(12) United States Patent
Zheng et al.

(10) Patent No.: US 7,927,798 B2
(45) Date of Patent: *Apr. 19, 2011

(54) DETECTION OF NUCLEIC ACIDS FROM WHOLE BLOOD

(75) Inventors: Zhi Zheng, Fremont, CA (US); Yuling Luo, San Ramon, CA (US); Gary McMaster, Ann Arbor, MI (US)

(73) Assignee: Panomics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/543,752

(22) Filed: Oct. 4, 2006

(65) Prior Publication Data

US 2007/0161015 A1 Jul. 12, 2007

Related U.S. Application Data

(60) Provisional application No. 60/724,205, filed on Oct. 5, 2005.

(51) Int. Cl.
*C12Q 1/68* (2006.01)
*C07H 21/02* (2006.01)
*C07H 21/04* (2006.01)

(52) U.S. Cl. .............................. 435/6; 536/23.1; 536/24.3

(58) Field of Classification Search ....... 435/6; 536/22.1, 536/23.1, 24.3
See application file for complete search history.

(56) References Cited

U.S. PATENT DOCUMENTS

| | | | |
|---|---|---|---|
| 4,868,105 A | 9/1989 | Urdea et al. | |
| 5,093,232 A | 3/1992 | Urdea et al. | |
| 5,122,599 A * | 6/1992 | Barnett et al. | 536/23.5 |
| 5,124,246 A | 6/1992 | Urdea et al. | |
| 5,185,244 A * | 2/1993 | Wallace | 435/6 |
| 5,198,357 A * | 3/1993 | Holmovist et al. | 435/408 |
| 5,334,499 A * | 8/1994 | Burdick et al. | 435/6 |
| 5,374,524 A * | 12/1994 | Miller | 435/6 |
| 5,393,672 A * | 2/1995 | Ness et al. | 436/94 |
| 5,543,305 A * | 8/1996 | Cummins et al. | 435/91.1 |
| 5,635,352 A * | 6/1997 | Urdea et al. | 435/6 |
| 5,681,697 A * | 10/1997 | Urdea et al. | 435/6 |
| 5,681,702 A | 10/1997 | Collins et al. | |
| 5,712,383 A | 1/1998 | Sheridan et al. | |
| 5,747,244 A | 5/1998 | Sheridan et al. | |
| 5,780,227 A | 7/1998 | Sheridan et al. | |
| 5,804,684 A * | 9/1998 | Su | 536/25.4 |
| 5,849,481 A | 12/1998 | Urdea et al. | |
| 5,945,515 A * | 8/1999 | Chomczynski | 530/412 |
| 6,007,994 A | 12/1999 | Ward et al. | |
| 6,221,589 B1 * | 4/2001 | Lane et al. | 435/6 |
| 6,232,462 B1 | 5/2001 | Collins et al. | |
| 6,235,465 B1 | 5/2001 | Kolberg et al. | |
| 6,268,147 B1 * | 7/2001 | Beattie et al. | 435/6 |
| 6,306,643 B1 | 10/2001 | Gentalen et al. | |
| 6,352,827 B1 * | 3/2002 | Lin et al. | 435/5 |
| 6,418,382 B2 | 7/2002 | Rothberg et al. | |
| 6,472,187 B1 * | 10/2002 | Tonoike et al. | 435/91.51 |
| 6,562,575 B1 * | 5/2003 | Dahl | 435/6 |
| 6,610,475 B1 * | 8/2003 | Kacian et al. | 435/6 |
| 6,670,464 B1 * | 12/2003 | Shimkets et al. | 536/23.5 |
| 6,673,914 B1 | 1/2004 | Hoon | |
| 6,852,490 B2 | 2/2005 | Gentalen et al. | |
| 7,033,758 B2 | 4/2006 | Kenny et al. | |
| 2002/0034754 A1 * | 3/2002 | Reed et al. | 435/6 |
| 2002/0172953 A1 | 11/2002 | Mirkin et al. | |
| 2002/0187470 A1 * | 12/2002 | Casey et al. | 435/6 |
| 2003/0211489 A1 | 11/2003 | Shen et al. | |
| 2004/0086930 A1 * | 5/2004 | Tereba et al. | 435/6 |
| 2004/0115686 A1 | 6/2004 | Dolginow et al. | |
| 2005/0009063 A1 * | 1/2005 | Xia et al. | 435/6 |
| 2005/0019842 A1 * | 1/2005 | Prober et al. | 435/7.9 |
| 2005/0170370 A1 | 8/2005 | Rabbani et al. | |
| 2005/0282220 A1 * | 12/2005 | Prober et al. | 435/6 |
| 2006/0172284 A1 | 8/2006 | Zheng et al. | |
| 2006/0263769 A1 * | 11/2006 | Luo et al. | 435/5 |
| 2006/0286583 A1 * | 12/2006 | Luo et al. | 435/6 |
| 2007/0015188 A1 | 1/2007 | Luo et al. | |
| 2008/0220979 A1 * | 9/2008 | Wang et al. | 506/9 |
| 2009/0170060 A1 * | 7/2009 | Kermekchiev et al. | 435/2 |

FOREIGN PATENT DOCUMENTS

| | | |
|---|---|---|
| EP | 1 428 892 A | 6/2004 |
| WO | WO 94/00598 A1 | 6/1994 |
| WO | WO 01/94632 A2 | 12/2001 |

OTHER PUBLICATIONS

Lo et al., Fetal DNA in Maternal plasma : Biology and Diagnostic Applications. Clinical Chemistry 46(12) : 1903-1906 (2000).*
Higuchi R., DNA from Whole blood for PCR (One page from the Jackson Laboratory) Amplifications 2 :1-3 (1989).*
Al-Soud et al. A sample preparation method which facilitates detection of bacteria in blood cultures by the polymerase chain reaction. J. Microbiol. Methods 32:217-224 (1998).*
Narayanan S. Overview of principles and current uses of DNA probes in clinical and laboratory medicine. Ann Clin Lab Sci 1992;22:353-376.*
Lewin et al., A simple method for DNA extraction from leukocytes for use in PCR. Biotechniques 13:522-524. (1992).*
Mercier B, Gaucher C, Feugeas O, Mazurier C. Direct PCR from whole blood, without DNA extraction. Nucleic Acids Res 18:5908 (1990).*
Balnaves ME, Nasioulas S, Dahl HH, Forrest S. Direct PCR from CVS, blood lysates for detection of cystic fibrosis and Duchenne muscular dystrophy deletions. Nucleic Acids Res 19:1155 (1991).*
Application Note : Total RNA purification from whole blood. Applied Biosystems (2002).*
Application Note : Whole genome amplification from crude blood lysates. Amersdham Biosciences. (2003).*
Zolg et al. High Salt Lysates: a Simple Method to Store Blood Samples Without Refrigeration for Subsequent Use with DNA Probes. Am. J. Trop. Med. Hyg., 39(1) : 33-40 (1988).*
De Vries et al. Cell lysates obtained from whole blood cicumvents DNA isolation. Clinical Chemistry 47 (9) :1701-1702 (2001).*
Ugozzoli et al. Detection of specific alleles by using allele—specific primer extension followed by capture on solid support. GATA 9(4) : 107-112 (1992).*

(Continued)

*Primary Examiner* — Ethan Whisenant

(74) *Attorney, Agent, or Firm* — Quine Intellectual Property Law Group, P.C.

(57) ABSTRACT

Methods of detecting one or more nucleic acids from whole blood or plasma are provided. The nucleic acids are captured on a solid support and detected. Compositions, kits, and systems related to the methods are also described.

24 Claims, 20 Drawing Sheets

OTHER PUBLICATIONS

Nordvag et al., Direct PCR of washed blood cells. Biotechniques 12:490-493 (1992).*

Van Cleve et al. (1998) "Direct quantification of HIV by flow cytometry using branched DNA signal amplification," *Molecular and Cellular Probes*, 12:243-247.

Malygin et al. (1996) "Hybridization of two oligodeoxynucleotides to both strands of an RNA hairpin structure increases the efficiency of RNA-DNA duplex formation," *FEBS Letters*, 392:114-116.

Player et al. (2001) "Single-copy gene detection using branched DNA (bDNA) in-situ hybridization," *The Journal of Histochemistry and Cytochemistry*, 49(5):603-611.

Schweitzer & Kingsmore (2001) "Combining nucleic acid amplification and detection," *Curr. Op Biotechnol.*, 12(1):21-27.

Shah et al. (1994) "Novel, ultrasensitive, Q-beta, replicase-amplified hybridization assay for detection of *Chlamydia trachomatis*," *J. Clin. Microbiol.*, 32(11):2718-2724.

Shah et al. (1995) "Detection of *Mycobacterium tuberculosis* directly from spiked human sputum by Q-beta replicase-amplified assay," *J. Clin. Microbiol.*, 33(2):322-328.

Shah et al. (2003) "Ultra-sensitive and specific detections of porcine endogenous retrovirus (PERV) using a sequence-capture real-time PCR approach," *J. Virol.Meth.*, 109:209-216.

Stone et al. (1996) "Detection of rRNA from four respiratory pathogens using an automated Qα replicase assay," *Mol. Cell. Probes*, 10:359-370.

Harris et al. (1996) "Detection of *Trypanosoma brucei* spp. In human blood by a nonradioactive branched DNA-based technique," *J. Clin. Microbiol.*, 34(10):2401-2407.

Nolte (1998) "Branched DNA signal amplification for direct quantitation of nucleic acid sequences in clinical specimens," *Advances in Clinical Chemistry*, 33(1):201-235.

Akane et al. (1994) "Identification of the heme compound copurified with deoxyribonucleic acid (DNA) from bloodstains, a major inhibitor of polymerase chain reaction (PCR) amplification," *J Forensic Sci* , 39(2):362-372.

Al-Soud & Radstrom (2001) "Purification and Characterization of PCR-Inhibitory Components in Blood Cells," *J. Clin. Microbiol*, 39(2):485-493.

Al-Soud et al. (2000) "Identification and Characterization of Immunoglobulin G in Blood as a Major Inhibitor of Diagnostic PCR," *J. Clin. Microbiol.* 38(1):345-350.

Baechler et al. (2004) "Expression levels for many genes in human peripheral blood cells are highly sensitive to ex vivo incubation," *Genes Immun*, 5(5):347-353.

Wettinger et al. (2005). "High throughput mRNA profiling highlights associations between myocardial infarction and aberrant expression of inflammatory molecules in blood cells," *Blood*, 105(5):2000-2006.

Breit et al. (2004) "Impact of pre-analytical handling on bone marrow mRNA gene expression," *Br J Haematol* , 126(2):231-243.

Bushnell et al. (1999) "ProbeDesigner: for the design of probesets for branched DNA (bDNA) signal amplification assays," *Bioinformatics* 15:348-355.

Bustin and Nolan (2004) "Pitfalls of quantitative real-time reverse-transcription polymerase chain reaction," *J Biomol Tech*, 15(3):155-166.

Bustin (2002) "Quantification of mRNA using real-time reverse transcription PCR (RT-PCR): trends and problems," *J Mol Endocrinol*, 29(1):23-39.

Bustin et al. (2005) "Quantitative real-time RT-PCR—a perspective," *J Mol Endocrinol* , 34(3): 597-601.

Collins et al. (1997) "A branched DNA signal amplification assay for quantification of nucleic acid targets below 100 molecules/ml," *Nucleic Acids Research*, 25(15):2979-2984.

Collins et al. (1998) "Branched DNA (bDNA) technology for direct quantification of nucleic acids: design and performance," in *Gene Quantification*, F. Ferre, ed.

De Groote et al. (1992) "Direct stimulation of cytokines (II-1 beta, TNF-alpha, IL-6, IL-2, IFN-gamma and GM-CSF) in whole blood. I. Comparison with isolated PBMC stimulation," *Cytokine*, 4(3):239-248.

Debey et al. (2004) "Comparison of different isolation techniques prior gene expression profiling of blood derived cells: impact on physiological responses, on overall expression and the role of different cell types," *Pharmacogenomics J*, 4(3):193-207.

Deprimo et al. (2003) "Expression profiling of blood samples from an SU5416 Phase III metastatic colorectal cancer clinical trial: a novel strategy for biomarker identification," *BMC Cancer*, 3:3.

Dimitrov and Zuker (2004) "Prediction of Hybridization and Melting for Double-Stranded Nucleic Acids," *Biophys. J.*, 87:215-226.

Eis et al. (2001). "An invasive cleavage assay for direct quantitation of specific RNAs," *Nat Biotechnol*.19: 673-676.

Fan and Hegde (2005) "The transcriptome in blood: challenges and solutions for robust expression profiling" *Curr Mol Med*, 5(1):3-10.

Feezor et al. (2004) "Whole blood and leukocyte RNA isolation for gene expression analyses," *Physiol. Genomics*, 19(3):247-254.

Flagella et al. (2006) "A multiplex branched DNA assay for parallel quantitative gene expression profiling," *Anal Biochem*, 352(1):50-60.

Fulton et al. (1997) "Advanced multiplexed analysis with the FlowMetrixTM system," *Clinical Chemistry*, 43:1749-1756.

Gentalen and Chee (1999) "A novel method for determining linkage between DNA sequences: hybridization to paired probe arrays," *Nucl Acids Research*, 27:1485-1491.

Gibbs et al. (Published online May 29, 2005) "Quantitative detection of changes in cytokine gene expression in peripheral blood mononuclear cells correlates with and precedes acute rejection in renal transplant recipients," *Transpl Immunol*, 14(2):99-108.

Gleaves et al. (2002) "Multicenter evaluation of the Bayer VERSANT HIV-1 RNA 3.0 assay: analytical and clinical performance," *J Clin Virol* , 25(2):205-216.

Goerttler et al. (2005) "Gene expression profiling in polycythaemia vera: overexpression of transcription factor NF-E2," *Br J Haematol*, 129(1):138-150.

Gomes et al. (2003) "Upregulation of the apoptosis regulators cFLIP, CD95 and CD95 ligand in peripheral blood mononuclear cells in relapsing-remitting multiple sclerosis," *J Neuroimmunol*, 135(1-2):126-134.

Haferlach et al. (2005) "Global approach to the diagnosis of leukemia using gene expression profiling," *Blood*, 106(4):1189-1198.

Hartel et al. (2001) "Ex vivo induction of cytokine mRNA expression in human blood samples, "*J Immunol Methods*, 249(1-2):63-71.

Hartley and Klaassen (2000) "Detection of Chemical-Induced Differential Expression of Rat Hepatic Cytochrome P450 mRNA Transcripts Using Branched DNA Signal Amplification Technology," *Drug Metab Dispos*, 28(5):608-616.

Hochhaus et al. (2000) "Detection and quantification of residual disease in chronic myelogenous leukemia," *Leukemia*, 14(6):998-1005.

Horwitz et al. (2004) "Detection of Cardiac Allograft Rejection and Response to Immunosuppressive Therapy With Peripheral Blood Gene Expression," *Circulation*, 110(25):3815-3821.

Jurzak et al. (2001) "Increased AST and GGT activity as marker of RT-PCR inhibition in RNA extracts from peripheral blood," *Med Sci Monit*, 7 Suppl 1:231-235.

Kellar and Iannone (2002) "Multiplexed microsphere-based flow cytometric assays," *Experimental Hematology*, 30:1227-1237.

Kern et al. (1996) "An enhanced-sensitivity branched-DNA assay for quantification of human immunodeficiency virus type 1 RNA in plasma," *J. Clin. Microbiol.*, 34(12):3196-3202.

Latham et al. (2005) "Total RNA from Whole Blood for Expression Profiling" *Ambion TechNotes*, 12(2).

Lossos et al. (2004) "Prediction of Survival in Diffuse Large-B-Cell Lymphoma Based on the Expression of Six Genes," *N. Engl J Med*, 350(18):1828-1837.

Martel et al. (2002). "Multiplexed Screening Assay for mRNA Combining Nuclease Protection with Luminescent Array Detection"*Assay Drug Dev Technology*, 1:61-71.

Mueller et al. (2004) "Quantitative Tissue Factor Gene Expression Analysis in Whole Blood: Development and Evaluation of a Real-Time PCR Platform" *Clinical Chemistry*, 50, (1):245-248.

Muller et al. (2004) "Standardization of preanalytical factors for minimal residual disease analysis in chronic myelogenous leukemia,". *Acta Haematol*, 112(1-2):30-33.

Ockenhouse et al. (Published online May 13, 2005) "Functional Genomic Relationships in HIV-1 Disease Revealed by Gene-Expression Profiling of Primary Human Peripheral Blood Mononuclear Cells," *J Infect Dis*, 191(12):2064-2074.

Pahl (2005) "Gene expression profiling using RNA extracted from whole blood: technologies and clinical applications," *Expert Rev Mol Diagn*, 5(1):43-52.

Potera (2003) "eTag, You're It!" *Environmental Health Perspectives*, 111(15):A808.

Presentation at qPCR 2005: 2$^{nd}$ International qPCR Symposium & Industrial Exhibition, Weihenstephan, Germany, Sep. 6, 2005.

Quantigene technical bulletin No. 8: Quantigene® reagent system for direct mRNA quantification from formalin-fixed paraffin embedded (FFPE) tissue, (est. 2002).

Rainen et al. (2002) "Stabilization of mRNA Expression in Whole Blood Samples," *Clin Chem*, 48(11):1883-1890.

Ransohoff (2004) "Rules of evidence for cancer molecular-marker discovery and validation," *Nat Rev Cancer*, 4(4):309-314.

Ransohoff (2005) "Bias as a threat to the validity of cancer molecular-marker research." *Nat Rev Cancer*, 5(2):142-149.

Schanke et al. (1998) "Detection of Blood-Borne Microbes with the MasterPure™ Complete DNA and RNA Purification Kit" *EPICENTRE Forum*, 5 (3).

Shen et al. (1998) "Quantification of cytokine mRNA in peripheral blood mononuclear cells using branched DNA (bDNA) technology," *Journal of Immunological Methods*, 215(1-2):123-134.

Shyamala et al. (1999) "High-throughput screening for ligand-induced c-fos mRNA expression by branched DNA assay in Chinese hamster ovary cells," *Anal. Biochem.*, 266(1):140-147.

Stordeur et al. (2002) "Analysis of spontaneous mRNA cytokine production in peripheral blood," *J Immunol Methods*, 261(1-2):195-197.

Tamul et al. (1995) "Comparison of the effects of Ficoll-Hypaque separation and whole blood lysis on results of immunophenotypic analysis of blood and bone marrow samples from patients with hematologic malignancies," *Clin Diagn Lab Immunol*, 2(3):337-342.

Tanner et al. (2002) "Substantial changes in gene expression level due to the storage temperature and storage duration of human whole blood," *Clinical and Laboratory Haematology*, 24(6):337-341.

Tenedini et al. (Published Jul. 22, 2004) "Gene expression profiling of normal and malignant CD34-derived megakaryocytic cells," *Blood*, 104(10):3126-3135.

Thach et al. (2003) "Assessment of two methods for handling blood in collection tubes with RNA stabilizing agent for surveillance of gene expression profiles with high density microarrays," *J Immunol Methods*, 283(1-2):269-279.

Theophilus (1998) "Extraction of RNA from fresh and frozen blood," *Methods Mol Biol*, 86:39-45.

Tian et al. (2004) "Multiplex mRNA assay using electrophoretic tags for high-throughput gene expression analysis," *Nucleic Acids Res*, 32(16):126.

Urdea et al. (1991) "Branched DNA amplification multimers for the sensitive, direct detection of human hepatitis viruses," *Nucleic Acids Symp Ser*, 24:197-200.

Van Leeuwen et al. (2005) "Differential Gene Expression in Human Peripheral Blood Mononuclear Cells Induced by Cigarette Smoke and Its Constituents," *Toxicol. Sci.*, 86(1):200-210.

Wang et al. (2004) "Optimizing RNA extraction yield from whole blood for microarray gene expression analysis" *Clin Biochem*, 37(9):741-744.

Wang et al. (1997) "Regulation of insulin preRNA splicing by glucose," *PNAS*, 94:4360-4365.

Wang et al. (1999) "Cytokine mRNA decay is accelerated by an inhibitor of p38-mitogen-activated protein kinase," *Inflamm Res*, 48:533-538.

Whitney et al. (Published Feb. 10, 2003) "Individuality and variation in gene expression patterns in human blood," *Proc Natl Acad Sci U S A*, 100(4):1896-18901.

Wilber & Urdea (1998) "Quantification of HCV RNA in clinical specimens by branched DNA (bDNA) technology," *Methods in Molecular Medicine: Hepatitis C* 19:71-78.

Wu et al. (2003) Globin reduction protocol. Affymetrix Technical Note http://www.affymetrix.com/support/technotes/blood2_technote.pdf.

Yang et al. (2001) "BADGE, Beads Array for the Detection of Gene Expression, a high-throughput diagnostic bioassay," *Genome Res.* 11:1888-1898.

Zheng et al (2006) "Sensitive and Quantitative Measurement of Gene Expression Directly from a Small Amount of Whole Blood," *Clin. Chem.* 52:1294-1302.

\* cited by examiner

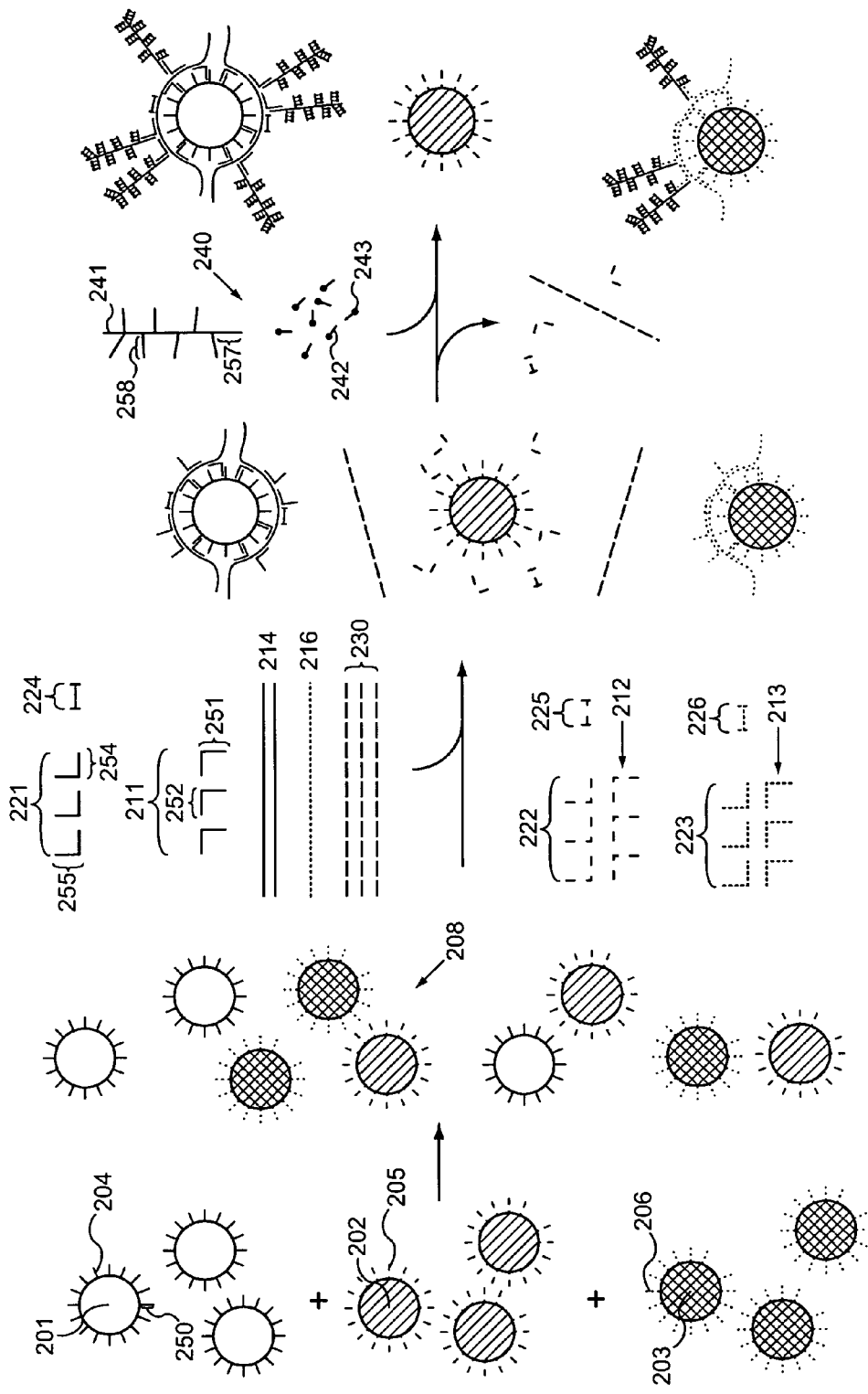

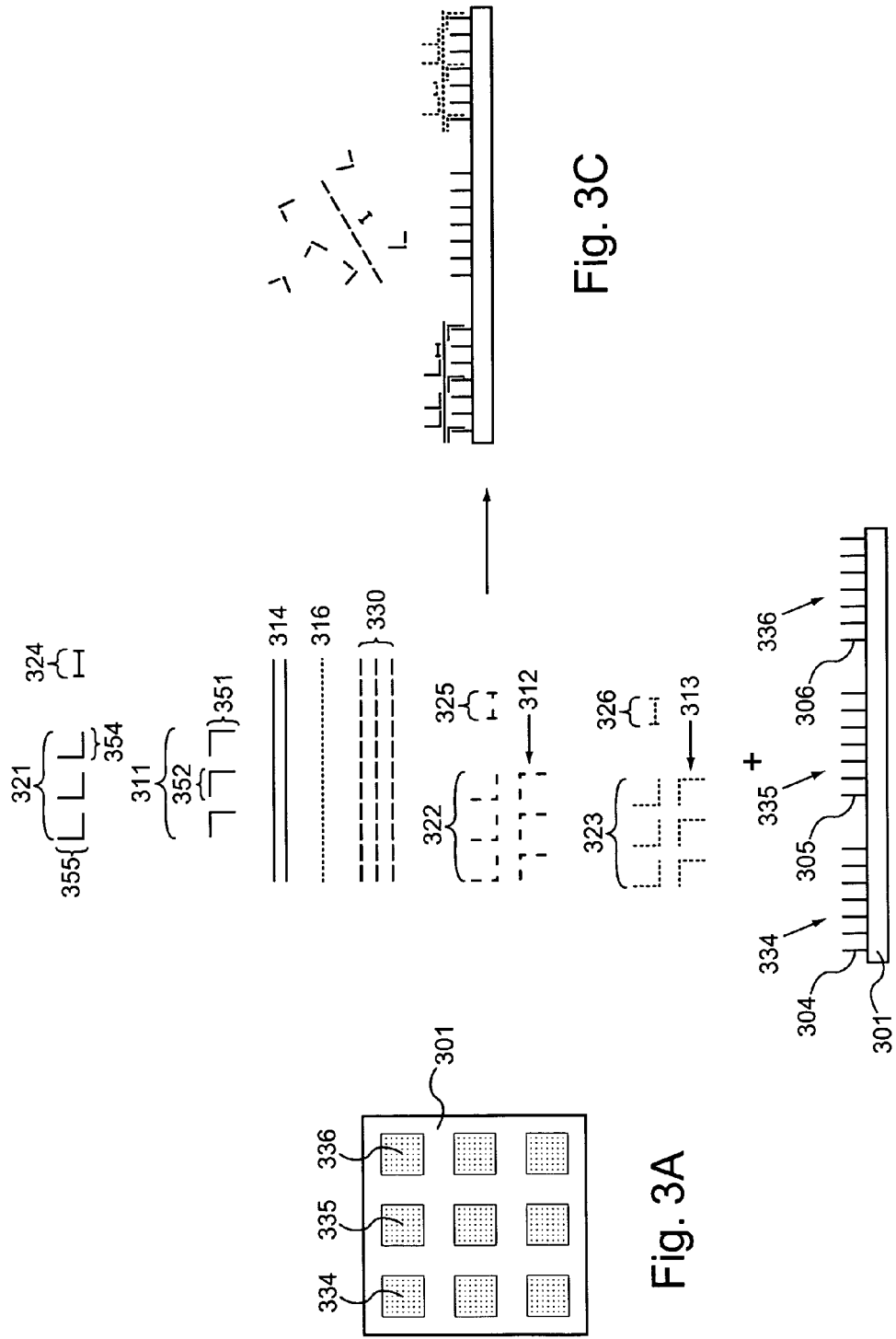

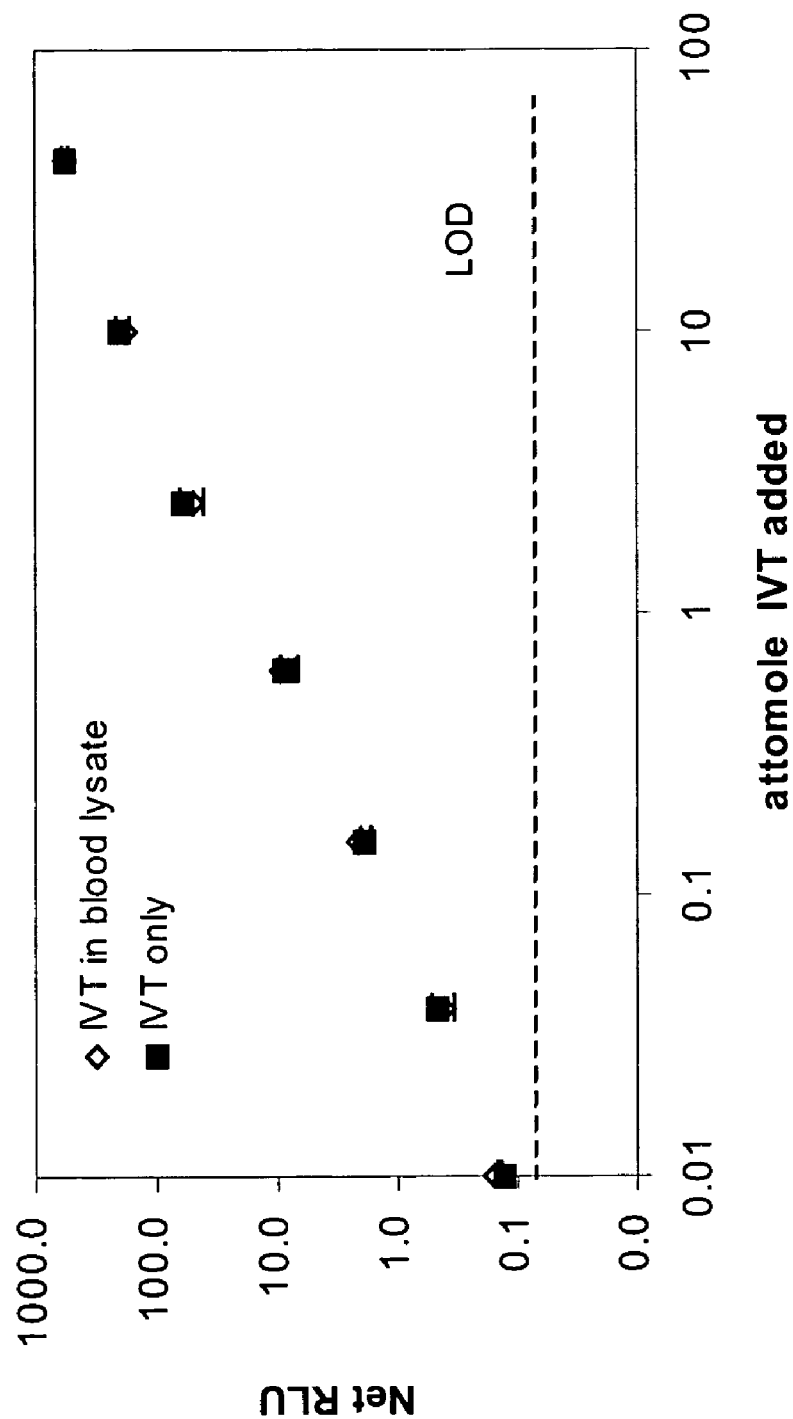

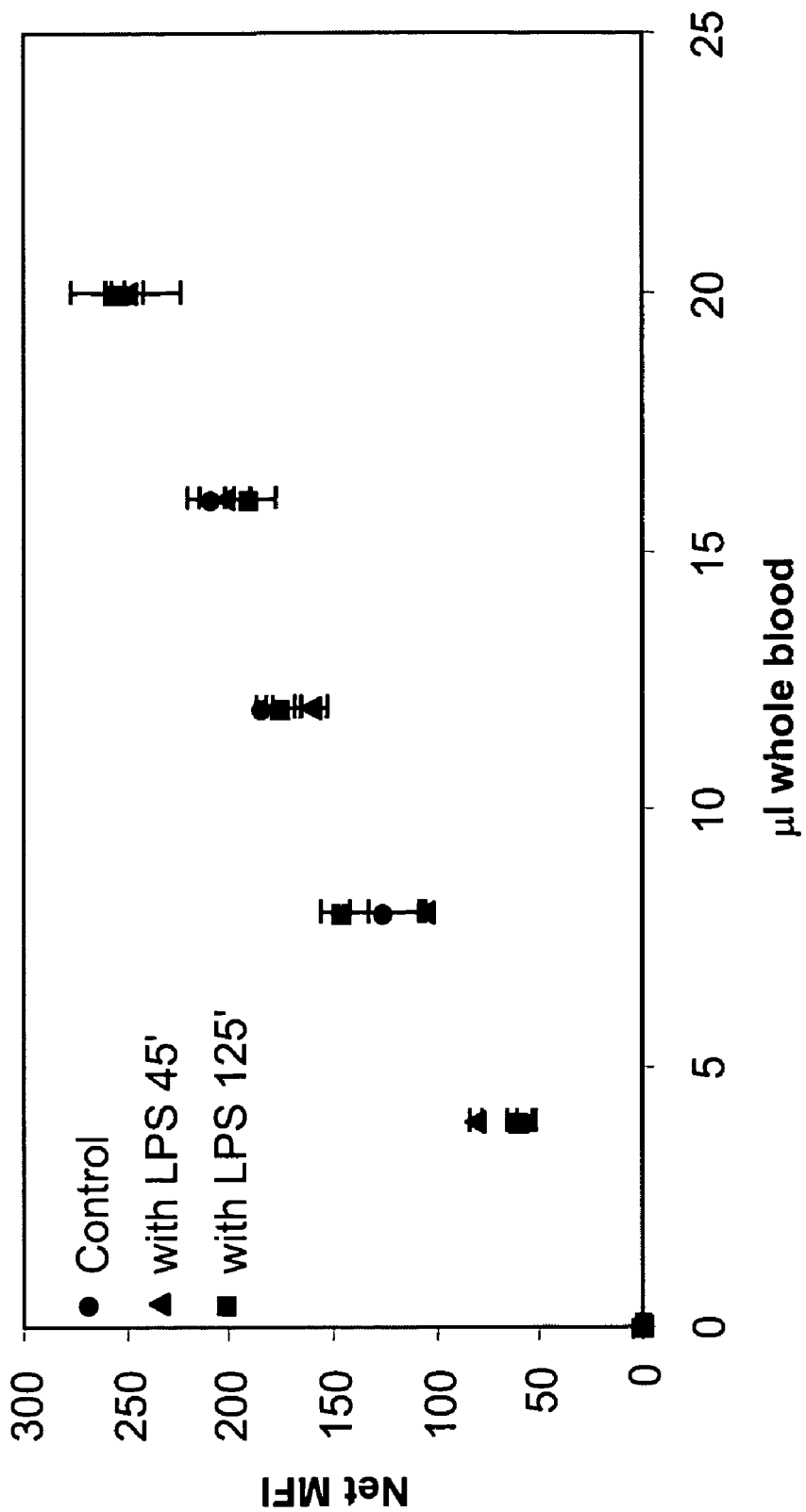

DETECTION OF NUCLEIC ACIDS FROM WHOLE BLOOD

CROSS-REFERENCE TO RELATED APPLICATIONS

This application is a non-provisional utility patent application claiming priority to and benefit of the following prior provisional patent application: U.S. Ser. No. 60/724,205, filed Oct. 5, 2005, entitled "DETECTION OF NUCLEIC ACIDS FROM WHOLE BLOOD" by Zhi Zheng et al., which is incorporated herein by reference in its entirety for all purposes.

FIELD OF THE INVENTION

The present invention is in the field of nucleic acid detection. The invention includes methods for detecting one or more nucleic acids from whole blood, peripheral blood cells, or plasma. The invention also includes compositions and kits related to the methods.

BACKGROUND OF THE INVENTION

Samples of peripheral whole blood are easily obtained from any of a wide variety of organisms, and thus blood would seem to be a rich source of material for gene expression studies. However, the composition of blood presents unusual challenges to the detection of nucleic acids from whole blood samples.

For example, whole blood includes a number of different cell types, including red blood cells (erythrocytes), platelets, and white blood cells (leukocytes). The white blood cells themselves include a variety of cell types, for example, granulocytes, such as neutrophils, basophils, and eosinophils, and mononuclear cells, such as monocytes and lymphocytes (including, e.g., T lymphocytes, B lymphocytes, and natural killer cells). Furthermore, when considering gene expression, only particular forms of particular white blood cell types may be of interest: e.g., active granular natural killer cells, Th-lymphocytes, or activated neutrophils, eosinophils, or basophils, to name only a few of the possible examples. Considering that red blood cells are estimated to occupy about 40-45% of the total blood volume while white blood cells and platelets together occupy only about 1-2% of the total blood volume, the difficulty of detecting a nucleic acid that is expressed only in white blood cells, or only in a particular subset or type of white blood cells, becomes clear.

Detection of nucleic acids from whole blood is further complicated, for example, by the high concentration of protein in blood (e.g., of hemoglobin from the red blood cells and of plasma proteins such as albumin, fibrinogen, and globulins) and by the prevalence of certain nucleic acids, particularly globin mRNA.

Current methods for analysis of gene expression in blood involve isolation of a particular type or group of cells (e.g., by red blood cell lysis, or by centrifugation to obtain peripheral blood mononuclear cells (PBMC)), purification of RNA from blood cells, and/or enzymatic manipulation (e.g., reverse transcription and/or target amplification) of the nucleic acids to be detected.

Among other aspects, the present invention provides methods for nucleic acid detection from whole blood that overcome the above noted difficulties. A complete understanding of the invention will be obtained upon review of the following.

SUMMARY OF THE INVENTION

In one aspect, the invention provides methods of detecting nucleic acids from whole blood. In another aspect, the invention provides methods of detecting nucleic acids from plasma. Compositions related to the methods (e.g., compositions useful in practicing the methods or formed while practicing the methods) are also provided, as are kits for detecting nucleic acids from whole blood or plasma.

A first general class of embodiments provides methods of detecting at least a first target nucleic acid. In the methods, a sample comprising whole blood is provided. The whole blood includes peripheral blood cells, which are lysed to produce a lysate comprising the first target nucleic acid. The first target nucleic acid is contacted with a first set of n capture extenders, wherein n is at least two; this first set of capture extenders is capable of hybridizing to the first target nucleic acid. The first target nucleic acid can be contacted with the first set of capture extenders by, for example, contacting the lysate with the first set of capture extenders. The first target nucleic acid is hybridized to the first set of capture extenders, and the first set of capture extenders is associated with a solid support. The first target nucleic acid is captured on the solid support by hybridizing the first target nucleic acid to the first set of capture extenders and associating the first set of capture extenders with the solid support, and the presence of the first target nucleic acid on the solid support is then detected. The hybridization and association steps can, e.g., be either simultaneous or sequential.

In one class of embodiments, the peripheral blood cells are lysed in the whole blood to produce a whole blood lysate that includes the first target nucleic acid. In this class of embodiments, contacting the first target nucleic acid with the first set of capture extenders typically comprises contacting the whole blood lysate with the first set of capture extenders. In one class of embodiments, the whole blood is applied to a matrix to produce a blood spot, and the blood spot is dried to produce a dried blood spot. The dried blood spot is contacted with an aqueous solution to produce the lysate. In one class of embodiments, the methods include contacting the peripheral blood cells and/or the lysate with an exogenously supplied protease, typically prior to contacting the first target nucleic acid with the first set of capture extenders.

The methods can be applied to detection of essentially any type of nucleic acids. For example, the first target nucleic acid can be a DNA or an RNA. In one class of embodiments, the peripheral blood cells include white blood cells, one or more of which white blood cells comprises the first target nucleic acid.

As noted, the first set of capture extenders includes n capture extenders, where n is at least two. Preferably, n is at least three, and n can be at least four or at least five or more. Typically, but not necessarily, n is at most ten. The capture extenders are optionally bound to the solid support, e.g., covalently or noncovalently, directly or through a linker. In one aspect, the capture extenders are associated with the solid support by hybridization of the capture extenders to one or more capture probes. Thus, in one class of embodiments, a first capture probe is bound to the solid support, and the first set of capture extenders is associated with the solid support by hybridizing the capture extenders to the first capture probe.

The solid support can be essentially any suitable support, including any of a variety of materials, configurations, and the like. For example, in one class of embodiments, the solid support is a substantially planar solid support. In another class of embodiments, the solid support comprises a plurality of particles, e.g., microspheres.

The methods can be conveniently multiplexed to detect two or more target nucleic acids simultaneously. Thus, in one class of embodiments, the lysate comprises a second target nucleic acid and the methods include contacting the second target nucleic acid with a second set of m capture extenders, wherein m is at least two; this second set of capture extenders is capable of hybridizing to the second target nucleic acid. The second target nucleic acid is hybridized to the second set of capture extenders, and the second set of capture extenders is associated with the solid support. Hybridizing the second target nucleic acid to the second set of capture extenders and associating the second set of capture extenders with the solid support captures the second target nucleic acid on the solid support. The presence of the second target nucleic acid on the solid support is then detected. It will be evident that n, the number of capture extenders in the first set, can but need not be the same as m, the number of capture extenders in the second set. As for the first target nucleic acid, the second target nucleic acid can be essentially any type of nucleic acid. It will be evident that third, fourth, fifth, etc. target nucleic acids are optionally also detected.

In one class of embodiments, the solid support is a substantially planar solid support, the first target nucleic acid is captured at a first selected position on the solid support, and the second target nucleic acid is captured at a second selected position on the solid support. For example, the first set of capture extenders can be hybridized to a first capture probe predisposed at the first selected position, while the second set of capture extenders is hybridized to a second capture probe predisposed at the second selected position.

In another class of embodiments, the solid support comprises a population of particles. The population includes at least two sets of particles, and the particles in each set are distinguishable from the particles in every other set. The first target nucleic acid is captured on a first set of the particles, and the second target nucleic acid is captured on a second set of the particles. For example, the first set of particles can comprise a first capture probe that is capable of hybridizing to the capture extenders comprising the first set of capture extenders (and thereby capturing the first target nucleic acid on the first set of particles), and the second set of particles can comprise a second capture probe that is capable of hybridizing to the capture extenders comprising the second set of capture extenders (and thereby capturing the second target nucleic acid on the second set of particles). In this class of embodiments, detecting the presence of the first and second nucleic acid on the solid support typically includes identifying at least a portion of the particles from each set and detecting the presence of nucleic acid on those particles.

In one aspect, the first target nucleic acid (and optional second, third, etc. target nucleic acid) is captured and its presence on the solid support is detected using a branched-chain DNA (bDNA) assay. Thus, in one class of embodiments, detecting the presence of the first target nucleic acid on the solid support includes hybridizing a first set of one or more label extenders (typically, two or more label extenders) and a label probe system comprising a label to the first target nucleic acid and detecting the presence of the label on the solid support. The label probe system typically includes an amplification multimer and a plurality of label probes, wherein the amplification multimer is capable of hybridizing simultaneously to a label extender and to a plurality of label probes. In another aspect, the label probe system includes a preamplifier, a plurality of amplification multimers, and a plurality of label probes, wherein the preamplifier hybridizes to one or more label extenders, and the amplification multimers hybridize to the preamplifier and to the plurality of label probes. As another example, the label probe system can include only label probes, which hybridize directly to the label extenders. The label probe can include the label, or it can be configured to bind to the label. Suitable labels include, but are not limited to, an enzyme or a fluorescent label. When an enzyme (e.g., alkaline phosphatase) is used as the label, its presence on the solid support can be detected by detecting its activity with a chemiluminescent, colorimetric, or similar assay as is well-known in the art. When a fluorescent label is used, detecting the presence of the label on the solid support typically comprises detecting a fluorescent signal from the label.

At any of various steps in the methods, materials not captured on the solid support are optionally separated from the support (and thus from any support-bound materials). The methods are optionally used to quantitate the amount of the first (and optional second, third, etc.) nucleic acid present in the whole blood sample. Thus, in one class of embodiments, detecting the presence of the first target nucleic acid on the solid support comprises detecting an amount of the first target nucleic acid on the solid support. It will be evident that the amount of the target nucleic acid captured on the solid support is proportional to the amount of the target nucleic acid present in the original sample.

Another general class of embodiments provides methods of detecting at least a first target nucleic acid from plasma. In the methods, plasma comprising the first target nucleic acid is provided. The plasma is contacted with a first set of n capture extenders, wherein n is at least two. The first set of capture extenders is capable of hybridizing to the first target nucleic acid. The first target nucleic acid is hybridized to the first set of capture extenders, and the first set of capture extenders is associated with a solid support. The first target nucleic acid is captured on the solid support by hybridizing the first target nucleic acid to the first set of capture extenders and associating the first set of capture extenders with the solid support. The presence of the first target nucleic acid on the solid support is then detected. The hybridization and association steps can be, e.g., either simultaneous or sequential. In one class of embodiments, the methods include contacting the plasma with an exogenously supplied protease, typically prior to contacting the plasma with the first set of capture extenders.

Essentially all of the features noted for the methods above apply to these embodiments as well, as relevant; for example, with respect to number of capture extenders per set, type of solid support, association of the capture extenders with the solid support, detection technique, composition of the optional label probe system, type of label, inclusion of blocking probes, type of target nucleic acid(s), quantitation of the target nucleic acid(s), separation of unbound materials from the solid support, and/or the like.

For example, in one preferred class of embodiments, a first capture probe is bound to the solid support, and associating the first set of capture extenders with the solid support comprises hybridizing the capture extenders to the first capture probe. As another example, the presence of the first target nucleic acid on the solid support is optionally detected by hybridizing a first set of one or more label extenders and a label probe system comprising a label to the first target nucleic acid and then detecting the presence of the label on the solid support.

As for the embodiments above, the methods can be conveniently multiplexed to detect two or more target nucleic acids simultaneously. Thus, in one class of embodiments, the plasma comprises a second target nucleic acid and the methods include contacting the second target nucleic acid with a second set of m capture extenders, wherein m is at least two; this second set of capture extenders is capable of hybridizing to the second target nucleic acid. The second target nucleic acid is hybridized to the second set of capture extenders, and the second set of capture extenders is associated with the solid support. Hybridizing the second target nucleic acid to the second set of capture extenders and associating the second set of capture extenders with the solid support captures the second target nucleic acid on the solid support. The presence of the second target nucleic acid on the solid support is then detected. It will be evident that n, the number of capture extenders in the first set, can but need not be the same as m, the number of capture extenders in the second set. As for the first target nucleic acid, the second target nucleic acid can be essentially any type of nucleic acid. It will be evident that third, fourth, fifth, etc. target nucleic acids are optionally also detected.

In one class of embodiments, the solid support is a substantially planar solid support, the first target nucleic acid is captured at a first selected position on the solid support, and the second target nucleic acid is captured at a second selected position on the solid support. For example, the first set of capture extenders can be hybridized to a first capture probe predisposed at the first selected position, while the second set of capture extenders is hybridized to a second capture probe predisposed at the second selected position.

In another class of embodiments, the solid support comprises a population of particles. The population includes at least two sets of particles, and the particles in each set are distinguishable from the particles in every other set. The first target nucleic acid is captured on a first set of the particles, and the second target nucleic acid is captured on a second set of the particles. For example, the first set of particles can comprise a first capture probe that is capable of hybridizing to the capture extenders comprising the first set of capture extenders (and thereby capturing the first target nucleic acid on the first set of particles), and the second set of particles can comprise a second capture probe that is capable of hybridizing to the capture extenders comprising the second set of capture extenders (and thereby capturing the second target nucleic acid on the second set of particles). In this class of embodiments, detecting the presence of the first and second nucleic acid on the solid support typically includes identifying at least a portion of the particles from each set and detecting the presence of nucleic acid on those particles.

Compositions related to the methods form another feature of the invention. Thus, one general class of embodiments provides a composition that includes a first set of n capture extenders, wherein n is at least two, and peripheral blood cell nucleic acids. The first set of capture extenders is capable of hybridizing to a first target nucleic acid. The first set of capture extenders is associated with, or is capable of being associated with, a solid support.

In one class of embodiments, the composition includes a whole blood lysate comprising the peripheral blood cell nucleic acids. The composition can include the first target nucleic acid. The peripheral blood cell nucleic acids optionally comprise the first target nucleic acid; alternatively, the first target nucleic acid can, e.g., be a nucleic acid found in the plasma.

In one class of embodiments, the composition includes an exogenously supplied protease. The composition optionally also includes reagents used to detect the first target nucleic acid. For example, in one class of embodiments, the composition includes a label probe system comprising a label and/or a first set of one or more label extenders, which first set of label extenders is capable of hybridizing to the first target nucleic acid.

The composition can include the solid support. The capture extenders are optionally bound to the solid support, e.g., covalently or noncovalently, directly or through a linker. In one preferred class of embodiments, a first capture probe is bound to the solid support. The first capture probe is capable of hybridizing to the capture extenders of the first set of capture extenders and thereby associating the capture extenders with the solid support. As noted above, the solid support can be essentially any suitable support, including any of a variety of materials, configurations, and the like. For example, in one class of embodiments, the solid support is a substantially planar solid support. In another class of embodiments, the solid support comprises a plurality of particles.

The composition optionally includes a second set of m capture extenders, wherein m is at least two. The second set of capture extenders is capable of hybridizing to a second target nucleic acid, and the second set of capture extenders is associated with, or is capable of being associated with, the solid support. In one class of embodiments, the solid support is a substantially planar solid support, wherein the first set of capture extenders is associated with or is capable of being associated with a first selected position on the solid support, and wherein the second set of capture extenders is associated with or is capable of being associated with a second selected position on the solid support. A first capture probe is optionally bound to the solid support at the first selected position while a second capture probe is bound to the solid support at the second selected position. In another class of embodiments, the solid support comprises a population of particles that includes at least two sets of particles, and the particles in each set are distinguishable from the particles in every other set. The first set of capture extenders is associated with or is capable of being associated with a first set of the particles, and the second set of capture extenders is associated with or is capable of being associated with a second set of the particles. Optionally, the first set of particles comprises a first capture probe capable of hybridizing to the capture extenders comprising the first set of capture extenders, while the second set of particles comprises a second capture probe capable of hybridizing to the capture extenders comprising the second set of capture extenders. The composition optionally includes the second target nucleic acid. It will be evident that the composition optionally also includes third, fourth, fifth, etc. target nucleic acids, sets of capture extenders, sets of particles or selected positions on the solid support, and/or the like.

Essentially all of the features noted for the methods above apply to these embodiments as well, as relevant; for example, with respect to number of capture extenders per set, composition of the label probe system, type of label, inclusion of blocking probes, type of target nucleic acid(s), and/or the like.

Another general class of embodiments provides a composition that includes a first set of n capture extenders, wherein n is at least two, and plasma. The first set of capture extenders is capable of hybridizing to a first target nucleic acid. The first set of capture extenders is associated with, or is capable of being associated with, a solid support.

The composition can include the first target nucleic acid (e.g., a DNA or RNA). In one class of embodiments, the composition includes an exogenously supplied protease. The composition optionally also includes reagents used to detect the first target nucleic acid. For example, in one class of embodiments, the composition includes a label probe system comprising a label and/or a first set of one or more label extenders, which first set of label extenders is capable of hybridizing to the first target nucleic acid.

The composition can include the solid support. In one class of embodiments, a first capture probe is bound to the solid support. The first capture probe is capable of hybridizing to the capture extenders of the first set of capture extenders and thereby associating the capture extenders with the solid support. As noted above, the solid support can be essentially any suitable support, including any of a variety of materials, configurations, and the like. For example, in one class of embodiments, the solid support is a substantially planar solid support, while in other embodiments, the solid support comprises a plurality of particles.

The composition optionally includes a second set of m capture extenders, wherein m is at least two. The second set of capture extenders is capable of hybridizing to a second target nucleic acid, and the second set of capture extenders is associated with, or is capable of being associated with, the solid support. In one class of embodiments, the solid support is a substantially planar solid support, wherein the first set of capture extenders is associated with or is capable of being associated with a first selected position on the solid support, and wherein the second set of capture extenders is associated with or is capable of being associated with a second selected position on the solid support. A first capture probe is optionally bound to the solid support at the first selected position while a second capture probe is bound to the solid support at the second selected position. In another class of embodiments, the solid support comprises a population of particles that includes at least two sets of particles, and the particles in each set are distinguishable from the particles in every other set. The first set of capture extenders is associated with or is capable of being associated with a first set of the particles, and the second set of capture extenders is associated with or is capable of being associated with a second set of the particles. Optionally, the first set of particles comprises a first capture probe capable of hybridizing to the capture extenders comprising the first set of capture extenders, while the second set of particles comprises a second capture probe capable of hybridizing to the capture extenders comprising the second set of capture extenders. The composition optionally includes the second target nucleic acid. It will be evident that the composition optionally also includes third, fourth, fifth, etc. target nucleic acids, sets of capture extenders, sets of particles or selected positions on the solid support, and/or the like.

Essentially all of the features noted for the embodiments above apply to these embodiments as well, as relevant; for example, with respect to number of capture extenders per set, composition of the label probe system, type of label, inclusion of blocking probes, type of target nucleic acid(s), and/or the like.

Yet another general class of embodiments provides a kit for detecting at least a first target nucleic acid. The kit includes a first capture probe bound to a solid support, a first set of n capture extenders, wherein n is at least two, a label probe system comprising a label, a first set of one or more label extenders, a first solution comprising a detergent, and a protease, packaged in one or more containers. Instructions for detecting the first target nucleic acid in whole blood, in peripheral blood cells, and/or in plasma with the kit are typically also included. The first set of capture extenders is capable of hybridizing to the first target nucleic acid and to the first capture probe, and the label extenders of the first set are capable of hybridizing to the first target nucleic acid and to the label probe system.

In one aspect, the kits are configured for multiplex detection of target nucleic acids. Thus, in one class of embodiments, the kit also includes a second capture probe bound to the solid support, a second set of m capture extenders, wherein m is at least two, and a second set of one or more label extenders. The second set of capture extenders is capable of hybridizing to a second target nucleic acid and to the second capture probe, and the label extenders of the second set are capable of hybridizing to the second target nucleic acid and to the label probe system.

Essentially all of the features noted for the embodiments above apply to these embodiments as well, as relevant; for example, with respect to number of capture extenders per set, type of solid support, association of the capture extenders with the solid support, composition of the label probe system, type of label, type of target nucleic acid(s), and/or the like.

Figure 1:
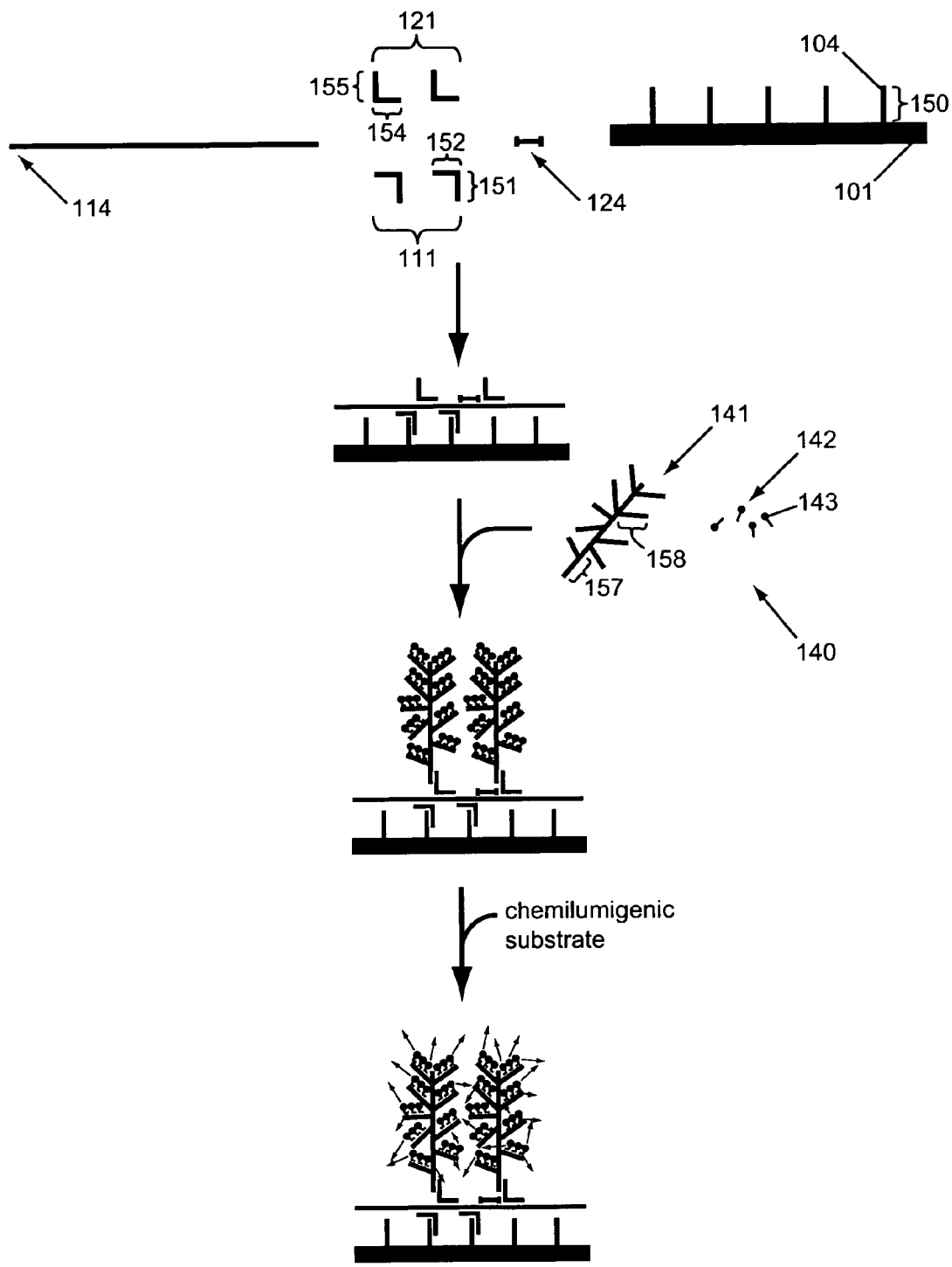
FIG. 1 schematically illustrates a typical standard bDNA assay.
Figure 2E:
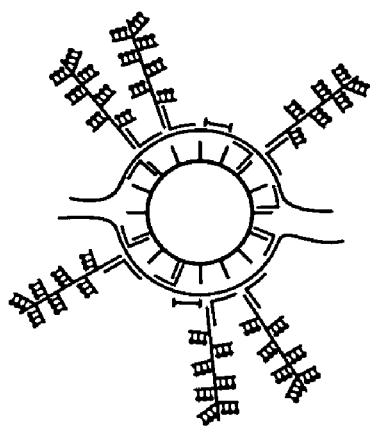
FIG. 2 Panels A-E schematically depict a multiplex bDNA assay, in which the target nucleic acids are captured on distinguishable subsets of microspheres and then detected.
Figure 2E:
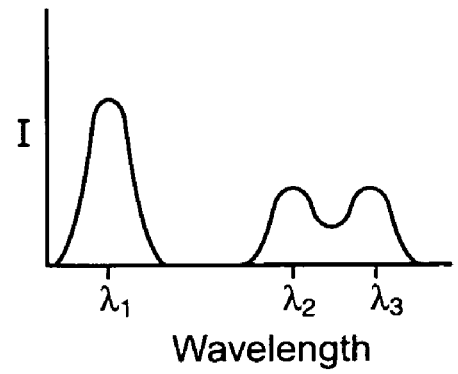
Figure 2E:
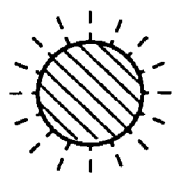
Figure 2E:
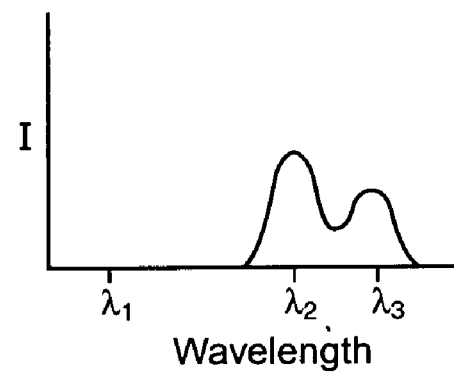
Figure 2E:
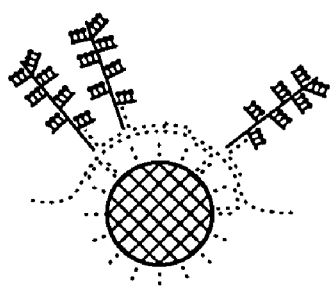
Figure 2E:
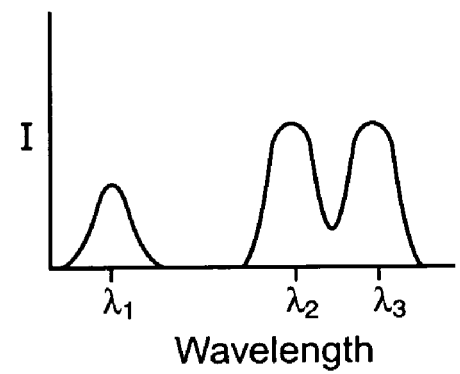

Schematic figures are not necessarily to scale.

Definitions

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

"Whole blood" is blood from which no constituent (e.g., plasma, platelets, or red blood cells) has been removed. Whole blood optionally includes an exogenously added anticoagulant. Whole blood can be obtained, e.g., from a human or from an animal.

"Peripheral blood cells" are the cellular components of blood, including red blood cells, white blood cells, and platelets. Peripheral blood cells typically include those cells found within the circulating pool of blood and not sequestered within the lymphatic system, spleen, liver, or bone marrow. Within a given sample of peripheral blood cells, all types of blood cells (e.g., red blood cells, white blood cells, and platelets) are represented or potentially represented; no cell type has been deliberately enriched in or removed from the sample.

"Peripheral blood cell nucleic acids" are nucleic acids (e.g., RNA and/or DNA) obtained from a sample of peripheral blood cells. Nucleic acids from all types of blood cells (e.g., red blood cells, white blood cells, and platelets) are represented or potentially represented, no cell type having been deliberately enriched in or removed from the sample of peripheral blood cells from which the nucleic acids were obtained.

"Plasma" is the liquid component of whole blood, in which the peripheral blood cells are suspended. Plasma is typically obtained by centrifuging whole blood to separate the plasma from the blood cells, optionally after addition of an anticoagulant.

A "target nucleic acid" is a nucleic acid to be detected.

The term "polynucleotide" (and the equivalent term "nucleic acid") encompasses any physical string of monomer units that can be corresponded to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, N.Y.), as well as in Ausubel, infra.

The term "complementary" refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A first polynucleotide that is "capable of hybridizing" (or "configured to hybridize") to a second polynucleotide comprises a first polynucleotide sequence that is complementary to a second polynucleotide sequence in the second polynucleotide.

A "capture extender" or "CP" is a polynucleotide that is capable of hybridizing to a nucleic acid of interest, and that is preferably also capable of hybridizing to a capture probe. The capture extender typically has a first polynucleotide sequence C-1, which is complementary to the capture probe, and a second polynucleotide sequence C-3, which is complementary to a polynucleotide sequence of the nucleic acid of interest. Sequences C-1 and C-3 are typically not complementary to each other. The capture extender is preferably single-stranded.

A "capture probe" or "CP" is a polynucleotide that is capable of hybridizing to at least one capture extender and that is tightly bound (e.g., covalently or noncovalently, directly or through a linker, e.g., streptavidin-biotin or the like) to a solid support, a spatially addressable solid support, a slide, a particle, a microsphere, or the like. The capture probe typically comprises at least one polynucleotide sequence C-2 that is complementary to polynucleotide sequence C-1 of at least one capture extender. The capture probe is preferably single-stranded.

A "label extender" or "LE" is a polynucleotide that is capable of hybridizing to a nucleic acid of interest and to a label probe system. The label extender typically has a first polynucleotide sequence L-1, which is complementary to a polynucleotide sequence of the nucleic acid of interest, and a second polynucleotide sequence L-2, which is complementary to a polynucleotide sequence of the label probe system (e.g., L-2 can be complementary to a polynucleotide sequence of an amplification multimer, a preamplifier, a label probe, or the like). The label extender is preferably single-stranded.

A "label" is a moiety that facilitates detection of a molecule. Common labels in the context of the present invention include fluorescent, luminescent, light-scattering, and/or colorimetric labels. Suitable labels include enzymes and fluorescent moieties, as well as radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "label probe system" comprises one or more polynucleotides that collectively comprise a label and a polynucleotide sequence M-1, which is capable of hybridizing to at least one label extender. The label provides a signal, directly or indirectly. Polynucleotide sequence M-1 is typically complementary to sequence L-2 in the label extenders. Typically, the label probe system includes a plurality of label probes (e.g., a plurality of identical label probes) and an amplification multimer; it optionally also includes a preamplifier or the like, or optionally includes only label probes, for example.

An "amplification multimer" is a polynucleotide comprising a plurality of polynucleotide sequences M-2, typically (but not necessarily) identical polynucleotide sequences M-2. Polynucleotide sequence M-2 is complementary to a polynucleotide sequence in the label probe. The amplification multimer also includes at least one polynucleotide sequence that is capable of hybridizing to a label extender or to a nucleic acid that hybridizes to the label extender, e.g., a preamplifier. For example, the amplification multimer optionally includes at least one polynucleotide sequence M-1; polynucleotide sequence M-1 is typically complementary to polynucleotide sequence L-2 of the label extenders. Similarly, the amplification multimer optionally includes at least one polynucleotide sequence that is complementary to a polynucleotide sequence in a preamplifier. The amplification multimer can be, e.g., a linear or a branched nucleic acid. As noted for all polynucleotides, the amplification multimer can include modified nucleotides and/or nonstandard internucleotide linkages as well as standard deoxyribonucleotides, ribonucleotides, and/or phosphodiester bonds. Suitable amplification multimers are described, for example, in U.S. Pat. Nos. 5,635,352, 5,124,246, 5,710,264, and 5,849,481.

A "label probe" or "LP" is a single-stranded polynucleotide that comprises a label (or optionally that is configured to bind to a label) that directly or indirectly provides a detectable signal. The label probe typically comprises a polynucleotide sequence that is complementary to the repeating polynucleotide sequence M-2 of the amplification multimer; however, if no amplification multimer is used in the bDNA assay, the label probe can, e.g., hybridize directly to a label extender.

A "preamplifier" is a nucleic acid that serves as an intermediate between at least one label extender and amplification multimer. Typically, the preamplifier is capable of hybridizing simultaneously to at least one label extender and to a plurality of amplification multimers.

The "$T_m$" (melting temperature) of a nucleic acid duplex under specified conditions (e.g., relevant assay conditions) is the temperature at which half of the base pairs in a population of the duplex are disassociated and half are associated. The $T_m$ for a particular duplex can be calculated and/or measured, e.g., by obtaining a thermal denaturation curve for the duplex (where the $T_m$ is the temperature corresponding to the midpoint in the observed transition from double-stranded to single-stranded form).

A "microsphere" is a small spherical, or roughly spherical, particle. A microsphere typically has a diameter less than about 1000 micrometers (e.g., less than about 100 micrometers, optionally less than about 10 micrometers).

A "microorganism" is an organism of microscopic or sub-microscopic size. Examples include, but are not limited to, bacteria, fungi, yeast, protozoans, microscopic algae (e.g., unicellular algae), viruses (which are typically included in this category although they are incapable of growth and reproduction outside of host cells), subviral agents, viroids, and mycoplasma.

A variety of additional terms are defined or otherwise characterized herein.

DETAILED DESCRIPTION

Analysis of gene expression in peripheral blood has been increasingly used for diagnosis, prognosis, tracking, and drug response monitoring of hematological diseases (Haferlach, T. et al. (2005) "A global approach to the diagnosis of leukemia using gene expression profiling" Blood 106:1189-1198; Lossos, I. S. et al. (2004) "Prediction of Survival in Diffuse Large-B-Cell Lymphoma Based on the Expression of Six Genes" N Engl J Med 350:1828-1837; Goerttler, P. S. et al. (2005) "Gene expression profiling in polycythaemia vera: overexpression of transcription factor NF-E2" Br J Haematol 129:138-50; Hochhaus, A. et al. (2000) "Detection and quantification of residual disease in chronic myelogenous leukemia" Leukemia 14:998-1005; and Wang, S. W. et al. (1999) "Cytokine mRNA decay is accelerated by an inhibitor of p38-mitogen-activated protein kinase" Inflamm Res 48:533-8). Due to the ease of collection of peripheral blood and its key role in the immune response, peripheral blood gene expression is also being explored for surrogate biomarker discovery in a wide range of non-hematological disorders (DePrimo, S. et al. (2003) "Expression profiling of blood samples from an SU5416 Phase m metastatic colorectal cancer clinical trial: a novel strategy for biomarker identification" BMC Cancer 3:3; Gibbs, P. J. et al. (2005) "Quantitative detection of changes in cytokine gene expression in peripheral blood mononuclear cells correlates with and precedes acute rejection in renal transplant recipients" Transpl Immunol 14:99-108; Ockenhouse, C. F. et al. (2005) "Functional Genomic Relationships in HIV-1 Disease Revealed by Gene-Expression Profiling of Primary Human Peripheral Blood Mononuclear Cells" J Infect Dis 191:2064-74; van Leeuwen, D. M. et al. (2005) "Differential Gene Expression in Human Peripheral Blood Mononuclear Cells Induced by Cigarette Smoke and Its Constituents" Toxicol. Sci. 86:200-210; and Horwitz, P. A. et al. (2004) "Detection of Cardiac Allograft Rejection and Response to Immunosuppressive Therapy With Peripheral Blood Gene Expression" Circulation 110: 3815-3821). However, validity and reproducibility of blood mRNA quantitation results are critical issues when considering potential clinical applications (Ransohoff, D. F. (2005) "Bias as a threat to the validity of cancer molecular-marker research" Nat Rev Cancer 5:142-9, and Ransohoff, D. F. (2004) "Rules of evidence for cancer molecular-marker discovery and validation" Nat Rev Cancer 4:309-14), and indeed, limitations associated with the techniques currently used in peripheral blood gene expression analysis have hindered wider application of genomics advances in the clinic (Pahl, A. (2005) "Gene expression profiling using RNA extracted from whole blood: technologies and clinical applications" Expert Rev Mol Diagn 5:43-52, and Bustin, S. A. et al. (2005) "Quantitative real-time RT-PCR—a perspective" J Mol Endocrinol 34:597-601). Robust, reproducible gene expression analysis in peripheral blood has been a challenge (Fan, H. and Hegde, P. S. (2005) "The transcriptome in blood: challenges and solutions for robust expression profiling" Curr Mol Med 5:3-10).

One major source of variation that is unique to peripheral blood mRNA analysis is the pre-analytical handling of the blood sample. Using current techniques for expression analysis, gene expression patterns are strongly dependent on choice of blood isolation and RNA preparation techniques (Fan and Hegde, supra, and Debey, S. et al. (2004) "Comparison of different isolation techniques prior gene expression profiling of blood derived cells: impact on physiological responses, on overall expression and the role of different cell types" Pharmacogenomics J 4:193-207). Partial purification of blood cells via density gradient centrifugation or selective red cell lysis can change gene expression, as blood cells are known to be sensitive to external environmental stress (Hartel, C. et al. (2001) "Ex vivo induction of cytokine mRNA expression in human blood samples" J Immunol Methods 249:63-71; Tamul, K R. et al. (1995) "Comparison of the effects of Ficoll-Hypaque separation and whole blood lysis on results of immunophenotypic analysis of blood and bone marrow samples from patients with hematologic malignancies" Clin Diagn Lab Immunol 2:337-42; Whitney, A. R. et al. (2003) "Individuality and variation in gene expression patterns in human blood" Proc Natl Acad Sci USA 100:1896-901; Rainen, L. et al. (2002) "Stabilization of mRNA Expression in Whole Blood Samples" Clin Chem 48:1883-1890; and Stordeur, P., Zhou, L. and Goldman, M. (2002) "Analysis of spontaneous mRNA cytokine production in peripheral blood" J Immunol Methods 261:195-7). Furthermore, significant gene expression changes can be detected within hours after phlebotomy, even without additional handling (Rainen et al., supra, and Tanner, M. A. et al. (2002) "Substantial changes in gene expression level due to the storage temperature and storage duration of human whole blood" Clinical and Laboratory Haematology 24:337-341). One way to minimize variations caused by storage and manipulation is to extract total RNA from fresh whole blood using phenol-chloroform extraction. However, this approach suffers from interference from the high concentration of plasma and erythrocyte proteins, leading to inconsistent yield and quality of the resulting purified RNA (Feezor, R. J. et al. (2004) "Whole blood and leukocyte RNA isolation for gene expression analyses" Physiol. Genomics 19:247-254). In addition, contaminating genomic DNA or PCR inhibitors such as heparin in the resulting purified RNA can reduce the accuracy of subsequent real-time quantitative PCR (RT-PCR) analysis (e.g., Bustin, S. A. and Nolan, T. (2004) "Pitfalls of quantitative real-time reverse-transcription polymerase chain reaction" J Biomol Tech 15:155-66), and the highly abundant red cell specific RNA can affect microarray profiling (Debey et al., supra).

Use of the blood-stabilizing reagent PAXgene® prior to RNA purification from the blood can prevent RNA degradation and time-dependent ex vivo induction of cytokine and immediate early response genes (Rainen et al., supra). However, signal to noise ratios are significantly reduced in microarray expression profiles of PAXgene®-treated blood RNA (Wu, K. et al. (2003) "Globin reduction protocol" Affymetrix Technical Note, available at www(dot)affymetrix (dot)com/support/technotes/blood2_technote(dot)pdf). In addition, the overall gene expression pattern from PAXgene® stabilized whole blood is quite distinct from that of the leukocytes (Feezor et al., supra). This difference has been attributed to the presence of an overwhelming amount of globin mRNA originating from the reticulocytes and remaining in the RNA purified from PAXgene®-treated blood; however, selective removal of globin mRNAs from PAXgene® purified RNA could not recover the leukocyte expression pattern (Feezor et al., supra). PAXgene® treated blood appears to give a low and variable yield of purified RNA, and the storage time of the PAXgene®-treated blood appears to significantly affect subsequent microarray profiling results as well, suggesting that stabilization is a complex process (Muller, M. C. et al. (2004) "Standardization of preanalytical factors for minimal residual disease analysis in chronic myelogenous leukemia" Acta Haematol 112:30-3; Thach, D. C. et al. (2003) "Assessment of two methods for handling blood in collection tubes with RNA stabilizing agent for surveillance of gene expression profiles with high density microarrays" J Immunol Methods 283:269-79; and Wang, J. et al. (2004) "Optimizing RNA extraction yield from whole blood for microarray gene expression analysis" Clin Biochem 37:741-4). In addition, the effect of PAXgene® treatment of blood samples on the expression of genes other than the dozen genes examined in Rainen et al., supra, has not been reported.

Currently, microarray analysis and RT-PCR are the most widely used methods for analyzing gene expression in blood. The relatively long experimental procedure and moderate sensitivity of microarrays have limited their use in high throughput expression profiling applications. More importantly, despite the high technical reproducibility of commercial microarrays, the overall reproducibility of the microarray data between runs, between laboratories, and between platforms is generally poor (Chen, J. J. et al. (2004) "Analysis of variance components in gene expression data" Bioinformatics 20:1436-1446; Kuo, W. P. et al. (2002) "Analysis of matched mRNA measurements from two different microarray technologies" Bioinformatics 18:405-12; Marshall, E. (2004) "Getting the noise out of gene arrays" Science 306:630-631; and Bammler, T. et al. (2005) "Standardizing global gene expression analysis between laboratories and across platforms" Nat Methods 2:351-6). Different blood RNA isolation procedures and different RNA labeling and amplification protocols used in different laboratories can give strikingly different expression patterns for even identical starting material (Feezor et al., supra, and Bammler, T. et al. (2005) "Standardizing global gene expression analysis between laboratories and across platforms" Nat Methods 2:351-6). Thus, significant variations can result, not necessarily from microarray hybridization itself, but from the processing steps used to prepare labeled RNA for hybridization.

RT-PCR offers greater sensitivity than microarray analysis, and it is widely used to validate microarray results. It has been used for quantitating specific mRNA levels in blood (Stordeur, P., Zhou, L. and Goldman, M. (2002) "Analysis of spontaneous mRNA cytokine production in peripheral blood" J Immunol Methods 261:195-7), but the approach has low multiplex capabilities. Moreover, as with microarray analysis, RT-PCR depends on purification and enzymatic manipulation (e.g., reverse transcription and subsequent amplification) of RNA from the blood. Variation in the overall quality of the RNA and in the efficiencies of reverse transcription and PCR are major factors that can reduce the accuracy and reproducibility of mRNA quantitation by RT-PCR (Bustin, S. A. and Nolan, T. (2004) "Pitfalls of quantitative real-time reverse-transcription polymerase chain reaction" J Biomol Tech 15:155-66 and Bustin, S. A. et al. (2002) "Quantification of mRNA using real-time reverse transcription PCR (RT-PCR): trends and problems" J Mol Endocrinol 29:23-39). In practice, RT-PCR quantitation of BCR-ABL mRNA in patients with chronic myelogenous leukemia has been affected by variations in sample preparation (Muller, M. C. et al. (2004) "Standardization of preanalytical factors for minimal residual disease analysis in chronic myelogenous leukemia" Acta Haematol 112:30-3).

Even typical techniques for mRNA detection that do not require prior purification of RNA (see, e.g., Martel et al. (2002) "Multiplexed screening assay for mRNA combining nuclease protection with luminescent array detection" Assay and Drug Development Technologies 1:61-71; Eis et al. (2001) "An invasive cleavage assay for direct quantitation of specific RNAs" Nature Biotechnology 19:673-676; and Tian et al. (2004) "Multiplex mRNA assay using electrophoretic tags for high-throughput gene expression analysis" Nucl Acids Res 32:e126) involve enzymatic manipulation of the RNA, and are thus subject to variability, have limited sensitivity, and/or require specialized probes, equipment, and data analysis software. In addition, such techniques may not all be suitable for use with whole blood samples.

In contrast, the present invention provides methods that permit rapid, simple, and sensitive detection of mRNAs (and other nucleic acids) from whole blood, without requiring isolation of a particular blood cell type, purification of RNA, and/or enzymatic manipulation of RNA. Following lysis of the blood cells, typically, in a sample of whole blood, one or more target nucleic acids are captured on a solid support and then detected, for example, using a branched-chain DNA (bDNA) assay. Methods for detecting nucleic acids directly from blood plasma are also provided, as are compositions and kits related to the methods. The methods of the invention are optionally used for gene expression analysis, clinical diagnosis, and/or detection of microorganisms, e.g., pathogens, among other applications.

Methods for Detecting Nucleic Acids from Blood

One general class of embodiments provides methods of detecting at least a first target nucleic acid. In the methods, a sample comprising whole blood is provided. The whole blood includes peripheral blood cells, which are lysed to produce a lysate comprising the first target nucleic acid. The first target nucleic acid is contacted with a first set of n capture extenders, wherein n is at least two; this first set of capture extenders is capable of hybridizing to the first target nucleic acid. The first target nucleic acid is hybridized to the first set of capture extenders, and the first set of capture extenders is associated with a solid support. The first target nucleic acid is captured on the solid support by hybridizing the first target nucleic acid to the first set of capture extenders and associating the first set of capture extenders with the solid support, and the presence of the first target nucleic acid on the solid support is then detected. The hybridization and association steps can, e.g., be either simultaneous or sequential.

Typically, the first target nucleic acid is contacted with the first set of capture extenders by contacting the lysate with the first set of capture extenders. The peripheral blood cells are optionally separated from the plasma (e.g., by centrifugation) prior to lysis of the peripheral blood cells, to provide a peripheral blood cell lysate; contacting the first target nucleic acid with the first set of capture extenders then comprises contacting the peripheral blood cell lysate with the first set of capture extenders. However, such separation is not necessary. Thus, in one class of embodiments, the peripheral blood cells are lysed in the whole blood (e.g., liquid whole blood) to produce a whole blood lysate that includes the first target nucleic acid (e.g., among other nucleic acids released from the peripheral blood cells and/or present in the plasma). In this class of embodiments, contacting the first target nucleic acid with the first set of capture extenders typically comprises contacting the whole blood lysate with the first set of capture extenders. Alternatively but less conveniently, nucleic acids (e.g., total nucleic acids, total RNA, total DNA, or the like) including the first target nucleic acid can be purified or partially purified from the lysate prior to contact with the capture extenders. For example, nucleic acids can be isolated from the whole blood lysate (or the peripheral blood cell lysate) by precipitation using techniques known in the art; such precipitated nucleic acids can be resuspended in an appropriate solution (e.g., a buffered aqueous solution) and then contacted with the first set of capture extenders. The whole blood is optionally treated with a stabilizing reagent such as PAXgene® prior to lysis of the peripheral blood cells, but it need not be (and preferably is not).

In one aspect, as described above, the peripheral blood cells are lysed in liquid whole blood to produce the lysate. In another aspect, the target nucleic acid(s) are detected from a dried blood spot. Thus, in one class of embodiments, the whole blood is applied to a matrix to produce a blood spot, and the blood spot is dried (e.g., air dried) to produce a dried blood spot. The dried blood spot is contacted with an aqueous solution to produce the lysate. The solution can comprise a buffered salt solution, a detergent, a protease, and/or the like, as described herein. The matrix to which the blood is applied is typically an absorbent matrix, for example, a specimen collection paper, filter paper, or the like.

A variety of techniques for lysing cells are known in the art and can be adapted to the practice of the present invention. For example, the peripheral blood cells can be lysed by contact with a detergent (e.g., an anionic detergent such as lithium lauryl sulfate), suspension in a low ionic strength buffer, sonication, freeze-thaw cycles, or a combination thereof.

In one class of embodiments, the methods include contacting the peripheral blood cells and/or the lysate with an exogenously supplied protease (a protease that is added to the peripheral blood cells and/or the lysate by a user of the methods, as opposed to a protease which is endogenous to whole blood and is thus already present), typically prior to contacting the first target nucleic acid with the first set of capture extenders. By digesting various blood proteins, the protease optionally inactivates ribonucleases and/or otherwise assists in increasing the integrity and/or availability of the target nucleic acid. A variety of proteases are known in the art and can be adapted to the practice of the present invention; an effective concentration of protease, time for which the lysate is incubated with the protease, and the like can be determined by routine experimentation, e.g., by ensuring that an exogenously added RNA can be quantitatively detected in the lysate.

In one embodiment, the protease is proteinase K. Proteinase K is commercially available from a number of suppliers, and it has little dependence on cofactors, remains active in the presence of fairly high concentrations of detergent (e.g., lithium lauryl sulfate or the like used to lyse the peripheral blood cells), and is active at elevated temperatures. In the example described below, proteinase K is employed at a concentration of at least 1 mg per ml of lysate; it will be evident that the concentration of protease can readily be varied, e.g., in conjunction with the duration of time for which the cells and/or lysate is incubated with the protease.

The volume of blood used in the assay is typically less than the volume of the resulting lysate, optionally substantially less. Thus, in one class of embodiments, the volume of whole blood in the sample is at most ½, at most ⅓, or at most ⅕ the volume of the lysate. For example, the volume of whole blood used can be at most 1/10, 1/50, 1/100, or 1/150 the volume of the lysate. The remainder of the volume of the lysate can comprise a buffered salt solution, a detergent, a protease, water, and/or the like.

The methods can be applied to detection of essentially any type of nucleic acids. For example, the first target nucleic acid can be a DNA or an RNA, e.g., an mRNA, rRNA, microRNA precursor, or essentially any other form of RNA. A target nucleic acid can, for example, be expressed by a peripheral blood cell or by an intracellular or extracellular pathogen, and can be located in the peripheral blood cells and/or in the plasma. Thus, in one class of embodiments, the peripheral blood cells include white blood cells, one or more of which white blood cells comprises the first target nucleic acid. The first target nucleic acid can, e.g., be endogenous to the white blood cells or it can be expressed as a result of infection of the white blood cells by a virus, bacterium, or other pathogen. The first target nucleic acid need not be expressed in all types of white blood cells, or even in all cells of a particular type or subtype; for example, the target nucleic acid can be found in one or more of: a granulocyte, mononuclear cell, neutrophil, basophil, eosinophil, monocyte, lymphocyte, T lymphocyte, B lymphocyte, natural killer cell, active granular natural killer cell, inactive agranular natural killer cell, Th-lymphocyte, Tc/k-lymphocyte, activated T cell, activated neutrophil, activated eosinophil, activated basophil, or the like. Similarly, the first target nucleic acid can be found in a red blood cell, platelet, bacterium, virion, or other pathogen.

It will be understood that if the first target nucleic acid is initially present in the whole blood in a double-stranded form, e.g., hybridized to a complementary nucleic acid, the double-stranded form is denatured prior to hybridizing the first target nucleic acid to the first set of capture extenders. Denaturation can be accomplished, for example, by thermal denaturation, exposure to alkaline conditions (which can have the added advantage of digesting extraneous RNA if the target nucleic acid is a DNA), or similar techniques. The methods can thus be used for detecting, e.g., double-stranded genomic DNA, double-stranded viral nucleic acids, and the like, as well as single-stranded nucleic acids such as mRNAs.

As noted, the first set of capture extenders includes n capture extenders, where n is at least two. Preferably, n is at least three, and n can be at least four or at least five or more. Typically, but not necessarily, n is at most ten. For example, n can be between three and ten, e.g., between five and ten or between five and seven, inclusive. Use of fewer capture extenders can be advantageous, for example, in embodiments in which target nucleic acids are to be specifically detected from samples including other nucleic acids with sequences very similar to that of the target nucleic acids. In other embodiments (e.g., embodiments in which capture of as much of the target nucleic acid as possible is desired), however, n can be more than 10, e.g., between 20 and 50. The n capture extenders in the first set preferably hybridize to nonoverlapping polynucleotide sequences in the first target nucleic acid. The nonoverlapping polynucleotide sequences can, but need not be, consecutive within the first target nucleic acid.

The capture extenders are optionally bound to the solid support, e.g., covalently or noncovalently, directly or through a linker, e.g., streptavidin-biotin or the like. In a preferred aspect, the capture extenders are associated with the solid support by hybridization of the capture extenders to one or more capture probes. Thus, in one class of embodiments, a first capture probe is bound to the solid support, and the first set of capture extenders is associated with the solid support by hybridizing the capture extenders to the first capture probe.

Each capture extender in the first set is capable of hybridizing to the first capture probe. The capture extender typically includes a polynucleotide sequence C-1 that is complementary to a polynucleotide sequence C-2 in the capture probe. C-1 and C-2 are typically, but need not be, 20 nucleotides or less in length. Hybridization of the capture extenders to the capture probe is optionally cooperative, e.g., as described in U.S. patent application 60/680,976 filed May 12, 2005 and Ser. No. 11/433,081 filed May 11, 2006, both by Luo et al. entitled "Multiplex branched-chain DNA assays." Thus, hybridizing the first set of capture extenders to the first capture probe is optionally performed at a hybridization temperature which is greater than a melting temperature ($T_m$) of a complex between each individual capture extender and the capture probe. Binding of a single capture extender and any associated nucleic acid to the capture probe is thus typically insufficient to capture the nucleic acid on the solid support.

The capture probe can include polynucleotide sequence in addition to C-2, or C-2 can comprise the entire polynucleotide sequence of the capture probe. For example, each capture probe optionally includes a linker sequence between the site of attachment of the capture probe to the solid support and sequence C-2 (e.g., a linker sequence containing 8 Ts, as just one possible example). Typically, each capture probe includes a single sequence C-2, and each capture extender in the first set includes the same nucleotide sequence as its sequence C-1. A number of other configurations are contemplated, however; for example, the capture probe can include two or more sequences C-2 (of the same or different nucleotide sequence), different capture extenders can include different nucleotide sequences as their sequence C-1, complementary to different sequences C-2 in a single or in different first capture probes, and the like.

The solid support can be essentially any suitable support, including any of a variety of materials, configurations, and the like. For example, in one class of embodiments, the solid support is a substantially planar solid support, e.g., an upper surface of the bottom of a well of a multiwell plate, a slide, or the like. Similarly, suitable solid supports include any surface of a well of a multiwell plate, whether planar or not. As another example, the solid support can comprise a plurality of particles, e.g., microspheres, beads, cylindrical particles, irregularly shaped particles, or the like. The particles are optionally identifiable, as will be described in greater detail below, and optionally have additional or other desirable characteristics. For example, the particles can be magnetic or paramagnetic, providing a convenient means for separating the particles from solution, e.g., to simplify separation of the particles from any materials not bound to the particles.

The methods can be conveniently multiplexed to detect two or more target nucleic acids simultaneously. Thus, in one class of embodiments, the lysate comprises a second target nucleic acid and the methods include contacting the second target nucleic acid with a second set of m capture extenders (e.g., by contacting the lysate with the second set of capture extenders, typically with the first and second sets simultaneously), wherein m is at least two; this second set of capture extenders is capable of hybridizing to the second target nucleic acid. The second target nucleic acid is hybridized to the second set of capture extenders, and the second set of capture extenders is associated with the solid support. Hybridizing the second target nucleic acid to the second set of capture extenders and associating the second set of capture extenders with the solid support captures the second target nucleic acid on the solid support. The presence of the second target nucleic acid on the solid support is then detected. It will be evident that n, the number of capture extenders in the first set, can but need not be the same as m, the number of capture extenders in the second set. As for the first target nucleic acid, the second target nucleic acid can be essentially any type of nucleic acid.

In one class of embodiments, the solid support is a substantially planar solid support, the first target nucleic acid is captured at a first selected position on the solid support, and the second target nucleic acid is captured at a second selected position on the solid support. For example, the first set of capture extenders can be hybridized to a first capture probe predisposed at the first selected position, while the second set of capture extenders is hybridized to a second capture probe predisposed at the second selected position. Techniques for forming such arrays of capture probes are well known and are, e.g., referenced below in the section entitled "Arrays." Spatially addressable non-planar solid supports can optionally also be employed in the methods. In this class of embodiments, detecting the presence of the first and second nucleic acid on the solid support typically includes detecting the presence of nucleic acid at each selected position on the solid support.

In another class of embodiments, the solid support comprises a population of particles. The population includes at least two sets of particles, and the particles in each set are distinguishable from the particles in every other set. The first target nucleic acid is captured on a first set of the particles, and the second target nucleic acid is captured on a second set of the particles. For example, the first set of particles can comprise a first capture probe that is capable of hybridizing to the capture extenders comprising the first set of capture extenders (and thereby capturing the first target nucleic acid on the first set of particles), and the second set of particles can comprise a second capture probe that is capable of hybridizing to the capture extenders comprising the second set of capture extenders (and thereby capturing the second target nucleic acid on the second set of particles). In this class of embodiments, detecting the presence of the first and second nucleic acid on the solid support typically includes identifying at least a portion of the particles from each set and detecting the presence of nucleic acid on particles from each set.

Essentially any suitable particles, e.g., particles having distinguishable characteristics and to which capture probes can be attached, can be used. For example, in one preferred class of embodiments, the particles are microspheres. The microspheres of each set can be distinguishable from those of the other sets, e.g., on the basis of their fluorescent emission spectrum, their diameter, or a combination thereof. For example, the microspheres of each set can be labeled with a unique fluorescent dye or mixture of such dyes, quantum dots with distinguishable emission spectra, and/or the like. As another example, the particles of each set can be identified by an optical barcode, unique to that set, present on the particles.

It will be evident that third, fourth, fifth, etc. target nucleic acids are optionally also detected. The at least one target nucleic acid to be detected thus optionally includes two or more, five or more, 10 or more, 20 or more, 30 or more, 40 or more, 50 or more, or even 100 or more target nucleic acids which are present or suspected to be present in the whole blood. A like number of sets of capture extenders, and typically a like number of selected positions on a substantially planar solid support or a like number of sets of particles, are also provided and used to capture and detect the target nucleic acids. For additional details on multiplex bDNA assays, see U.S. patent application No. 60/680,976 filed May 12, 2005 and Ser. No. 11/433,081 filed May 11, 2006, both by Luo et al. entitled "Multiplex branched-chain DNA assays" and the examples below.

The presence of the first target nucleic acid (and optional second, third, etc. nucleic acids) on the solid support can be detected by any of a variety of techniques known in the art. For example, the first target nucleic acid can comprise a label (including, e.g., one or two or more labels per molecule), and detecting the presence of the first target nucleic acid can comprise detecting the label. The label can be covalently associated with the nucleic acid (e.g., a fluorescent label can be incorporated into the nucleic acid using a chemical or enzymatic labeling technique), or the nucleic acid can be configured to bind the label (e.g., a biotinylated nucleic acid can bind a streptavidin-associated label). The label can be essentially any convenient label that directly or indirectly provides a detectable signal. For example, the label can be a fluorescent label (e.g., a quantum dot or fluorophore, e.g., Cy™3 or Cy™5), a luminescent label, a light-scattering label (e.g., colloidal gold particles), or an enzyme (e.g., horseradish peroxidase (HRP) or alkaline phosphatase). As another example, at least one detection probe (a polynucleotide comprising a label or configured to bind a label) can be provided and hybridized to the first target nucleic acid, and detecting the presence of the first target nucleic acid can comprise detecting the label. For example, a labeled molecular dendrimer can be hybridized to the first target nucleic acid, for example, a dendrimer such as 3DNA™ from Genisphere Inc.; an exemplary 3DNA dendrimer includes 1-15 oligonucleotides complementary to the target nucleic acid and 30-900 fluorescent labels such as Cy™3, Cy™5, Alexa Fluor 546 or Alexa Fluor 647. As yet another example, the target nucleic acid can be amplified. A wide variety of techniques for amplifying nucleic acids are known in the art, including, but not limited to, PCR (polymerase chain reaction), rolling circle amplification, and transcription mediated amplification. (See, e.g., Hatch et al. (1999) "Rolling circle amplification of DNA immobilized on solid surfaces and its application to multiplex mutation detection" Genet Anal. 15:35-40; Baner et al. (1998) "Signal amplification of padlock probes by rolling circle replication" Nucleic Acids Res. 26:5073-8; and Nallur et al. (2001) "Signal amplification by rolling circle amplification on DNA microarrays" Nucleic Acids Res. 29:E118.) A labeled primer and/or labeled nucleotides are optionally incorporated during amplification.

In one aspect, the first target nucleic acid (and optional second, third, etc. target nucleic acid) is captured and its presence on the solid support is detected using a branched-chain DNA (bDNA) assay. Thus, in one preferred class of embodiments, detecting the presence of the first target nucleic acid on the solid support includes hybridizing a first set of one or more label extenders (typically, two or more label extenders) and a label probe system comprising a label to the first target nucleic acid and detecting the presence of the label on the solid support. The label probe system optionally includes an amplification multimer and a plurality of label probes, where the amplification multimer is capable of hybridizing simultaneously to a label extender and to a plurality of label probes. In another aspect, the label probe system includes a preamplifier, a plurality of amplification multimers, and a plurality of label probes, wherein the preamplifier hybridizes to a label extender, and the amplification multimers hybridize to the preamplifier and to the plurality of label probes. As another example, the label probe system can include only label probes, which hybridize directly to the label extenders. The label probe can include the label, or it can be configured to bind to the label (for example, a biotinylated label probe can bind to a streptavidin-associated label). Suitable labels include, but are not limited to, an enzyme or a fluorescent label. When an enzyme (e.g., alkaline phosphatase) is used as the label, its activity can be detected with a chemiluminescent, calorimetric, or similar assay as is well-known in the art. When a fluorescent label is used, detecting the presence of the label on the solid support typically comprises detecting a fluorescent signal from the label. Two or more label extenders optionally hybridize to a component of the label probe system (e.g., a single amplification multimer or preamplifier), and such hybridization is optionally cooperative; see U.S. patent application Ser. No. 11/471,025 filed Jun. 19, 2006 by Luo et al. entitled "Multiplex detection of nucleic acids."

An exemplary embodiment in which a single target nucleic acid is captured and detected using a bDNA assay is schematically illustrated in FIG. 1. Peripheral blood cells in a sample of whole blood are lysed to produce a lysate including first target nucleic acid 114. First target nucleic acid 114 (e.g., an mRNA whose expression is to be detected in whole blood) is captured by capture probe 104 on solid support 101 (e.g., a well of a microtiter plate) through first set 111 of synthetic oligonucleotide capture extenders. Each capture extender has first polynucleotide sequence C-3 (152) that can hybridize to the target nucleic acid and second polynucleotide sequence C-1 (151) that can hybridize to the capture probe through sequence C-2 (150) in the capture probe. Typically, two or more capture extenders are used. Each label extender in first set 121 of label extenders hybridizes to a different sequence on the target nucleic acid, through sequence L-1 (154) that is complementary to the target nucleic acid, and to sequence M-1 (157) on amplification multimer 141, through sequence L-2 (155). Blocking probes, which hybridize to sequences in the target nucleic acid not bound by either capture extenders or label extenders, are often used in bDNA assays to reduce non-specific target probe binding. A probe set for a given target nucleic acid thus consists of capture extenders, label extenders, and optional blocking probes for the target nucleic acid. The capture extenders, label extenders, and optional blocking probes are complementary to nonoverlapping sequences in the target nucleic acid, and are typically, but not necessarily, contiguous. In this example, a single blocking probe is used (124).

Signal amplification begins with the binding of the label extenders to the target nucleic acid. The amplification multimer is then hybridized to the label extenders. The amplification multimer has multiple copies of sequence M-2 (158) that is complementary to label probe 142. (It is worth noting that the amplification multimer is typically, but not necessarily, a branched-chain nucleic acid; for example, the amplification multimer can be a branched, forked, or comb-like nucleic acid or a linear nucleic acid.) Label 143, for example, alkaline phosphatase, is covalently attached to each label probe. (Alternatively, the label can, e.g., be noncovalently associated with the label probes.) In the final step, labeled complexes are detected, e.g., by the alkaline phosphatase-mediated degradation of a chemilumigenic substrate, e.g., dioxetane. Luminescence is reported as relative luminescence units (RLUs) on a microplate reader. The amount of chemiluminescence is proportional to the level of first target nucleic acid originally present in the sample of whole blood.

In the preceding example, the amplification multimer and the label probes comprise label probe system 140. In another example, the label probe system also comprises a preamplifier, e.g., as described in U.S. Pat. Nos. 5,635,352 and 5,681,697, which further amplifies the signal from a single target mRNA. See also U.S. patent application Ser. No. 11/471,025. In yet another example, the label extenders hybridize directly to the label probes and no amplification multimer or preamplifier is used, so the signal from a single target mRNA molecule is only amplified by the number of distinct label extenders that hybridize to that mRNA (and the number of label probes that bind to a single label extender).

Basic bDNA assays have been well described and have been used, e.g., to detect and quantify mRNA transcripts in cell lines and to determine viral loads. The bDNA assay provides direct quantification of nucleic acid molecules at physiological levels. Several advantages of the technology distinguish it from other DNA/RNA amplification technologies, including linear amplification, good sensitivity and dynamic range, great precision and accuracy, simple sample preparation procedure, and reduced sample-to-sample variation. For additional details on bDNA assays, see, e.g., U.S. Pat. No. 4,868,105 to Urdea et al. entitled "Solution phase nucleic acid sandwich assay"; U.S. Pat. No. 5,635,352 to Urdea et al. entitled "Solution phase nucleic acid sandwich assays having reduced background noise"; U.S. Pat. No. 5,681,697 to Urdea et al. entitled "Solution phase nucleic acid sandwich assays having reduced background noise and kits therefor"; U.S. Pat. No. 5,124,246 to Urdea et al. entitled "Nucleic acid multimers and amplified nucleic acid hybridization assays using same"; U.S. Pat. No. 5,624,802 to Urdea et al. entitled "Nucleic acid multimers and amplified nucleic acid hybridization assays using same"; U.S. Pat. No. 5,849,481 to Urdea et al. entitled "Nucleic acid hybridization assays employing large comb-type branched polynucleotides"; U.S. Pat. No. 5,710,264 to Urdea et al. entitled "Large comb type branched polynucleotides"; U.S. Pat. No. 5,594,118 to Urdea and Horn entitled "Modified N-4 nucleotides for use in amplified nucleic acid hybridization assays"; U.S. Pat. No. 5,093,232 to Urdea and Horn entitled "Nucleic acid probes"; U.S. Pat. No. 4,910,300 to Urdea and Horn entitled "Method for making nucleic acid probes"; U.S. Pat. Nos. 5,359,100; 5,571,670; 5,614,362; 6,235,465; 5,712,383; 5,747,244; 6,232,462; 5,681,702; 5,780,610; 5,780,227 to Sheridan et al. entitled "Oligonucleotide probe conjugated to a purified hydrophilic alkaline phosphatase and uses thereof"; U.S. patent application Publication No. US2002172950 by Kenny et al. entitled "Highly sensitive gene detection and localization using in situ branched-DNA hybridization"; Wang et al. (1997) "Regulation of insulin preRNA splicing by glucose" Proc Nat Acad Sci USA 94:4360-4365; Collins et al. (1998) "Branched DNA (bDNA) technology for direct quantification of nucleic acids: Design and performance" in Gene Quantification, F Ferre, ed.; and Wilber and Urdea (1998) "Quantification of HCV RNA in clinical specimens by branched DNA (bDNA) technology" Methods in Molecular Medicine: Hepatitis C 19:71-78. In addition, reagents for performing basic bDNA assays (e.g., QuantiGene® kits, amplification multimers, alkaline phosphatase labeled label probes, chemilumigenic substrate, capture probes immobilized on a solid support, and the like) are commercially available, e.g., from Panomics, Inc. (www(dot)panomics(dot)com), and can be adapted for the practice of the present invention. Software for designing probe sets for a given mRNA target (i.e., for designing the regions of the capture extenders, label extenders, and optional blocking probes that are complementary to the target) is also commercially available (e.g., ProbeDesigner™ from Panomics, Inc.); see also Bushnell et al. (1999) "ProbeDesigner: for the design of probe sets for branched DNA (bDNA) signal amplification assays Bioinformatics 15:348-55.

Another exemplary embodiment is schematically illustrated in FIG. 2. This example demonstrates multiplex capture and detection of target nucleic acids with a bDNA assay, where the solid support comprises a population of particles (in this example, a population of microspheres, where each set of microspheres has a characteristic fluorescent emission spectrum). Panel A illustrates three distinguishable sets of microspheres 201, 202, and 203, which have associated therewith capture probes 204, 205, and 206, respectively. Each capture probe includes a sequence C-2 (250), which is different from set to set of microspheres. The three sets of microspheres are combined to form population 208 (Panel B). A set of three capture extenders is provided for each target nucleic acid; set 211 for nucleic acid 214, set 212 for nucleic acid 215 which is not present, and set 213 for nucleic acid 216. Each capture extender includes sequences C-1 (251, complementary to the respective capture probe's sequence C-2) and C-3 (252, complementary to a sequence in the corresponding target nucleic acid). Three sets of label extenders (221, 222, and 223 for nucleic acids 214, 215, and 216, respectively) and three sets of blocking probes (224, 225, and 226 for nucleic acids 214, 215, and 216, respectively) are also provided. Each label extender includes sequences L-1 (254, complementary to a sequence in the corresponding target nucleic acid) and L-2 (255, complementary to M-1).

The sample comprising whole blood is provided and the peripheral blood cells are lysed, providing a lysate (e.g., a whole blood lysate) including target nucleic acids 214 and 216. Non-target nucleic acids 230 are also present. Target nucleic acids 214 and 216 are contacted with and hybridized to their corresponding set of capture extenders (211 and 213, respectively), and the capture extenders are hybridized to the corresponding capture probes (204 and 206, respectively), capturing target nucleic acids 214 and 216 on microspheres 201 and 203, respectively (Panel C). Materials not bound to the microspheres (e.g., capture extenders 212, nucleic acids 230, etc.) are optionally separated from the microspheres by washing. Label probe system 240 including amplification multimer 241 (which includes sequences M-1 257 and M-2 258) and label probe 242 (which contains label 243) is hybridized to label extenders 221 and 223, which are hybridized to nucleic acids 214 and 216, respectively (Panel D). Materials not captured on the microspheres are optionally removed by washing the microspheres. Microspheres from each set are identified, e.g., by their fluorescent emission spectrum ($\lambda_2$ and $\lambda_3$, Panel E), and the presence or absence of the label on each set of microspheres is detected ($\lambda_1$, Panel E). (It is worth noting that in embodiments such as this, in which both the label and the particles are fluorescent, fluorescent emission by the label is typically distinguishable from fluorescent emission by the particles, e.g., microspheres, and many suitable fluorescent label-fluorescent microsphere combinations are possible.) Since each target nucleic acid is associated with a distinct set of microspheres via hybridization with the corresponding set of capture extenders and capture probe, the presence of the label on a given set of microspheres correlates with the presence of the corresponding target nucleic acid on the microspheres and thus in the original sample.

As depicted in FIG. 2, all of the label extenders in all of the sets typically include an identical sequence L-2. Optionally, however, different label extenders (e.g., label extenders in different sets) can include different sequences L-2. Also as depicted in FIG. 2, each capture probe typically includes a single sequence C-2 and thus hybridizes to a single capture extender. Optionally, however, a capture probe can include two or more sequences C-2 and hybridize to two or more capture extenders. Similarly, as depicted, each of the capture extenders in a particular set typically includes an identical sequence C-1, and thus only a single capture probe is needed for each set of particles; however, different capture extenders within a set optionally include different sequences C-1 (and thus hybridize to different sequences C-2, within a single capture probe or different capture probes on the surface of the corresponding set of particles).

One or more of the sets of particles is optionally isolated, whereby the associated target nucleic acid is isolated. The isolated nucleic acid can optionally be removed from the particles and/or subjected to further manipulation, if desired (e.g., amplification by PCR or the like).

Figure 3D:
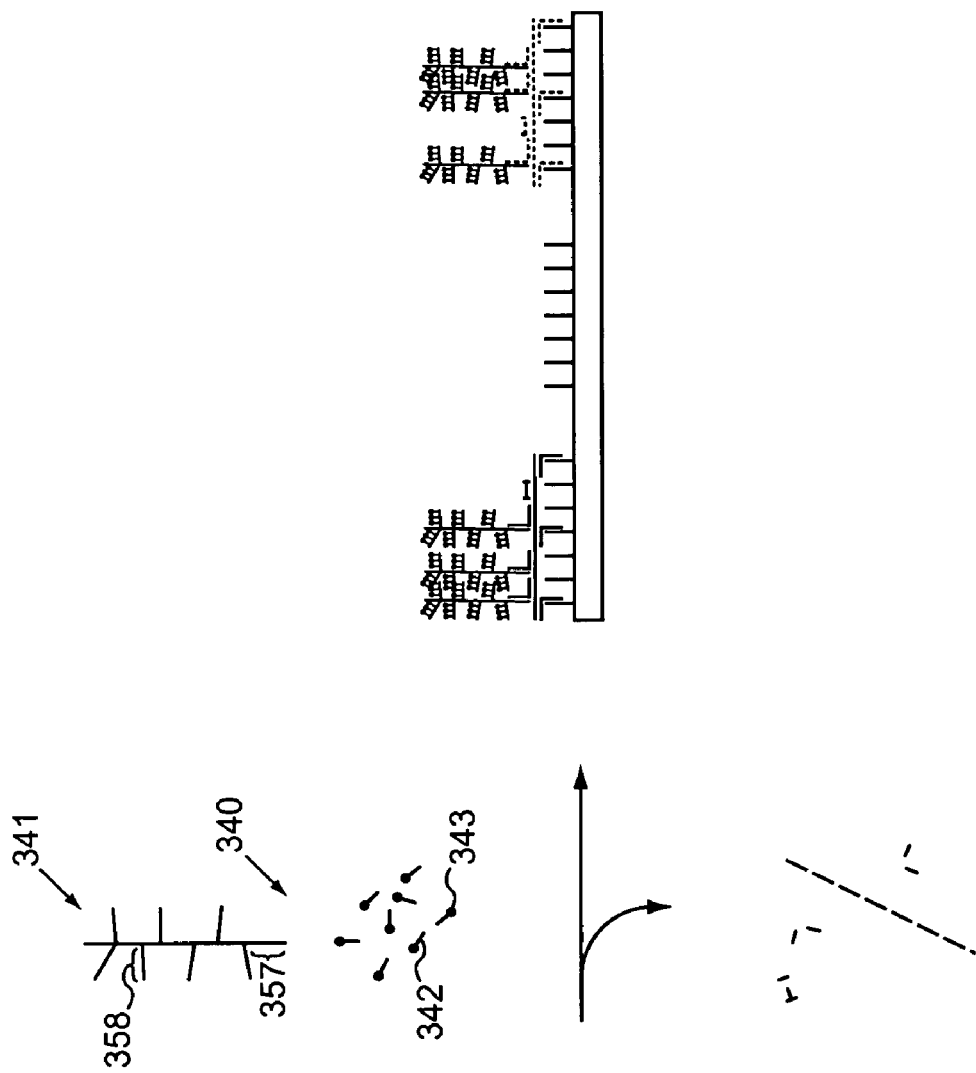
FIG. 3 Panels A-D schematically depict a multiplex bDNA assay, in which the target nucleic acids are captured at selected positions on a solid support and then detected. Panel A shows a top view of the solid support, while Panels B-D show the support in cross-section.

Yet another exemplary embodiment is schematically illustrated in FIG. 3. This example demonstrates multiplex capture and detection of target nucleic acids, using a bDNA assay and a substantially planar solid support. Panel A depicts solid support 301 having nine capture probes provided on it at nine selected positions (e.g., 334-336). Panel B depicts a cross section of solid support 301, with distinct capture probes 304, 305, and 306 at different selected positions on the support (334, 335, and 336, respectively). A set of capture extenders is provided for each target nucleic acid. Only three sets are depicted; set 311 for nucleic acid 314, set 312 for nucleic acid 315 which is not present, and set 313 for nucleic acid 316. Each capture extender includes sequences C-1 (351, complementary to the respective capture probe's sequence C-2) and C-3 (352, complementary to a sequence in the corresponding target nucleic acid). Three sets of label extenders (321, 322, and 323 for nucleic acids 314, 315, and 316, respectively) and three sets of blocking probes (324, 325, and 326 for nucleic acids 314, 315, and 316, respectively) are also depicted (although nine would typically be provided, one for each nucleic acid of interest). Each label extender includes sequences L-1 (354, complementary to a sequence in the corresponding target nucleic acid) and L-2 (355, complementary to M-1).

A sample comprising whole blood is provided and the peripheral blood cells are lysed, producing a lysate (e.g., a whole blood lysate) including target nucleic acids 314 and 316; non-target nucleic acids 330 are also present in the lysate. Nucleic acids 314 and 316 are contacted with and hybridized to their corresponding set of capture extenders (311 and 313, respectively), and the capture extenders are hybridized to the corresponding capture probes (304 and 306, respectively), capturing nucleic acids 314 and 316 at selected positions 334 and 336, respectively (Panel C). Materials not bound to the solid support (e.g., capture extenders 312, nucleic acids 330, etc.) are optionally separated from the support by washing. Label probe system 340 including amplification multimer 341 (which includes sequences M-1 357 and M-2 358) and label probe 342 (which contains label 343) is hybridized to label extenders 321 and 323, which are hybridized to nucleic acids 314 and 316, respectively (Panel D). Materials not captured on the solid support are optionally removed by washing the support, and the presence or absence of the label at each position on the solid support is detected. Since each target nucleic acid is associated with a distinct selected position on the solid support via hybridization with the corresponding set of capture extenders and capture probe, the presence of the label at a given position on the solid support correlates with the presence of the corresponding target nucleic acid at that position and thus its presence in the original sample.

At any of various steps in the methods, materials not captured on the solid support are optionally separated from the support (and thus from any support-bound materials). For example, when detection is performed with a bDNA assay, after the capture extenders, nucleic acids, label extenders, blocking probes, and support-bound capture probes are hybridized, the solid support is optionally washed to remove unbound nucleic acids and probes; after the label extenders and amplification multimer are hybridized, the solid support is optionally washed to remove unbound amplification multimer; and/or after the label probes are hybridized to the amplification multimer, the solid support is optionally washed to remove unbound label probe prior to detection of the label.

The methods are optionally used to quantitate the amount of the first (and optional second, third, etc.) nucleic acid present in the whole blood sample. Thus, in one class of embodiments, detecting the presence of the first target nucleic acid on the solid support comprises detecting an amount of the first target nucleic acid on the solid support. It will be evident that the amount of the target nucleic acid captured on the solid support is proportional to the amount of the target nucleic acid present in the original sample. For example, in one class of embodiments in which a label is used, an intensity of a signal from the label can be measured (e.g., for each set of particles or each selected position on the solid support, in multiplex embodiments), and correlated with a quantity of the corresponding target nucleic acid present.

Due to efficient capture of each target nucleic acid by hybridization to multiple capture extenders, for example, even target nucleic acids present at low concentration can be captured and detected. Thus, in one class of embodiments, the first target nucleic acid is present in the sample in a non-zero amount of 100 amol or less, 50 amol or less, 10 amol or less, 1 amol or less, 0.1 amol or less, 0.05 amol or less, or even 0.01 amol or less. Similarly, two target nucleic acids can be captured and detected simultaneously, even when they differ greatly in concentration (e.g., by 1000-fold or more) in the sample. The methods are thus extremely versatile.

Capture of a particular target nucleic acid is optionally quantitative. Thus, in one exemplary class of embodiments, at least 30%, at least 50%, at least 80%, at least 90%, at least 95%, or even at least 99% of a total amount of the first target nucleic acid present in the sample is captured on the solid support. Second, third, etc. nucleic acids can similarly be quantitatively captured. Such quantitative capture can occur without capture of a significant amount of undesired nucleic acids, even those of very similar sequence to the target nucleic acid.

Thus, in one class of embodiments, in addition to the first target nucleic acid, the sample comprises or is suspected of comprising a nucleic acid which has a polynucleotide sequence which is 95% or more identical to that of the first target nucleic acid (e.g., 96% or more, 97% or more, 98% or more, or even 99% or more identical). The first target nucleic acid is captured on the solid support, while the other nucleic acid comprises 1% or less of a total amount of nucleic acid captured on the solid support (e.g., 0.5% or less, 0.2% or less, or even 0.1% or less; for multiplex embodiments, percent capture is assessed, e.g., on the corresponding first set of particles or first selected position on the solid support). The other nucleic acid can be another target nucleic acid or simply any nucleic acid. Typically, capture extenders are chosen that hybridize to regions of the first target nucleic acid having the greatest sequence difference from the other nucleic acid.

A capture probe and/or capture extender optionally comprises at least one non-natural nucleotide. For example, a capture probe and the corresponding capture extender optionally comprise, at complementary positions, at least one pair of non-natural nucleotides that base pair with each other but that do not Watson-Crick base pair with the bases typical to biological DNA or RNA (i.e., A, C, G, T, or U). Examples of nonnatural nucleotides include, but are not limited to, Locked NucleicAcid™ nucleotides (available from Exiqon A/S, www(dot)exiqon(dot)com; see, e.g., Santa Lucia Jr. (1998) Proc Natl Acad Sci 95:1460-1465) and isoG, isoC, and other nucleotides used in the AEGIS system (Artificially Expanded Genetic Information System, available from EraGen Biosciences, www(dot)eragen(dot)com; see, e.g., U.S. Pat. Nos. 6,001,983, 6,037,120, and 6,140,496). Use of such non-natural base pairs (e.g., isoG-isoC base pairs) in the capture probes and capture extenders can, for example, reduce background and/or simplify probe design by decreasing cross hybridization, or it can permit use of shorter capture probes and capture extenders when the non-natural base pairs have higher binding affinities than do natural base pairs. Non-natural nucleotides can similarly be included in the label extenders, amplification multimers, and/or label probes, if desired.

Methods for Detecting Nucleic Acids from Plasma

Similar methods can be used to detect nucleic acids from blood plasma. Although current techniques typically involve concentration of RNA from large volumes of plasma prior to detection, e.g., by passing the plasma through a column to collect circulating RNAs on the column or by isolation of viral particles, the methods of the present invention facilitate detection of nucleic acids directly from the plasma.

Thus, one general class of embodiments provides methods of detecting at least a first target nucleic acid. In the methods, plasma comprising the first target nucleic acid is provided. The plasma is contacted with a first set of n capture extenders, wherein n is at least two. The first set of capture extenders is capable of hybridizing to the first target nucleic acid. The first target nucleic acid is hybridized to the first set of capture extenders, and the first set of capture extenders is associated with a solid support. The first target nucleic acid is captured on the solid support by hybridizing the first target nucleic acid to the first set of capture extenders and associating the first set of capture extenders with the solid support. The presence of the first target nucleic acid on the solid support is then detected. The hybridization and association steps can be, e.g., either simultaneous or sequential.

In one class of embodiments, the methods include contacting the plasma with an exogenously supplied protease (a protease that is added to the plasma by a user of the methods, as opposed to a protease which is endogenous to plasma and is thus already present), typically prior to contacting the plasma with the first set of capture extenders. As for the methods above, a variety of proteases are known in the art and can be adapted to the practice of the present invention; an effective concentration of protease, time for which the lysate is incubated with the protease, and the like can be determined by routine experimentation, e.g., by ensuring that an exogenously added RNA can be quantitatively detected in the plasma. In one embodiment, the protease is proteinase K.

The plasma is optionally contacted with the protease in a digestion mixture, and the volume of plasma in the mixture is optionally at most ½, at most ⅓, or at most ⅕ the volume of the mixture. For example, the volume of plasma used can be at most 1/10, 1/50, 1/100, or 1/150 the volume of the mixture. The remainder of the volume of the mixture can comprise a buffered salt solution, a detergent (e.g., lithium lauryl sulfate), water, and/or the like; for example, the plasma can be mixed with a lysis buffer such as that described in Example 1 below.

The methods can be applied to detection of essentially any type of nucleic acids. For example, the first target nucleic acid can be a DNA or an RNA. A target nucleic acid can, for example, be expressed by the organism from which the plasma is obtained or by a pathogen, and can be, e.g., free in the plasma or associated with one or more proteins, lipids, and/or the like, e.g. as a virion.

It will be understood that if the first target nucleic acid is initially present in the plasma in a double-stranded form, e.g., hybridized to a complementary nucleic acid, the double-stranded form is denatured prior to hybridizing the first target nucleic acid to the first set of capture extenders. Denaturation can be accomplished, for example, by thermal denaturation, exposure to alkaline conditions (which can have the added advantage of digesting extraneous RNA if the target nucleic acid is a DNA), or similar techniques. The methods can thus be used for detecting, e.g., double-stranded genomic DNA, double-stranded viral nucleic acids, and the like, as well as single-stranded nucleic acids such as mRNAs.

Essentially all of the features noted for the methods above apply to these embodiments as well, as relevant; for example, with respect to number of capture extenders per set, type of solid support, association of the capture extenders with the solid support, detection technique, composition of the optional label probe system, type of label, inclusion of blocking probes, quantitation of the target nucleic acid(s), separation of unbound materials from the solid support, and/or the like.

For example, in one preferred class of embodiments, a first capture probe is bound to the solid support, and associating the first set of capture extenders with the solid support comprises hybridizing the capture extenders to the first capture probe. As another example, the presence of the first target nucleic acid on the solid support is optionally detected by hybridizing a first set of one or more label extenders and a label probe system comprising a label to the first target nucleic acid and then detecting the presence of the label on the solid support.

As for the embodiments above, the methods can be conveniently multiplexed to detect two or more target nucleic acids simultaneously. Thus, in one class of embodiments, the plasma comprises a second target nucleic acid and the methods include contacting the plasma with a second set of m capture extenders, wherein m is at least two (preferably at the same time the plasma is contacted with the first set of capture extenders); this second set of capture extenders is capable of hybridizing to the second target nucleic acid. The second target nucleic acid is hybridized to the second set of capture extenders, and the second set of capture extenders is associated with the solid support. Hybridizing the second target nucleic acid to the second set of capture extenders and associating the second set of capture extenders with the solid support captures the second target nucleic acid on the solid support. The presence of the second target nucleic acid on the solid support is then detected. It will be evident that n, the number of capture extenders in the first set, can but need not be the same as m, the number of capture extenders in the second set. As for the first target nucleic acid, the second target nucleic acid can be essentially any type of nucleic acid.

In one class of embodiments, the solid support is a substantially planar solid support, the first target nucleic acid is captured at a first selected position on the solid support, and the second target nucleic acid is captured at a second selected position on the solid support. For example, the first set of capture extenders can be hybridized to a first capture probe predisposed at the first selected position, while the second set of capture extenders is hybridized to a second capture probe predisposed at the second selected position. As for the embodiments above, essentially any suitable solid support can be employed.

In another class of embodiments, the solid support comprises a population of particles. The population includes at least two sets of particles, and the particles in each set are distinguishable from the particles in every other set. The first target nucleic acid is captured on a first set of the particles, and the second target nucleic acid is captured on a second set of the particles. For example, the first set of particles can comprise a first capture probe that is capable of hybridizing to the capture extenders comprising the first set of capture extenders (and thereby capturing the first target nucleic acid on the first set of particles), and the second set of particles can comprise a second capture probe that is capable of hybridizing to the capture extenders comprising the second set of capture extenders (and thereby capturing the second target nucleic acid on the second set of particles). In this class of embodiments, detecting the presence of the first and second nucleic acid on the solid support typically includes identifying at least a portion of the particles from each set and detecting the presence of nucleic acid on particles from each set. As for the embodiments above, essentially any suitable particles, e.g., particles having distinguishable characteristics and to which capture probes can be attached, can be used. For example, in one preferred class of embodiments, the particles are microspheres.

It will be evident that third, fourth, fifth, etc. target nucleic acids are optionally also detected. The at least one target nucleic acid to be detected thus optionally includes two or more, five or more, 10 or more, 20 or more, 30 or more, 40 or more, 50 or more, or even 100 or more target nucleic acids which are present or suspected to be present in the whole blood. A like number of sets of capture extenders, and typically a like number of selected positions on a substantially planar solid support or a like number of sets of particles, are also provided and used to capture and detect the target nucleic acids.

Compositions

Compositions related to the methods are another feature of the invention. Thus, one general class of embodiments provides a composition that includes a first set of n capture extenders, wherein n is at least two, and peripheral blood cell nucleic acids. The first set of capture extenders is capable of hybridizing to (and optionally is hybridized to) a first target nucleic acid. The first set of capture extenders is associated with, or is capable of being associated with, a solid support.

In one class of embodiments, the composition includes a whole blood lysate comprising the peripheral blood cell nucleic acids. The volume of whole blood from which the lysate is produced is optionally at most ½, ⅓, ⅕, ¹⁄₁₀, ¹⁄₅₀, ¹⁄₁₀₀, or ¹⁄₁₅₀ the volume of the composition. In another class of embodiments, the composition includes a peripheral blood cell lysate comprising the peripheral blood cell nucleic acids.

The composition can include the first target nucleic acid. The peripheral blood cell nucleic acids optionally comprise the first target nucleic acid; alternatively, the first target nucleic acid can, e.g., be a nucleic acid found in the plasma. The composition optionally includes nucleic acids from whole blood, where nucleic acids from plasma and all blood cell types (e.g., red blood cells, white blood cells, and platelets) are represented or potentially represented, no plasma, cells, or cell type having been deliberately enriched in or removed from the sample of whole blood.

In one class of embodiments, the composition includes an exogenously supplied protease (e.g., proteinase K) and/or a detergent. The composition optionally also includes reagents used to detect the first target nucleic acid. For example, in one class of embodiments, the composition includes a first set of one or more label extenders, which first set of label extenders is capable of hybridizing to (and optionally is hybridized to) the first target nucleic acid. The composition optionally also includes a label probe system comprising a label.

The composition can include the solid support. The capture extenders are optionally bound to the solid support, e.g., covalently or noncovalently, directly or through a linker, e.g., streptavidin-biotin or the like. In one preferred class of embodiments, a first capture probe is bound to the solid support. The first capture probe is capable of hybridizing to (and optionally is hybridized to) the capture extenders of the first set of capture extenders and thereby associating the capture extenders with the solid support. As noted above, the solid support can be essentially any suitable support, including any of a variety of materials, configurations, and the like. For example, in one class of embodiments, the solid support is a substantially planar solid support, e.g., an upper surface of the bottom of a well of a multiwell plate, a slide, or the like. Similarly, suitable solid supports include any surface of a well of a multiwell plate, whether planar or not. As another example, the solid support can comprise a plurality of particles, e.g., microspheres, beads, cylindrical particles, irregularly shaped particles, or the like. The particles are optionally identifiable, and optionally have additional or other desirable characteristics.

The composition optionally includes a second set of m capture extenders, wherein m is at least two. The second set of capture extenders is capable of hybridizing to (and optionally is hybridized to) a second target nucleic acid, and the second set of capture extenders is associated with, or is capable of being associated with, the solid support. In one class of embodiments, the solid support is a substantially planar solid support, wherein the first set of capture extenders is associated with or is capable of being associated with a first selected position on the solid support, and wherein the second set of capture extenders is associated with or is capable of being associated with a second selected position on the solid support. A first capture probe capable of hybridizing to the capture extenders of the first set is optionally bound to the solid support at the first selected position while a second capture probe capable of hybridizing to the capture extenders of the second set is bound to the solid support at the second selected position. In another class of embodiments, the solid support comprises a population of particles that includes at least two sets of particles, and the particles in each set are distinguishable from the particles in every other set. The first set of capture extenders is associated with or is capable of being associated with a first set of the particles, and the second set of capture extenders is associated with or is capable of being associated with a second set of the particles. Optionally, the first set of particles comprises a first capture probe capable of hybridizing to the capture extenders comprising the first set of capture extenders, while the second set of particles comprises a second capture probe capable of hybridizing to the capture extenders comprising the second set of capture extenders. The composition optionally includes the second target nucleic acid. It will be evident that the composition optionally also includes third, fourth, fifth, etc. target nucleic acids, sets of capture extenders, sets of particles or selected positions on the solid support, and/or the like.

Essentially all of the features noted for the methods above apply to these embodiments as well, as relevant; for example, with respect to number of capture extenders per set, composition of the label probe system, type of label, inclusion of blocking probes, type of target nucleic acid(s), and/or the like.

Another general class of embodiments provides a composition that includes a first set of n capture extenders, wherein n is at least two, and plasma. The first set of capture extenders is capable of hybridizing to (and optionally is hybridized to) a first target nucleic acid. The first set of capture extenders is associated with, or is capable of being associated with, a solid support.

The composition can include the first target nucleic acid. In one class of embodiments, the composition includes an exogenously supplied protease (e.g., proteinase K) and/or a detergent. The volume of the plasma is optionally at most $\frac{1}{2}$, $\frac{1}{3}$, $\frac{1}{5}$, $\frac{1}{10}$, $\frac{1}{50}$, $\frac{1}{100}$, or $\frac{1}{150}$ the volume of the composition. The composition optionally also includes reagents used to detect the first target nucleic acid. For example, in one class of embodiments, the composition includes a first set of one or more label extenders, which first set of label extenders is capable of hybridizing to the first target nucleic acid. The composition optionally also includes a label probe system comprising a label.

The composition can include the solid support. The capture extenders are optionally bound to the solid support, e.g., covalently or noncovalently, directly or through a linker, e.g., streptavidin-biotin or the like. In one preferred class of embodiments, a first capture probe is bound to the solid support. The first capture probe is capable of hybridizing to the capture extenders of the first set of capture extenders and thereby associating the capture extenders with the solid support. As noted above, the solid support can be essentially any suitable support, including any of a variety of materials, configurations, and the like. For example, in one class of embodiments, the solid support is a substantially planar solid support, e.g., an upper surface of the bottom of a well of a multiwell plate, a slide, or the like. Similarly, suitable solid supports include any surface of a well of a multiwell plate, whether planar or not. As another example, the solid support can comprise a plurality of particles, e.g., microspheres, beads, cylindrical particles, irregularly shaped particles, or the like. The particles are optionally identifiable, and optionally have additional or other desirable characteristics.

The composition optionally includes a second set of m capture extenders, wherein m is at least two. The second set of capture extenders is capable of hybridizing to (and optionally is hybridized to) a second target nucleic acid, and the second set of capture extenders is associated with, or is capable of being associated with, the solid support. In one class of embodiments, the solid support is a substantially planar solid support, wherein the first set of capture extenders is associated with or is capable of being associated with a first selected position on the solid support, and wherein the second set of capture extenders is associated with or is capable of being associated with a second selected position on the solid support. A first capture probe capable of hybridizing to the capture extenders of the first set is optionally bound to the solid support at the first selected position while a second capture probe capable of hybridizing to the capture extenders of the second set is bound to the solid support at the second selected position. In another class of embodiments, the solid support comprises a population of particles that includes at least two sets of particles, and the particles in each set are distinguishable from the particles in every other set. The first set of capture extenders is associated with or is capable of being associated with a first set of the particles, and the second set of capture extenders is associated with or is capable of being associated with a second set of the particles. Optionally, the first set of particles comprises a first capture probe capable of hybridizing to the capture extenders comprising the first set of capture extenders, while the second set of particles comprises a second capture probe capable of hybridizing to the capture extenders comprising the second set of capture extenders. The composition optionally includes the second target nucleic acid. It will be evident that the composition optionally also includes third, fourth, fifth, etc. target nucleic acids, sets of capture extenders, sets of particles or selected positions on the solid support, and/or the like.

Essentially all of the features noted for the embodiments above apply to these embodiments as well, as relevant; for example, with respect to number of capture extenders per set, composition of the label probe system, type of label, inclusion of blocking probes, type of target nucleic acid(s), and/or the like.

Kits

Yet another general class of embodiments provides a kit for detecting at least a first target nucleic acid. The kit includes a first capture probe bound to a solid support, a first set of n capture extenders, wherein n is at least two, a label probe system comprising a label, a first set of one or more label extenders, a first solution comprising a detergent, a protease, and instructions for detecting the first target nucleic acid in whole blood, in peripheral blood cells, and/or in plasma with the kit, packaged in one or more containers. The first set of capture extenders is capable of hybridizing to the first target nucleic acid and to the first capture probe, and the label extenders of the first set are capable of hybridizing to the first target nucleic acid and to the label probe system.

The protease can be included in the first solution, provided in another solution, or provided in dried form, for example. The first solution typically includes a buffer, salt, and/or the like in addition to the detergent (e.g., a detergent such as lithium lauryl sulfate). The kit optionally also includes additional buffered solutions (e.g., diluent, hybridization buffer, and/or wash buffer), standards comprising one or more nucleic acids at known concentration, blocking probes, and/or the like.

In one aspect, the kits are configured for multiplex detection of target nucleic acids. Thus, in one class of embodiments, the kit also includes a second capture probe bound to the solid support, a second set of m capture extenders, wherein m is at least two, and a second set of one or more label extenders. The second set of capture extenders is capable of hybridizing to a second target nucleic acid and to the second capture probe, and the label extenders of the second set are capable of hybridizing to the second target nucleic acid and to the label probe system. It will be evident that third, fourth, fifth, etc. support-bound capture probes, sets of capture extenders, and sets of label extenders are optionally also included in the kit, for detection of third, fourth, fifth, etc. target nucleic acids.

Essentially all of the features noted for the embodiments above apply to these embodiments as well, as relevant; for example, with respect to number of capture extenders per set, type of solid support, association of the capture extenders with the solid support, composition of the label probe system, type of label, type of target nucleic acid(s), and/or the like.

Systems

In one aspect, the invention includes systems, e.g., systems used to practice the methods herein and/or comprising the compositions described herein. The system can include, e.g., a fluid and/or particle (e.g., microsphere) handling element, a fluid and/or particle containing element, a laser for exciting a fluorescent label and/or fluorescent particles, a detector for detecting light emissions from a chemiluminescent reaction or fluorescent emissions from a fluorescent label and/or fluorescent particles, and/or a robotic element that moves other components of the system from place to place as needed (e.g., a multiwell plate handling element). For example, in one class of embodiments, a composition of the invention is contained in a flow cytometer, a Luminex® 100™ or HTS™ instrument, a microplate reader, a microarray reader, a luminometer, a colorimeter, or like instrument.

The system can optionally include a computer. The computer can include appropriate software for receiving user instructions, either in the form of user input into a set of parameter fields, e.g., in a GUI, or in the form of preprogrammed instructions, e.g., preprogrammed for a variety of different specific operations. The software optionally converts these instructions to appropriate language for controlling the operation of components of the system (e.g., for controlling a fluid handling element, robotic element and/or laser). The computer can also receive data from other components of the system, e.g., from a detector, and can interpret the data, provide it to a user in a human readable format, or use that data to initiate further operations, in accordance with any programming by the user.

Labels

A wide variety of labels are well known in the art and can be adapted to the practice of the present invention. For example, luminescent labels and light-scattering labels (e.g., colloidal gold particles) have been described. See, e.g., Csaki et al. (2002) "Gold nanoparticles as novel label for DNA diagnostics" Expert Rev Mol Diagn 2:187-93.

As another example, a number of fluorescent labels are well known in the art, including but not limited to, hydrophobic fluorophores (e.g., phycoerythrin, rhodamine, Alexa Fluor 488 and fluorescein), green fluorescent protein (GFP) and variants thereof (e.g., cyan fluorescent protein and yellow fluorescent protein), and quantum dots. See e.g., Haughland (2003) Handbook of Fluorescent Probes and Research Products, Ninth Edition or Web Edition, from Molecular Probes, Inc., for descriptions of fluorophores emitting at various different wavelengths (including tandem conjugates of fluorophores that can facilitate simultaneous excitation and detection of multiple labeled species). For use of quantum dots as labels for biomolecules, see e.g., Dubertret et al. (2002) Science 298:1759; Nature Biotechnology (2003) 21:41-46; and Nature Biotechnology (2003) 21:47-51.

Labels can be introduced to molecules, e.g. polynucleotides, during synthesis or by postsynthetic reactions by techniques established in the art; for example, kits for fluorescently labeling polynucleotides with various fluorophores are available from Molecular Probes, Inc. (www(dot)molecularprobes(dot)com), and fluorophore-containing phosphoramidites for use in nucleic acid synthesis are commercially available. Similarly, signals from the labels (e.g., absorption by and/or fluorescent emission from a fluorescent label) can be detected by essentially any method known in the art. For example, multicolor detection, detection of FRET, fluorescence polarization, and the like, are well known in the art.

Microspheres

Microspheres are preferred particles in certain embodiments described herein since they are generally stable, are widely available in a range of materials, surface chemistries and uniform sizes, and can be fluorescently dyed. Microspheres can be distinguished from each other by identifying characteristics such as their size (diameter) and/or their fluorescent emission spectra, for example.

Luminex Corporation (www(dot)luminexcorp(dot)com), for example, offers 100 sets of uniform diameter polystyrene microspheres. The microspheres of each set are internally labeled with a distinct ratio of two fluorophores. A flow cytometer or other suitable instrument can thus be used to classify each individual microsphere according to its predefined fluorescent emission ratio. Fluorescently-coded microsphere sets are also available from a number of other suppliers, including Radix Biosolutions (www(dot)radixbiosolutions(dot)com) and Upstate Biotechnology (www(dot)upstatebiotech(dot)com). Alternatively, BD Biosciences (www(dot)bd(dot)com) and Bangs Laboratories, Inc. (www(dot)bangslabs(dot)com) offer microsphere sets distinguishable by a combination of fluorescence and size. As another example, microspheres can be distinguished on the basis of size alone, but fewer sets of such microspheres can be multiplexed in an assay because aggregates of smaller microspheres can be difficult to distinguish from larger microspheres.

Microspheres with a variety of surface chemistries are commercially available, from the above suppliers and others (e.g., see additional suppliers listed in Kellar and Iannone (2002) "Multiplexed microsphere-based flow cytometric assays" Experimental Hematology 30:1227-1237 and Fitzgerald (2001) "Assays by the score" The Scientist 15[11]: 25). For example, microspheres with carboxyl, hydrazide or maleimide groups are available and permit covalent coupling of molecules (e.g., polynucleotide capture probes with free amine, carboxyl, aldehyde, sulfhydryl or other reactive groups) to the microspheres. As another example, microspheres with surface avidin or streptavidin are available and can bind biotinylated capture probes; similarly, microspheres coated with biotin are available for binding capture probes conjugated to avidin or streptavidin. In addition, services that couple a capture reagent of the customer's choice to microspheres are commercially available, e.g., from Radix Biosolutions (www(dot)radixbiosolutions(dot)com).

Protocols for using such commercially available microspheres (e.g., methods of covalently coupling polynucleotides to carboxylated microspheres for use as capture probes, methods of blocking reactive sites on the microsphere surface that are not occupied by the polynucleotides, methods of binding biotinylated polynucleotides to avidin-functionalized microspheres, and the like) are typically supplied with the microspheres and are readily utilized and/or adapted by one of skill. In addition, coupling of reagents to microspheres is well described in the literature. For example, see Yang et al. (2001) "BADGE, Beads Array for the Detection of Gene Expression, a high-throughput diagnostic bioassay" Genome Res. 11:1888-98; Fulton et al. (1997) "Advanced multiplexed analysis with the FlowMetrix™ system" Clinical Chemistry 43:1749-1756; Jones et al. (2002) "Multiplex assay for detection of strain-specific antibodies against the two variable regions of the G protein of respiratory syncytial virus" 9:633-638; Camilla et al. (2001) "Flow cytometric microsphere-based immunoassay: Analysis of secreted cytokines in whole-blood samples from asthmatics" Clinical and Diagnostic Laboratory Immunology 8:776-784; Martins (2002) "Development of internal controls for the Luminex instrument as part of a multiplexed seven-analyte viral respiratory antibody profile" Clinical and Diagnostic Laboratory Immunology 9:41-45; Kellar and Iannone (2002) "Multiplexed microsphere-based flow cytometric assays" Experimental Hematology 30:1227-1237; Oliver et al. (1998) "Multiplexed analysis of human cytokines by use of the FlowMetrix system" Clinical Chemistry 44:2057-2060; Gordon and McDade (1997) "Multiplexed quantification of human IgG, IgA, and IgM with the FlowMetrix™ system" Clinical Chemistry 43:1799-1801; U.S. Pat. No. 5,981,180 entitled "Multiplexed analysis of clinical specimens apparatus and methods" to Chandler et al. (Nov. 9, 1999); U.S. Pat. No. 6,449,562 entitled "Multiplexed analysis of clinical specimens apparatus and methods" to Chandler et al. (Sep. 10, 2002); and references therein.

Methods of analyzing microsphere populations (e.g. methods of identifying microsphere subsets by their size and/or fluorescence characteristics, methods of using size to distinguish microsphere aggregates from single uniformly sized microspheres and eliminate aggregates from the analysis, methods of detecting the presence or absence of a fluorescent label on the microsphere subset, and the like) are also well described in the literature. See, e.g., the above references.

Suitable instruments, software, and the like for analyzing microsphere populations to distinguish subsets of microspheres and to detect the presence or absence of a label (e.g., a fluorescently labeled label probe) on each subset are commercially available. For example, flow cytometers are widely available, e.g., from Becton-Dickinson (www(dot)bd(dot)com) and Beckman Coulter (www(dot)beckman(dot)com). Luminex® 100™ and Luminex HTS™ systems (which use microfluidics to align the microspheres and two lasers to excite the microspheres and the label) are available from Luminex Corporation (www(dot)luminexcorp(dot)com); the similar Bio-Plex™ Protein Array System is available from Bio-Rad Laboratories, Inc. (www(dot)bio-rad(dot)com). A confocal microplate reader suitable for microsphere analysis, the FMAT™ System 8100, is available from Applied Biosystems (www(dot)appliedbiosystems(dot)com).

As another example of particles that can be adapted for use in the present invention, sets of microbeads that include optical barcodes are available from CyVera, now part of illumina, Inc. (www(dot)illumina(dot)com). The optical barcodes are holographically inscribed digital codes that diffract a laser beam incident on the particles, producing an optical signature unique for each set of microbeads.

Molecular Biological Techniques

In practicing the present invention, many conventional techniques in molecular biology, microbiology, and recombinant DNA technology are optionally used. These techniques are well known and are explained in, for example, Berger and Kimmel, Guide to Molecular Cloning Techniques, Methods in Enzymology volume 152 Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2000 and Current Protocols in Molecular Biology, F. M. Ausubel et al., eds., Current Protocols, a joint venture between Greene Publishing Associates, Inc. and John Wiley & Sons, Inc., (supplemented through 2005). Other useful references, e.g. for cell isolation and culture (e.g., for subsequent nucleic acid or protein isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York) and Atlas and Parks (Eds.) The Handbook of Microbiological Media (1993) CRC Press, Boca Raton, Fla.

Making Polynucleotides

Methods of making nucleic acids (e.g., by in vitro amplification, purification from cells, or chemical synthesis), methods for manipulating nucleic acids (e.g., by restriction enzyme digestion, ligation, etc.) and various vectors, cell lines and the like useful in manipulating and making nucleic acids are described in the above references. In addition, methods of making branched polynucleotides (e.g., amplification multimers) are described in U.S. Pat. Nos. 5,635,352, 5,124, 246, 5,710,264, and 5,849,481, as well as in other references mentioned above.

In addition, essentially any polynucleotide (including, e.g., labeled or biotinylated polynucleotides) can be custom or standard ordered from any of a variety of commercial sources, such as The Midland Certified Reagent Company (www(dot) mcrc(dot)com), The Great American Gene Company (www (dot)genco(dot)com), ExpressGen Inc. (www(dot)expressgen(dot)com), Qiagen (on the internet at oligos(dot)qiagen (dot)com) and many others.

A label, biotin, or other moiety can optionally be introduced to a polynucleotide, either during or after synthesis. For example, a biotin phosphoramidite can be incorporated during chemical synthesis of a polynucleotide. Alternatively, any nucleic acid can be biotinylated using techniques known in the art; suitable reagents are commercially available, e.g., from Pierce Biotechnology (www(dot)piercenet(dot)com). Similarly, any nucleic acid can be fluorescently labeled, for example, by using commercially available kits such as those from Molecular Probes, Inc. (www(dot)molecularprobes (dot)com) or Pierce Biotechnology (www(dot)piercenet(dot) com) or by incorporating a fluorescently labeled phosphoramidite during chemical synthesis of a polynucleotide.

Arrays

In an array of capture probes on a solid support (e.g., a membrane, a glass or plastic slide, a silicon or quartz chip, a plate, or other spatially addressable solid support), each capture probe is typically bound (e.g., electrostatically or covalently bound, directly or via a linker) to the support at a unique selected location. Methods of making, using, and analyzing such arrays (e.g., microarrays) are well known in the art. See, e.g., Baldi et al. (2002) DNA Microarrays and Gene Expression: From Experiments to Data Analysis and Modeling, Cambridge University Press; Beaucage (2001) "Strategies in the preparation of DNA oligonucleotide arrays for diagnostic applications" Curr Med Chem 8:1213-1244; Schena, ed. (2000) Microarray Biochip Technology, pp. 19-38, Eaton Publishing; technical note "Agilent SurePrint Technology: Content centered microarray design enabling speed and flexibility" available at www(dot)chem(dot)agilent(dot)com/temp/rad01539/00039489(dot)pdf; and references therein. Arrays of pre-synthesized polynucleotides can be formed (e.g., printed), for example, using commercially available instruments such as a GMS 417 Arrayer (Affymetrix, Santa Clara, Calif.). Alternatively, the polynucleotides can be synthesized at the selected positions on the solid support; see, e.g., U.S. Pat. Nos. 6,852,490 and 6,306,643, each to Gentanlen and Chee entitled "Methods of using an array of pooled probes in genetic analysis."

Suitable solid supports are commercially readily available. For example, a variety of membranes (e.g., nylon, PVDF, and nitrocellulose membranes) are commercially available, e.g., from Sigma-Aldrich, Inc. www(dot)sigmaaldrich(dot)com). As another example, surface-modified and pre-coated slides with a variety of surface chemistries are commercially available, e.g., from TeleChem International (www(dot)arrayit (dot)com), Corning, Inc. (Corning, N.Y.), or Greiner Bio-One, Inc. (www(dot)greinerbiooneinc(dot)com). For example, silanated and silylated slides with free amino and aldehyde groups, respectively, are available and permit covalent coupling of molecules (e.g., polynucleotides with free aldehyde, amine, or other reactive groups) to the slides. As another example, slides with surface streptavidin are available and can bind biotinylated capture probes. In addition, services that produce arrays of polynucleotides of the customer's choice are commercially available, e.g., from TeleChem International (www(dot)arrayit(dot)com) and Agilent Technologies (Palo Alto, Calif.).

Suitable instruments, software, and the like for analyzing arrays to distinguish selected positions on the solid support and to detect the presence or absence of a label (e.g., a fluorescently labeled label probe) at each position are commercially available. For example, microarray readers are available, e.g., from Agilent Technologies (Palo Alto, Calif.), Affymetrix (Santa Clara, Calif.), and Zeptosens (Switzerland).

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Sensitive and Quantitative Measurement of Gene Expression Directly from Peripheral Whole Blood The following sets forth a series of experiments that demonstrate detection of nucleic acids from whole blood using bDNA assays. Both singleplex and multiplex assays are described.

Using current techniques, gene expression analysis of whole blood requires cell isolation, RNA purification, and/or target amplification. This example, however, describes an assay to measure single- or multiplexed gene expression directly from whole blood without RNA purification, labeling, or amplification. The assay can detect, e.g., as little as 0.01 attomol (singleplex) or 0.04 attomol (multiplex) of a target mRNA in 30 μl of blood, with a coefficient of variation less than 10% and a dynamic range of 3-4 logs. The assay is sensitive enough to quantitatively measure gene expression from cells in the minority in whole blood, with signals that are several times higher than those from assays using RNA purified from an equivalent amount of blood. The assay was used to evaluate the impact of blood processing on gene expression and indicated that PAXgene® treatment induced expression of known antiapoptotic genes during processing of the whole blood.

The method can directly measure RNA in whole blood lysates, with excellent sensitivity and reproducibility. The assay does not require blood processing (other than direct lysis), RNA extraction, or enzymatic manipulation of sample RNA. Because detection is based on hybridization between a target RNA and oligonucleotide probes, no enzymatic manipulation of the target is needed; the measured signal is directly proportional to the target RNA, instead of to any derivatives of it such as cDNA, cRNA, or an amplified product. The assay is presented in a singleplex format using a multi-well plate and chemiluminescent detection, and in a multiplex format combining the Luminex xMAP® encoded bead platform with fluorescent detection.

Overview of the Assay

Analogous to an ELISA sandwich assay, this exemplary assay utilizes nucleic acid sandwich binding to capture target RNAs in whole blood lysates to a solid support. The ability to quantify an mRNA transcript without target labeling lies in the design of a set of target-specific oligonucleotide probes (e.g., about 20 probes per target as in this example). The detection signal is amplified using branched-DNA (bDNA) signal amplification technology (Urdea, M. S. et al. (1991) "Branched DNA amplification multimers for the sensitive: direct detection of human hepatitis viruses" Nucleic Acids Symp Ser 24:197-200). An overview of the assay is shown in FIG. 1.

Assay Performance bDNA assays have been used successfully to quantify gene expression in total RNA and tissue culture lysates and in viral particles purified from human plasma (Urdea, M. S. et al. (1991) "Branched DNA amplification multimers for the sensitive:direct detection of human hepatitis viruses" Nucleic Acids Symp Ser 24:197-200; Hartley, D. P. and Klaassen, C. D. (2000) "Detection of Chemical-Induced Differential Expression of Rat Hepatic Cytochrome P450 mRNA Transcripts Using Branched DNA Signal Amplification Technology" Drug Metab Dispos 28:608-616; Wang, J. et al. (1997) Regulation of insulin preRNA splicing by glucose" PNAS 94:4360-4365; and Gleaves, C. A. et al. (2002) "Multicenter evaluation of the Bayer VERSANT HIV-1 RNA 3.0 assay: analytical and clinical performance" J Clin Virol 25:205-16). However, there has been no report on the use of bDNA to directly detect RNA in whole blood, presumably because of the unique challenges presented by whole blood that are not found in other tissues or cultured cells, including high protein content from plasma and red cells and high ribonuclease activity. Initial attempts to apply bDNA technology to measurement of mRNA from whole blood failed to generate specific signals. The complex content in blood lysates resulted in nonspecific binding of probes and high background, and the addition of blood lysate into purified in vitro transcripts resulted in significant loss of transcript signals, suggesting the presence of residual ribonuclease activity in the whole blood lysate.

However, the methods described herein, which include incubating the lysate with an effective concentration of protease for an effective time at an effective temperature and limiting the blood to lysis buffer ratio, can enable detection of mRNA from whole blood. Using these methods, a linear signal response was observed for GAPDH (FIG. 4 Panel A, diamonds; $R^2=0.9898$) and other genes tested in 1-30 µl of whole blood, as well as in solubilized RNA pellets formed from equivalent amounts of whole blood stabilized in PAXgene® (FIG. 4 Panel B; $R^2=0.9927$). The average coefficient of variation was 7% (representing 16 sample measurements, each in triplicate) with a range of 0.4%-16%.

Figure 4A:
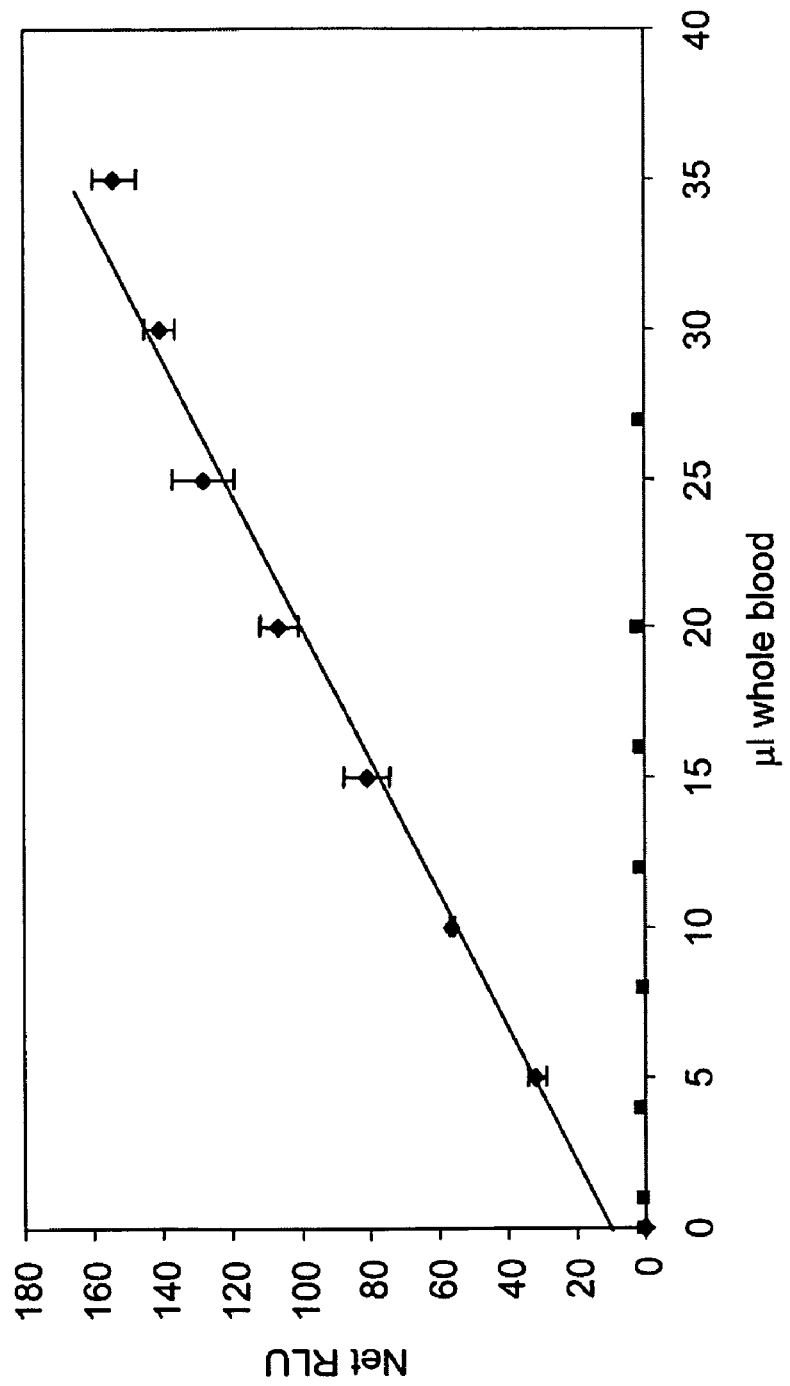
FIG. 4 Panel A depicts a graph illustrating quantitative detection of GAPDH mRNA in whole blood. Fresh, heparinized whole blood from a healthy donor was lysed and assayed for GAPDH expression using a probe set specific for GAPDH mRNA (diamond). No signal from hybridizing with genomic DNA can be detected using probes designed to bind the antisense strand of the target gene (square). Panel B depicts a graph illustrating GAPDH expression in PAXgene® stabilized whole blood. The nucleic acid pellet formed from PAXgene® stabilized blood was solubilized and assayed for GAPDH expression. Panel C depicts a graph illustrating detection of exogenous in vitro dapB transcripts (IVT) in the presence (diamond) and absence (square) of whole blood lysate. Mean±SD (standard deviation) values are graphed.
Figure 4B:
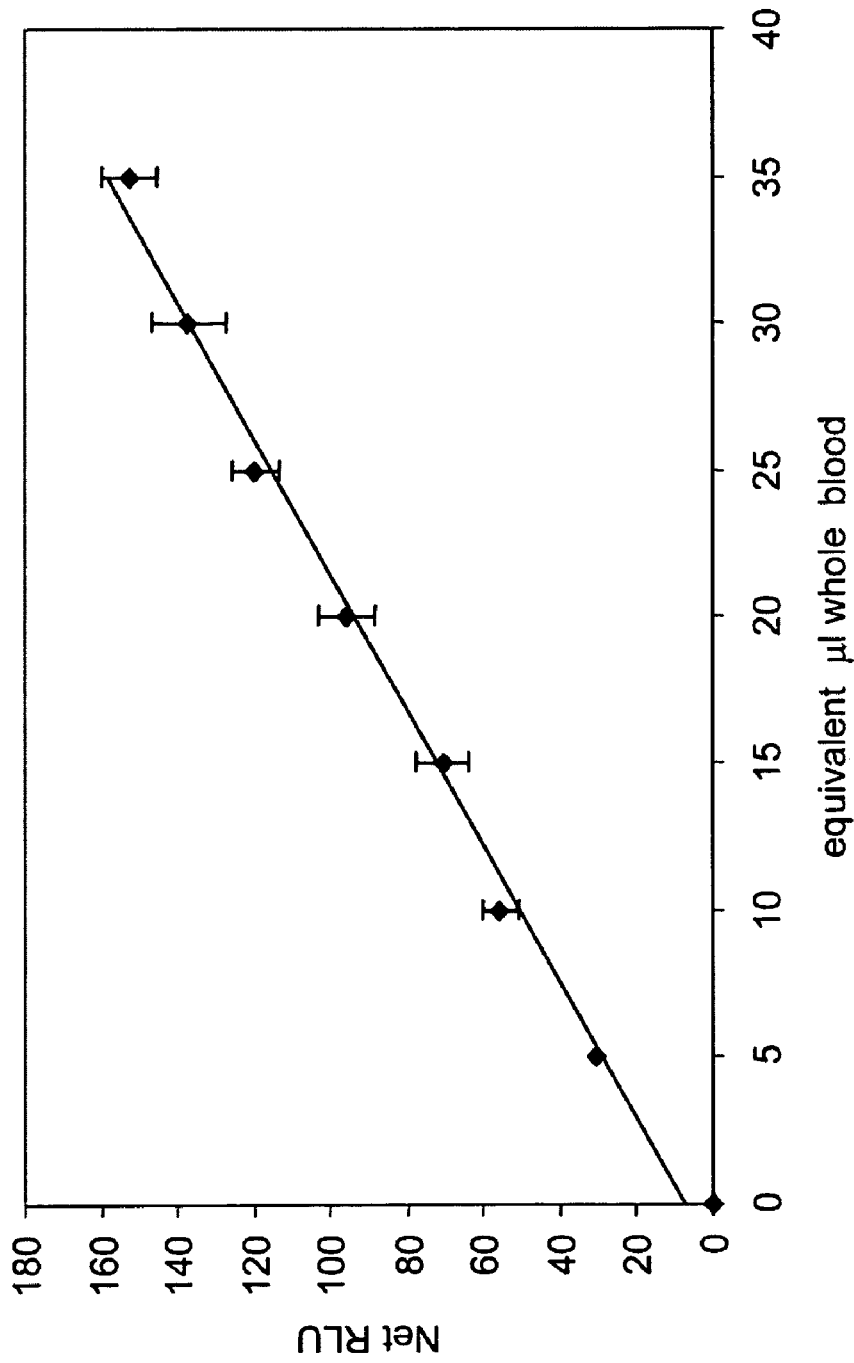

It is important to note that although both RNA and genomic DNA are present in the blood lysate, only RNA hybridizes to the probes under the assay conditions, since the genomic DNAs apparently remain annealed. Probes complementary to the antisense strand of a target gene did not give significant signal from whole blood lysate under standard assay conditions (FIG. 4 Panel A, squares). In a separate experiment, 500 ng of purified human genomic DNA (equivalent to DNA from 20 µl whole blood) was hybridized with GAPDH probes under standard assay conditions, and no specific hybridization signals could be detected.

Known amounts of an exogenous *E. coli* transcript (dapB, which does not cross hybridize with any known mammalian RNA) were added to the whole blood lysate to assess the assay's analytical sensitivity. An in vitro *E. coli* dapB transcript was serially diluted, added to lysate produced from 30 µl whole blood, and quantitated using dapB specific probes. As shown in FIG. 4 Panel C, the assay can specifically detect as little as 6000 copies (0.01 attomole) of target in the background of 30 µl blood, which includes about $2 \times 10^5$ white blood cells and $1.5 \times 10^8$ red blood cells. Linear regression $R^2$ values for both curves are 0.99, and all signals are above the indicated Limit of Detection (LOD). The complex components in blood lysate do not interfere with the detection of the specific mRNA target. Nearly 100% of the target molecules were captured onto the solid surface, as indicated by the generation of only minimal signals in a second assay measuring the amount of target remaining in the unbound supernatant of the first assay. The dynamic range of this method spans 4 logs. Importantly, at all concentrations tested, target signals in the absence or presence of blood lysate are essentially identical (FIG. 4 Panel C). A similar result was obtained by adding transcripts of IL2, which was not detectable in unstimulated whole blood. These results indicate that this method permits specific quantitation of RNA, avoiding interference by blood constituents such as blood proteins and the high concentration of reticulocyte-specific RNAs such as globin.

To obtain a practical sense of the assay sensitivity, mRNAs of several blood cell surface markers were assayed in singleplex in 30 µl fresh whole blood (Table 1). mRNAs from all major blood subtypes in normal blood can be detected, including the minority cell types (e.g., B cells and NK cells). Thus, this assay provides the means to directly monitor gene expression in subpopulations of blood cells without blood fractionation.

TABLE 1

Detection of cell-type specific mRNA in whole blood.

|  | T cell | T cell | NK cell | B cell | Monocyte | platelet (reticulated) | platelet (reticulated) |
|---|---|---|---|---|---|---|---|
| Approx. cell number per µl | 1600 | 1600 | 300 | 300 | 500 | 9200 | 9200 |
| mRNA | CD3E | CD5 | CD56 | CD19 | CD14 | CD61 | CD41 |
| 30 µl Blood (SD)* | 7.0 (1.1) | 3.0 (0.3) | 1.5 (0.1) | 1.7 (0.2) | 21.8 (1.1) | 11.1 (1.9) | 5.3 (0.6) |
| Control (SD)*,** | 0.4 (0.02) | 0.3 (0.01) | 0.5 (0.03) | 0.3 (0.03) | 0.4 (0.06) | 0.5 (0.06) | 0.4 (0.05) |

*units are RLUs
**no blood

Figure 5A:
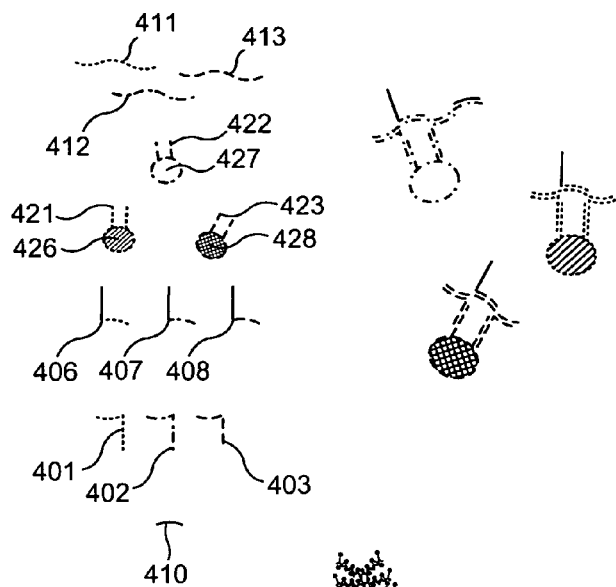
FIG. 5 Panels A-C schematically depict an overview of a multiplex bDNA assay.
Figure 5B:
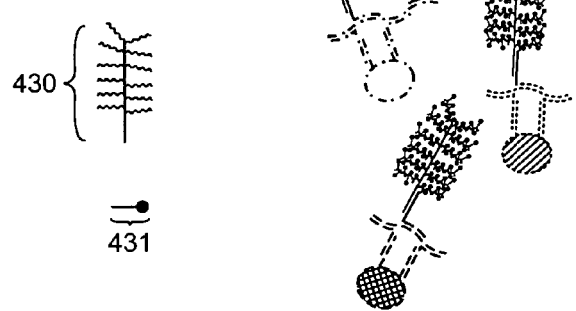
Figure 5C:
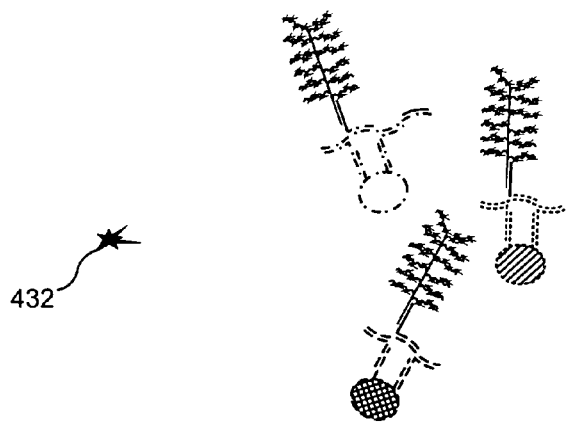
Figure 6A:
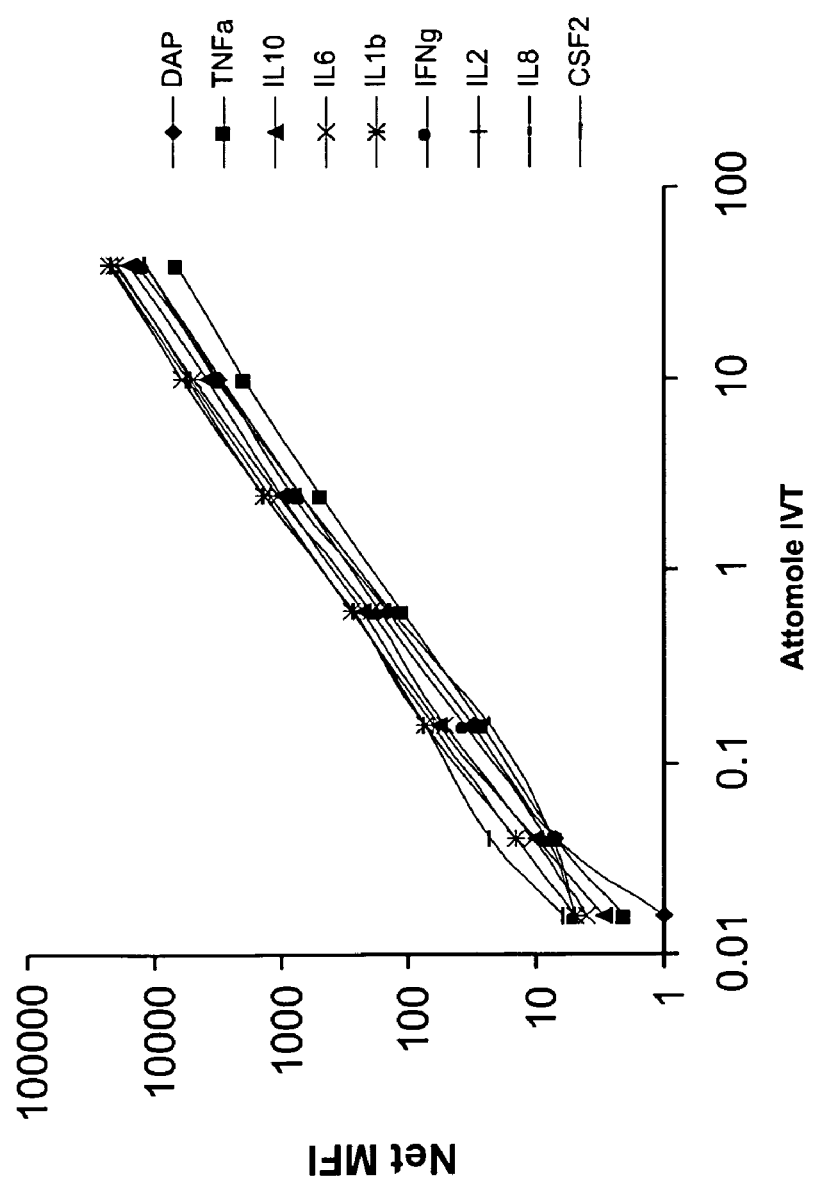
FIG. 6 Panel A depicts a graph illustrating simultaneous detection of multiple genes in the multiplexed assay. A mixture of 9 target IVTs was serially diluted, added to lysate produced from 20 µl whole blood, and assayed using the multiplexed bead assay. MFI: mean fluorescent intensity. Panel B depicts a graph illustrating specificity of multiplex detection. A mixture of 9 target IVTs were assayed simultaneously using the multiplexed bead assay. Signals for $E.\ coli$ DapB transcript detected in the absence (square) or presence (diamond) of lysate produced from 20 µl human whole blood are shown. LOD for this target is 0.04 attomole. Panel C depicts a bar graph illustrating simultaneous detection of multiple cytokine mRNAs in LPS stimulated whole blood. Whole blood was incubated at 37° C. for 125 min with or without LPS. Sixteen microliters were removed and assayed in multiplex for cytokine gene expressions. Control is blood sample at $t_0$. Mean+s.d. (standard deviation) values are shown. Panel D depicts a bar graph illustrating simultaneous detection of multiple mRNAs associated with antigen presenting cell activation, detected as described in Panel C. Panel E depicts graphs illustrating consistent measurement of cytokines in LPS activated whole blood using singleplex (left axis, bar graph) and multiplex (right axis, line graph) assay formats. Panel F depicts a graph illustrating GAPDH expression during LPS stimulation of whole blood. Mean+s.d values are shown. Panel G depicts a graph illustrating IL-1 beta expression during LPS stimulation of whole blood.
Figure 6B:
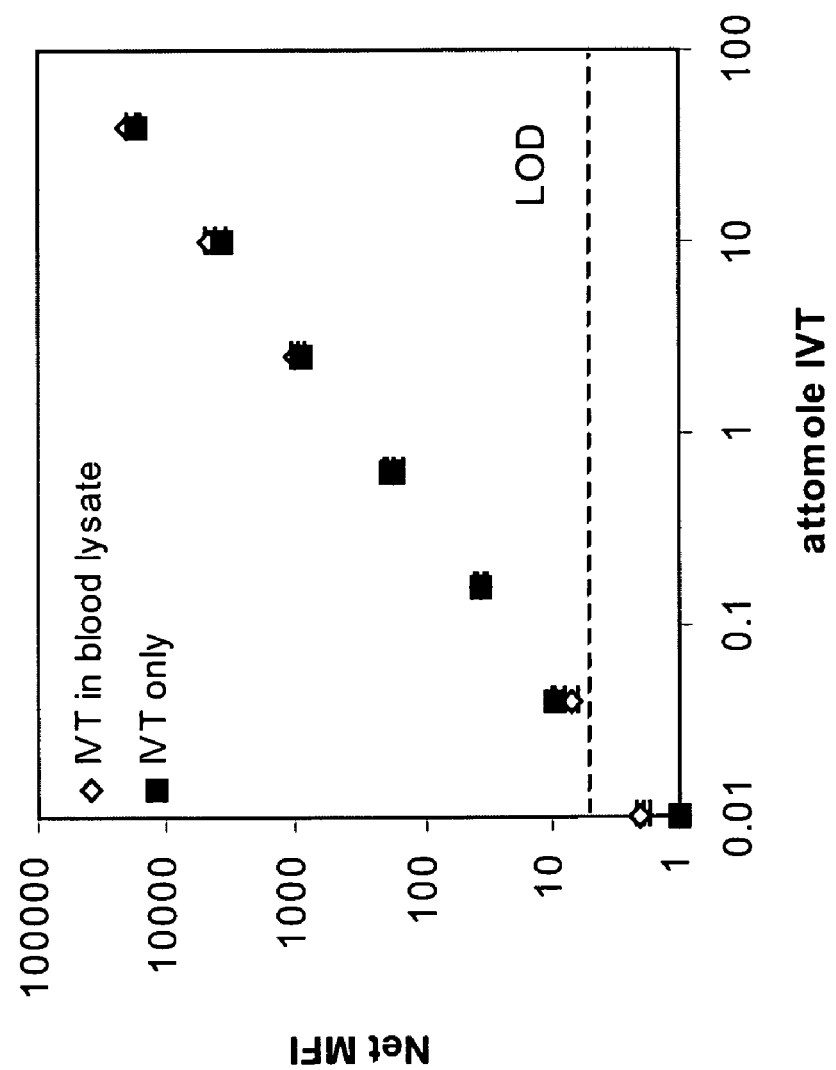
Figure 6C:
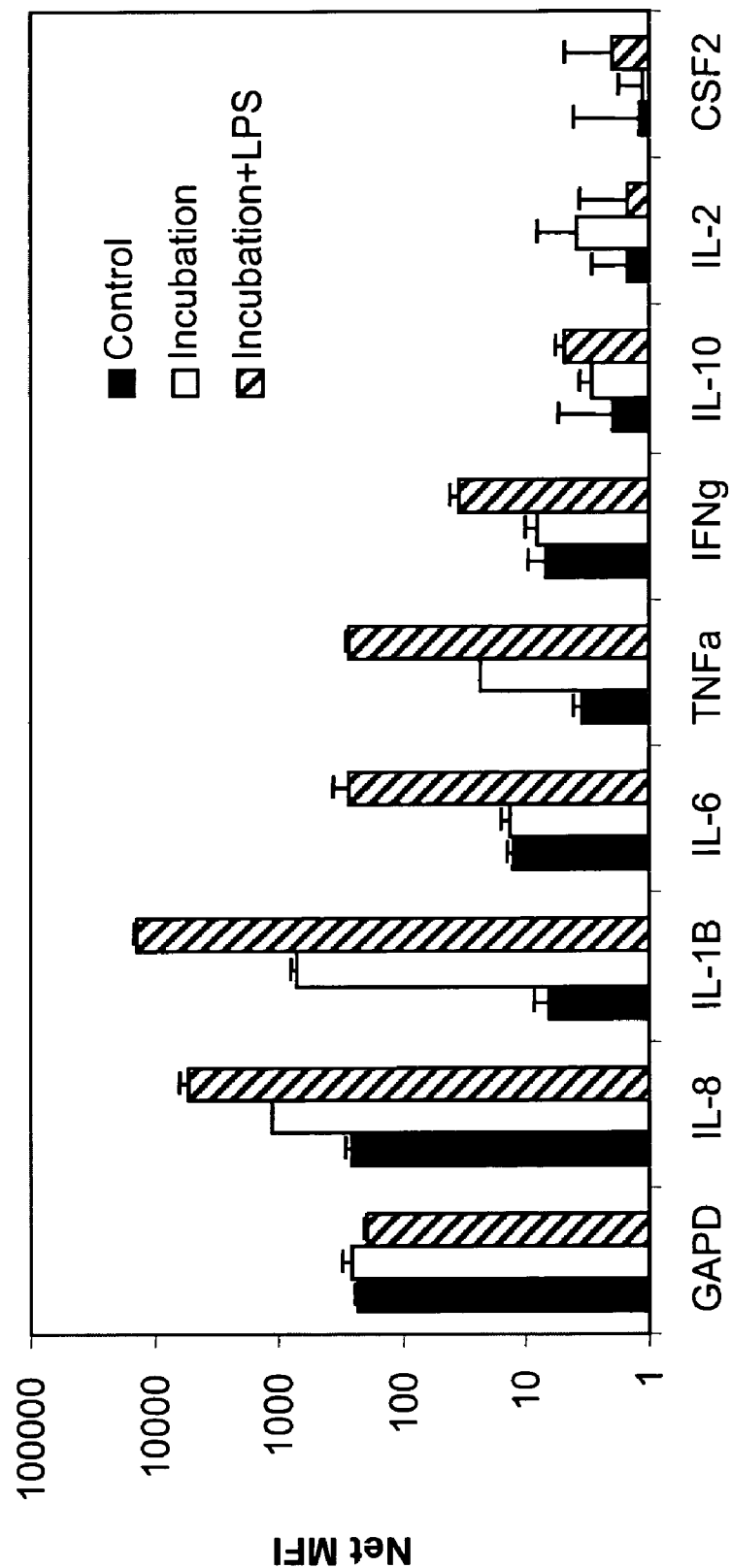
Figure 6D:
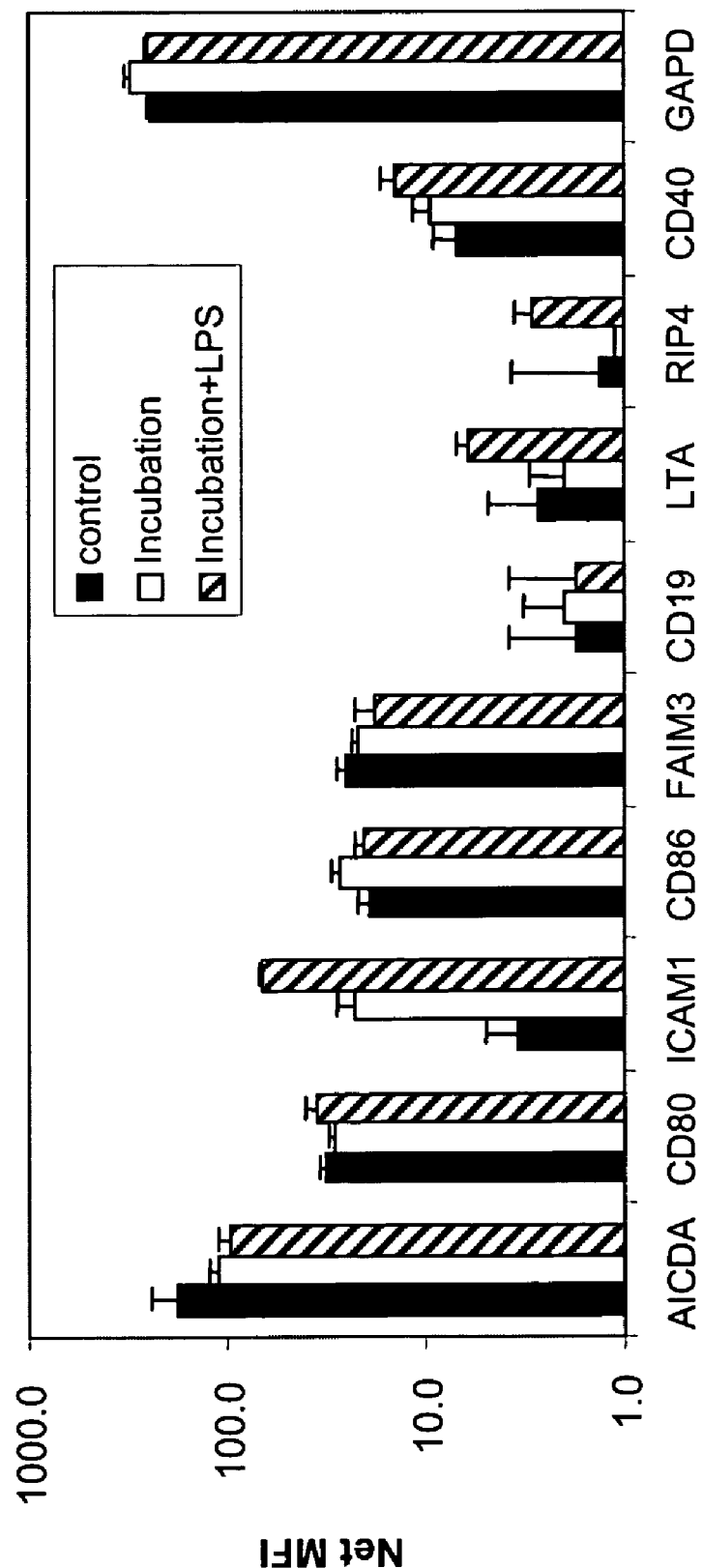
Figure 6E:
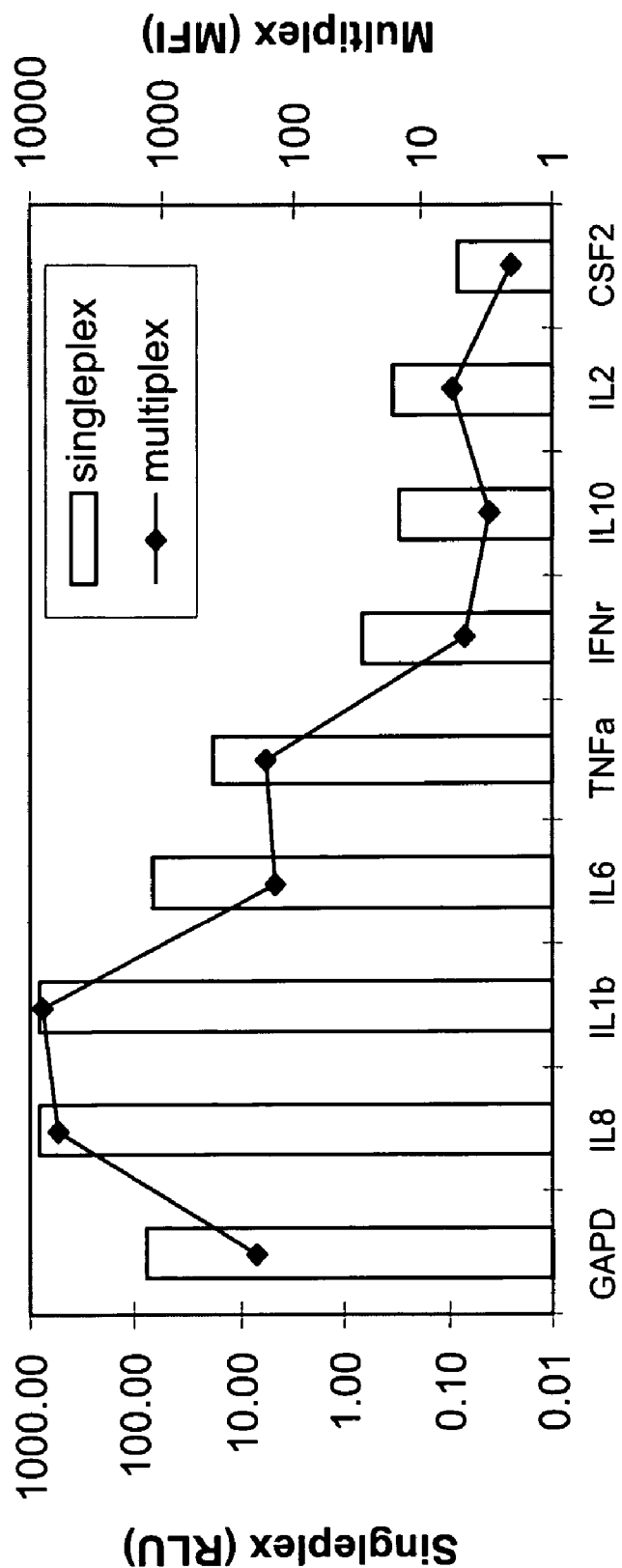
Figure 6G:
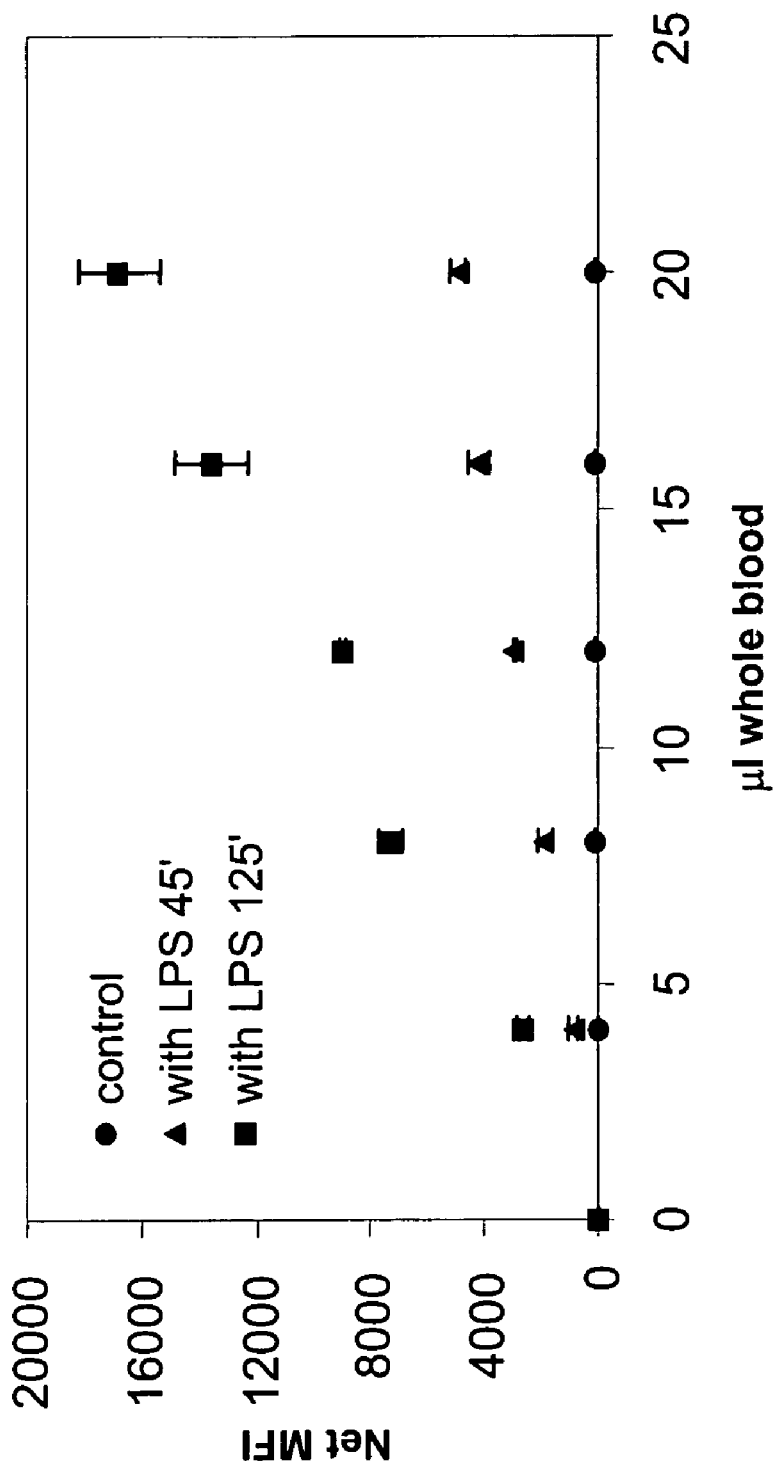
Figure 7A:
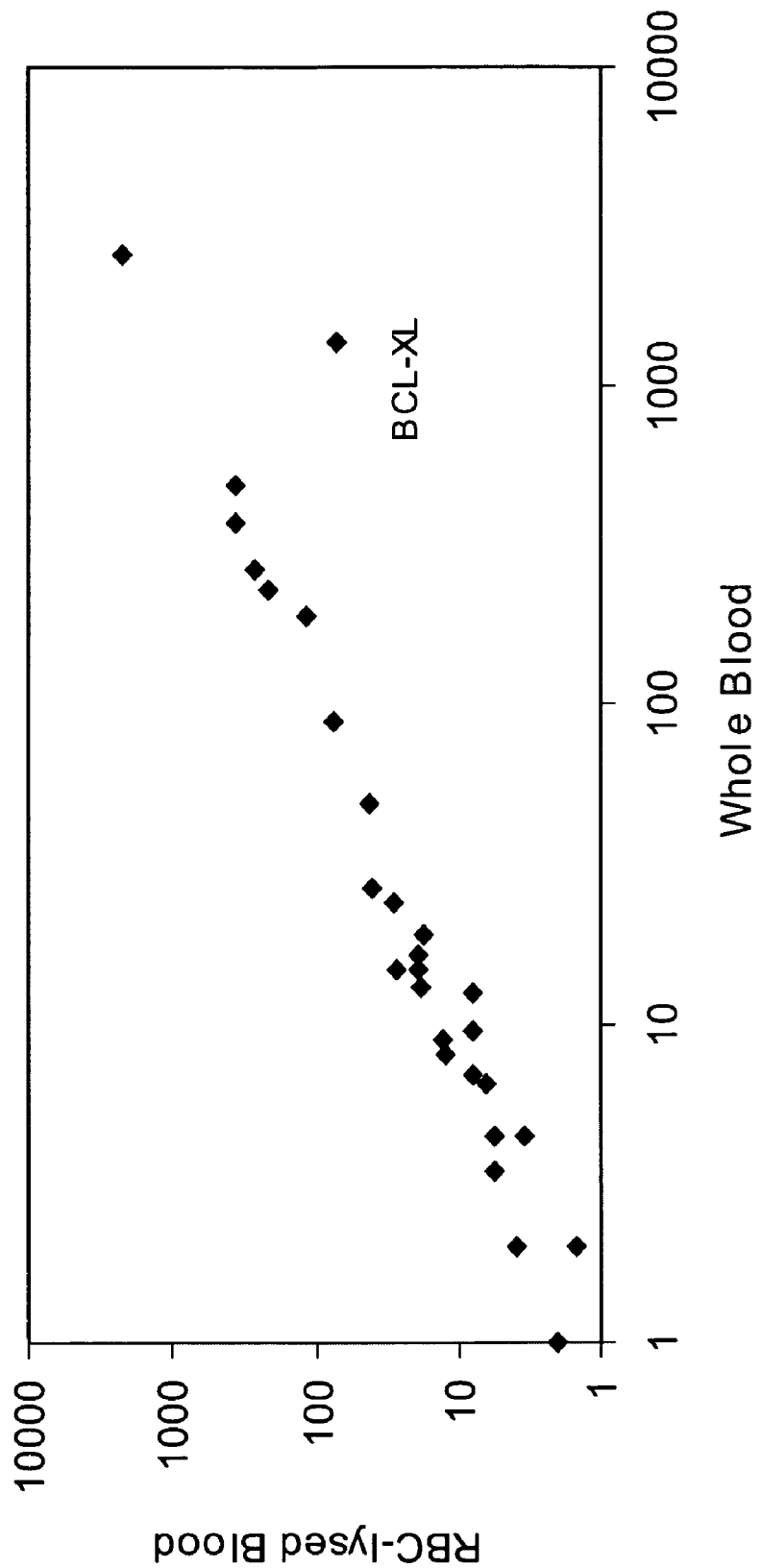
FIG. 7 Panel A depicts a graph illustrating correlation of the gene expression pattern in whole blood and red blood cell (RBC)-lysed blood. Signals are mean fluorescent intensities. Panel B depicts a graph illustrating correlation of the gene expression pattern between whole blood lysate and RNA. Panel C depicts a graph illustrating correlation of gene expression patterns between whole blood lysate and lysate from PAXgene® blood pellet. Panel D depicts a bar graph illustrating that PAXgene® reagent induces gene expression in whole blood. Error bar: s.d. Data is representative of assays of three independent samples.
Figure 7B:
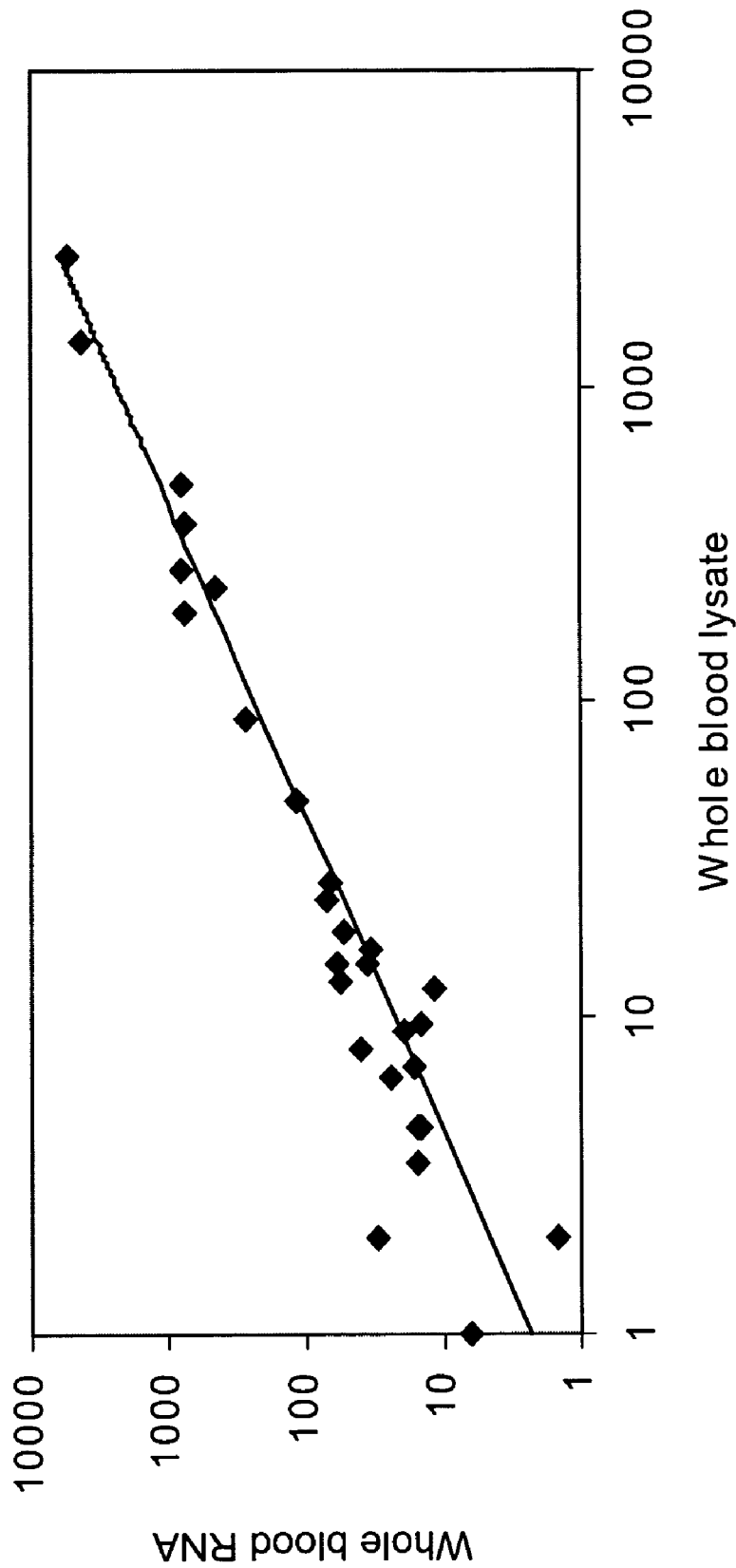
Figure 7C:
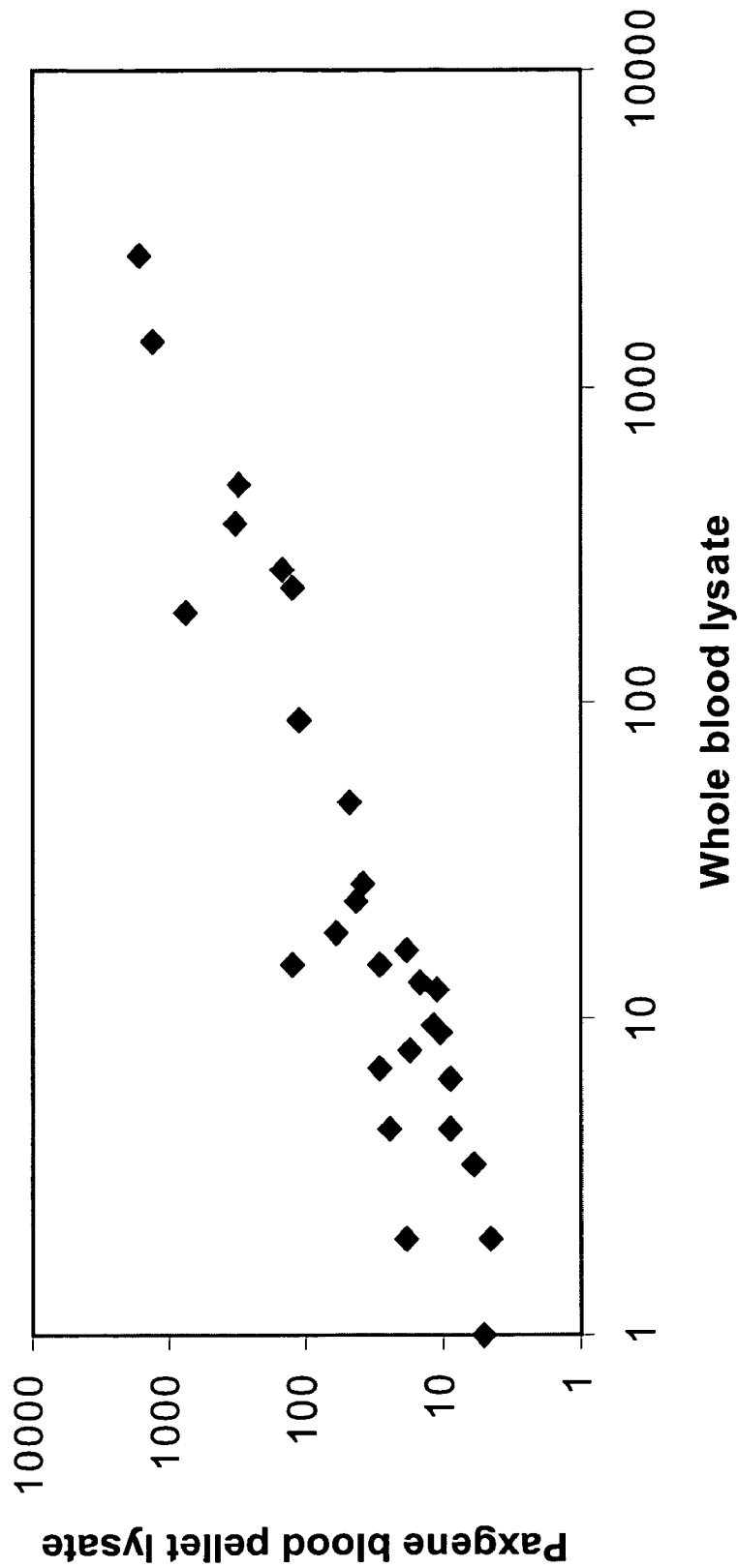
Figure 7D:
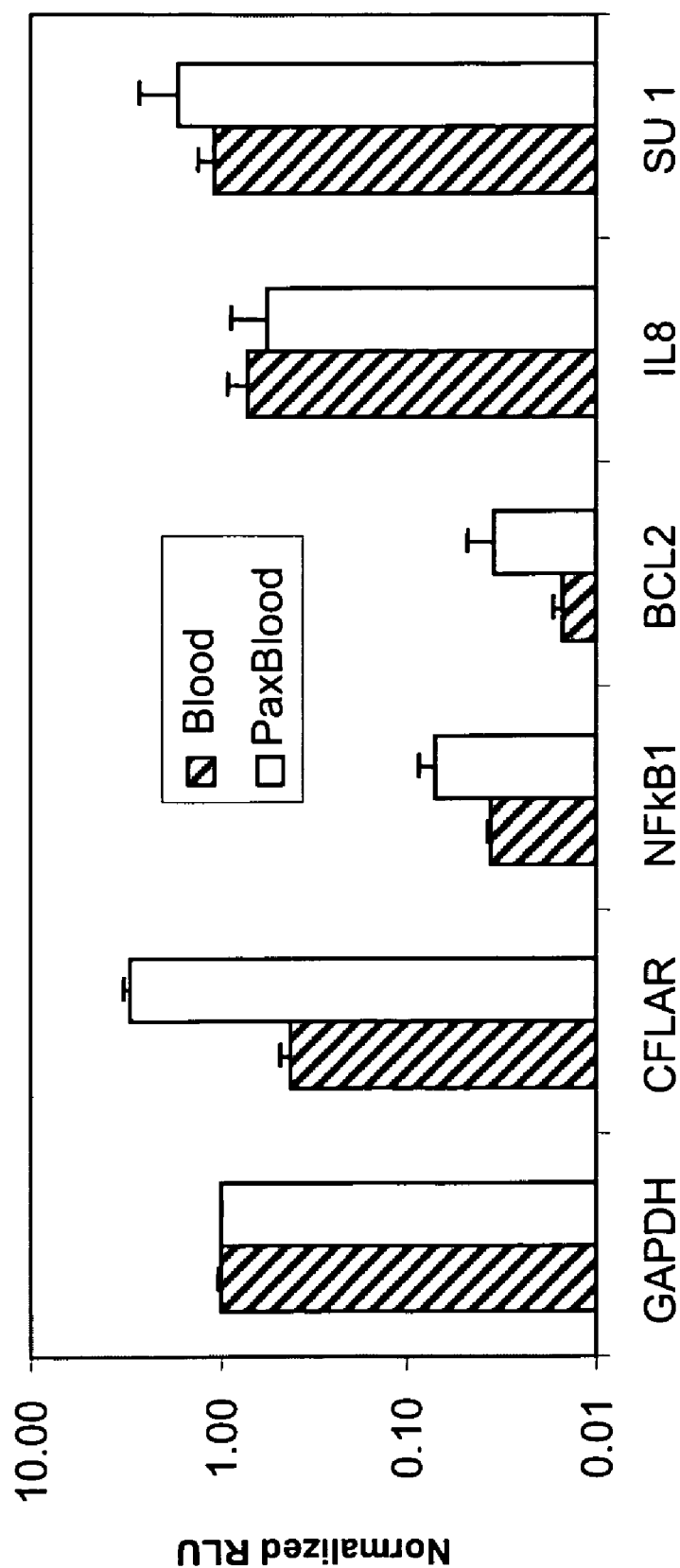

A multiplexed assay for simultaneous detection of multiple messages in whole blood was also developed. The assay exploits Luminex encoded-bead technology and flow cytometry. As schematically depicted in FIG. 5 Panel A, fluorescently distinguishable latex beads (426, 427, and 428) were conjugated with distinctive capture probe sequences (421, 422, and 423), pooled, and added to the assay well. Whole blood or PAXgene®-treated blood was lysed to release target mRNAs (411, 412, and 413), which bind to their respective capture extender (CE; e.g., 401, 402, and 403), label extender (LE; e.g., 406, 407, and 408), and blocking probe (BP; 410)

probes. The CEs for different genes of interest carry distinctive extender sequences, each of which is complementary to the capture probe on the respective set of beads. After hybridization to capture the target on beads, bDNA amplifier molecules (430) were added and hybridized to the universal LE extender on each target, and biotinylated label probe oligos (431) were added to bind to the branches of the amplifier molecule (FIG. 5 Panel B). Strepavidin-conjugated phycoerythrin (SAPE; 432) was added to bind to the biotin on the label probes (FIG. 5 Panel C), and the beads were assayed by flow cytometry (e.g., on the Luminex® 100™ IS flow system). The characteristic intrinsic fluorescence color code of each bead (which is spectrally distinct from the SAPE fluorescence) identifies the target gene being assayed, and the SAPE fluorescence intensity on the bead measures the target concentration. The current capability of the Luminex platform (100 sets of distinctively coded beads) allows for up to 100 genes to be simultaneously assayed with this technology.

Experiments with added in vitro transcripts, in which a mixture of 9 target IVTs was serially diluted, added to lysate produced from 20 µl whole blood, and assayed using the multiplexed bead assay, indicated a good linearity of response (FIG. 6 Panel A) as well as high specificity (FIG. 6 Panel B). As shown in FIG. 6 Panel B, components of the whole blood lysate do not interfere with the specific detection of mRNA target. The multiplexed assay as described in this example has a detection limit of 0.04 amol (25,000 copies) of each target molecule per assay of lysate produced from 20 µl of blood (which can be lowered, e.g., by use of more LEs per target) (FIG. 6 Panel B), with an average coefficient of variation of 8.1%. The reduced sensitivity compared to the singleplex assay (FIG. 4 Panel C) resulted in part from the use of fluorescence detection instead of the more sensitive chemiluminescence detection.

The assay was validated by demonstrating the upregulation of inflammatory cytokine genes in whole blood in response to *E. coli* LPS stimulation. As determined by a 9-plex bead assay, after a 2 hour incubation of fresh whole blood at 37° C. with 10 µg/ml LPS, expression of IL-1beta, IL8, IL6, and TNF-alpha were significantly induced, while expression of IL2, IL10 and GM-CSF (CSF2) remains stable during this period (FIG. 6 Panel C), consistent with previously reported measurements of cytokine proteins (De Groote, D. et al. (1992) "Direct stimulation of cytokines (IL-1 beta, TNF-alpha, IL-6, IL-2, IFN-gamma and GM-CSF) in whole blood. I. Comparison with isolated PBMC stimulation" Cytokine 4:239-48). Signals are linear with increasing blood volume, and were detected even in the lowest volume (4 µl) tested (FIG. 6 Panels F and G). Interestingly, 37° C. ex vivo incubation alone (no LPS) caused significant basal induction of IL1b, IL8 and TNF-alpha, but not IL6, in whole blood (FIG. 6 Panel C), consistent with the sensitivity to environmental conditions whole blood displays. In contrast to the rapid response of inflammatory cytokine producing cells, the acquired immune response in whole blood was scarcely activated by LPS within 2 hours, as indicated by the lack of induction of several genes associated with antigen presenting cell activation (FIG. 6 Panel D); only ICAM1 showed significant induction. Results from the multiplex and singleplex platforms are highly consistent (FIG. 6 Panel E).

Assessment of the Effect of Blood Handling on Gene Expression

The assay having been demonstrated to represent a sensitive and quantitative method to directly assay blood RNA expression relatively free of biases, it was used to assess the impact of common pre-analytical blood handling procedures on gene expression. Similar attempts could previously only assess the combined impact from blood handling, RNA extraction, and post-extraction processing. A panel of about 30 genes including cytokines and apoptosis related genes was used to assess the blood state, since these genes are among the most sensitive to stress during ex vivo incubation (Baechler, E. C. et al. (2004) "Expression levels for many genes in human peripheral blood cells are highly sensitive to ex vivo incubation" Genes Immun 5:347-53). Identical blood samples were processed by red blood cell lysis, by Ficoll-Hipaque centrifugation (PBMC), by phenol/chloroform extraction of whole blood RNA, and by blood stabilization using the PAXgene® reagent. These processed blood samples (or RNA) were then lysed and assayed together with unprocessed whole blood lysates. The correlation coefficients of gene expression patterns between unprocessed and various processed blood samples are presented in Table 2.

TABLE 2

Correlation of the expression pattern of a panel of 26 genes between whole blood and processed blood. Gene expression was determined by the multiplex assay described.
Samples assayed are the following: WB: Fresh whole blood lysate.
RBC-lys: Lysate of blood that underwent selective red cell lysis and was washed. PaxPellet: Solubilized PAXgene ® blood pellet.
WB RNA: Whole blood RNA purified by phenol/chloroform extraction.
RNA from 8x equivalent volume of blood was used.
PaxRNA: RNA purified from PAXgene ® blood using recommended protocol. RNA from 10x equivalent volume of blood was used. PBMC: Lysate of peripheral blood mononuclear cells.
List of genes assayed was the same as for FIG. 7 Panel A.

| R square | WB | RBC-lys* | PaxPellet | WB RNA | PaxRNA | PBMC* |
|---|---|---|---|---|---|---|
| WB | 1 | 0.998 | 0.87 | 0.96 | 0.86 | 0.95 |
| RBC-lys* | | 1 | 0.85 | 0.99 | 0.88 | 0.95 |
| PaxPellet | | | 1 | 0.93 | 0.84 | 0.82 |
| WB RNA | | | | 1 | 0.77 | 0.93 |
| PaxRNA | | | | | 1 | 0.84 |
| PBMC* | | | | | | 1 |

*Excluding BCL-XL

FIG. 7 Panel A depicts a graph illustrating correlation of the gene expression pattern in whole blood and red blood cell (RBC)-lysed blood. Lysates from 20 µl of whole blood and an equivalent volume of RBC-lysed blood were assayed in multiplex for expression of IL2, TNFa, IL10, IL6, IL1B, IFNg, IL8, CSF2, GAPDH, RELB, A20, CDKN1, NFKB1, NFKB2, RELA, NFKBIA, BAK, FASL, FAS, RAFTK, BAD, BCL-2, IL6R, BCL-XL, ACTB and CFLAR as described herein. The lysis of red blood cells resulted in little change in expression of the genes assayed, except for a significant reduction in expression of BCL-XL, a gene expressed in erythrocytes and having an important antiapoptotic role during erythropoiesis (Gregoli, P. A. and Bondurant, M. C. (1997) "The Roles of Bcl-XL and Apopain in the Control of Erythropoiesis by Erythropoietin" Blood 90:630-640). Linear regression (with BCL-XL excluded) showed good correlation in expression pattern; excluding BCL-XL, signals from genes in the panel show a strong correlation between whole blood and red blood cell lysed whole blood ($R^2=0.998$, Table 2 and FIG. 7 Panel A). Ficoll centrifugation for PBMC resulted in changes in blood cell composition and not unexpectedly, the correlation with whole blood expression was lower ($R^2=0.95$, Table 2).

When expression signals from whole blood lysates are compared with phenol/chloroform-purified total RNA, correlation is generally good except for some genes with low expression, where measurement precision is expectedly reduced ($R^2=0.96$, Table 2 and FIG. 7 Panel B). However, the signals from direct lysates are 2-10 times stronger than the signals from purified RNA, depending on RNA extraction efficiency. The reduced signal in purified RNA appeared to be due to RNA loss during the purification procedure, since after normalization against an exogenous transcript spiked into the lysate before RNA extraction, the signals are equivalent. To produce the graph shown in FIG. 7 Panel B, lysates of whole blood (20 µl) and RNA extracted from whole blood were assayed in multiplex for expression of the genes listed for FIG. 7 Panel A. RNA equivalent to 160 µl whole blood was assayed to yield sufficient signals for most genes. Linear regression generates a straight line with slope of 2.34, significantly lower than the expected slope of 8, indicating that RNA extraction resulted in significant RNA loss.

Lysates from 20 µl of whole blood as well as from a pellet formed in an equivalent amount of whole blood stabilized at room temperature overnight in PAXgene® reagent were assayed in multiplex for expression of genes listed for FIG. 7 Panel A. PAXgene® caused significant changes in gene expression compared to direct whole blood measurement (Table 2 and FIG. 7 Panel C; $R^2$=0.8759). Twenty microliters of whole blood and PAXgene® stabilized blood were assayed in singleplex format in the same plate; signals were normalized to GAPDH (FIG. 7 Panel D). The apoptosis genes such as CFLAR are particularly sensitive to PAXgene® reagent treatment (FIG. 7 Panel D), although their signals are comparable among direct lysate, purified RNA, and other processed blood samples. When CFLAR data was removed, the correlation significantly improved ($R^2$=0.95 for PAXgene® pellet and $R^2$=0.94 for PAXgene® purified RNA). As expected, the correlation became poorer as more handling steps were involved with any one sample. The lowest correlation resulted when comparing RNA purified from whole blood and RNA purified from PAXgene® stabilized blood ($R^2$=0.77, Table 2).

Advantages

In contrast to microarray or RT-PCR analysis, which, e.g., rely on single probe-target interactions for target capture or detection, this exemplary assay used on average 20 probes, hybridizing to 500-600 contiguous bases of one target sequence. The multiple probe per target design offers significantly improved sensitivity and reproducibility for the assay. In addition to the benefit that multiple LE reporters are bound to one target, the assay optionally takes advantage of the fact that the interactions between contiguous probes and a target result in stronger, more stable helix formation due to base stacking effects (Dimitrov, R. A. and Zuker, M. (2004) "Prediction of Hybridization and Melting for Double-Stranded Nucleic Acids" Biophys. J. 87:215-226). The multidentate interaction between the solid surface and the many CEs bound to one target also ensures more robust and reproducible target capture. Finally, use of multiple probes minimizes the impact of the design of individual probes on signal, reducing assay variations. As a result the target capture efficiency in the singleplex plate assay approaches 100%, and the average CV (coefficient of variance) of this assay from replicate blood samples is routinely below 10%. In comparison, the CV from replicate blood samples in microarray analysis is 37% (Feezor, R. J. et al. (2004) "Whole blood and leukocyte RNA isolation for gene expression analyses" Physiol. Genomics 19:247-254), and for Taqman RT-PCR the CV for copy numbers is around 16% (Rainen et al., supra).

Another important benefit afforded by the multi-probe per target design is high specificity. Unlike in traditional microarray experiments, the high concentration of globin RNAs does not interfere with the assay. The bDNA assay requires both CEs and LEs to bind to the same RNA molecule in order for the RNA to give a signal, and multiple CEs typically have to bind to the same RNA target in order for the RNA to be captured on the solid surface, since the interaction between a single CE and a surface capture probe is optionally thermodynamically unstable at the assay hybridization temperature.

This assay can be used for quantitation of absolute gene expression by incorporating standard curves with known amounts of in vitro transcripts for each gene of interest. It is superior to quantitative RT-PCR for several reasons, including: 1) curves generated are linear, not logarithmic, 2) the product measured represents the actual amount of a given transcript, 3) hybridization efficiency is the same for samples and standards (FIG. 4 Panel C), whereas in RT-PCR amplification efficiency may not be the same, 4) results can be meaningfully expressed as copies per unit blood, not copies per unit RNA purified or copies relative to a unit housekeeper copy number, and 5) the assay can be conveniently multiplexed.

An important and unique advantage of this assay is its accurate result, free of biases from blood cell and RNA isolation procedures. The processing of clinical specimens such as peripheral blood samples is rarely ideal. The results with a panel of cytokine and apoptosis genes presented herein show that impact to expression pattern increases with increases in the number of processing steps, including RNA purification. Although PAXgene®D may stabilize the expression pattern of some genes, the use of PAxgene® may result in invalid RNA quantitation for other genes, including certain apoptosis related genes such as CFLAR. Induction of selected genes by PAXgene® stabilization was also observed on human bone marrow aspirates (Breit, S. et al. 1 (2004) "Impact of pre-analytical handling on bone marrow mRNA gene expression" Br J Haematol 126:231-43). For biomarker discovery study using PAXgene® stabilized blood samples, especially if CFLAR is identified as one of the biomarkers (Horwitz, P. A. et al. (2004) "Detection of Cardiac Allograft Rejection and Response to Immunosuppressive Therapy With Peripheral Blood Gene Expression" Circulation 110:3815-3821), it is prudent to validate the markers using blood without PAXgene® treatment.

Blood biomarker studies often involve microarray profiling on a limited number of samples, followed by clinical validation of dozens of genes in a larger number of independent samples. The multiplexed bead assay described herein is well suited for the validation workflow, with its medium gene throughput and the high sample throughput capability. With proper probe design, the assay can be adapted to high multiplex formats such as microarrays and used in high throughput applications such as expression profiling of whole blood, without the need to purify, label, and amplify the RNA targets. The methods of the invention thus remove the most significant roadblock to the broader application of expression profiling in clinical applications.

The assays of the invention can significantly simplify clinical expression analysis. Blood drawn from, e.g., an ear bleed may be sufficient for some expression analyses. Similarly, RNA analysis can now be performed for infants or patients where only limited amounts of blood are available. The absence of the RNA purification requirement is especially useful for large-scale studies where sample analysis throughput has been limited by laborious RNA purification. The exceptional accuracy, consistency of the results, and the time saved in sample preparation and data analysis are significant advantages of these assays when compared with other assays for blood gene expression.

As described above, the methods of the invention can be used, for example, to detect target nucleic acid(s) from peripheral blood cells lysed in liquid whole blood. As another example, the methods can also be used to detect target nucleic acid(s) from a blood sample that is applied to a matrix (e.g., filter paper) and dried. The dried blood spot is contacted with blood lysis buffer (such as that described below) to lyse the peripheral blood cells (if necessary) and to elute the nucleic acid(s) from the filter paper or other matrix. The nucleic acid(s) in the resulting lysate are then hybridized to CE, LE, and BP sets and detected in singleplex or multiplex assays as described. The methods are similarly applicable to detection of target nucleic acids from plasma (e.g., liquid plasma or plasma dried on a matrix).

Experimental Protocol

Singleplex Assay for Whole Blood

Fresh, anticoagulated blood (with EDTA, heparin, or citrate as the anticoagulant) from healthy donors (Stanford Blood Center, Stanford, Calif.) was refrigerated and assayed within 1 hour (hr) after blood was drawn. One to thirty microliters (μl) of whole blood was added to the lysis solution to a final volume of 150 μl containing 50% Blood Lysis Buffer, at least 1 mg per ml proteinase K (e.g., 2 mg/ml), and $H_2O$. The Lysis Mixture reagent commercially available, e.g., in Panomics's QuantiGene® Explore Kit or as catalog number QG0502 or QP0522, was used as the Blood Lysis Buffer in these experiments; as noted previously, a large number of suitable buffers can be prepared by one of skill in the art (for example, the capture diluent described in Collins M L et al. (1997) Nucleic Acid Research 25:2979-2984 (127 mM LiCl, 5% lithium lauroyl sulfate, 9 mM EDTA, 50 mM HEPES (pH 7.5), 0.05% hespan (DuPont Pharmaceuticals), 0.05% ProClin 300 (Supelco), 0.2% casein (Research Organics, Hammarsten quality)). The mixture was shaken at 1000 rpm at 60° C. for 1 hour in a heated shaker (Vortemp) to lyse the cells. The lysate was then transferred to an assay well in a 96-well plate covalently coated with capture probe oligo (5'-CACTTCACTTTCTTCCAAGAG-3', SEQ ID NO:1). The probe set for a target gene, containing 50, 100, and 200 fmol of CE, BP, and LE, respectively, was added to the blood lysate and incubated for 16 hr at 53° C. (This incubation is optionally performed, e.g., at 58° C. instead.) The well was washed three times with 200 μl Wash Buffer (0.1×SSC, 0.3% lithium lauryl sulfate), followed by sequential hybridization at 53° C. for 1 hour with 100 μl of a 1:1000 dilution of branched-DNA amplifier (Panomics) and 46° C. for 1 hour with 100 μl of 50 fmol of 3'-alkaline phosphatase-conjugated label probe oligo (5'-AAGTACGACAACCACATC-3', SEQ ID NO:2), with three washes after each incubation. After a final wash, the alkaline phosphatase substrate dioxetane (Panomics) was added to wells and incubated at 46° C. for 30 minutes (min) to develop the luminescent signal, which was detected using a Lmax microtiter plate luminometer (Molecular Device).

Singleplex Assay for PAXgene® Stabilized Blood

PAXgene® stabilized blood was prepared according to the manufacturer's protocol (PreAnalytiX, Hombrechtikon, Switzerland). 9.5 ml stabilized blood is equivalent of 2.5 ml of whole blood. After 16 hr storage at room temperature, the stabilized blood was centrifuged for 5 min at 3000 g. The supernatant was removed by decanting or pipetting. The pellet was sequentially washed with $H_2O$ (1000 μl per ml of stabilized blood) and 2 M LiCl (400 μl per ml of stabilized blood), before being solubilized at 60° C. with shaking for 30 minutes in Pax Lysis Buffer (265 μl per ml of stabilized blood) with 0.25 mg per ml proteinase K. In these experiments, the Homogenizing Solution commercially available from Panomics, catalog number QG0515, was used as the Pax Lysis Buffer; it will be evident that a large number of suitable buffers can be prepared by one of skill in the art (e.g., buffers including a chaotropic agent such as guanidine HCl and/or a detergent such as SDS). One to thirty μl of lysate, corresponding to the same volume of the original whole blood, was mixed with 75 μl of Blood Lysis Buffer and $H_2O$ to a final volume of 150 μl. The mixture was transferred to an assay well in a 96-well plate coated with capture probe. The probe set for a target gene, containing 50, 100, and 200 fmol of CE, BP, and LE, respectively, was added to the lysate and incubated for 16 hr at 53° C. (This incubation is optionally performed, e.g., at 58° C. instead.) Subsequent steps were the same as the post 16 hr hybridization steps described in "Singleplex assay for whole blood" above.

Multiplex Assay

A panel of 10 oligonucleotide capture probes, each with a unique sequence of 15 bases, were synthesized with a 5'-amino linker (BioSearch, San Carlos, Calif.) and each was covalently linked to carboxylated fluorescent-encoded beads (Luminex, Austin, Tex.) following the recommended conjugation procedure (one capture probe per identifiable set of the beads). Beads conjugated with different capture probes were pooled in equal proportions before use. One hundred microliters of whole blood lysate or PAXgene® blood lysate prepared above were mixed with the multiplex panel probe sets and the pooled capture beads (2000 beads each type) in a round bottom well and hybridized for 16 hours at 53° C. in a final volume of 110 μl. (The incubation is optionally performed, e.g., at 58° C. instead.) The assay mix was transferred to a MultiScreen filter plate (Milipore), and unbound material was filter-washed from the wells three times with Wash Buffer. The plate was then hybridized at 53° C. for 1 hour with 100 μl of a 3:1000 dilution of bDNA amplifier in amplifier diluent (3M tetramethyl ammonium chloride, 0.1% Sarkosyl, 50 mM Tris-HCl, 4 mM EDTA, 4% dextran sulfate, 1% BSA and 0.5% v/v Micr-O-protect (Roche Molecular Systems, Pleasanton, Calif.)). After filter-washing twice with Wash Buffer, the plate was incubated at 46° C. for 1 hour with 100 μl of 150 fmol 5'-dT(Biotin)-conjugated label probe (Biosearch) diluted in amplifier diluent without the dextran sulfate. After two washes, streptavidin conjugated R-phycoerythrin (SA-PE, Prozyme, San Leandro, Calif.) at 6 μg/ml diluted in SAPE diluent (20 mM Tris-HCl, 400 mM Lithium Chloride, 0.1% v/v TWEEN 20, 0.1% v/v BSA, 0.5% v/v Micr-O-protect) was added and the plate was incubated at room temperature for 30 min. The beads were washed to remove unbound SA-PE, followed by analysis with Luminex® 100™ IS system (Luminex) or Bio-Plex system (Bio-Rad). The level of SA-PE fluorescence measured from each set of beads is proportional to the number of mRNA transcripts captured by that set of beads.

LPS Stimulation of Whole Blood

Fresh whole blood (Stanford Blood Center) with or without added 10 μg/ml *E. coli* LPS (Sigma) was incubated at 37° C. with shaking in a cell culture incubator for 30-135 minutes, before being lysed in the vessel and assayed in multiplex as described above.

Probe Design for Singleplex and Multiplex bDNA Assays

Modified probe design software (Bushnell, S. et al. (1999) "ProbeDesigner: for the design of probesets for branched DNA (bDNA) signal amplification assays" Bioinformatics 15:348-355) was developed to design probe sets for target genes in both singleplex and multiplex bDNA assays. For each target sequence, the software algorithm identifies regions that can serve as annealing templates for CEs (5-7 per gene), LEs (10-15 per gene), or BPs. Potential CEs and LEs were examined for possible interactions with other components of the multiplex assay, and CEs and LEs expected to cross-hybridize were not selected for use; CE-LE, CE-bDNA, CE-label probe, and LE-capture probe interactions having highly negative ΔG were removed to minimize non-specific hybridization. Probe sets are essentially the same for both singleplex and multiplex bDNA assays except for the portion of the CE probes that hybridize with capture probe. Three 10-plex panels were developed for assessment of the effect of common blood handling procedures. Gene names and reference sequence accession numbers are shown along with probe sets in Tables 3-5. All deoxyoligonucleotides were synthesized and HPLC purified (Biosearch, Calif.).

Data Analysis & Statistics

Three replicate assays (n=3) were performed for all described experimental samples unless noted otherwise. For all samples, background signal levels in the absence of target mRNAs were determined and subtracted from signals obtained in the presence of target mRNAs to get the net signal. Statistical significance of biological studies was tested using Student's t-test or ANOVA where appropriate (P<0.01).

Additional discussion of the singleplex and multiplex assays can be found in Zheng et al. (2006) "Sensitive and Quantitative Measurement of Gene Expression Directly from a Small Amount of Whole Blood" Clinical Chemistry 52:1294-1302, which is hereby incorporated by reference in its entirety.

TABLE 3

Cytokine probe set. Accession number and symbol are listed for each target, along with probe type and the sequence of the probe.

| Type | Sequence | SEQ ID NO: |
|---|---|---|
| NM_002046 GAPDH | | |
| BP | CGGAGGGGCCATCCAC | 3 |
| LE | cccacttgattttggagggaTTTTTaggcataggacccgtgtct | 4 |
| CE | agcttcccgttctcagcctTTTTTctcttggaaagaaagt | 5 |
| LE | ccttccacgataccaaagttgtTTTTTaggcataggacccgtgtct | 6 |
| CE | cctttggctcccccctTTTTTctcttggaaagaaagt | 7 |
| LE | ccagtggactccacgacgtacTTTTTaggcataggacccgtgtct | 8 |
| CE | tgacggtgccatggaatttTTTTTctcttggaaagaaagt | 9 |
| LE | ggcatggactgtggtcatgagtTTTTTaggcataggacccgtgtct | 10 |
| LE | gggtgctaagcagttggtggtTTTTTaggcataggacccgtgtct | 11 |
| LE | agtcttctgggtggcagtgatTTTTTaggcataggacccgtgtct | 12 |
| BP | AACATGGGGCATCAGCA | 13 |
| BP | CATGGTTCACACCCATGACG | 14 |
| BP | gcaggaggcattgctgatga | 15 |
| LE | cacagccttggcagcgcTTTTTaggcataggacccgtgtct | 16 |
| LE | ccagtgagcttcccgttcaTTTTTaggcataggacccgtgtct | 17 |
| BP | GAGGGGGCAGAGATGATGAC | 18 |
| LE | tcttgaggctgttgtcatacttctTTTTTaggcataggacccgtgtct | 19 |
| CE | catggatgaccttggccagTTTTTctcttggaaagaaagt | 20 |
| BP | TGGAGAGCCCCGCGG | 21 |
| CE | gctcagggatgaccttgccTTTTTctcttggaaagaaagt | 22 |
| LE | ttctccatggtggtgaagacgTTTTTaggcataggacccgtgtct | 23 |
| LE | ccatcacgccacagtttccTTTTTaggcataggacccgtgtct | 24 |
| LE | gatgggatttccattgatgacaTTTTTaggcataggacccgtgtct | 25 |
| CE | gcaaatgagccccagccTTTTTctcttggaaagaaagt | 26 |
| CE | tctcgctcctggaagatggtTTTTTctcttggaaagaaagt | 27 |
| LE | cagtagaggcagggatgatgttcTTTTTaggcataggacccgtgtct | 28 |
| BP | TCAGCGCCAGCATCGC | 29 |
| NM_000584 IL8 | | |
| LE | aattcttgcacaaatatttgatgcTTTTTaggcataggacccgtgtct | 30 |
| LE | gaaattcaaatttaaccaggaatctTTTTTaggcataggacccgtgtct | 31 |
| LE | tgtattgcatctggcaaccctaTTTTTaggcataggacccgtgtct | 32 |
| BP | AGTGTTGAAGTAGATTTGCTTGAAGT | 33 |
| BP | AAGTTACACTTGAAAATAATTTATGTTATG | 34 |
| LE | ggtaagatggtggctaatacttttTTTTTaggcataggacccgtgtct | 35 |
| BP | AAAAAATCCAGGATTTCCAGCt | 36 |
| BP | CTAGGGTTGCCAGATTTAACAGA | 37 |
| BP | CATGTCCTCACAACATCACTGTGA | 38 |
| BP | CCACTTAGAAATAAAGGAGAAACCA | 39 |
| CE | tgcacccagttttccttggTTTTTctcttggaaagaaagt | 40 |
| BP | GTACAATGAAAAACTATTCATTGTTTACT | 41 |
| LE | ggtccagacagagctctcttccTTTTTaggcataggacccgtgtct | 42 |
| BP | TTTTTTGTAGATTCAAATAAATAATACTTTA | 43 |
| BP | GCTTCAAATATCACATTCTAGCAAAC | 44 |
| BP | CAAAAACTTCTCCACAACCCTC | 45 |
| LE | catataagtatgttctggatatttcatgTTTTTaggcataggacccgtgtct | 46 |
| LE | ccattcaattcctgaaattaaagttTTTTTaggcataggacccgtgtct | 47 |
| LE | ttggataccacagagaatgaatttTTTTTaggcataggacccgtgtct | 48 |
| LE | ttctcccgtgcaatatctaggaTTTTTaggcataggacccgtgtct | 49 |
| BP | ATAAAACATCATTTAATATCTAAAATAAAAT | 50 |
| BP | CAACAGACCCACACAATACATGA | 51 |
| LE | ttcactggcatcttcactgattcTTTTTaggcataggacccgtgtct | 52 |
| LE | caatgattcatcttctatttttccaTTTTTaggcataggacccgtgtct | 53 |
| LE | aaatttactataacatctttataactattcaatTTTTTaggcataggacccgtgtct | 54 |

TABLE 3-continued

Cytokine probe set. Accession number and symbol are listed for each target, along with probe type and the sequence of the probe.

| Type | Sequence | SEQ ID NO: |
|---|---|---|
| LE | aggcacagtggaacaaggactTTTTTaggcataggacccgtgtct | 55 |
| CE | cggatattctcttggcccttTTTTTctcttggaaagaaagt | 56 |
| CE | ttttatgaattctcagccctcttTTTTTctcttggaaagaaagt | 57 |
| BP | TAAAAACCCTGATTGAAATTTATCTA | 58 |
| LE | ggcctcaattttgctatttgtataTTTTTaggcataggacccgtgtct | 59 |
| BP | TTAATAATACATAAATAATAAATAGGTTAAT | 60 |
| BP | ATGAAAAAACTTAAAGTGCTTCCA | 61 |
| CE | tgtggatcctggctagcagaTTTTTctcttggaaagaaagt | 62 |
| LE | attgtcccatcattttttatgtgatTTTTTaggcataggacccgtgtct | 63 |
| BP | AAATCCTTATATTTAAAAATTATTTGTTG | 64 |
| CE | acccaattgtttgtttgtttaatcTTTTTctcttggaaagaaagt | 65 |
| LE | aaatttgactttatggcaaaatttTTTTTaggcataggacccgtgtct | 66 |

NM_000600 IL6

| Type | Sequence | SEQ ID NO: |
|---|---|---|
| BP | CTGCAGGAACTCCTTAAAGCTG | 67 |
| LE | aactggaccgaaggcgctTTTTTaggcataggacccgtgtct | 68 |
| LE | aagttctgtgcccagtggacaTTTTTaggcataggacccgtgtct | 69 |
| LE | tgtgcctgcagcttcgtcaTTTTTaggcataggacccgtgtct | 70 |
| LE | ctgcaggaactggatcaggacTTTTTaggcataggacccgtgtct | 71 |
| BP | CCTCAAACTCCAAAAGACCAGTG | 72 |
| LE | gcatctagattctttgccttttTTTTTaggcataggacccgtgtct | 73 |
| CE | gagcttctctttcgttcccgTTTTTctcttggaaagaaagt | 74 |
| CE | agccccaggagaaggcTTTTTctcttggaaagaaagt | 75 |
| LE | gaatttgtttgtcaattcgttctgTTTTTaggcataggacccgtgtct | 76 |
| LE | gatgccgtcgaggatgtaccTTTTTaggcataggacccgtgtct | 77 |
| BP | TTTGGAAGGTTCAGGTTGTTTT | 78 |
| CE | tgtggagaaggagttcatagctgTTTTTctcttggaaagaaagt | 79 |
| LE | ggcttgttcctcactactctcaaTTTTTaggcataggacccgtgtct | 80 |
| LE | atctgttctggaggtactctaggtataTTTTTaggcataggacccgtgtct | 81 |
| LE | ttttgtactcatctgcacagctctTTTTTaggcataggacccgtgtct | 82 |
| LE | gcaggcaacaccaggagcTTTTTaggcataggacccgtgtct | 83 |
| LE | ggtttctgaccagaagaaggaatgTTTTTaggcataggacccgtgtct | 84 |
| LE | tgcccatgctacatttgccTTTTTaggcataggacccgtgtct | 85 |
| LE | aagaggtgagtggctgtctgtgTTTTTaggcataggacccgtgtct | 86 |
| BP | TGGGGCGGCTACATCTTT | 87 |
| LE | gcatccatcttttcagccatcTTTTTaggcataggacccgtgtct | 88 |
| LE | atgattttcaccaggcaagtctTTTTTaggcataggacccgtgtct | 89 |
| CE | tgtctcctttctcagggctgaTTTTTctcttggaaagaaagt | 90 |
| BP | TGGCGCAGGGAAGGCA | 91 |
| LE | gcaggctggcatttgtggTTTTTaggcataggacccgtgtct | 92 |
| LE | ctgccagtgcctctttgctTTTTTaggcataggacccgtgtct | 93 |
| LE | tgtcctgcagccactggttcTTTTTaggcataggacccgtgtct | 94 |
| CE | gaagagccccaggctggaTTTTTctcttggaaagaaagt | 95 |
| BP | CCCATTAACAACAACAATCTGAGG | 96 |
| BP | TTGGGTCAGGGGTGGTTATT | 97 |
| BP | GGAATCTTCTCCTGGGGGTAC | 98 |
| LE | cgcagaatgagatgagttgtcaTTTTTaggcataggacccgtgtct | 99 |
| LE | ggctcctggaggcgagataTTTTTaggcataggacccgtgtct | 100 |
| CE | cctcattgaatccagattggaaTTTTTctcttggaaagaaagt | 101 |
| BP | GCTTTCACACATGTTACTCTTGTTACA | 102 |

NM_000619 IFNG

| Type | Sequence | SEQ ID NO: |
|---|---|---|
| BP | AAATGCCTAAGAAAAGAGTTCCA | 103 |
| BP | TGCATTAAAATATTTCTTAAGGTTTTCT | 104 |
| BP | AAAAAGTTTGAAGTAAAAGGAGACAAT | 105 |
| LE | gcttcttttacatatgggtcctggTTTTTaggcataggacccgtgtct | 106 |
| LE | gcaggcaggacaaccattactgTTTTTaggcataggacccgtgtct | 107 |
| BP | AATAAATAGATTTAGATTTAAAATTCAAATATT | 108 |
| LE | aaaaacttgacattcatgtcttccTTTTTaggcataggacccgtgtct | 109 |
| BP | GGATGCTCTTCGACCTTGAAAC | 110 |
| CE | tctcgtttcttttttgttgctattgTTTTTctcttggaaagaaagt | 111 |
| LE | aatacttatttgattgatgagtctaaaaatTTTTTaggcataggacccgtgtct | 112 |
| CE | atattcccatataaataatgttaaatattTTTTTctcttggaaagaaagt | 113 |
| CE | ttggctctgcattatttttctgtTTTTTctcttggaaagaaagt | 114 |
| LE | tggacattcaagtcagttaccgaTTTTTaggcataggacccgtgtct | 115 |
| LE | agcatctgactccttttttcgcTTTTTaggcataggacccgtgtct | 116 |
| BP | GATGCTCTGGTCATCTTTAAAGTTTTT | 117 |
| LE | ataattagtcagcttttcgaagtcaTTTTTaggcataggacccgtgtct | 118 |
| LE | cgacagttcagccatcacttggTTTTTaggcataggacccgtgtct | 119 |
| LE | ttatccgctacatctgaatgaccTTTTTaggcataggacccgtgtct | 120 |

TABLE 3-continued

Cytokine probe set. Accession number and symbol are
listed for each target, along with probe type and
the sequence of the probe.

| Type | Sequence | SEQ ID NO: |
|---|---|---|
| CE | atgagttcatgtattgctttgcgtTTTTTctcttggaaagaaagt | 121 |
| LE | ttgatggtctccacactctttttgTTTTTaggcataggacccgtgtct | 122 |
| CE | ttccctgttttagctgctggTTTTTctcttggaaagaaagt | 123 |
| CE | cactctcctctttccaattcttcaTTTTTTTctcttggaaagaaagt | 124 |

NM_000758 CSF2

| LE | gcagtgtctctactcaggttcaggTTTTTaggcataggacccgtgtct | 125 |
|---|---|---|
| BP | CCGCAGGCCCTGCTTG | 126 |
| BP | GGGCTGGGCGAGCGG | 127 |
| LE | gggttgcacaggaagtttccTTTTTaggcataggacccgtgtct | 128 |
| LE | caggccacagtgcccaagTTTTTaggcataggacccgtgtct | 129 |
| BP | GGGGTTGGAGGGCAGTGC | 130 |
| BP | TCATGGTCAAGGGGCCCT | 131 |
| LE | agcagaaagtccttcaggttctcTTTTTaggcataggacccgtgtct | 132 |
| CE | tgagcttggtgaggctgccTTTTTctcttggaaagaaagt | 133 |
| CE | agcagcaggctctgcagcTTTTTctcttggaaagaaagt | 134 |
| LE | tgtaggcaggtcggctcctTTTTTaggcataggacccgtgtct | 135 |
| LE | tttgaaactttcaaaggtgataatctTTTTTaggcataggacccgtgtct | 136 |
| LE | tggatggcattcacatgctcTTTTTaggcataggacccgtgtct | 137 |
| BP | CCAGGGCTGCGTGCTG | 138 |
| CE | tacagctccaggcgggtcTTTTTctcttggaaagaaagt | 139 |
| LE | ctcactcctggactggctccTTTTTaggcataggacccgtgtct | 140 |
| BP | CAGCAGTCAAAGGGGATGACA | 141 |
| LE | ttctactgtttcattcatctcagcaTTTTTaggcataggacccgtgtct | 142 |
| LE | ggaggtcaaacatttctgagatgacTTTTTaggcataggacccgtgtct | 143 |
| BP | AGACGCCGGGCCTCC | 144 |
| CE | gcgggtgcagagatgctgTTTTTctcttggaaagaaagt | 145 |
| CE | tgcttgtagtggctggccaTTTTTctcttggaaagaaagt | 146 |

NM_000572 IL10

| LE | gtcttcactctgctgaaggcatTTTTTaggcataggacccgtgtct | 147 |
|---|---|---|
| CE | ctgggtcttggttctcagcttTTTTTctcttggaaagaaagt | 148 |
| BP | GGTAAAACTGGATCATCTCAGACAA | 149 |
| LE | tgatgaagatgtcaaactcactcatTTTTTaggcataggacccgtgtct | 150 |
| BP | gactgggtgccctggcc | 151 |
| LE | tgtcctagagtctatagagtcgccaTTTTTaggcataggacccgtgtct | 152 |
| BP | GGCTTTGTAGATGCCTTTCTCT | 153 |
| LE | TaggcaggttgcctgggaTTTTTaggcataggacccgtgtct | 154 |
| LE | cattgtcatgtaggcttctatgtagtTTTTTaggcataggacccgtgtct | 155 |
| CE | ctcggagatctcgaagcatgtTTTTTctcttggaaagaaagt | 156 |
| BP | GGGGCATCACCTCCTCCA | 157 |
| CE | ccgattttggagacctctaatttaTTTTTctcttggaaagaaagt | 158 |
| CE | gctgatccttcatttgaaagaaaTTTTTctcttggaaagaaagt | 159 |
| LE | tggagcttattaaaggcattcttTTTTTaggcataggacccgtgtct | 160 |
| CE | agtgggtgcagctgttctcaTTTTTctcttggaaagaaagt | 161 |
| LE | gctatcccagagccccagatTTTTTaggcataggacccgtgtct | 162 |
| LE | ccctgatgtctcagtttcgtatcttTTTTTaggcataggacccgtgtct | 163 |
| LE | actccttttaacaacaagttgtccaTTTTTaggcataggacccgtgtct | 164 |
| LE | cacctgctccacggccttTTTTTaggcataggacccgtgtct | 165 |
| BP | GTTCACATGCGCCTTGATGT | 166 |
| LE | aatcgatgacagcgccgtaTTTTTaggcataggacccgtgtct | 167 |
| BP | GCTCTTGTTTTCACAGGGAAGA | 168 |
| LE | ggcttggcaacccaggtaacTTTTTaggcataggacccgtgtct | 169 |
| LE | caggttctcccccagggaTTTTTaggcataggacccgtgtct | 170 |
| CE | gcctcagcctgagggtcttTTTTTctcttggaaagaaagt | 171 |
| LE | ccttaaagtcctccagcaaggTTTTTaggcataggacccgtgtct | 172 |

NM_000594 TNF

| LE | gcggctgatggtgtgggTTTTTaggcataggacccgtgtct | 173 |
|---|---|---|
| LE | aggtacaggccctctgatggTTTTTaggcataggacccgtgtct | 174 |
| LE | tcactccaaagtgcagcaggTTTTTaggcataggacccgtgtct | 175 |
| CE | tcgggccgattgatctcaTTTTTctcttggaaagaaagt | 176 |
| BP | AGGCTTGTCACTCGGGGTT | 177 |
| BP | GAGGTCCCTGGGGAACTCTT | 178 |
| LE | gcgctgagtcggtcaccctTTTTTaggcataggacccgtgtct | 179 |
| LE | tctccagctggaagaccccTTTTTaggcataggacccgtgtct | 180 |
| LE | agactcggcaaagtcgagatagTTTTTaggcataggacccgtgtct | 181 |
| CE | gtctggtaggagacggcgatTTTTTctcttggaaagaaagt | 182 |
| BP | TGGGGCAGGGGAGGC | 183 |

TABLE 3-continued

Cytokine probe set. Accession number and symbol are listed for each target, along with probe type and the sequence of the probe.

| Type | Sequence | SEQ ID NO: |
|---|---|---|
| BP | CCCCTCTGGGGTCTCCCTC | 184 |
| LE | caggagggcattggcccTTTTTaggcataggacccgtgtct | 185 |
| BP | ggccagagggctgattagaga | 186 |
| LE | gtcctcctcacagggcaatgTTTTTaggcataggacccgtgtct | 187 |
| CE | tcccagatagatgggctcatacTTTTTctcttggaaagaaagt | 188 |
| LE | cagggcttggcctcagcTTTTTaggcataggacccgtgtct | 189 |
| BP | tgaagaggacctgggagtagatg | 190 |
| BP | GGGCAGCCTTGGCCCT | 191 |
| CE | cgagaagatgatctgactgcctgTTTTTctcttggaaagaaagt | 192 |
| LE | cagaagaggttgagggtgtctgaTTTTTaggcataggacccgtgtct | 193 |
| CE | gctgcccctcagcttgagTTTTTctcttggaaagaaagt | 194 |
| LE | ggcggttcagccactggaTTTTTaggcataggacccgtgtct | 195 |
| LE | caccaccagctggttatctctcTTTTTaggcataggacccgtgtct | 196 |
| LE | ggtttgctacaacatgggctacTTTTTaggcataggacccgtgtct | 197 |
| BP | AGGAGGGGGTAATAAAGGGAT | 198 |
| CE | cccccaattctcttttttgagcTTTTTctcttggaaagaaagt | 199 |
| BP | TGGCAGCGGCTCTTGATG | 200 |
| BP | CCCTCTCGGGGCCGA | 201 |
| LE | gcttgggttccgaccctaagTTTTTaggcataggacccgtgtct | 202 |
| LE | atcccaaagtagacctgcccTTTTTaggcataggacccgtgtct | 203 |
| BP | GTTTGGCAAGGTTGGATGTTC | 204 |
| LE | gcagagaggaggttgaccttgTTTTTaggcataggacccgtgtct | 205 |
| LE | tgaggagcacatgggtggagTTTTTaggcataggacccgtgtct | 206 |
| LE | agctccacgccattggcTTTTTaggcataggacccgtgtct | 207 |

NM_000586 IL2

| LE | aaacttaaatgtgagcatcctggTTTTTaggcataggacccgtgtct | 208 |
|---|---|---|
| CE | ctccagaggtttgagttcttcttcTTTTTctcttggaaagaaagt | 209 |
| LE | agtgggaagcacttaattatcaagTTTTTaggcataggacccgtgtct | 210 |
| BP | CCTGGGTCTTAAGTGAAAGTTTTT | 211 |
| LE | gctgtgttttctttgtagaacttgaTTTTTaggcataggacccgtgtct | 212 |
| LE | gctttgagctaaatttagcacttcTTTTTaggcataggacccgtgtct | 213 |
| BP | AGCATATTCACACATGAATGTTGTT | 214 |
| LE | attacgttgatattgctgattaagtcTTTTTaggcataggacccgtgtct | 215 |
| LE | agtaggtgcactgtttgtgacaagTTTTTaggcataggacccgtgtct | 216 |
| CE | tcagatccctttagttccagaactTTTTTctcttggaaagaaagt | 217 |
| CE | aataaaatagaaggcctgatatgttttaTTTTTctcttggaaagaaagt | 218 |
| LE | tcagtgttgagatgatgctttgacTTTTTaggcataggacccgtgtct | 219 |
| BP | AAAAGGTAATCCATCTGTTCAGAAA | 220 |
| LE | ttctacaatggttgctgtctcatcTTTTTaggcataggacccgtgtct | 221 |
| LE | cagcagtaaatgctccagttgtaTTTTTaggcataggacccgtgtct | 222 |
| LE | tagacactgaagatgtttcagttctgTTTTTaggcataggacccgtgtct | 223 |
| CE | tggccttcttgggcatgtaTTTTTctcttggaaagaaagt | 224 |
| LE | aatagttacaataggtagcaaaccatacTTTTTaggcataggacccgtgtct | 225 |
| BP | ATTCAACAATAAATATAAAATTTAAATATTTA | 226 |
| BP | TTCCATTCAAAATCATCTGTAAATC | 227 |
| CE | tgagtttgggattcttgtaattattaaTTTTTctcttggaaagaaagt | 228 |

NM_000576 IL1B

| CE | ggagagctttcagttcatatggaTTTTTctcttggaaagaaagt | 229 |
|---|---|---|
| LE | ttatcccatgtgtcgaagaagataTTTTTaggcataggacccgtgtct | 230 |
| BP | ccagacatcaccaagctttttt | 231 |
| CE | tgaagcccttgctgtagtggtTTTTTctcttggaaagaaagt | 232 |
| LE | catcgtgcacataagcctcgTTTTTaggcataggacccgtgtct | 233 |
| CE | cctggaaggtctgtgggcaTTTTTctcttggaaagaaagt | 234 |
| LE | gcagttcagtgatcgtacaggtgTTTTTaggcataggacccgtgtct | 235 |
| LE | ggtcggagattcgtagctggTTTTTaggcataggacccgtgtct | 236 |
| CE | gcagaggtccaggtcctggTTTTTctcttggaaagaaagt | 237 |
| LE | gggaaccagcatcttcctcaTTTTTaggcataggacccgtgtct | 238 |
| CE | ccatatcctgtccctggaggtTTTTTctcttggaaagaaagt | 239 |
| LE | atggagaacaccacttgttgctTTTTTaggcataggacccgtgtct | 240 |
| LE | atgccgccatccagaggTTTTTaggcataggacccgtgtct | 241 |
| LE | aggcacaggtattttgtcattTTTTTaggcataggacccgtgtct | 242 |
| CE | aaagaaggtgctcaggtcattctTTTTTctcttggaaagaaagt | 243 |
| LE | actttcttctccttgtacaaaggacTTTTTaggcataggacccgtgtct | 244 |
| BP | ACTGACGCGGCCTGCC | 245 |
| LE | gccatcagcttcaaagaacaagTTTTTaggcataggacccgtgtct | 246 |
| LE | gctgtgagtcccggagcgtTTTTTaggcataggacccgtgtct | 247 |
| CE | attcttttccttgaggcccaTTTTTctcttggaaagaaagt | 248 |
| LE | gcttgtccatggccacaacaTTTTTaggcataggacccgtgtct | 249 |

TABLE 3-continued

Cytokine probe set. Accession number and symbol are listed for each target, along with probe type and the sequence of the probe.

| Type | Sequence | SEQ ID NO: |
|---|---|---|
| LE | aaggagcacttcatctgtttaggTTTTTaggcataggacccgtgtct | 250 |
| LE | ggttcttcttcaaagatgaagggTTTTTaggcataggacccgtgtct | 251 |

NM_003376 VEGF

| Type | Sequence | SEQ ID NO: |
|---|---|---|
| CE | atctttctttggtctgcattcacTTTTTctcttggaaagaaagt | 252 |
| CE | aaggctccaatgcacccaTTTTTctcttggaaagaaagt | 253 |
| LE | ggcccacagggaacgctTTTTTaggcataggacccgtgtct | 254 |
| BP | GCAGCCCCGCATCG | 255 |
| LE | gatgattctgccctcctccttTTTTTaggcataggacccgtgtct | 256 |
| LE | accagggtctcgattggatgTTTTTaggcataggacccgtgtct | 257 |
| LE | tgggaccacttggcatggTTTTTaggcataggacccgtgtct | 258 |
| LE | tccatgaacttcaccacttcgtTTTTTaggcataggacccgtgtct | 259 |
| LE | ttgcgctttcgttttgcTTTTTaggcataggacccgtgtct | 260 |
| LE | tggaggtagagcagcaaggcTTTTTaggcataggacccgtgtct | 261 |
| LE | gcttgaagatgtactcgatctcatcTTTTTaggcataggacccgtgtct | 262 |
| LE | ctgatttttttcttgtcttgctctTTTTTaggcataggacccgtgtct | 263 |
| LE | agggtactcctggaagatgtccTTTTTaggcataggacccgtgtct | 264 |
| BP | CTCCTCAGTGGGCACACACTC | 265 |
| LE | caggccctcgtcattgcaTTTTTaggcataggacccgtgtct | 266 |
| CE | ccctttcccttcctcgaaTTTTTctcttggaaagaaagt | 267 |
| CE | ccaggacttataccgggatttcTTTTTctcttggaaagaaagt | 268 |
| LE | gcagtagctgcgctgatagacaTTTTTaggcataggacccgtgtct | 269 |
| BP | CATCAGGGGCACACAGGATG | 270 |
| LE | atttgttgtgctgtaggaagctcTTTTTaggcataggacccgtgtct | 271 |
| CE | ctgccatgggtgcagccTTTTTctcttggaaagaaagt | 272 |
| CE | atctctcctatgtgctggcctTTTTTctcttggaaagaaagt | 273 |
| LE | TaatctgcatggtgatgttggaTTTTTaggcataggacccgtgtct | 274 |
| CE | tggtgaggtttgatccgcaTTTTTctcttggaaagaaagt | 275 |

TABLE 4

Apoptosis 1 probe set. Accession number and symbol are listed for each target, along with probe type and the sequence of the probe.

| Type | Sequence | SEQ ID NO: |
|---|---|---|

NM_001188 BAK1

| Type | Sequence | SEQ ID NO: |
|---|---|---|
| LE | ccatgctggtagacgtgtagggTTTTTaggcataggacccgtgtct | 276 |
| LE | tctctgccgtgggctgcTTTTTaggcataggacccgtgtct | 277 |
| LE | gccccaattgatgccactcTTTTTaggcataggacccgtgtct | 278 |
| BP | GGGGCAGCCACCCCTTC | 279 |
| BP | gggaggacctgggccttg | 280 |
| BP | GGCGGTAAAAAACCTAGCTG | 281 |
| BP | CGGAAAACCTCCTCTGTGTCC | 282 |
| BP | TGGCGAGCTGCCGTCC | 283 |
| LE | ccaagttcagggctgccacTTTTTaggcataggacccgtgtct | 284 |
| CE | cagcctgccgggatcctTTTTTctcttggaaagaaagt | 285 |
| BP | ggcctaggaagccagtcagg | 286 |
| LE | ccagaagagccaccacacgTTTTTaggcataggacccgtgtct | 287 |
| LE | gaccatctctgggtcggcaTTTTTaggcataggacccgtgtct | 288 |
| LE | aggtgctgcaacatggtctgTTTTTaggcataggacccgtgtct | 289 |
| BP | AGCAGAGGGCAGGGCAG | 290 |
| BP | TCTTGGTGAAGTACTCATAGGCAT | 291 |
| BP | ccagccacccctctgtgc | 292 |
| CE | ccccgaagccatttttcaTTTTTctcttggaaagaaagt | 293 |
| CE | tgctaggttgcagaggtaaggtTTTTTctcttggaaagaaagt | 294 |
| LE | tcaaacaggctggtggcaaTTTTTaggcataggacccgtgtct | 295 |
| LE | cacctgcccatggtgcTTTTTaggcataggacccgtgtct | 296 |
| LE | gttcaggatgggaccattgcTTTTTaggcataggacccgtgtct | 297 |
| LE | aatccaccgggcaatgcTTTTTaggcataggacccgtgtct | 298 |
| LE | ttgatgtcgtccccgatgaTTTTTaggcataggacccgtgtct | 299 |
| CE | tgggctacctgctcctcagaTTTTTctcttggaaagaaagt | 300 |
| BP | gaactctgagtcatagcgtcgg | 301 |
| LE | ccacgaagcgggtcaccttTTTTTaggcataggacccgtgtct | 302 |

TABLE 4-continued

Apoptosis 1 probe set. Accession number and symbol are listed for each target, along with probe type and the sequence of the probe.

| Type | Sequence | SEQ ID NO: |
|---|---|---|
| LE | ggtctcagtggaggacgggatTTTTTaggcataggacccgtgtct | 303 |
| BP | AGTGATGCAGCATGAAGTCGA | 304 |
| CE | ccagacggtagccgaagcTTTTTctcttggaaagaaagt | 305 |
| CE | agcctcctgttcctgctgatTTTTTctcttggaaagaaagt | 306 |
| LE | gctctccgcactcctgcctTTTTTaggcataggacccgtgtct | 307 |

NM_000565 IL6R

| Type | Sequence | SEQ ID NO: |
|---|---|---|
| LE | gcacgaagctgcaccacgtTTTTTaggcataggacccgtgtct | 308 |
| CE | ttcagcccgatatctgagctcTTTTTctcttggaaagaaagt | 309 |
| LE | aaaccgtagtctgtagaaagatgagtTTTTTaggcataggacccgtgtct | 310 |
| LE | ccaggtgacactgagccagcTTTTTaggcataggacccgtgtct | 311 |
| LE | cgacactactggcgacgcaTTTTTaggcataggacccgtgtct | 312 |
| LE | gcagtgactgtgatgttggcaTTTTTaggcataggacccgtgtct | 313 |
| BP | CATGGACACTATGTAGAAAGAGCTG | 314 |
| BP | gctggaggtccttgaccatc | 315 |
| CE | tgagttttgctgaacttgctccTTTTTctcttggaaagaaagt | 316 |
| LE | ttctgtccaaggcgtgccTTTTTaggcataggacccgtgtct | 317 |
| BP | CATGGCCTCCGGGCTC | 318 |
| LE | catgttgtgaatgtctttgaccgTTTTTaggcataggacccgtgtct | 319 |
| BP | GGGGGTTTCTGGCCACG | 320 |
| LE | caccaagagcacagcctttgtTTTTTaggcataggacccgtgtct | 321 |
| LE | gcgtcgtggatgacacagtgatTTTTTaggcataggacccgtgtct | 322 |
| CE | ccggactgttctgaaacttcctTTTTTctcttggaaagaaagt | 323 |
| LE | gattccacaaccctgaaaggttTTTTTaggcataggacccgtgtct | 324 |
| LE | gactcctgggaatactggcacTTTTTaggcataggacccgtgtct | 325 |
| CE | gcctcaggccgctccagTTTTTctcttggaaagaaagt | 326 |
| CE | tctccctccgggactgctTTTTTctcttggaaagaaagt | 327 |
| LE | ggcggatcaggctgcaaTTTTTaggcataggacccgtgtct | 328 |
| BP | AACTGGCAGGAGAACTTCTGG | 329 |
| BP | TCCAGGAGTGGGGGTCTTG | 330 |
| LE | ggctcctggaagtcttcggTTTTTaggcataggacccgtgtct | 331 |
| BP | cactcgctccactcgcct | 332 |
| CE | tgcccgaactcctcctggTTTTTctcttggaaagaaagt | 333 |

NM_138578 BCL2L1

| Type | Sequence | SEQ ID NO: |
|---|---|---|
| LE | cggttgaagcgttcctggTTTTTaggcataggacccgtgtct | 334 |
| LE | gctgcattgttcccatagagttcTTTTTaggcataggacccgtgtct | 335 |
| LE | gccatccaagctgcgatcTTTTTaggcataggacccgtgtct | 336 |
| CE | gctcccggttgctctgagaTTTTTctcttggaaagaaagt | 337 |
| BP | CACAAAAGTATCCCAGCCGC | 338 |
| BP | CACAGTGCCCCGCCG | 339 |
| LE | cgactcaccaatacctgcatctTTTTTaggcataggacccgtgtct | 340 |
| LE | gggcctcagtcctgttctcttTTTTTaggcataggacccgtgtct | 341 |
| BP | CACCTCCCGGGCATCC | 342 |
| LE | gctgggatgtcaggtcactgaaTTTTTaggcataggacccgtgtct | 343 |
| BP | TGGCACTGGGGGTCTCCA | 344 |
| BP | TGCCCGCCGGTACCG | 345 |
| LE | cgttctcctggatccaaggcTTTTTaggcataggacccgtgtct | 346 |
| CE | tgtatcctttctgggaaagcttTTTTTctcttggaaagaaagt | 347 |
| CE | cctccctcagcgcttgctTTTTTctcttggaaagaaagt | 348 |
| LE | cctgttcaaagctctgatatgctgTTTTTaggcataggacccgtgtct | 349 |
| LE | caggatgggttgccattgaTTTTTaggcataggacccgtgtct | 350 |
| LE | tctccgattcagtcccttctgTTTTTaggcataggacccgtgtct | 351 |
| BP | TTACTGCTGCCATGGGAT | 352 |
| LE | ccttgtctacgctttccacgTTTTTaggcataggacccgtgtct | 353 |
| LE | gtaggagagaaagtcaaccaccaTTTTTaggcataggacccgtgtct | 354 |
| LE | cagttcaaactcgtcgcctgTTTTTaggcataggacccgtgtct | 355 |
| CE | aaactgctgctgtggccagTTTTTctcttggaaagaaagt | 356 |
| LE | cgaccccagtttaccccaTTTTTaggcataggacccgtgtct | 357 |
| BP | ccacatcactaaactgactccagc | 358 |
| LE | tggctccattcaccgcgTTTTTaggcataggacccgtgtct | 359 |
| LE | tctaggtggtcattcaggtaagtgTTTTTaggcataggacccgtgtct | 360 |
| BP | AAGGAGAAAAAGGCCACAATG | 361 |
| CE | gggctgtctgccaggtgcTTTTTctcttggaaagaaagt | 362 |
| LE | tcccggaagagttcattcactaTTTTTaggcataggacccgtgtct | 363 |
| CE | ccctttcggctctcggctTTTTTctcttggaaagaaagt | 364 |
| BP | TCCCTGGGGTGATGTGGA | 365 |

TABLE 4-continued

Apoptosis 1 probe set. Accession number and symbol are listed for each target, along with probe type and the sequence of the probe.

| Type | Sequence | SEQ ID NO: |
|---|---|---|
| NM_003879 CFLAR | | |
| LE | tctgctgttccaatcatacatgtaTTTTTaggcataggacccgtgtct | 366 |
| CE | gccctcgcttctgagcctTTTTTctcttggaaagaaagt | 367 |
| LE | tgaattccacattcttcatcgcTTTTTaggcataggacccgtgtct | 368 |
| LE | tggcctcccaaagtgctgTTTTTaggcataggacccgtgtct | 369 |
| CE | gcccagccttttggtttcttaTTTTTctcttggaaagaaagt | 370 |
| LE | ttcttgtctcagtttctgggagaTTTTTaggcataggacccgtgtct | 371 |
| LE | tggcccatccaccctccaTTTTTaggcataggacccgtgtct | 372 |
| BP | TGGCCCTCTGACACCACATAG | 373 |
| LE | gcgtttaccatgttggccaTTTTTaggcataggacccgtgtct | 374 |
| LE | cataatatttctccttggcagaaacTTTTTaggcataggacccgtgtct | 375 |
| LE | ggtgagctgtgagactgctccaTTTTTaggcataggacccgtgtct | 376 |
| LE | ttccctgctagataagggcatTTTTTaggcataggacccgtgtct | 377 |
| LE | ggattacaggtgtgagccactacTTTTTaggcataggacccgtgtct | 378 |
| BP | TTCTGAATAAAAAACATCTTTGGC | 379 |
| LE | ggcactgcaggtacagggacTTTTTaggcataggacccgtgtct | 380 |
| BP | CACAGGCTCCAGAAGAAGTCAG | 381 |
| LE | tgtgtaggagaggataagtttctttctTTTTTaggcataggacccgtgtct | 382 |
| CE | cagagtgtgctgcagccagaTTTTTctcttggaaagaaagt | 383 |
| CE | agaggctgctgttctccagcTTTTTctcttggaaagaaagt | 384 |
| LE | gccattgagttcaatgtgaagatTTTTTaggcataggacccgtgtct | 385 |
| CE | ggctggtctcgaactcctgaTTTTTctcttggaaagaaagt | 386 |
| LE | cttctcggtgaactgtgcacaTTTTTaggcataggacccgtgtct | 387 |
| LE | attttttgcattttttactagggacaTTTTTaggcataggacccgtgtct | 388 |
| CE | ccaggagtgggcgttttctTTTTTctcttggaaagaaagt | 389 |
| BP | CCTGAAGTGATCTGCCCTCCT | 390 |
| LE | gcagggacatgtccgcagtaTTTTTaggcataggacccgtgtct | 391 |
| NM_000639 TNFSF6 | | |
| BP | TCCTGGGGATACTTAGAGTTCCT | 392 |
| BP | CCCGGAAGTATACTTTGGAATATA | 393 |
| CE | ttggacttgcctgttaaatggTTTTTctcttggaaagaaagt | 394 |
| LE | agagctgaaacatccccaggTTTTTaggcataggacccgtgtct | 395 |
| LE | tcccctccatcatcaccagaTTTTTaggcataggacccgtgtct | 396 |
| LE | catgtagaccttgtggctcaggTTTTTaggcataggacccgtgtct | 397 |
| LE | atcacaaggccacccttcttaTTTTTaggcataggacccgtgtct | 398 |
| BP | GCGGGCCCACATCTGC | 399 |
| CE | ccagctccttctgtaggtggaTTTTTctcttggaaagaaagt | 400 |
| LE | ggcaggttgttgcaagattgacTTTTTaggcataggacccgtgtct | 401 |
| LE | cccaatcctaccaaggcaacTTTTTaggcataggacccgtgtct | 402 |
| BP | ccagaggcatggaccttgag | 403 |
| CE | ggtggcagcggtagtggagTTTTTctcttggaaagaaagt | 404 |
| CE | tggttccctctcttcttcaggTTTTTctcttggaaagaaagt | 405 |
| LE | ccagtagtgcagtagctcatcatctTTTTTaggcataggacccgtgtct | 406 |
| CE | gctggtagactctcggagttctgTTTTTctcttggaaagaaagt | 407 |
| LE | aagatgatgctgtgtgcatctgTTTTTaggcataggacccgtgtct | 408 |
| LE | ggagacacaggcctgtgctgTTTTTaggcataggacccgtgtct | 409 |
| CE | tgccccaggtagctgctTTTTTctcttggaaagaaagt | 410 |
| BP | CAGAACCATGAAAAACATCACAA | 411 |
| BP | AATTCCATAGGTGTCTTCCCATT | 412 |
| BP | tacttcactccagaaagcaggac | 413 |
| CE | gcggcggaggtggtagtTTTTTctcttggaaagaaagt | 414 |
| BP | TTTTCAGGGGGTGGACTGG | 415 |
| BP | gccactttcctcagctcctt | 416 |
| LE | caaagtacagcccagtttcattgTTTTTaggcataggacccgtgtct | 417 |
| BP | GCAGTGGTGGCGGCG | 418 |
| LE | ggtggcctatttgcttctccaTTTTTaggcataggacccgtgtct | 419 |
| NM_001101 ACTB | | |
| LE | cgtggtggtgaagctgtagcTTTTTaggcataggacccgtgtct | 420 |
| BP | CGCAGGATGGCATGGGG | 421 |
| LE | acaggtctttgcggatgtccTTTTTaggcataggacccgtgtct | 422 |
| CE | acaggactccatgcccaggTTTTTctcttggaaagaaagt | 423 |
| BP | CGATTTCCCGCTCGGC | 424 |
| LE | gggcacagtgtgggtgaccTTTTTaggcataggacccgtgtct | 425 |
| LE | agacagcactgtgttggcgtTTTTTaggcataggacccgtgtct | 426 |
| LE | tcggtcagcagcacgggTTTTTaggcataggacccgtgtct | 427 |
| LE | ccagggcgacgtagcacaTTTTTaggcataggacccgtgtct | 428 |
| LE | catgaggtagtcagtcaggtcccTTTTTaggcataggacccgtgtct | 429 |

TABLE 4-continued

Apoptosis 1 probe set. Accession number and symbol are listed for each target, along with probe type and the sequence of the probe.

| Type | Sequence | SEQ ID NO: |
|---|---|---|
| CE | ctcgtagctcttctccagggaTTTTTctcttggaaagaaagt | 430 |
| LE | tctcaaacatgatctgggtcatcTTTTTaggcataggacccgtgtct | 431 |
| BP | TGGCTGGGGTGTTGAAGG | 432 |
| CE | ggagctggaagcagccgtTTTTTctcttggaaagaaagt | 433 |
| LE | ggccatctcttgctcgaagtTTTTTaggcataggacccgtgtct | 434 |
| CE | aaggaaggctggaagagtgcTTTTTctcttggaaagaaagt | 435 |
| CE | cgcgctcggtgaggatcttTTTTTctcttggaaagaaagt | 436 |
| LE | ctcagggcagcggaaccTTTTTaggcataggacccgtgtct | 437 |
| LE | ccgtcaccggagtccatcaTTTTTaggcataggacccgtgtct | 438 |
| LE | gagggcataccctcgtagatTTTTTaggcataggacccgtgtct | 439 |
| BP | ACGTCACACTTCATGATGGAGTT | 440 |
| LE | gcttctccttaatgtcacgcaTTTTTaggcataggacccgtgtct | 441 |
| BP | acctggccgtcaggcag | 442 |
| LE | cgatgccagtggtacggcTTTTTaggcataggacccgtgtct | 443 |
| LE | cagcctggatagcaacgtacaTTTTTaggcataggacccgtgtct | 444 |
| LE | gaaggtagtttcgtggatgccTTTTTaggcataggacccgtgtct | 445 |
| CE | gctcattgccaatggtgatgTTTTTctcttggaaagaaagt | 446 |
| LE | cagaggcgtacaggqgatacaTTTTTaggcataggacccgtgtct | 447 |
| BP | GGCCAGCCACGTCCAGA | 448 |
| CE | ttctcgcggttggccttTTTTTctcttggaaagaaagt | 449 |
| BP | GGGGTTCAGGGGGGCC | 450 |

NM_000043 TNFRSF6

| Type | Sequence | SEQ ID NO: |
|---|---|---|
| LE | gaactgaatttgttgtttttcactctTTTTTaggcataggacccgtgtct | 451 |
| LE | ttgccactgttttcaggatttaaTTTTTaggcataggacccgtgtct | 452 |
| LE | tccatgaagttgatgccaattaTTTTTaggcataggacccgtgtct | 453 |
| CE | gattggcttttttgagatctttaatTTTTTctcttggaaagaaagt | 454 |
| LE | ccccaagttagatctggatcctTTTTTaggcataggacccgtgtct | 455 |
| LE | agaccaagctttggatttcattTTTTTaggcataggacccgtgtct | 456 |
| CE | cgaagcagttgaactttctgttcTTTTTctcttggaaagaaagt | 457 |
| CE | tgactccagcaatagtggtgatatatTTTTTctcttggaaagaaagt | 458 |
| LE | tcctcttttgcacttggtgttgTTTTTaggcataggacccgtgtct | 459 |
| LE | catgttttctgtacttccttttctcttTTTTTaggcataggacccgtgtct | 460 |
| LE | tgctgtgtcttggacattgtcatTTTTTaggcataggacccgtgtct | 461 |
| LE | tctgaagtttgaattttctgagtcaTTTTTaggcataggacccgtgtct | 462 |
| CE | ggttttcctttctgtgctttctgTTTTTctcttggaaagaaagt | 463 |
| LE | ctagtaatgtccttgaggatgatagtcTTTTTaggcataggacccgtgtct | 464 |
| LE | agtatttacagccagctattaagaatcTTTTTaggcataggacccgtgtct | 465 |
| LE | ttttcaaacactaattgcatatactcaTTTTTaggcataggacccgtgtct | 466 |
| BP | GCAAAAGAAGAAGACAAAGCCA | 467 |
| LE | ggttggagattcatgagaaccttTTTTTaggcataggacccgtgtct | 468 |
| BP | ATGTACCCAGTAAAAAACCAAGC | 469 |
| LE | cattgacaccattctttcgaacaTTTTTaggcataggacccgtgtct | 470 |
| LE | ttactcaagtcaacatcagataaaatttaTTTTTaggcataggacccgtgtct | 471 |
| LE | caatgtgtcatacgcttcttttcttTTTTTaggcataggacccgtgtct | 472 |
| LE | cacccaaacaattagtggaatttTTTTTaggcataggacccgtgtct | 473 |
| LE | aagcctttaacttgacttagtgtcaTTTTTaggcataggacccgtgtct | 474 |
| LE | tcttgatctcatctattttggcttTTTTTaggcataggacccgtgtct | 475 |
| CE | ctcttcagcgctaataaatgataaaTTTTTctcttggaaagaaagt | 476 |
| LE | tgaattttctctgcaagagtacaaaTTTTTaggcataggacccgtgtct | 477 |

NM_004103 PTK2B

| Type | Sequence | SEQ ID NO: |
|---|---|---|
| LE | aagtactgcctggccctccTTTTTaggcataggacccgtgtct | 478 |
| LE | gggccttcgcagggtttcTTTTTaggcataggacccgtgtct | 479 |
| BP | GGACAAGGCCTGGGGGG | 480 |
| BP | TCCAGCGGGAGGCACC | 481 |
| LE | caccttcaatgcccagctgTTTTTaggcataggacccgtgtct | 482 |
| CE | gctggcggatccctttaggTTTTTctcttggaaagaaagt | 483 |
| LE | cttggtgctcaccctgcagTTTTTaggcataggacccgtgtct | 484 |
| CE | ctgctagggatgaggttttgatTTTTTctcttggaaagaaagt | 485 |
| LE | ggaactgtttgggcttaagttTTTTTaggcataggacccgtgtct | 486 |
| LE | aaggtctgctggatcatcttccTTTTTaggcataggacccgtgtct | 487 |
| LE | gttccgcttctcaccatctttTTTTTaggcataggacccgtgtct | 488 |
| LE | ccggcagtagccgtctatgaTTTTTaggcataggacccgtgtct | 489 |
| LE | gacgcactcctcctccctgTTTTTaggcataggacccgtgtct | 490 |
| LE | gccaatgaccaggtccacagtTTTTTaggcataggacccgtgtct | 491 |
| LE | agcgaggcgtactgctggTTTTTaggcataggacccgtgtct | 492 |
| CE | acagcggtaggtctcctggtTTTTTctcttggaaagaaagt | 493 |
| LE | ctgagaggtgggaccgccTTTTTaggcataggacccgtgtct | 494 |
| CE | gggcctccaggtttagcatgTTTTTctcttggaaagaaagt | 495 |

TABLE 4-continued

Apoptosis 1 probe set. Accession number and symbol are listed for each target, along with probe type and the sequence of the probe.

| Type | Sequence | SEQ ID NO: |
|---|---|---|
| BP | ACTCGGCCAGGCAGGTG | 496 |
| LE | cgatgttggcgaagccgTTTTTaggcataggacccgtgtct | 497 |
| BP | AATGTTCCATCCTTGAATGAGTTC | 498 |
| CE | gtctgactctatgctgcagctctTTTTTctcttggaaagaaagt | 499 |
| LE | cctaggatggatgatgagagagcTTTTTaggcataggacccgtgtct | 500 |
| LE | ggtcagccatgttctcagcctTTTTTaggcataggacccgtgtct | 501 |
| BP | GGGATCTGGGGCAGGCT | 502 |
| CE | gcgagagtgttgaagaacttcatTTTTTctcttggaaagaaagt | 503 |
| LE | ggctttgcgtcctgactagtcaTTTTTaggcataggacccgtgtct | 504 |
| LE | tgatggacctgatctgcttgaTTTTTaggcataggacccgtgtct | 505 |
| LE | gtcgggaatctctgcgtagatTTTTTaggcataggacccgtgtct | 506 |

NM_004322 BAD

| Type | Sequence | SEQ ID NO: |
|---|---|---|
| BP | tgctgctggttggctgct | 507 |
| LE | cctgctcactcggctcaaactTTTTTaggcataggacccgtgtct | 508 |
| LE | ctgggatctggaacatgctctTTTTTaggcataggacccgtgtct | 509 |
| BP | tggaaggcagaggcaggta | 510 |
| LE | cccccatcccttcgtcgTTTTTaggcataggacccgtgtct | 511 |
| BP | CCGGAGCCTGAGGGCC | 512 |
| LE | cgtagtcaaggcacagctggTTTTTaggcataggacccgtgtct | 513 |
| BP | cgggtctggcctggcag | 514 |
| CE | ggagctgaggctgtcggcTTTTTctcttggaaagaaagt | 515 |
| BP | cccacaggaggcctggg | 516 |
| CE | gagctcgcggccatagcTTTTTctcttggaaagaaagt | 517 |
| BP | GCCCGCCAGGCCTCC | 518 |
| BP | ACCGTAGCGCCCCCAG | 519 |
| CE | agcgcctccatgatggcTTTTTctcttggaaagaaagt | 520 |
| CE | gcctggcgatgatgcttgTTTTTctcttggaaagaaagt | 521 |
| BP | TCCTCCGTCCCCGCG | 522 |
| LE | tgggccctcatctgtctgcTTTTTaggcataggacccgtgtct | 523 |
| CE | cccctggcttcctctcccTTTTTctcttggaaagaaagt | 524 |
| LE | gctgtgctgcccagaggttTTTTTaggcataggacccgtgtct | 525 |
| BP | GCGAGCGGCCCCG | 526 |
| CE | cctgctggtgactggcgtTTTTTctcttggaaagaaagt | 527 |
| LE | tcaggacctcagtctcccctcTTTTTaggcataggacccgtgtct | 528 |
| BP | TGGGGCCCAGGCCC | 529 |
| LE | agtcccttcttaaaggagtccacTTTTTaggcataggacccgtgtct | 530 |
| BP | GGCCAACGGTGGCCC | 531 |
| CE | ctctctgcagagctggagtcttTTTTTctcttggaaagaaagt | 532 |
| BP | AAAGGGGCTGGGCTCCT | 533 |
| BP | CGTCCCCTGCGGGGC | 534 |
| BP | GGGGGGCGCCGAGC | 535 |
| LE | ccggatctccacagccccTTTTTaggcataggacccgtgtct | 536 |
| LE | gggtaggagctgtggcgactTTTTTaggcataggacccgtgtct | 537 |
| LE | aaactcgtcactcatcctccgTTTTTaggcataggacccgtgtct | 538 |
| LE | gggctgtgaggacaagatgttaTTTTTaggcataggacccgtgtct | 539 |

NM_000633 BCL2

| Type | Sequence | SEQ ID NO: |
|---|---|---|
| BP | TCTTCAATACAAAATAGGGATGGTT | 540 |
| LE | cggagacgacccgatggcTTTTTaggcataggacccgtgtct | 541 |
| CE | tttgtgcagcgagggactgTTTTTctcttggaaagaaagt | 542 |
| BP | AATCTTGATTATTATAACTCCTCTCGAT | 543 |
| BP | CCCCAATTTGGAAAGTGCATAt | 544 |
| LE | ctgggccagagctacatctttaTTTTTaggcataggacccgtgtct | 545 |
| LE | catagaccctgtcagctgtcattcTTTTTaggcataggacccgtgtct | 546 |
| CE | tctgcccctgccaaatctttTTTTTctcttggaaagaaagt | 547 |
| LE | ctctgttgcccaactgcaaaTTTTTaggcataggacccgtgtct | 548 |
| CE | ctcagatgttcttctcctttggTTTTTctcttggaaagaaagt | 549 |
| BP | CATCTGAACACAGAGAGGTAAGTGAGc | 550 |
| BP | GATGATAAGCATTTACTAATAAAACAAA | 551 |
| LE | cagtgtaaagaggagtacatacagaggTTTTTaggcataggacccgtgtct | 552 |
| LE | tgtggagagaatgttggcgtTTTTTaggcataggacccgtgtct | 553 |
| LE | gatcacatataaatggaaggccaTTTTTaggcataggacccgtgtct | 554 |
| CE | cttgtttgaactaaattgaggtgcTTTTTctcttggaaagaaagt | 555 |
| BP | ACTCTATTTAACTCTGACCCTGGC | 556 |
| LE | ggagggccgaggaggtttTTTTTaggcataggacccgtgtct | 557 |
| CE | actgttttttcattcataaagagcaTTTTTctcttggaaagaaagt | 558 |
| LE | gttaagatgcagatgtgaatcccTTTTTaggcataggacccgtgtct | 559 |
| LE | ggattgcccgattatttacatttTTTTTaggcataggacccgtgtct | 560 |
| CE | aaatcttaagcctgccagagtttTTTTTctcttggaaagaaagt | 561 |

TABLE 4-continued

Apoptosis 1 probe set. Accession number and symbol are listed for each target, along with probe type and the sequence of the probe.

| Type | Sequence | SEQ ID NO: |
|---|---|---|
| LE | tggcctctcttgcggagtaTTTTTaggcataggacccgtgtct | 562 |
| LE | tataatcacttcctaattttcccaTTTTTaggcataggacccgtgtct | 563 |
| LE | ttccttgattctgtgactttattccTTTTTaggcataggacccgtgtct | 564 |
| CE | ggcttttttagagcccttgtTTTTTctcttggaaagaaagt | 565 |

TABLE 5

Apoptosis 2 probe set. Accession number and symbol are listed for each target, along with probe type and the sequence of the probe.

| Type | Sequence | SEQ ID NO: |
|---|---|---|
| NM_006509 RELB | | |
| CE | ggcttttttcttccgccgTTTTTctcttggaaagaaagt | 566 |
| LE | tccacgccgtagctgtcatTTTTTaggcataggacccgtgtct | 567 |
| BP | CGGCGTCTTGAACACAATGG | 568 |
| LE | tgactgtcacgggctcgacTTTTTaggcataggacccgtgtct | 569 |
| LE | ccccgtttccgcttcttgTTTTTaggcataggacccgtgtct | 570 |
| LE | tgaaaggcaatggctcgcTTTTTaggcataggacccgtgtct | 571 |
| LE | gcccgaccttcccaggagTTTTTaggcataggacccgtgtct | 572 |
| CE | caatctggcggtgcacgTTTTTctcttggaaagaaagt | 573 |
| CE | gccgctgcaggaagacgtTTTTTctcttggaaagaaagt | 574 |
| LE | gcaaatccgcagctctgatgTTTTTaggcataggacccgtgtct | 575 |
| LE | gccctgctgaacaccactgaTTTTTaggcataggacccgtgtct | 576 |
| LE | tgcagacccatcggtgaTTTTTaggcataggacccgtgtct | 577 |
| BP | gggctcggaaagcacagg | 578 |
| CE | aatctccaggtcctcgtagggTTTTTctcttggaaagaaagt | 579 |
| LE | cgcagagcaagtagagctcctcTTTTTaggcataggacccgtgtct | 580 |
| LE | atccatccggcgcatctTTTTTaggcataggacccgtgtct | 581 |
| BP | ggtcgcgaggcaggtacg | 582 |
| BP | ccaaggacgtcgggcatc | 583 |
| CE | ccgctttccttgttaattcgTTTTTctcttggaaagaaagt | 584 |
| BP | TGTTTGTGGATTTCTTGTCATAGAC | 585 |
| LE | atgaggcctggaagcagatcTTTTTaggcataggacccgtgtct | 586 |
| BP | GCCACCGGTGCACGGC | 587 |
| CE | gtccctgctggtcccgatTTTTTctcttggaaagaaagt | 588 |
| LE | tttgctctcgatgccatggTTTTTaggcataggacccgtgtct | 589 |
| BP | TATGTCCTCTTTCTGCACCTTGT | 590 |
| LE | tcggcctgggagaagtcaTTTTTaggcataggacccgtgtct | 591 |
| LE | gggtcagagctgttcagctccTTTTTaggcataggacccgtgtct | 592 |
| NM_000389 CDKN1A | | |
| BP | GGGGAGGGACAGCAGCAG | 593 |
| BP | AGGGGAATTGCAGAGCCC | 594 |
| LE | ttttgatgatgcccccactcTTTTTaggcataggacccgtgtct | 595 |
| BP | TGTCCCTTCCCCTTCCAGT | 596 |
| CE | aagaattcaggtctgagtgtccagTTTTTctcttggaaagaaagt | 597 |
| CE | ttgagctgcctgaggtagaactTTTTTctcttggaaagaaagt | 598 |
| BP | gggtgggacaggcacctc | 599 |
| BP | CCATTGAGCTGGGGGTGG | 600 |
| BP | AGGGTGCCCTTCTTCTTGTG | 601 |
| BP | GGAGGGATGGGGTGGATG | 602 |
| LE | tgccaccacatgggacccTTTTTaggcataggacccgtgtct | 603 |
| BP | GGGGGCGGTCGCTGC | 604 |
| BP | CCCAGTGCAGGTCAGAGGG | 605 |
| CE | tgtctgactccttgttccgctTTTTTctcttggaaagaaagt | 606 |
| CE | agctggagaagaagggtaagctTTTTTctcttggaaagaaagt | 607 |
| LE | caagagccaggagggtaccaTTTTTaggcataggacccgtgtct | 608 |
| CE | ctcctagaaagatctactccccTTTTTctcttggaaagaaagt | 609 |
| BP | GAGGTGAGGGGACTCCAAAGT | 610 |
| LE | agagccacctggagcatgagTTTTTaggcataggacccgtgtct | 611 |
| LE | gctcaacactgagacgggctcTTTTTaggcataggacccgtgtct | 612 |
| BP | GCTAATCAAAGTGCAATGAACTGG | 613 |
| BP | GGGAGCCAAAGAGGGAAAAG | 614 |

TABLE 5-continued

Apoptosis 2 probe set. Accession number and symbol are listed for each target, along with probe type and the sequence of the probe.

| Type | Sequence | SEQ ID NO: |
|---|---|---|
| BP | AGGGTACTGAAGGGAAAGACAAG | 615 |
| BP | CCCACTCAAGGGGGCCTG | 616 |
| BP | ATCATATACCCCTAACACAGAGATAAC | 617 |
| LE | ccatctgtttacttctcaaatgaaaTTTTTaggcataggacccgtgtct | 618 |
| LE | gggtggtctgctccagtaccTTTTTaggcataggacccgtgtct | 619 |
| LE | tcaccccacagctagaggaTTTTTaggcataggacccgtgtct | 620 |
| LE | caccctgcccaaccttagagTTTTTaggcataggacccgtgtct | 621 |
| BP | GCCATGAGGGCAGGCG | 622 |
| CE | ggtccccagctcagccctaTTTTTctcttggaaagaaagt | 623 |
| LE | ccaccttcccccctgcctTTTTTaggcataggacccgtgtct | 624 |
| LE | aggaaggtcgctggacgatTTTTTaggcataggacccgtgtct | 625 |
| BP | TTGAGGGGCCAGTGTCTCC | 626 |
| BP | TCACAAGACAGAGGGGGTAT | 627 |
| BP | GGGGCTCCTCAAAAGGTACAG | 628 |
| BP | GGTGAGGCCCCTTCAAAGTG | 629 |
| LE | ggctgtgctcacttcagggtTTTTTaggcataggacccgtgtct | 630 |

NM_002046 GAPDH

| BP | CGGAGGGGCCATCCAC | 3 |
|---|---|---|
| LE | cccacttgattttggagggaTTTTTaggcataggacccgtgtct | 4 |
| CE | agcttcccgttctcagcctTTTTTctcttggaaagaaagt | 5 |
| LE | ccttccacgataccaaagttgtTTTTTaggcataggacccgtgtct | 6 |
| CE | cctttggctccccccTTTTTctcttggaaagaaagt | 7 |
| LE | ccagtggactccacgacgtacTTTTTaggcataggacccgtgtct | 8 |
| CE | tgacggtgccatggaatttTTTTTctcttggaaagaaagt | 9 |
| LE | ggcatggactgtggtcatgagtTTTTTaggcataggacccgtgtct | 10 |
| LE | gggtgctaagcagttggtggtTTTTTaggcataggacccgtgtct | 11 |
| LE | agtcttctgggtggcagtgatTTTTTaggcataggacccgtgtct | 12 |
| BP | AACATGGGGGCATCAGCA | 13 |
| BP | CATGGTTCACACCCATGACG | 14 |
| BP | gcaggaggcattgctgatga | 15 |
| LE | cacagccttggcagcgcTTTTTaggcataggacccgtgtct | 16 |
| LE | ccagtgagcttcccgttcaTTTTTaggcataggacccgtgtct | 17 |
| BP | GAGGGGGCAGAGATGATGAC | 18 |
| LE | tcttgaggctgttgtcatacttctTTTTTaggcataggacccgtgtct | 19 |
| CE | catggatgaccttggccagTTTTTctcttggaaagaaagt | 20 |
| BP | TGGAGAGCCCCGCGG | 21 |
| CE | gctcagggatgaccttgccTTTTTctcttggaaagaaagt | 22 |
| LE | ttctccatggtggtgaagacgTTTTTaggcataggacccgtgtct | 23 |
| LE | ccatcacgccacagtttccTTTTTaggcataggacccgtgtct | 24 |
| LE | gatgggatttccattgatgacaTTTTTaggcataggacccgtgtct | 25 |
| CE | gcaaatgagccccagccTTTTTctcttggaaagaaagt | 26 |
| CE | tctcgctcctggaagatggtTTTTTctcttggaaagaaagt | 27 |
| LE | cagtagaggcagggatgatgttcTTTTTaggcataggacccgtgtct | 28 |
| BP | TCAGCGCCAGCATCGC | 29 |

NM_020529 NFKBIA

| LE | ggcccagctgctgctgtatTTTTTaggcataggacccgtgtct | 631 |
|---|---|---|
| BP | CTGAGCATTGACATCAGCACC | 632 |
| CE | tgcgaggtgaagggcagtTTTTTctcttggaaagaaagt | 633 |
| CE | gtcctctgtgaactccgtgaacTTTTTctcttggaaagaaagt | 634 |
| LE | ggatagaggctaagtgtagacacgTTTTTaggcataggacccgtgtct | 635 |
| LE | ctctgttgacatcagccccaTTTTTaggcataggacccgtgtct | 636 |
| LE | cacttcaacaggagtgacaccagTTTTTaggcataggacccgtgtct | 637 |
| LE | ccggccattacagggctcTTTTTaggcataggacccgtgtct | 638 |
| LE | gtcaggattttgcaggtccacTTTTTaggcataggacccgtgtct | 639 |
| LE | tgtggccattgtagttggtagcTTTTTaggcataggacccgtgtct | 640 |
| BP | gccccaggtgagctggta | 641 |
| BP | TCATCCTCACTCTCTGGCAGC | 642 |
| LE | gacgctggcctccaaacaTTTTTaggcataggacccgtgtct | 643 |
| CE | cgatgcccaggtagccatTTTTTctcttggaaagaaagt | 644 |
| CE | gggagaatagccctggtaggtaaTTTTTctcttggaaagaaagt | 645 |
| BP | CGGGGTGGTGCAGGACT | 646 |
| CE | gccaggcagccctgctcTTTTTctcttggaaagaaagt | 647 |
| BP | CAAGGACACCAAAAGCTCCA | 648 |
| BP | CCGGGTGCTTGGGCG | 649 |
| CE | cttcaggatggagtggaggtgTTTTTctcttggaaagaaagt | 650 |
| LE | tctgactctgtgtcatagctctccTTTTTaggcataggacccgtgtct | 651 |
| LE | gagtcaggactcccacgctgTTTTTaggcataggacccgtgtct | 652 |
| BP | cacagtcatcatagggcagctc | 653 |

TABLE 5-continued

Apoptosis 2 probe set. Accession number and symbol are listed for each target, along with probe type and the sequence of the probe.

| Type | Sequence | SEQ ID NO: |
|---|---|---|
| LE | atctgaaggttttctagtgtcagctTTTTTaggcataggacccgtgtct | 654 |
| LE | ccctttgcactcataacgtcaTTTTTaggcataggacccgtgtct | 655 |

NM_002502 NFKB2

| BP | CGAGGTGGGTCACTGTGTGTTAC | 656 |
|---|---|---|
| LE | caggtccacctcgatcttggTTTTTaggcataggacccgtgtct | 657 |
| LE | tactcagatccatcaccttcttcaTTTTTaggcataggacccgtgtct | 658 |
| LE | ccagactgtgggcatgagcaTTTTTaggcataggacccgtgtct | 659 |
| LE | cgcacagagcctgctgtcttTTTTTaggcataggacccgtgtct | 660 |
| LE | gtccattcgagaaatcttcaggTTTTTaggcataggacccgtgtct | 661 |
| BP | gcccttctcactggaggcac | 662 |
| LE | actggctctaaggaaggcagaTTTTTaggcataggacccgtgtct | 663 |
| BP | AGGGGCCTTCACAGCCAT | 664 |
| BP | ctggtccctcgtagttacagatct | 665 |
| LE | tgggccccacagaaacgTTTTTaggcataggacccgtgtct | 666 |
| CE | atcgaaatcggaagcctctcTTTTTctcttggaaagaaagt | 667 |
| CE | cctccgtaaggccctgggTTTTTctcttggaaagaaagt | 668 |
| LE | tgacagtgggataggtctttcgTTTTTaggcataggacccgtgtct | 669 |
| BP | gaagcgcagccgcacta | 670 |
| BP | TGCCTCTGAAGTTTTTGTATCATAGT | 671 |
| BP | ttgctatcatggatgggctg | 672 |
| CE | gttctttggcctcttgctccTTTTTctcttggaaagaaagt | 673 |
| LE | ttaaattgggcagtcatgtcctTTTTTaggcataggacccgtgtct | 674 |
| LE | catgcaggacacccaggttgTTTTTaggcataggacccgtgtct | 675 |
| CE | ggaggtgactggcttcagggTTTTTctcttggaaagaaagt | 676 |
| BP | AGCTCCCGCTGCTCGG | 677 |
| LE | gcctagagcggagccgcTTTTTaggcataggacccgtgtct | 678 |
| CE | cgagcattgcttgcccaTTTTTctcttggaaagaaagt | 679 |
| LE | gcagggagaaggagccatcTTTTTaggcataggacccgtgtct | 680 |
| LE | gcgcagatccccagctcTTTTTaggcataggacccgtgtct | 681 |
| LE | ccccatcatgttcttcttagtcaTTTTTaggcataggacccgtgtct | 682 |
| CE | tttgatgccccggagatTTTTTctcttggaaagaaagt | 683 |
| LE | cgggcagtcctccatgggTTTTTaggcataggacccgtgtct | 684 |

NM_021975 RELA

| BP | AGGCCGAGGCCTGGC | 685 |
|---|---|---|
| LE | gctgaaactcggagttgtcgaTTTTTaggcataggacccgtgtct | 686 |
| CE | cgttccttccccagcctgTTTTTctcttggaaagaaagt | 687 |
| CE | acgtaaagggatagggctggTTTTTctcttggaaagaaagt | 688 |
| LE | ccatggtgggaaactcatcatTTTTTaggcataggacccgtgtct | 689 |
| LE | gtcttcatcatcaaactgcagctTTTTTaggcataggacccgtgtct | 690 |
| BP | GGTGCTGGCTTGGGGACA | 691 |
| BP | GGACTGGGACAGGGGCTG | 692 |
| CE | tgccctggttcagcagctTTTTTctcttggaaagaaagt | 693 |
| LE | ccaagcaaggcccccagTTTTTaggcataggacccgtgtct | 694 |
| CE | cggatgccaggtctgtgaacaTTTTTctcttggaaagaaagt | 695 |
| BP | gataccatggctggagcagg | 696 |
| BP | GGGCCTGGGCCAGAGCT | 697 |
| BP | GGTGGGCTTGGGGGCA | 698 |
| BP | GGTGGGGCCACAGCCTG | 699 |
| LE | gaaggtctcatatgtccttttacgtTTTTTaggcataggacccgtgtct | 700 |
| LE | gcgagttatagcctcagggtactcTTTTTaggcataggacccgtgtct | 701 |
| BP | CAGCTGGGTCTGTGCTGTTG | 702 |
| BP | ggcacagcaatgcgtcga | 703 |
| BP | AGGAGGGCCTGGGGCTA | 704 |
| BP | GGTGGAGGCCGGGGG | 705 |
| BP | GGCAGCGGCTGGAGCCT | 706 |
| BP | GGGGCAGGACTTGGGGA | 707 |
| CE | aggactcttcttcatgatgctcttTTTTTctcttggaaagaaagt | 708 |
| CE | tgatctgcccagaaggaaacaTTTTTctcttggaaagaaagt | 709 |
| BP | gcagcagggcctctgacag | 710 |
| LE | ttctcctcaatccggtgacgTTTTTaggcataggacccgtgtct | 711 |
| LE | ggcctctgggctgtcactagTTTTTaggcataggacccgtgtct | 712 |
| BP | GTGGGGGCCACAGGTA | 713 |
| BP | GAAGCTGAGCTGCGGGAA | 714 |
| BP | catcagcatgggctcagttgt | 715 |
| BP | GGGGCCGGGGCCA | 716 |
| LE | agttgatggtgctcagggatgTTTTTaggcataggacccgtgtct | 717 |
| LE | tcggtgggtccgctgaaTTTTTaggcataggacccgtgtct | 718 |

TABLE 5-continued

Apoptosis 2 probe set. Accession number and symbol are listed for each target, along with probe type and the sequence of the probe.

| Type | Sequence | SEQ ID NO: |
|---|---|---|
| NM_003998 NFKB1 | | |
| CE | ccaggattatagccccttatacaTTTTTctcttggaaagaaagt | 719 |
| BP | TGTCACATGAAGTATACCCAGGTTT | 720 |
| BP | TCTGGATTAAATATTGTATGAGTCAAAG | 721 |
| LE | gcgaagccgaccaccatTTTTTaggcataggacccgtgtct | 722 |
| LE | tttccatttgtgaccaactgaaTTTTTaggcataggacccgtgtct | 723 |
| CE | tcaggccttcccaaatatggTTTTTctcttggaaagaaagt | 724 |
| LE | catagttgcagattttgacctgagTTTTTaggcataggacccgtgtct | 725 |
| LE | ctgcttggcggattagctcTTTTTaggcataggacccgtgtct | 726 |
| CE | ggttgctctaatatttgaaggtatgTTTTTctcttggaaagaaagt | 727 |
| LE | aaggatccaaatgaaacatttgtTTTTTaggcataggacccgtgtct | 728 |
| LE | ggccatctgctgttggcaTTTTTaggcataggacccgtgtct | 729 |
| LE | gtgttttccaccaggctgtTTTTTaggcataggacccgtgtct | 730 |
| LE | ggtaagacttcttgttcttttcactagaTTTTTaggcataggacccgtgtct | 731 |
| LE | gtgccatctgtggttgaaatactTTTTTaggcataggacccgtgtct | 732 |
| BP | GGATGGGCCTTCACATACATAAC | 733 |
| LE | ggcaccaggtagtccaccatgTTTTTaggcataggacccgtgtct | 734 |
| BP | AGTGCAGATCCCATCCTCACA | 735 |
| CE | tttttcccgatctcccagcTTTTTctcttggaaagaaagt | 736 |
| BP | TCCAGTGTTTCAAATACTTTTTTCTT | 737 |
| BP | GGAAACGAAATCCTCTCTGTTTA | 738 |
| CE | gggcatgcaggtggatatttTTTTTctcttggaaagaaagt | 739 |
| LE | cttctgcttgcaaataggcaaTTTTTaggcataggacccgtgtct | 740 |
| LE | ggtcagggtgcaccaagagtTTTTTaggcataggacccgtgtct | 741 |
| LE | cgcctctgtcattcgtgctTTTTTaggcataggacccgtgtct | 742 |
| CE | gtccttgggtccagcagttacTTTTTctcttggaaagaaagt | 743 |
| BP | TGCCGGTCCCCTCCAC | 744 |
| LE | caataacctttgctggtcccaTTTTTaggcataggacccgtgtct | 745 |
| NM_006290 TNFAIP3 | | |
| BP | ggcgtcgtttccagctctg | 746 |
| CE | gggccttgaggtgctttgTTTTTctcttggaaagaaagt | 747 |
| LE | gatgctgacactccatgcagaTTTTTaggcataggacccgtgtct | 748 |
| BP | GCGCTGGCTCGATCTCAGTT | 749 |
| LE | gtgggactgactttccctgagTTTTTaggcataggacccgtgtct | 750 |
| BP | GAGTCCCAAAATACACGCAGC | 751 |
| LE | cgtccccgtcctgtcccTTTTTaggcataggacccgtgtct | 752 |
| CE | cgcgagggatctgacttggaTTTTTctcttggaaagaaagt | 753 |
| BP | GGCCCGGGCGCACTT | 754 |
| BP | TGCAAAAGCCCTTGTTTTCTG | 755 |
| LE | gccaggatgttcttgcaggaTTTTTaggcataggacccgtgtct | 756 |
| LE | acgctggtgacaggaaggagTTTTTaggcataggacccgtgtct | 757 |
| LE | caatgaaacacttctggcagtatcTTTTTaggcataggacccgtgtct | 758 |
| CE | catgaaatctctgattctgagcttTTTTTctcttggaaagaaagt | 759 |
| LE | ggaggctggtgctgaggcTTTTTaggcataggacccgtgtct | 760 |
| CE | gctcctcgctgcggcagTTTTTctcttggaaagaaagt | 761 |
| CE | cggcttttctgcacttgctTTTTTctcttggaaagaaagt | 762 |
| BP | TGGAGGAGGCCTCTGCTGT | 763 |
| LE | agatcccattaaatgtcctggtaTTTTTaggcataggacccgtgtct | 764 |
| LE | tgttctggaacctggacgctTTTTTaggcataggacccgtgtct | 765 |
| BP | TCTCTGTACTCGATGAAACACAGTG | 766 |
| LE | tgtggttcgaggcacatctctTTTTTaggcataggacccgtgtct | 767 |
| BP | TGGCAAGAATGCGGGGA | 768 |
| BP | GCAGCAGCAAAATGTTTGTTT | 769 |
| LE | agtccttttgaagcaagtactgcTTTTTaggcataggacccgtgtct | 770 |
| BP | CAGGAGTCCGTGCAGCTTG | 771 |
| LE | cttcaaacatggtgcttccaaTTTTTaggcataggacccgtgtct | 772 |
| LE | gctcttctgtcctttggcctTTTTTaggcataggacccgtgtct | 773 |
| BP | agacaggcagccagcagg | 774 |
| BP | GGGGCTCCGGACGAGC | 775 |
| CE | ccccaggcacggaatggTTTTTctcttggaaagaaagt | 776 |
| BP | GGGTGCCGCATTCCCT | 777 |
| NM_000600 IL6 | | |
| BP | TCTAGGTATACCTCAAACTCCAAAG | 778 |
| LE | atgtaccgaatttgtttgtcaattTTTTTaggcataggacccgtgtct | 779 |
| CE | cgttctgaagaggtgagtggctTTTTTctcttggaaagaaagt | 780 |
| LE | caagtctcctcattgaatccagatTTTTTaggcataggacccgtgtct | 781 |

TABLE 5-continued

Apoptosis 2 probe set. Accession number and symbol are listed for each target, along with probe type and the sequence of the probe.

| Type | Sequence | SEQ ID NO: |
|---|---|---|
| LE | aacaacataagttctgtgcccagTTTTTaggcataggacccgtgtct | 782 |
| BP | CCATCTTTGGAAGGTTCAGGT | 783 |
| CE | cctttttctgcaggaactggatTTTTTctcttggaaagaaagt | 784 |
| LE | catctttggaatcttctcctggTTTTTaggcataggacccgtgtct | 785 |
| LE | caggacttttgtactcatctgcacTTTTTaggcataggacccgtgtct | 786 |
| LE | ttgttacatgtctcctttctcaggTTTTTaggcataggacccgtgtct | 787 |
| CE | gctgagatgccgtcgaggTTTTTctcttggaaagaaagt | 788 |
| BP | TGCTGCTTTCACACATGTTACTC | 789 |
| LE | tggaagcatccatcttttcagTTTTTaggcataggacccgtgtct | 790 |
| CE | ccttaaagctgcgcagaatgTTTTTctcttggaaagaaagt | 791 |
| BP | GGGTACTGGGGCAGGGAA | 792 |
| BP | GTCTGTGTGGGGCGGCTA | 793 |
| BP | ccactggttctgtgcctgca | 794 |
| LE | agatgagttgtcatgtcctgcagTTTTTaggcataggacccgtgtct | 795 |
| LE | accagtgatgattttcaccaggTTTTTaggcataggacccgtgtct | 796 |
| LE | ggcagcaggcaacaccagTTTTTaggcataggacccgtgtct | 797 |
| LE | acatttgccgaagagccctTTTTTaggcataggacccgtgtct | 798 |
| LE | catttgtggttgggtcagggTTTTTaggcataggacccgtgtct | 799 |
| BP | AAGGAATGCCCATTAACAACAA | 800 |
| LE | tggacaggtttctgaccagaagTTTTTaggcataggacccgtgtct | 801 |
| LE | tgttttctgccagtgcctcttTTTTTaggcataggacccgtgtct | 802 |
| LE | actctcaaatctgttctggaggtacTTTTTaggcataggacccgtgtct | 803 |
| LE | agctctggcttgttcctcactTTTTTaggcataggacccgtgtct | 804 |
| CE | cgctcatacttttagttctccatagagTTTTTctcttggaaagaaagt | 805 |
| CE | caatctgaggtgcccatgctTTTTTctcttggaaagaaagt | 806 |
| LE | caggctggactgcaggaactTTTTTaggcataggacccgtgtct | 807 |
| LE | gtggttattgcatctagattctttgTTTTTaggcataggacccgtgtct | 808 |
| BP | gcttcgtcagcaggctgg | 809 |

NM_000594 TNF

| Type | Sequence | SEQ ID NO: |
|---|---|---|
| CE | cgagaagatgatctgactgcctgTTTTTctcttggaaagaaagt | 810 |
| LE | cagaagaggttgagggtgtctgaTTTTTaggcataggacccgtgtct | 811 |
| LE | gcggctgatggtgtgggTTTTTaggcataggacccgtgtct | 812 |
| LE | aggtacaggccctctgatggTTTTTaggcataggacccgtgtct | 813 |
| CE | gctgcccctcagcttgagTTTTTctcttggaaagaaagt | 814 |
| CE | tcgggccgattgatctcaTTTTTctcttggaaagaaagt | 815 |
| LE | ggcggttcagccactggaTTTTTaggcataggacccgtgtct | 816 |
| BP | AGGCTTGTCACTCGGGGTT | 817 |
| BP | tctccagctggaagacccc | 818 |
| BP | caccaccagctggttatctctc | 819 |
| LE | ggccagagggctgattagagaTTTTTaggcataggacccgtgtct | 820 |
| BP | AGGAGGGGGTAATAAAGGGAT | 821 |
| LE | ggtttgctacaacatgggctacTTTTTaggcataggacccgtgtct | 822 |
| LE | agactcggcaaagtcgagatagTTTTTaggcataggacccgtgtct | 823 |
| CE | cccccaattctcttttttgagcTTTTTctcttggaaagaaagt | 824 |
| BP | TGGCAGGGGCTCTTGATG | 825 |
| CE | gtctggtaggagacggcgatTTTTTctcttggaaagaaagt | 826 |
| LE | gcttgggttccgaccctaagTTTTTaggcataggacccgtgtct | 827 |
| BP | TGGGGCAGGGGAGGC | 828 |
| BP | GTTTGGGAAGGTTGGATGTTC | 829 |
| LE | atcccaaagtagacctgcccTTTTTaggcataggacccgtgtct | 830 |
| BP | CCCCTCTGGGGTCTCCCTC | 831 |
| LE | caggagggcattggcccTTTTTaggcataggacccgtgtct | 832 |
| LE | gcagagaggaggttgaccttgTTTTTaggcataggacccgtgtct | 833 |
| LE | gtcctcctcacagggcaatgTTTTTaggcataggacccgtgtct | 834 |
| CE | tcccagatagatgggctcatacTTTTTctcttggaaagaaagt | 835 |
| LE | cagggcttggcctcagcTTTTTaggcataggacccgtgtct | 836 |
| LE | tgaggagcacatgggtggagTTTTTaggcataggacccgtgtct | 837 |
| BP | tgaagaggacctgggagtagatg | 838 |
| BP | GCGCTGAGTCGGTCACCCT | 839 |
| LE | agctccacgccattggcTTTTTaggcataggacccgtgtct | 840 |
| BP | GGGCAGCCTTGGCCCT | 841 |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of detecting at least a first target nucleic acid, the method comprising:
   providing a sample comprising whole blood, which whole blood comprises peripheral blood cells;
   lysing the peripheral blood cells in the whole blood to produce a whole blood lysate, which whole blood lysate comprises the first target nucleic acid;
   contacting the peripheral blood cells and/or the whole blood lysate with an exogenously supplied protease;
   contacting the first target nucleic acid with a first set of n capture extenders, wherein n is at least two, which first set of capture extenders is capable of hybridizing to the first target nucleic acid, wherein contacting the first target nucleic acid with the first set of capture extenders comprises contacting the whole blood lysate with the first set of capture extenders;
   hybridizing the first target nucleic acid to the first set of capture extenders;
   providing a solid support, wherein a first capture probe is bound to the solid support;
   associating the first set of capture extenders with the solid support by hybridizing the capture extenders to the first capture probe at a hybridization temperature which is greater than a melting temperature ($T_m$) of a complex between each individual capture extender and the capture probe,
   whereby hybridizing the first target nucleic acid to the first set of capture extenders and associating the first set of capture extenders with the solid support captures the first target nucleic acid on the solid support; and
   detecting, while the first target nucleic acid is captured on the solid support, the presence of the first target nucleic acid on the solid support.

2. The method of claim 1, wherein the first target nucleic acid is an RNA.

3. The method of claim 1, wherein the first target nucleic acid is a DNA.

4. The method of claim 1, wherein the peripheral blood cells comprise white blood cells, one or more of which white blood cells comprises the first target nucleic acid.

5. The method of claim 1, wherein n is at least three.

6. The method of claim 1, wherein n is at most 10.

7. The method of claim 1, wherein the solid support is a substantially planar solid support.

8. The method of claim 1, wherein the solid support comprises a plurality of particles.

9. The method of claim 1, wherein the whole blood lysate comprises a second target nucleic acid, and wherein a second capture probe is bound to the solid support, the method comprising:
   contacting the second target nucleic acid with a second set of m capture extenders, wherein m is at least two, which second set of capture extenders is capable of hybridizing to the second target nucleic acid, wherein contacting the second target nucleic acid with the second set of capture extenders comprises contacting the second set of capture extenders with the whole blood lysate;
   hybridizing the second target nucleic acid to the second set of capture extenders;
   associating the second set of capture extenders with the solid support by hybridizing the capture extenders of the second set to the second capture probe at a hybridization temperature which is greater than a melting temperature ($T_m$) of a complex between each individual capture extender and the capture probe,
   whereby hybridizing the second target nucleic acid to the second set of capture extenders and associating the second set of capture extenders with the solid support captures the second target nucleic acid on the solid support; and
   detecting, while the second target nucleic acid is captured on the solid support, the presence of the second target nucleic acid on the solid support.

10. The method of claim 9, wherein the solid support is a substantially planar solid support; wherein the first capture probe is predisposed at a first selected position on the solid support, whereby the first target nucleic acid is captured at the first selected position on the solid support; and wherein the second capture probe is predisposed at a second selected position on the solid support, whereby the second target nucleic acid is captured at the second selected position on the solid support.

11. The method of claim 9, wherein the solid support comprises a population of particles, the population comprising at least two sets of particles, the particles in each set being distinguishable from the particles in every other set; wherein the first target nucleic acid is captured on a first set of the particles, which first set of particles comprises the first capture probe; and wherein the second target nucleic acid is captured on a second set of the particles, which second set of particles comprises the second capture probe.

12. The method of claim 1, wherein detecting the presence of the first target nucleic acid on the solid support comprises hybridizing a first set of one or more label extenders and a label probe system comprising a label to the first target nucleic acid and detecting the presence of the label on the solid support.

13. The method of claim 12, wherein the label probe system comprises an amplification multimer and a plurality of label probes, wherein the amplification multimer is capable of hybridizing simultaneously to a label extender and to a plurality of label probes.

14. The method of claim 13, wherein the label probe comprises the label.

15. The method of claim 12, wherein the label is a fluorescent label, and wherein detecting the presence of the label on the solid support comprises detecting a fluorescent signal from the label.

16. The method of claim 12, wherein the label is an enzyme.

17. The method of claim 1, wherein detecting the presence of the first target nucleic acid on the solid support comprises detecting an amount of the first target nucleic acid on the solid support.

18. The method of claim 1, comprising separating materials not captured on the solid support from the solid support.

19. The method of claim 1, wherein the exogenously supplied protease is proteinase K at a concentration of at least 1 mg per ml of the whole blood lysate.

20. The method of claim 1, wherein the volume of the whole blood in which the peripheral blood cells are lysed is at most ⅕ the volume of the resulting whole blood lysate.

21. A method of detecting at least a first target nucleic acid, the method comprising:
providing a sample comprising whole blood, which whole blood comprises peripheral blood cells;
applying the whole blood to a matrix to produce a blood spot;
drying the blood spot to produce a dried blood spot;
lysing the peripheral blood cells to produce a lysate, which lysate comprises the first target nucleic acid, by contacting the dried blood spot with an aqueous solution to produce the lysate;
contacting the peripheral blood cells and/or the lysate with an exogenously supplied protease;
contacting the first target nucleic acid with a first set of n capture extenders, wherein n is at least two, which first set of capture extenders is capable of hybridizing to the first target nucleic acid, wherein contacting the first target nucleic acid with the first set of capture extenders comprises contacting the lysate with the first set of capture extenders;
hybridizing the first target nucleic acid to the first set of capture extenders;
providing a solid support, wherein a first capture probe is bound to the solid support;
associating the first set of capture extenders with the solid support by hybridizing the capture extenders to the first capture probe at a hybridization temperature which is greater than a melting temperature ($T_m$) of a complex between each individual capture extender and the capture probe,
whereby hybridizing the first target nucleic acid to the first set of capture extenders and associating the first set of capture extenders with the solid support captures the first target nucleic acid on the solid support; and
detecting, while the first target nucleic acid is captured on the solid support, the presence of the first target nucleic acid on the solid support.

22. The method of claim 9, wherein the whole blood lysate comprises five or more target nucleic acids, and wherein five or more capture probes are bound to the solid support, the method comprising:
contacting each of the target nucleic acids with a corresponding set of at least two capture extenders capable of hybridizing to the target nucleic acid, by contacting the sets of capture extenders with the whole blood lysate;
hybridizing each of the target nucleic acids to its corresponding set of capture extenders;
associating each set of capture extenders with the solid support by hybridizing the capture extenders of each set to their corresponding capture probe at a hybridization temperature which is greater than a melting temperature ($T_m$) of a complex between each individual capture extender and the capture probe,
whereby the target nucleic acids are captured on the solid support; and
detecting, while the target nucleic acids are captured on the solid support, the presence of the target nucleic acids on the solid support.

23. The method of claim 1, wherein the presence of the label on the solid support, and therefore the presence of the first target nucleic acid on the solid support, is detectable when as few as 6000 copies of the first target nucleic acid are present in the whole blood lysate.

24. The method of claim 21, wherein the lysate comprises five or more target nucleic acids, and wherein five or more capture probes are bound to the solid support, the method comprising:
contacting each of the target nucleic acids with a corresponding set of at least two capture extenders capable of hybridizing to the target nucleic acid, by contacting the sets of capture extenders with the lysate;
hybridizing each of the target nucleic acids to its corresponding set of capture extenders;
associating each set of capture extenders with the solid support by hybridizing the capture extenders of each set to their corresponding capture probe at a hybridization temperature which is greater than a melting temperature ($T_m$) of a complex between each individual capture extender and the capture probe,
whereby the target nucleic acids are captured on the solid support; and
detecting, while the target nucleic acids are captured on the solid support, the presence of the target nucleic acids on the solid support.

* * * * *

SEQUENCE LISTING

<160> NUMBER OF SEQ ID NOS: 841

<210> SEQ ID NO 1
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 1
cacttcactt tctttccaag ag                                              22

<210> SEQ ID NO 2
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 2
aagtacgaca accacatc                                                   18

<210> SEQ ID NO 3
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 3
cggaggggcc atccac                                                     16

<210> SEQ ID NO 4
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 4
cccacttgat tttggaggga tttttaggca taggacccgt gtct                      44

<210> SEQ ID NO 5
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 5
agcttcccgt tctcagcctt ttttctcttg gaaagaaagt                           40

<210> SEQ ID NO 6
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 6
ccttccacga taccaaagtt gttttttagg cataggaccc gtgtct                    46

-continued

<210> SEQ ID NO 7
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 7 cctttggct cccccctttt ttctcttgga aagaaagt                     38

<210> SEQ ID NO 8
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 8
ccagtggact ccacgacgta cttttaggc ataggacccg tgtct             45

<210> SEQ ID NO 9
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 9
tgacggtgcc atggaatttt ttttctcttg gaaagaaagt                  40

<210> SEQ ID NO 10
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 10
ggcatggact gtggtcatga gttttttagg cataggaccc gtgtct           46

<210> SEQ ID NO 11
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 11
gggtgctaag cagttggtgg tttttaggc ataggacccg tgtct             45

<210> SEQ ID NO 12
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 12
agtcttctgg gtggcagtga tttttaggc ataggacccg tgtct             45

<210> SEQ ID NO 13
<211> LENGTH: 18
<212> TYPE: DNA
<213> ORGANISM: Artificial
<220> FEATURE:
<223> OTHER INFORMATION: synthetic oligonucleotide probe -continued

```
<400> SEQUENCE: 13
aacatggggg catcagca                                                    18

<210> SEQ ID NO 14
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 14
catggttcac acccatgacg                                                  20

<210> SEQ ID NO 15
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 15
gcaggaggca ttgctgatga                                                  20

<210> SEQ ID NO 16
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 16
cacagccttg gcagcgcttt ttaggcatag gacccgtgtc t                          41

<210> SEQ ID NO 17
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 17
ccagtgagct tcccgttcat ttttaggcat aggacccgtg tct                        43

<210> SEQ ID NO 18
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 18
gagggggcag agatgatgac                                                  20

<210> SEQ ID NO 19
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 19
tcttgaggct gttgtcatac ttctttttta ggcataggac ccgtgtct                   48
```

```
<210> SEQ ID NO 20
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 20
catggatgac cttggccagt ttttctcttg gaaagaaagt                              40

<210> SEQ ID NO 21
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 21
tggagagccc cgcgg                                                        15

<210> SEQ ID NO 22
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 22
gctcagggat gaccttgcct ttttctcttg gaaagaaagt                              40

<210> SEQ ID NO 23
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 23
ttctccatgg tggtgaagac gttttaggc ataggacccg tgtct                         45

<210> SEQ ID NO 24
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 24
ccatcacgcc acagtttcct ttttaggcat aggacccgtg tct                          43

<210> SEQ ID NO 25
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 25
gatgggattt ccattgatga cattttagg cataggaccc gtgtct                        46

<210> SEQ ID NO 26
<211> LENGTH: 38
<212> TYPE: DNA
<213> ORGANISM: Artificial
<220> FEATURE:
<223> OTHER INFORMATION: synthetic oligonucleotide probe
```

-continued

<400> SEQUENCE: 26
gcaaatgagc cccagccttt ttctcttgga aagaaagt                                38

<210> SEQ ID NO 27
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 27
tctcgctcct ggaagatggt tttttctctt ggaaagaaag t                            41

<210> SEQ ID NO 28
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 28
cagtagaggc agggatgatg ttcttttag gcataggacc cgtgtct                       47

<210> SEQ ID NO 29
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 29
tcagcgccag catcgc                                                        16

<210> SEQ ID NO 30
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 30
aattcttgca caaatatttg atgcttttta ggcataggac ccgtgtct                     48

<210> SEQ ID NO 31
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 31
gaaattcaaa tttaaccagg aatctttttt aggcatagga cccgtgtct                    49

<210> SEQ ID NO 32
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 32
tgtattgcat ctggcaaccc tatttttagg cataggaccc gtgtct                       46

-continued

```
<210> SEQ ID NO 33
<211> LENGTH: 26
<212> TYPE: DNA
<213> ORGANISM: Artificial
<220> FEATURE:
<223> OTHER INFORMATION: synthetic oligonucleotide probe

<400> SEQUENCE: 33
agtgttgaag tagatttgct tgaagt                                        26

<210> SEQ ID NO 34
<211> LENGTH: 30
<212> TYPE: DNA
<213> ORGANISM: Artificial
<220> FEATURE:
<223> OTHER INFORMATION: synthetic oligonucleotide probe

<400> SEQUENCE: 34
aagttacact tgaaaataat ttatgttatg                                    30

<210> SEQ ID NO 35
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 35
ggtaagatgg tggctaatac tttttttttt aggcatagga cccgtgtct               49

<210> SEQ ID NO 36
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 36
aaaaaatcca ggatttccag ct                                            22

<210> SEQ ID NO 37
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 37
ctagggttgc cagatttaac aga                                           23

<210> SEQ ID NO 38
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 38
catgtcctca caacatcact gtga                                          24

<210> SEQ ID NO 39
<211> LENGTH: 25
<212> TYPE: DNA
<213> ORGANISM: Artificial
<220> FEATURE:
<223> OTHER INFORMATION: synthetic oligonucleotide probe
```

-continued

<400> SEQUENCE: 39
ccacttagaa ataaaggaga aacca                                        25

<210> SEQ ID NO 40
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 40
tgcacccagt tttccttggt ttttctcttg gaaagaaagt                        40

<210> SEQ ID NO 41
<211> LENGTH: 29
<212> TYPE: DNA
<213> ORGANISM: Artificial
<220> FEATURE:
<223> OTHER INFORMATION: synthetic oligonucleotide probe

<400> SEQUENCE: 41
gtacaatgaa aaactattca ttgtttact                                    29

<210> SEQ ID NO 42
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 42
ggtccagaca gagctctctt ccttttagg cataggaccc gtgtct                  46

<210> SEQ ID NO 43
<211> LENGTH: 31
<212> TYPE: DNA
<213> ORGANISM: Artificial
<220> FEATURE:
<223> OTHER INFORMATION: synthetic oligonucleotide probe

<400> SEQUENCE: 43 tttttttgtag attcaaataa ataatactttt a                               31

<210> SEQ ID NO 44
<211> LENGTH: 26
<212> TYPE: DNA
<213> ORGANISM: Artificial
<220> FEATURE:
<223> OTHER INFORMATION: synthetic oligonucleotide probe

<400> SEQUENCE: 44
gcttcaaata tcacattcta gcaaac                                       26

<210> SEQ ID NO 45
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 45
caaaaacttc tccacaaccc tc                                           22

<210> SEQ ID NO 46
<211> LENGTH: 52
<212> TYPE: DNA
<213> ORGANISM: Artificial
<220> FEATURE:
<223> OTHER INFORMATION: synthetic oligonucleotide probe

<400> SEQUENCE: 46
catataagta tgttctggat atttcatgtt tttaggcata ggacccgtgt ct         52

<210> SEQ ID NO 47
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 47
ccattcaatt cctgaaatta aagttttttt aggcatagga cccgtgtct             49

<210> SEQ ID NO 48
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 48
ttggatacca cagagaatga atttttttta ggcataggac ccgtgtct              48

<210> SEQ ID NO 49
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 49
ttctcccgtg caatatctag gattttagg cataggaccc gtgtct                 46

<210> SEQ ID NO 50
<211> LENGTH: 31
<212> TYPE: DNA
<213> ORGANISM: Artificial
<220> FEATURE:
<223> OTHER INFORMATION: synthetic oligonucleotide probe

<400> SEQUENCE: 50
ataaaacatc atttaatatc taaaataaaa t                                31

<210> SEQ ID NO 51
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 51
caacagaccc acacaataca tga                                         23

<210> SEQ ID NO 52
<211> LENGTH: 47
<212> TYPE: DNA
<213> ORGANISM: Artificial
<220> FEATURE:
<223> OTHER INFORMATION: synthetic oligonucleotide probe -continued

<400> SEQUENCE: 52
ttcactggca tcttcactga ttcttttag gcataggacc cgtgtct        47

<210> SEQ ID NO 53
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 53
caatgattca tcttctattt ttccattttt aggcatagga cccgtgtct    49

<210> SEQ ID NO 54
<211> LENGTH: 57
<212> TYPE: DNA
<213> ORGANISM: Artificial
<220> FEATURE:
<223> OTHER INFORMATION: synthetic oligonucleotide probe

<400> SEQUENCE: 54
aaatttacta taacatcttt ataactattc aattttttag gcataggacc cgtgtct    57

<210> SEQ ID NO 55
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 55
aggcacagtg gaacaaggac ttttttaggc ataggacccg tgtct    45

<210> SEQ ID NO 56
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 56
cggatattct cttggccctt ttttctctt ggaaagaaag t    41

<210> SEQ ID NO 57
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 57
ttttatgaat tctcagccct cttttttct cttggaaaga aagt    44

<210> SEQ ID NO 58
<211> LENGTH: 26
<212> TYPE: DNA
<213> ORGANISM: Artificial
<220> FEATURE:
<223> OTHER INFORMATION: synthetic oligonucleotide probe

<400> SEQUENCE: 58
taaaaaccct gattgaaatt tatcta    26

-continued

<210> SEQ ID NO 59
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 59
ggcctcaatt ttgctatttg tatattttta ggcataggac ccgtgtct        48

<210> SEQ ID NO 60
<211> LENGTH: 33
<212> TYPE: DNA
<213> ORGANISM: Artificial
<220> FEATURE:
<223> OTHER INFORMATION: synthetic oligonucleotide probe

<400> SEQUENCE: 60
ttaaataaat acataaataa taaataggtt aat        33

<210> SEQ ID NO 61
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 61
atgaaaaaac ttaaagtgct tcca        24

<210> SEQ ID NO 62
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 62
tgtggatcct ggctagcaga ttttctctt ggaaagaaag t        41

<210> SEQ ID NO 63
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 63
attgtcccat cattttatg tgattttta ggcataggac ccgtgtct        48

<210> SEQ ID NO 64
<211> LENGTH: 29
<212> TYPE: DNA
<213> ORGANISM: Artificial
<220> FEATURE:
<223> OTHER INFORMATION: synthetic oligonucleotide probe

<400> SEQUENCE: 64
aaatccttat atttaaaaat tatttgttg        29

<210> SEQ ID NO 65
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 65
acccaattgt tgtttgttt aatctttttc tcttggaaag aaagt                45

<210> SEQ ID NO 66
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 66
aaatttgact ttatggcaaa attttttta ggcataggac ccgtgtct             48

<210> SEQ ID NO 67
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 67
ctgcaggaac tccttaaagc tg                                         22

<210> SEQ ID NO 68
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 68
aactggaccg aaggcgcttt tttaggcata ggacccgtgt ct                   42

<210> SEQ ID NO 69
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 69
aagttctgtg cccagtggac atttttaggc ataggacccg tgtct                45

<210> SEQ ID NO 70
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 70
tgtgcctgca gcttcgtcat ttttaggcat aggacccgtg tct                  43

<210> SEQ ID NO 71
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 71
ctgcaggaac tggatcagga cttttaggc ataggacccg tgtct                 45

-continued

```
<210> SEQ ID NO 72
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 72
cctcaaactc caaaagacca gtg                                          23

<210> SEQ ID NO 73
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 73
gcatctagat tctttgcctt ttttttttag gcataggacc cgtgtct                47

<210> SEQ ID NO 74
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 74
gagcttctct ttcgttcccg tttttctctt ggaaagaaag t                      41

<210> SEQ ID NO 75
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 75
agccccaggg agaaggcttt ttctcttgga aagaaagt                          38

<210> SEQ ID NO 76
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 76
gaatttgttt gtcaattcgt tctgttttta ggcataggac ccgtgtct               48

<210> SEQ ID NO 77
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 77
gatgccgtcg aggatgtacc tttttaggca taggacccgt gtct                   44

<210> SEQ ID NO 78
<211> LENGTH: 22
<212> TYPE: DNA
<213> ORGANISM: Artificial
<220> FEATURE:
<223> OTHER INFORMATION: synthetic oligonucleotide probe
```

-continued

```
<400> SEQUENCE: 78
tttggaaggt tcaggttgtt tt                                    22

<210> SEQ ID NO 79
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 79
tgtggagaag gagttcatag ctgttttct cttggaaaga aagt              44

<210> SEQ ID NO 80
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 80
ggcttgttcc tcactactct caatttttag gcataggacc cgtgtct          47

<210> SEQ ID NO 81
<211> LENGTH: 51
<212> TYPE: DNA
<213> ORGANISM: Artificial
<220> FEATURE:
<223> OTHER INFORMATION: synthetic oligonucleotide probe

<400> SEQUENCE: 81
atctgttctg gaggtactct aggtatattt ttaggcatag gacccgtgtc t     51

<210> SEQ ID NO 82
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 82
ttttgtactc atctgcacag ctcttttta ggcataggac ccgtgtct          48

<210> SEQ ID NO 83
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 83
gcaggcaaca ccaggagctt tttaggcata ggacccgtgt ct               42

<210> SEQ ID NO 84
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 84
ggtttctgac cagaagaagg aatgttttta ggcataggac ccgtgtct         48
```

```
<210> SEQ ID NO 85
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 85
tgcccatgct acatttgcct ttttaggcat aggacccgtg tct                43

<210> SEQ ID NO 86
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 86
aagaggtgag tggctgtctg tgtttttagg cataggaccc gtgtct             46

<210> SEQ ID NO 87
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 87
tggggcggct acatcttt                                            18

<210> SEQ ID NO 88
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 88
gcatccatct ttttcagcca tctttttagg cataggaccc gtgtct             46

<210> SEQ ID NO 89
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 89
atgattttca ccaggcaagt ctttttagg cataggaccc gtgtct              46

<210> SEQ ID NO 90
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 90
tgtctccttt ctcagggctg attttctct tggaaagaaa gt                  42

<210> SEQ ID NO 91
<211> LENGTH: 16
<212> TYPE: DNA
<213> ORGANISM: Artificial
<220> FEATURE:
<223> OTHER INFORMATION: synthetic oligonucleotide probe
```

```
<400> SEQUENCE: 91
tggggcaggg aaggca                                                    16

<210> SEQ ID NO 92
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 92
gcaggctggc atttgtggtt tttaggcata ggacccgtgt ct                        42

<210> SEQ ID NO 93
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 93
ctgccagtgc ctctttgctt ttttaggcat aggacccgtg tct                       43

<210> SEQ ID NO 94
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 94
tgtcctgcag ccactggttc tttttaggca taggacccgt gtct                      44

<210> SEQ ID NO 95
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 95
gaagagccct caggctggat ttttctcttg gaaagaaagt                           40

<210> SEQ ID NO 96
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 96
cccattaaca acaacaatct gagg                                           24

<210> SEQ ID NO 97
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 97
ttgggtcagg ggtggttatt                                                20
```

```
<210> SEQ ID NO 98
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 98
ggaatcttct cctgggggta c                                              21

<210> SEQ ID NO 99
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 99
cgcagaatga gatgagttgt cattttttagg cataggaccc gtgtct                   46

<210> SEQ ID NO 100
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 100
ggctcctgga ggcgagatat ttttaggcat aggaccctg tct                        43

<210> SEQ ID NO 101
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 101
cctcattgaa tccagattgg aattttttctc ttggaaagaa agt                      43

<210> SEQ ID NO 102
<211> LENGTH: 27
<212> TYPE: DNA
<213> ORGANISM: Artificial
<220> FEATURE:
<223> OTHER INFORMATION: synthetic oligonucleotide probe

<400> SEQUENCE: 102
gctttcacac atgttactct tgttaca                                         27

<210> SEQ ID NO 103
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 103
aaatgcctaa gaaaagagtt cca                                             23

<210> SEQ ID NO 104
<211> LENGTH: 28
<212> TYPE: DNA
<213> ORGANISM: Artificial
<220> FEATURE:
<223> OTHER INFORMATION: synthetic oligonucleotide probe
```

<400> SEQUENCE: 104
tgcattaaaa tatttcttaa ggttttct                                    28

<210> SEQ ID NO 105
<211> LENGTH: 27
<212> TYPE: DNA
<213> ORGANISM: Artificial
<220> FEATURE:
<223> OTHER INFORMATION: synthetic oligonucleotide probe

<400> SEQUENCE: 105
aaaaagtttg aagtaaaagg agacaat                                     27

<210> SEQ ID NO 106
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 106
gcttctttta catatgggtc ctggtttta ggcataggac ccgtgtct               48

<210> SEQ ID NO 107
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 107
gcaggcagga caaccattac tgtttttagg cataggaccc gtgtct                46

<210> SEQ ID NO 108
<211> LENGTH: 33
<212> TYPE: DNA
<213> ORGANISM: Artificial
<220> FEATURE:
<223> OTHER INFORMATION: synthetic oligonucleotide probe

<400> SEQUENCE: 108
aataaataga tttagattta aaattcaaat att                              33

<210> SEQ ID NO 109
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 109
aaaaacttga cattcatgtc ttcctttta ggcataggac ccgtgtct               48

<210> SEQ ID NO 110
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 110
ggatgctctt cgaccttgaa ac                                          22

<210> SEQ ID NO 111
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 111
tctcgtttct ttttgttgct attgtttttc tcttggaaag aaagt            45

<210> SEQ ID NO 112
<211> LENGTH: 54
<212> TYPE: DNA
<213> ORGANISM: Artificial
<220> FEATURE:
<223> OTHER INFORMATION: synthetic oligonucleotide probe

<400> SEQUENCE: 112
aatacttatt tgattgatga gtctaaaaat tttttaggca taggacccgt gtct            54

<210> SEQ ID NO 113
<211> LENGTH: 51
<212> TYPE: DNA
<213> ORGANISM: Artificial
<220> FEATURE:
<223> OTHER INFORMATION: synthetic oligonucleotide probe

<400> SEQUENCE: 113
atattcccca tataaataat gttaaatatt tttttctctt ggaaagaaag t            51

<210> SEQ ID NO 114
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 114
ttggctctgc attattttc tgttttttct cttggaaaga aagt            44

<210> SEQ ID NO 115
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 115
tggacattca agtcagttac cgattttag gcataggacc cgtgtct            47

<210> SEQ ID NO 116
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 116
agcatctgac tccttttcg cttttaggc ataggacccg tgtct            45

<210> SEQ ID NO 117
<211> LENGTH: 27
<212> TYPE: DNA
<213> ORGANISM: Artificial
<220> FEATURE:
<223> OTHER INFORMATION: synthetic oligonucleotide probe

```
<400> SEQUENCE: 117
gatgctctgg tcatctttaa agttttt                                    27

<210> SEQ ID NO 118
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 118
ataattagtc agcttttcga agtcattttt aggcatagga cccgtgtct            49

<210> SEQ ID NO 119
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 119
cgacagttca gccatcactt ggttttagg cataggaccc gtgtct                46

<210> SEQ ID NO 120
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 120
ttatccgcta catctgaatg accttttag gcataggacc cgtgtct                47

<210> SEQ ID NO 121
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 121
atgagttcat gtattgcttt gcgttttttc tcttggaaag aaagt                 45

<210> SEQ ID NO 122
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 122
ttgatggtct ccacactctt ttgttttag gcataggacc cgtgtct                47

<210> SEQ ID NO 123
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 123
ttccctgttt tagctgctgg tttttctctt ggaaagaaag t                     41
```

```
<210> SEQ ID NO 124
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 124
cactctcctc tttccaattc ttcatttttt tctcttggaa agaaagt          47

<210> SEQ ID NO 125
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 125
gcagtgtctc tactcaggtt caggttttta ggcataggac ccgtgtct         48

<210> SEQ ID NO 126
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 126
ccgcaggccc tgcttg                                            16

<210> SEQ ID NO 127
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 127
gggctgggcg agcgg                                             15

<210> SEQ ID NO 128
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 128
gggttgcaca ggaagtttcc tttttaggca taggacccgt gtct             44

<210> SEQ ID NO 129
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 129
caggccacag tgcccaagtt tttaggcata ggacccgtgt ct               42

<210> SEQ ID NO 130
<211> LENGTH: 18
<212> TYPE: DNA
<213> ORGANISM: Artificial
<220> FEATURE:
<223> OTHER INFORMATION: synthetic oligonucleotide probe
```

```
<400> SEQUENCE: 130 gggggttggag ggcagtgc                                                18

<210> SEQ ID NO 131
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 131
tcatggtcaa ggggccct                                                 18

<210> SEQ ID NO 132
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 132
agcagaaagt ccttcaggtt ctcttttag gcataggacc cgtgtct                  47

<210> SEQ ID NO 133
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 133
tgagcttggt gaggctgcct ttttctcttg gaaagaaagt                         40

<210> SEQ ID NO 134
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 134
agcagcaggc tctgcagctt tttctcttgg aaagaaagt                          39

<210> SEQ ID NO 135
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 135
tgtaggcagg tcggctcctt ttttaggcat aggacccgtg tct                     43

<210> SEQ ID NO 136
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 136
tttgaaactt tcaaaggtga taatcttttt taggcatagg acccgtgtct              50
```

```
<210> SEQ ID NO 137
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 137
tggatggcat tcacatgctc tttttaggca taggacccgt gtct            44

<210> SEQ ID NO 138
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 138
ccagggctgc gtgctg                                            16

<210> SEQ ID NO 139
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 139
tacagctcca ggcgggtctt tttctcttgg aaagaaagt                   39

<210> SEQ ID NO 140
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 140
ctcactcctg gactggctcc tttttaggca taggacccgt gtct            44

<210> SEQ ID NO 141
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 141
cagcagtcaa agggatgac a                                       21

<210> SEQ ID NO 142
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 142
ttctactgtt tcattcatct cagcattttt aggcatagga cccgtgtct        49

<210> SEQ ID NO 143
<211> LENGTH: 49
<212> TYPE: DNA
<213> ORGANISM: Artificial
<220> FEATURE:
<223> OTHER INFORMATION: synthetic oligonucleotide probe
```

```
<400> SEQUENCE: 143
ggaggtcaaa catttctgag atgactttt aggcatagga cccgtgtct          49

<210> SEQ ID NO 144
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 144
agacgccggg cctcc                                              15

<210> SEQ ID NO 145
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 145
gcgggtgcag agatgctgtt tttctcttgg aaagaaagt                    39

<210> SEQ ID NO 146
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 146
tgcttgtagt ggctggccat ttttctcttg gaaagaaagt                   40

<210> SEQ ID NO 147
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 147
gtcttcactc tgctgaaggc attttttagg cataggaccc gtgtct            46

<210> SEQ ID NO 148
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 148
ctgggtcttg gttctcagct ttttttctct tggaaagaaa gt                42

<210> SEQ ID NO 149
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 149
ggtaaaactg gatcatctca gacaa                                   25
```

-continued

```
<210> SEQ ID NO 150
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 150
tgatgaagat gtcaaactca ctcattttttt aggcatagga cccgtgtct              49

<210> SEQ ID NO 151
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 151
gactgggtgc cctggcc                                                  17

<210> SEQ ID NO 152
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 152
tgtcctagag tctatagagt cgccattttt aggcatagga cccgtgtct               49

<210> SEQ ID NO 153
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 153
ggctttgtag atgcctttct ct                                            22

<210> SEQ ID NO 154
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 154
taggcaggtt gcctgggatt tttaggcata ggacccgtgt ct                      42

<210> SEQ ID NO 155
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 155
cattgtcatg taggcttcta tgtagttttt taggcatagg acccgtgtct              50

<210> SEQ ID NO 156
<211> LENGTH: 42
<212> TYPE: DNA
<213> ORGANISM: Artificial
<220> FEATURE:
<223> OTHER INFORMATION: synthetic oligonucleotide probe
```

```
<400> SEQUENCE: 156
ctcggagatc tcgaagcatg ttttttctct tggaaagaaa gt                    42

<210> SEQ ID NO 157
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 157
ggggcatcac ctcctcca                                              18

<210> SEQ ID NO 158
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 158
ccgattttgg agacctctaa tttatttttc tcttggaaag aaagt                 45

<210> SEQ ID NO 159
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 159
gctgatcctt catttgaaag aaattttct cttggaaaga aagt                   44

<210> SEQ ID NO 160
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 160
tggagcttat taaaggcatt ctttttttag gcataggacc cgtgtct               47

<210> SEQ ID NO 161
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 161
agtgggtgca gctgttctca ttttctctt ggaaagaaag t                      41

<210> SEQ ID NO 162
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 162
gctatcccag agccccagat ttttaggca taggacccgt gtct                   44
```

<210> SEQ ID NO 163
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 163
ccctgatgtc tcagtttcgt atcttttttt aggcatagga cccgtgtct            49

<210> SEQ ID NO 164
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 164
actcctttaa caacaagttg tccatttta ggcataggac ccgtgtct              48

<210> SEQ ID NO 165
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 165
cacctgctcc acggccttt tttaggcata ggacccgtgt ct                    42

<210> SEQ ID NO 166
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 166
gttcacatgc gccttgatgt                                            20

<210> SEQ ID NO 167
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 167
aatcgatgac agcgccgtat ttttaggcat aggacccgtg tct                  43

<210> SEQ ID NO 168
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 168
gctcttgttt tcacagggaa ga                                         22

<210> SEQ ID NO 169
<211> LENGTH: 44
<212> TYPE: DNA
<213> ORGANISM: Artificial
<220> FEATURE:
<223> OTHER INFORMATION: synthetic oligonucleotide probe

```
<400> SEQUENCE: 169
ggcttggcaa cccaggtaac tttttaggca taggacccgt gtct                    44

<210> SEQ ID NO 170
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 170
caggttctcc cccagggatt tttaggcata ggacccgtgt ct                      42

<210> SEQ ID NO 171
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 171
gcctcagcct gagggtcttt ttttctcttg gaaagaaagt                         40

<210> SEQ ID NO 172
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 172
ccttaaagtc ctccagcaag gtttttaggc ataggacccg tgtct                   45

<210> SEQ ID NO 173
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 173
gcggctgatg gtgtgggttt ttaggcatag gacccgtgtc t                       41

<210> SEQ ID NO 174
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 174
aggtacaggc cctctgatgg tttttaggca taggacccgt gtct                    44

<210> SEQ ID NO 175
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 175
tcactccaaa gtgcagcagg tttttaggca taggacccgt gtct                    44
```

```
<210> SEQ ID NO 176
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 176
tcgggccgat tgatctcatt tttctcttgg aaagaaagt                        39

<210> SEQ ID NO 177
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 177
aggcttgtca ctcggggtt                                              19

<210> SEQ ID NO 178
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 178
gaggtccctg gggaactctt                                             20

<210> SEQ ID NO 179
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 179
gcgctgagtc ggtcacccTt ttttaggcat aggacccgtg tct                   43

<210> SEQ ID NO 180
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 180
tctccagctg gaagacccct ttttaggcat aggacccgtg tct                   43

<210> SEQ ID NO 181
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 181
agactcggca aagtcgagat agtttttagg cataggaccc gtgtct                46

<210> SEQ ID NO 182
<211> LENGTH: 41
<212> TYPE: DNA
<213> ORGANISM: Artificial
<220> FEATURE:
<223> OTHER INFORMATION: synthetic oligonucleotide probe
```

-continued

<400> SEQUENCE: 182
gtctggtagg agacggcgat tttttctctt ggaaagaaag t         41

<210> SEQ ID NO 183
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 183
tggggcaggg gaggc         15

<210> SEQ ID NO 184
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 184
cccctctggg gtctccctc         19

<210> SEQ ID NO 185
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 185
caggagggca ttggcccttt ttaggcatag gacccgtgtc t         41

<210> SEQ ID NO 186
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 186
ggccagaggg ctgattagag a         21

<210> SEQ ID NO 187
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 187
gtcctcctca cagggcaatg tttttaggca taggacccgt gtct         44

<210> SEQ ID NO 188
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 188
tcccagatag atgggctcat acttttttctc ttggaaagaa agt         43

```
<210> SEQ ID NO 189
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 189
cagggcttgg cctcagcttt ttaggcatag gacccgtgtc t                 41

<210> SEQ ID NO 190
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 190
tgaagaggac ctgggagtag atg                                     23

<210> SEQ ID NO 191
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 191
gggcagcctt ggccct                                             16

<210> SEQ ID NO 192
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 192
cgagaagatg atctgactgc ctgttttttct cttggaaaga aagt             44

<210> SEQ ID NO 193
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 193
cagaagaggt tgagggtgtc tgattttag gcataggacc cgtgtct            47

<210> SEQ ID NO 194
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 194
gctgcccctc agcttgagtt tttctcttgg aaagaaagt                    39

<210> SEQ ID NO 195
<211> LENGTH: 42
<212> TYPE: DNA
<213> ORGANISM: Artificial
<220> FEATURE:
<223> OTHER INFORMATION: synthetic oligonucleotide probe
```

```
<400> SEQUENCE: 195
ggcggttcag ccactggatt tttaggcata ggacccgtgt ct                    42

<210> SEQ ID NO 196
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 196
caccaccagc tggttatctc tcttttagg cataggaccc gtgtct                 46

<210> SEQ ID NO 197
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 197
ggtttgctac aacatgggct acttttagg cataggaccc gtgtct                 46

<210> SEQ ID NO 198
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 198 aggaggggt aataaaggga t                                            21

<210> SEQ ID NO 199
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 199
cccccaattc tcttttgag cttttctct tggaaagaaa gt                      42

<210> SEQ ID NO 200
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 200
tggcaggggc tcttgatg                                               18

<210> SEQ ID NO 201
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 201
ccctctgggg gccga                                                  15
```

<210> SEQ ID NO 202
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 202
gcttgggttc cgaccctaag tttttaggca taggacccgt gtct                44

<210> SEQ ID NO 203
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 203
atcccaaagt agacctgccc tttttaggca taggacccgt gtct                44

<210> SEQ ID NO 204
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 204
gtttgggaag gttggatgtt c                                         21

<210> SEQ ID NO 205
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 205
gcagagagga ggttgacctt gtttttaggc ataggacccg tgtct               45

<210> SEQ ID NO 206
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 206
tgaggagcac atgggtggag tttttaggca taggacccgt gtct                44

<210> SEQ ID NO 207
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 207
agctccacgc cattggcttt ttaggcatag gacccgtgtc t                   41

<210> SEQ ID NO 208
<211> LENGTH: 47
<212> TYPE: DNA
<213> ORGANISM: Artificial
<220> FEATURE:
<223> OTHER INFORMATION: synthetic oligonucleotide probe -continued

<400> SEQUENCE: 208
aaacttaaat gtgagcatcc tggtttttag gcataggacc cgtgtct           47

<210> SEQ ID NO 209
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 209
ctccagaggt ttgagttctt cttcttttc tcttggaaag aaagt              45

<210> SEQ ID NO 210
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 210
agtgggaagc acttaattat caagttttta ggcataggac ccgtgtct          48

<210> SEQ ID NO 211
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 211
cctgggtctt aagtgaaagt tttt                                    24

<210> SEQ ID NO 212
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 212
gctgtgtttt ctttgtagaa cttgattttt aggcatagga cccgtgtct         49

<210> SEQ ID NO 213
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 213
gctttgagct aaatttagca cttcttttta ggcataggac ccgtgtct          48

<210> SEQ ID NO 214
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 214
agcatattca cacatgaatg ttgtt                                   25

<210> SEQ ID NO 215
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 215
attacgttga tattgctgat taagtctttt taggcatagg acccgtgtct                50

<210> SEQ ID NO 216
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 216
agtaggtgca ctgtttgtga caagttttta ggcataggac ccgtgtct                48

<210> SEQ ID NO 217
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 217
tcagatccct ttagttccag aacttttttc tcttggaaag aaagt                45

<210> SEQ ID NO 218
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 218
aataaataga aggcctgata tgttttattt ttctcttgga aagaaagt                48

<210> SEQ ID NO 219
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 219
tcagtgttga gatgatgctt tgacttttta ggcataggac ccgtgtct                48

<210> SEQ ID NO 220
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 220
aaaaggtaat ccatctgttc agaaa                25

<210> SEQ ID NO 221
<211> LENGTH: 48
<212> TYPE: DNA
<213> ORGANISM: Artificial
<220> FEATURE:
<223> OTHER INFORMATION: synthetic oligonucleotide probe -continued

<400> SEQUENCE: 221
ttctacaatg gttgctgtct catcttttta ggcataggac ccgtgtct    48

<210> SEQ ID NO 222
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 222
cagcagtaaa tgctccagtt gtatttttag gcataggacc cgtgtct    47

<210> SEQ ID NO 223
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 223
tagacactga agatgtttca gttctgtttt taggcatagg acccgtgtct    50

<210> SEQ ID NO 224
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 224
tggccttctt gggcatgtat ttttctcttg gaaagaaagt    40

<210> SEQ ID NO 225
<211> LENGTH: 52
<212> TYPE: DNA
<213> ORGANISM: Artificial
<220> FEATURE:
<223> OTHER INFORMATION: synthetic oligonucleotide probe

<400> SEQUENCE: 225
aatagttaca ataggtagca aaccatactt tttaggcata ggacccgtgt ct    52

<210> SEQ ID NO 226
<211> LENGTH: 32
<212> TYPE: DNA
<213> ORGANISM: Artificial
<220> FEATURE:
<223> OTHER INFORMATION: synthetic oligonucleotide probe

<400> SEQUENCE: 226
attcaacaat aaatataaaa tttaaatatt ta    32

<210> SEQ ID NO 227
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 227
ttccattcaa aatcatctgt aaatc    25

<210> SEQ ID NO 228
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 228
tgagtttggg attcttgtaa ttattaattt ttctcttgga aagaaagt   48

<210> SEQ ID NO 229
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 229
ggagagcttt cagttcatat ggatttttct cttggaaaga aagt   44

<210> SEQ ID NO 230
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 230
ttatcccatg tgtcgaagaa gatattttta ggcataggac ccgtgtct   48

<210> SEQ ID NO 231
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 231
ccagacatca ccaagctttt tt   22

<210> SEQ ID NO 232
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 232
tgaagccctt gctgtagtgg tttttttctct tggaaagaaa gt   42

<210> SEQ ID NO 233
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 233
catcgtgcac ataagcctcg tttttaggca taggacccgt gtct   44

<210> SEQ ID NO 234
<211> LENGTH: 40
<212> TYPE: DNA
<213> ORGANISM: Artificial
<220> FEATURE:
<223> OTHER INFORMATION: synthetic oligonucleotide probe

```
<400> SEQUENCE: 234
cctggaaggt ctgtgggcat ttttctcttg gaaagaaagt                              40

<210> SEQ ID NO 235
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 235
gcagttcagt gatcgtacag gtgttttag gcataggacc cgtgtct                      47

<210> SEQ ID NO 236
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 236
ggtcggagat tcgtagctgg ttttaggca taggacccgt gtct                         44

<210> SEQ ID NO 237
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 237
gcagaggtcc aggtcctggt ttttctcttg gaaagaaagt                              40

<210> SEQ ID NO 238
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 238
gggaaccagc atcttcctca ttttaggca taggacccgt gtct                         44

<210> SEQ ID NO 239
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 239
ccatatcctg tccctggagg ttttttctct tggaaagaaa gt                           42

<210> SEQ ID NO 240
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 240
atggagaaca ccacttgttg cttttttagg cataggaccc gtgtct                      46
```

```
<210> SEQ ID NO 241
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 241
atgccgccat ccagaggttt ttaggcatag gacccgtgtc t                 41

<210> SEQ ID NO 242
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 242
aggccacagg tattttgtca tttttttagg cataggaccc gtgtct           46

<210> SEQ ID NO 243
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 243
aaagaaggtg ctcaggtcat tctttttttct cttggaaaga aagt             44

<210> SEQ ID NO 244
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 244
actttcttct ccttgtacaa aggactttttt aggcatagga cccgtgtct        49

<210> SEQ ID NO 245
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 245
actgacgcgg cctgcc                                             16

<210> SEQ ID NO 246
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 246
gccatcagct tcaaagaaca agtttttagg cataggaccc gtgtct            46

<210> SEQ ID NO 247
<211> LENGTH: 43
<212> TYPE: DNA
<213> ORGANISM: Artificial
<220> FEATURE:
<223> OTHER INFORMATION: synthetic oligonucleotide probe
```

-continued

<400> SEQUENCE: 247
gctgtgagtc ccggagcgtt ttttaggcat aggacccgtg tct                43

<210> SEQ ID NO 248
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 248 attctttttcc ttgaggccca tttttctctt ggaaagaaag t                 41

<210> SEQ ID NO 249
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 249
gcttgtccat ggccacaaca tttttaggca taggacccgt gtct               44

<210> SEQ ID NO 250
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 250
aaggagcact tcatctgttt aggttttag gcataggacc cgtgtct             47

<210> SEQ ID NO 251
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 251
ggttcttctt caaagatgaa gggttttag gcataggacc cgtgtct             47

<210> SEQ ID NO 252
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 252 atctttctttt ggtctgcatt cacttttct cttggaaaga aagt               44

<210> SEQ ID NO 253
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 253
aaggctccaa tgcacccatt tttctcttgg aaagaaagt                     39

```
<210> SEQ ID NO 254
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 254
ggcccacagg gaacgctttt ttaggcatag gacccgtgtc t                    41

<210> SEQ ID NO 255
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 255
gcagcccccg catcg                                                 15

<210> SEQ ID NO 256
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 256
gatgattctg ccctcctcct tttttttaggc ataggacccg tgtct               45

<210> SEQ ID NO 257
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 257
accagggtct cgattggatg tttttaggca taggacccgt gtct                 44

<210> SEQ ID NO 258
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 258
tgggaccact tggcatggtt tttaggcata ggacccgtgt ct                   42

<210> SEQ ID NO 259
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 259
tccatgaact tcaccacttc gtttttttagg cataggaccc gtgtct              46

<210> SEQ ID NO 260
<211> LENGTH: 42
<212> TYPE: DNA
<213> ORGANISM: Artificial
<220> FEATURE:
<223> OTHER INFORMATION: synthetic oligonucleotide probe
```

```
<400> SEQUENCE: 260
ttgcgctttc gtttttgctt tttaggcata ggacccgtgt ct                    42

<210> SEQ ID NO 261
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 261
tggaggtaga gcagcaaggc tttttaggca taggacccgt gtct                  44

<210> SEQ ID NO 262
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 262
gcttgaagat gtactcgatc tcatcttttt aggcatagga cccgtgtct             49

<210> SEQ ID NO 263
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 263 ctgattttt tcttgtctt gctcttttt aggcatagga cccgtgtct                49

<210> SEQ ID NO 264
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 264
agggtactcc tggaagatgt cctttttagg cataggaccc gtgtct                46

<210> SEQ ID NO 265
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 265
ctcctcagtg ggcacacact c                                           21

<210> SEQ ID NO 266
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 266
caggccctcg tcattgcatt tttaggcata ggacccgtgt ct                    42
```

```
<210> SEQ ID NO 267
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 267
ccctttccct ttcctcgaat ttttctcttg gaaagaaagt                          40

<210> SEQ ID NO 268
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 268
ccaggactta taccgggatt tcttttttctc ttggaaagaa agt                     43

<210> SEQ ID NO 269
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 269
gcagtagctg cgctgataga catttttagg cataggaccc gtgtct                  46

<210> SEQ ID NO 270
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 270
catcaggggc acacaggatg                                               20

<210> SEQ ID NO 271
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 271
atttgttgtg ctgtaggaag ctcttttag gcataggacc cgtgtct                  47

<210> SEQ ID NO 272
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 272
ctgccatggg tgcagccttt ttctcttgga aagaaagt                           38

<210> SEQ ID NO 273
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 273
```
atctctccta tgtgctggcc tttttctct tggaaagaaa gt                42

<210> SEQ ID NO 274
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 274
taatctgcat ggtgatgttg gatttttagg cataggaccc gtgtct          46

<210> SEQ ID NO 275
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 275
tggtgaggtt tgatccgcat ttttctcttg gaaagaaagt                 40

<210> SEQ ID NO 276
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 276
ccatgctggt agacgtgtag ggtttttagg cataggaccc gtgtct          46

<210> SEQ ID NO 277
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 277
tctctgccgt gggctgcttt ttaggcatag gacccgtgtc t               41

<210> SEQ ID NO 278
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 278
gccccaattg atgccactct ttttaggcat aggacccgtg tct             43

<210> SEQ ID NO 279
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 279
ggggcagcca ccccttc                                          17

<210> SEQ ID NO 280
<211> LENGTH: 18
<212> TYPE: DNA
<213> ORGANISM: Artificial

```
<220> FEATURE:
<223> OTHER INFORMATION: synthetic oligonucleotide probe

<400> SEQUENCE: 280
gggaggacct gggccttg                                               18

<210> SEQ ID NO 281
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 281
ggcggtaaaa aacgtagctg                                             20

<210> SEQ ID NO 282
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 282
cggaaaacct cctctgtgtc c                                           21

<210> SEQ ID NO 283
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 283
tggcgagctg ccgtcc                                                 16

<210> SEQ ID NO 284
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 284
ccaagttcag ggctgccact ttttaggcat aggacccgtg tct                   43

<210> SEQ ID NO 285
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 285
cagcctgccg ggatccttt ttctcttgga aagaaagt                          38

<210> SEQ ID NO 286
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 286
ggcctaggaa gccagtcagg                                             20
```

```
<210> SEQ ID NO 287
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 287
ccagaagagc caccacacgt ttttaggcat aggacccgtg tct              43

<210> SEQ ID NO 288
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 288
gaccatctct gggtcggcat ttttaggcat aggacccgtg tct              43

<210> SEQ ID NO 289
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 289
aggtgctgca acatggtctg tttttaggca taggacccgt gtct             44

<210> SEQ ID NO 290
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 290
agcagagggc agggcag                                           17

<210> SEQ ID NO 291
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 291
tcttggtgaa gtactcatag gcat                                   24

<210> SEQ ID NO 292
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 292
ccagccaccc ctctgtgc                                          18

<210> SEQ ID NO 293
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 293
``` cccgaagcc attttttcatt tttctcttgg aaagaaagt 39

<210> SEQ ID NO 294
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 294
tgctaggttg cagaggtaag gttttttctc ttggaaagaa agt 43

<210> SEQ ID NO 295
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 295
tcaaacaggc tggtggcaat ttttaggcat aggacccgtg tct 43

<210> SEQ ID NO 296
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 296
cacctgcccc atggtgcttt ttaggcatag gacccgtgtc t 41

<210> SEQ ID NO 297
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 297
gttcaggatg ggaccattgc ttttttaggca taggacccgt gtct 44

<210> SEQ ID NO 298
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 298
aatccaccgg gcaatgcttt ttaggcatag gacccgtgtc t 41

<210> SEQ ID NO 299
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 299
ttgatgtcgt ccccgatgat ttttaggcat aggacccgtg tct 43

<210> SEQ ID NO 300
<211> LENGTH: 41
<212> TYPE: DNA
<213> ORGANISM: Artificial

```
<220> FEATURE:
<223> OTHER INFORMATION: synthetic oligonucleotide probe

<400> SEQUENCE: 300
tgggctacct gctcctcaga tttttctctt ggaaagaaag t                41

<210> SEQ ID NO 301
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 301
gaactctgag tcatagcgtc gg                                     22

<210> SEQ ID NO 302
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 302
ccacgaagcg ggtcaccttt tttaggcata ggacccgtgt ct               42

<210> SEQ ID NO 303
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 303
ggtctcagtg gaggacggga ttttttaggc ataggacccg tgtct            45

<210> SEQ ID NO 304
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 304
agtgatgcag catgaagtcg a                                      21

<210> SEQ ID NO 305
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 305
ccagacggta gccgaagctt tttctcttgg aaagaaagt                   39

<210> SEQ ID NO 306
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 306
agcctcctgt tcctgctgat tttttctctt ggaaagaaag t                41
```

```
<210> SEQ ID NO 307
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 307
gctctccgca ctcctgcctt ttttaggcat aggacccgtg tct                    43

<210> SEQ ID NO 308
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 308
gcacgaagct gcaccacgtt ttttaggcat aggacccgtg tct                    43

<210> SEQ ID NO 309
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 309
ttcagcccga tatctgagct cttttttctct tggaaagaaa gt                    42

<210> SEQ ID NO 310
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 310
aaaccgtagt ctgtagaaag atgagttttt taggcatagg acccgtgtct             50

<210> SEQ ID NO 311
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 311
ccaggtgaca ctgagccagc ttttaggca taggaccgt gtct                     44

<210> SEQ ID NO 312
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 312
cgacactact ggcgacgcat ttttaggcat aggacccgtg tct                    43

<210> SEQ ID NO 313
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 313
```
gcagtgactg tgatgttggc atttttaggc ataggacccg tgtct            45

<210> SEQ ID NO 314
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 314
catggacact atgtagaaag agctg            25

<210> SEQ ID NO 315
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 315
gctggaggtc cttgaccatc            20

<210> SEQ ID NO 316
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 316
tgagttttgc tgaacttgct ccttttctc ttggaaagaa agt            43

<210> SEQ ID NO 317
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 317
ttctgtccaa ggcgtgcctt tttaggcata ggacccgtgt ct            42

<210> SEQ ID NO 318
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 318
catggcctcc gggctc            16

<210> SEQ ID NO 319
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 319
catgttgtga atgtctttga ccgtttttag gcataggacc cgtgtct            47

<210> SEQ ID NO 320
<211> LENGTH: 17
<212> TYPE: DNA
<213> ORGANISM: Artificial

```
<220> FEATURE:
<223> OTHER INFORMATION: synthetic oligonucleotide probe

<400> SEQUENCE: 320
gggggtttct ggccacg                                                        17

<210> SEQ ID NO 321
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 321
caccaagagc acagcctttg tttttttaggc ataggacccg tgtct                        45

<210> SEQ ID NO 322
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 322
gcgtcgtgga tgacacagtg atttttttagg cataggaccc gtgtct                       46

<210> SEQ ID NO 323
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 323
ccggactgtt ctgaaacttc ctttttttctc ttggaaagaa agt                          43

<210> SEQ ID NO 324
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 324
gattccacaa ccctgaaagg tttttttagg cataggaccc gtgtct                        46

<210> SEQ ID NO 325
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 325
gactcctggg aatactggca cttttttaggc ataggacccg tgtct                        45

<210> SEQ ID NO 326
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 326
gcctcaggcc gctccagttt ttctcttgga aagaaagt                                 38
```

```
<210> SEQ ID NO 327
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 327
tctccctccg ggactgcttt tttctcttgg aaagaaagt                    39

<210> SEQ ID NO 328
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 328
ggcggatcag gctgcaattt ttaggcatag gacccgtgtc t                 41

<210> SEQ ID NO 329
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 329
aactggcagg agaacttctg g                                       21

<210> SEQ ID NO 330
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 330
tccaggagtg ggggtcttg                                          19

<210> SEQ ID NO 331
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 331
ggctcctgga agtcttcggt ttttaggcat aggacccgtg tct               43

<210> SEQ ID NO 332
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 332
cactcgctcc actcgcct                                           18

<210> SEQ ID NO 333
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 333
```
tgcccgaact cctcctggtt tttctcttgg aaagaaagt                39

<210> SEQ ID NO 334
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 334
cggttgaagc gttcctggtt tttaggcata ggacccgtgt ct             42

<210> SEQ ID NO 335
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 335
gctgcattgt tcccatagag ttcttttag gcataggacc cgtgtct         47

<210> SEQ ID NO 336
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 336
gccatccaag ctgcgatctt tttaggcata ggacccgtgt ct             42

<210> SEQ ID NO 337
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 337
gctcccggtt gctctgagat ttttctcttg gaaagaaagt                40

<210> SEQ ID NO 338
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 338
cacaaaagta tcccagccgc                                      20

<210> SEQ ID NO 339
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 339
cacagtgccc cgccg                                           15

<210> SEQ ID NO 340
<211> LENGTH: 46
<212> TYPE: DNA
<213> ORGANISM: Artificial

```
<220> FEATURE:
<223> OTHER INFORMATION: synthetic oligonucleotide probe

<400> SEQUENCE: 340
cgactcacca atacctgcat cttttttagg cataggaccc gtgtct                46

<210> SEQ ID NO 341
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 341
gggcctcagt cctgttctct tttttaggc ataggacccg tgtct                  45

<210> SEQ ID NO 342
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 342
cacctcccgg gcatcc                                                 16

<210> SEQ ID NO 343
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 343
gctgggatgt caggtcactg aattttagg cataggaccc gtgtct                 46

<210> SEQ ID NO 344
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 344
tggcactggg ggtctcca                                               18

<210> SEQ ID NO 345
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 345
tgcccgccgg taccg                                                  15

<210> SEQ ID NO 346
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 346
cgttctcctg gatccaaggc ttttaggca taggacccgt gtct                   44
```

<210> SEQ ID NO 347
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 347
tgtatccttt ctgggaaagc ttttttctc ttggaaagaa agt                43

<210> SEQ ID NO 348
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 348
cctccctcag cgcttgcttt tttctcttgg aaagaaagt                    39

<210> SEQ ID NO 349
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 349
cctgttcaaa gctctgatat gctgttttta ggcataggac ccgtgtct          48

<210> SEQ ID NO 350
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 350
caggatgggt tgccattgat ttttaggcat aggacccgtg tct               43

<210> SEQ ID NO 351
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 351
tctccgattc agtcccttct gttttaggc ataggacccg tgtct              45

<210> SEQ ID NO 352
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 352
ttactgctgc catggggat                                          19

<210> SEQ ID NO 353
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 353
ccttgtctac gctttccacg tttttaggca taggacccgt gtct          44

<210> SEQ ID NO 354
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 354
gtaggagaga aagtcaacca ccattttag gcataggacc cgtgtct          47

<210> SEQ ID NO 355
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 355
cagttcaaac tcgtcgcctg tttttaggca taggacccgt gtct          44

<210> SEQ ID NO 356
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 356
aaactgctgc tgtggccagt ttttctcttg gaaagaaagt          40

<210> SEQ ID NO 357
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 357 cgacccagt ttaccccatt tttaggcata ggaccgtgt ct          42

<210> SEQ ID NO 358
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 358
ccacatcact aaactgactc cagc          24

<210> SEQ ID NO 359
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 359
tggctccatt caccgcgttt ttaggcatag gacccgtgtc t          41

<210> SEQ ID NO 360
<211> LENGTH: 48
<212> TYPE: DNA
<213> ORGANISM: Artificial

```
<220> FEATURE:
<223> OTHER INFORMATION: synthetic oligonucleotide probe

<400> SEQUENCE: 360
tctaggtggt cattcaggta agtgttttta ggcataggac ccgtgtct          48

<210> SEQ ID NO 361
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 361
aaggagaaaa aggccacaat g                                       21

<210> SEQ ID NO 362
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 362
gggctgtctg ccaggtgctt tttctcttgg aaagaaagt                    39

<210> SEQ ID NO 363
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 363
tcccggaaga gttcattcac tattttagg cataggaccc gtgtct             46

<210> SEQ ID NO 364
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 364
ccctttcggc tctcggcttt tttctcttgg aaagaaagt                    39

<210> SEQ ID NO 365
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 365
tccctggggt gatgtgga                                           18

<210> SEQ ID NO 366
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 366
tctgctgttc caatcataca tgtattttta ggcataggac ccgtgtct          48
```

```
<210> SEQ ID NO 367
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 367
gccctcgctt ctgagccttt tttctcttgg aaagaaagt                     39

<210> SEQ ID NO 368
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 368
tgaattccac attcttcatc gcttttagg cataggaccc gtgtct              46

<210> SEQ ID NO 369
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 369
tggcctccca aagtgctgtt tttaggcata ggacccgtgt ct                 42

<210> SEQ ID NO 370
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 370
gcccagcctt ttggtttctt atttttctct tggaaagaaa gt                 42

<210> SEQ ID NO 371
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 371
ttcttgtctc agtttctggg agatttttag gcataggacc cgtgtct            47

<210> SEQ ID NO 372
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 372
tggcccatcc acctccattt ttaggcatag gacccgtgtc t                  41

<210> SEQ ID NO 373
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 373
```
tggccctctg acaccacata g                                              21

<210> SEQ ID NO 374
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 374
gcgtttacca tgttggccat ttttaggcat aggacccgtg tct                      43

<210> SEQ ID NO 375
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 375
cataatattt ctccttggca gaaactttt aggcatagga cccgtgtct                 49

<210> SEQ ID NO 376
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 376
ggtgagctgt gagactgctc catttttagg cataggaccc gtgtct                   46

<210> SEQ ID NO 377
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 377
ttccctgcta gataagggca ttttttaggc ataggacccg tgtct                    45

<210> SEQ ID NO 378
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 378
ggattacagg tgtgagccac tactttttag gcataggacc cgtgtct                  47

<210> SEQ ID NO 379
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 379
ttctgaataa aaaacatctt tggc                                           24

<210> SEQ ID NO 380
<211> LENGTH: 44
<212> TYPE: DNA
<213> ORGANISM: Artificial

```
<220> FEATURE:
<223> OTHER INFORMATION: synthetic oligonucleotide probe

<400> SEQUENCE: 380
ggcactgcag gtacagggac tttttaggca taggacccgt gtct                    44

<210> SEQ ID NO 381
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 381
cacaggctcc agaagaagtc ag                                            22

<210> SEQ ID NO 382
<211> LENGTH: 51
<212> TYPE: DNA
<213> ORGANISM: Artificial
<220> FEATURE:
<223> OTHER INFORMATION: synthetic oligonucleotide probe

<400> SEQUENCE: 382
tgtgtaggag aggataagtt tctttctttt ttaggcatag gacccgtgtc t             51

<210> SEQ ID NO 383
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 383
cagagtgtgc tgcagccaga ttttttctctt ggaaagaaag t                       41

<210> SEQ ID NO 384
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 384
agaggctgct gttctccagc ttttttctctt ggaaagaaag t                       41

<210> SEQ ID NO 385
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 385
gccattgagt tcaatgtgaa gatttttag gcataggacc cgtgtct                   47

<210> SEQ ID NO 386
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 386
ggctggtctc gaactcctga ttttttctctt ggaaagaaag t                       41
```

```
<210> SEQ ID NO 387
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 387
cttctcggtg aactgtgcac atttttaggc ataggacccg tgtct            45

<210> SEQ ID NO 388
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 388
atttttgcat ttttactagg gacatttttta ggcataggac ccgtgtct        48

<210> SEQ ID NO 389
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 389
ccaggagtgg gcgttttctt ttttctcttg gaaagaaagt                   40

<210> SEQ ID NO 390
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 390
cctgaagtga tctgccctcc t                                       21

<210> SEQ ID NO 391
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 391
gcagggacat gtccgcagta tttttaggca taggacccgt gtct              44

<210> SEQ ID NO 392
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 392
tcctggggat acttagagtt cct                                     23

<210> SEQ ID NO 393
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 393
```
cccggaagta tactttggaa tata                                      24

<210> SEQ ID NO 394
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 394
ttggacttgc ctgttaaatg gttttctct tggaaagaaa gt                   42

<210> SEQ ID NO 395
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 395
agagctgaaa catccccagg tttttaggca taggacccgt gtct                44

<210> SEQ ID NO 396
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 396
tcccctccat catcaccaga tttttaggca taggacccgt gtct                44

<210> SEQ ID NO 397
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 397
catgtagacc ttgtggctca ggttttagg cataggaccc gtgtct               46

<210> SEQ ID NO 398
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 398
atcacaaggc caccttctt attttaggc ataggacccg tgtct                 45

<210> SEQ ID NO 399
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 399
gcgggcccac atctgc                                               16

<210> SEQ ID NO 400
<211> LENGTH: 42
<212> TYPE: DNA
<213> ORGANISM: Artificial

```
<220> FEATURE:
<223> OTHER INFORMATION: synthetic oligonucleotide probe

<400> SEQUENCE: 400
ccagctcctt ctgtaggtgg atttttctct tggaaagaaa gt                          42

<210> SEQ ID NO 401
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 401
ggcaggttgt tgcaagattg acttttagg cataggaccc gtgtct                       46

<210> SEQ ID NO 402
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 402
cccaatccta ccaaggcaac tttttaggca taggacccgt gtct                        44

<210> SEQ ID NO 403
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 403
ccagaggcat ggaccttgag                                                   20

<210> SEQ ID NO 404
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 404
ggtggcagcg gtagtggagt ttttctcttg gaaagaaagt                             40

<210> SEQ ID NO 405
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 405
tggttccctc tcttcttcag gttttctct tggaaagaaa gt                           42

<210> SEQ ID NO 406
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 406
ccagtagtgc agtagctcat catctttttt aggcatagga cccgtgtct                   49
```

```
<210> SEQ ID NO 407
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 407
gctggtagac tctcggagtt ctgttttct cttggaaaga aagt                44

<210> SEQ ID NO 408
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 408
aagatgatgc tgtgtgcatc tgttttagg cataggaccc gtgtct              46

<210> SEQ ID NO 409
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 409
ggagacacag gcctgtgctg ttttaggca taggacccgt gtct                44

<210> SEQ ID NO 410
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 410
tgcccccagg tagctgcttt tttctcttgg aaagaaagt                     39

<210> SEQ ID NO 411
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 411
cagaaccatg aaaaacatca caa                                      23

<210> SEQ ID NO 412
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 412
aattccatag gtgtcttccc att                                      23

<210> SEQ ID NO 413
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 413
```

```
tacttcactc cagaaagcag gac                                              23

<210> SEQ ID NO 414
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 414
gcggcggagg tggtagtttt ttctcttgga aagaaagt                              38

<210> SEQ ID NO 415
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 415
ttttcagggg gtggactgg                                                   19

<210> SEQ ID NO 416
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 416
gccactttcc tcagctcctt t                                                21

<210> SEQ ID NO 417
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 417
caaagtacag cccagtttca ttgttttag gcataggacc cgtgtct                     47

<210> SEQ ID NO 418
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 418
gcagtggtgg cggcg                                                       15

<210> SEQ ID NO 419
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 419
ggtggcctat ttgcttctcc atttttaggc ataggacccg tgtct                      45

<210> SEQ ID NO 420
<211> LENGTH: 44
<212> TYPE: DNA
<213> ORGANISM: Artificial
```

```
<220> FEATURE:
<223> OTHER INFORMATION: synthetic oligonucleotide probe

<400> SEQUENCE: 420
cgtggtggtg aagctgtagc tttttaggca taggacccgt gtct            44

<210> SEQ ID NO 421
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 421
cgcaggatgg catgggg                                          17

<210> SEQ ID NO 422
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 422
acaggtcttt gcggatgtcc tttttaggca taggacccgt gtct            44

<210> SEQ ID NO 423
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 423
acaggactcc atgcccaggt ttttctcttg gaaagaaagt                 40

<210> SEQ ID NO 424
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 424
cgatttcccg ctcggc                                           16

<210> SEQ ID NO 425
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 425
gggcacagtg tgggtgacct ttttaggcat aggacccgtg tct             43

<210> SEQ ID NO 426
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 426
agacagcact gtgttggcgt tttttaggca taggacccgt gtct            44
```

```
<210> SEQ ID NO 427
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 427
tcggtcagca gcacgggttt ttaggcatag gacccgtgtc t                41

<210> SEQ ID NO 428
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 428
ccagggcgac gtagcacatt tttaggcata ggacccgtgt ct               42

<210> SEQ ID NO 429
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 429
catgaggtag tcagtcaggt cccttttag gcataggacc cgtgtct           47

<210> SEQ ID NO 430
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 430
ctcgtagctc ttctccaggg atttttctct tggaaagaaa gt               42

<210> SEQ ID NO 431
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 431
tctcaaacat gatctgggtc atctttttag gcataggacc cgtgtct          47

<210> SEQ ID NO 432
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 432
tggctggggt gttgaagg                                          18

<210> SEQ ID NO 433
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 433
```

```
ggagctggaa gcagccgttt tttctcttgg aaagaaagt                      39

<210> SEQ ID NO 434
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 434
ggccatctct tgctcgaagt tttttaggca taggacccgt gtct               44

<210> SEQ ID NO 435
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 435
aaggaaggct ggaagagtgc tttttctctt ggaaagaaag t                   41

<210> SEQ ID NO 436
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 436
cgcgctcggt gaggatcttt ttttctcttg gaaagaaagt                     40

<210> SEQ ID NO 437
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 437
ctcagggcag cggaaccttt ttaggcatag gacccgtgtc t                   41

<210> SEQ ID NO 438
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 438
ccgtcaccgg agtccatcat ttttaggcat aggacccgtg tct                 43

<210> SEQ ID NO 439
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 439
gagggcatac ccctcgtaga tttttaggc ataggacccg tgtct                45

<210> SEQ ID NO 440
<211> LENGTH: 23
<212> TYPE: DNA
<213> ORGANISM: Artificial
```

```
<220> FEATURE:
<223> OTHER INFORMATION: synthetic oligonucleotide probe

<400> SEQUENCE: 440
acgtcacact tcatgatgga gtt                                              23

<210> SEQ ID NO 441
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 441
gcttctcctt aatgtcacgc atttttaggc ataggacccg tgtct                      45

<210> SEQ ID NO 442
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 442
acctggccgt caggcag                                                     17

<210> SEQ ID NO 443
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 443
cgatgccagt ggtacggctt tttaggcata ggacccgtgt ct                         42

<210> SEQ ID NO 444
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 444
cagcctggat agcaacgtac atttttaggc ataggacccg tgtct                      45

<210> SEQ ID NO 445
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 445
gaaggtagtt tcgtggatgc ctttttaggc ataggacccg tgtct                      45

<210> SEQ ID NO 446
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 446
gctcattgcc aatggtgatg tttttctctt ggaaagaaag t                          41
```

```
<210> SEQ ID NO 447
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 447
cagaggcgta cagggatagc attttttaggc ataggacccg tgtct            45

<210> SEQ ID NO 448
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 448
ggccagccag gtccaga                                             17

<210> SEQ ID NO 449
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 449
ttctcgcggt tggccttttt ttctcttgga aagaaagt                      38

<210> SEQ ID NO 450
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 450
ggggttcagg ggggcc                                              16

<210> SEQ ID NO 451
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 451
gaactgaatt tgttgttttt cactcttttt taggcatagg acccgtgtct         50

<210> SEQ ID NO 452
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 452
ttgccactgt ttcaggattt aattttttagg cataggaccc gtgtct            46

<210> SEQ ID NO 453
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 453
```
tccatgaagt tgatgccaat tattttagg cataggaccc gtgtct          46

<210> SEQ ID NO 454
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 454
gattggcttt tttgagatct ttaattttt ctcttggaaa gaaagt          46

<210> SEQ ID NO 455
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 455
ccccaagtta gatctggatc ctttttagg cataggaccc gtgtct          46

<210> SEQ ID NO 456
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 456
agaccaagct ttggatttca tttttagg cataggaccc gtgtct          46

<210> SEQ ID NO 457
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 457
cgaagcagtt gaactttctg ttctttttct cttggaaaga aagt          44

<210> SEQ ID NO 458
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 458
tgactccagc aatagtggtg atatatttt tctcttggaa agaaagt          47

<210> SEQ ID NO 459
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 459
tcctctttgc acttggtgtt gtttttaggc ataggacccg tgtct          45

<210> SEQ ID NO 460
<211> LENGTH: 50
<212> TYPE: DNA
<213> ORGANISM: Artificial

```
<220> FEATURE:
<223> OTHER INFORMATION: synthetic oligonucleotide probe

<400> SEQUENCE: 460
catgttttct gtacttcctt tctctttttt taggcatagg acccgtgtct          50

<210> SEQ ID NO 461
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 461
tgctgtgtct tggacattgt cattttttag gcataggacc cgtgtct             47

<210> SEQ ID NO 462
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 462
tctgaagttt gaattttctg agtcattttt aggcatagga cccgtgtct           49

<210> SEQ ID NO 463
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 463
ggttttcctt tctgtgcttt ctgttttttct cttggaaaga aagt               44

<210> SEQ ID NO 464
<211> LENGTH: 51
<212> TYPE: DNA
<213> ORGANISM: Artificial
<220> FEATURE:
<223> OTHER INFORMATION: synthetic oligonucleotide probe

<400> SEQUENCE: 464
ctagtaatgt ccttgaggat gatagtcttt ttaggcatag gacccgtgtc t        51

<210> SEQ ID NO 465
<211> LENGTH: 51
<212> TYPE: DNA
<213> ORGANISM: Artificial
<220> FEATURE:
<223> OTHER INFORMATION: synthetic oligonucleotide probe

<400> SEQUENCE: 465
agtatttaca gccagctatt aagaatcttt ttaggcatag gacccgtgtc t        51

<210> SEQ ID NO 466
<211> LENGTH: 51
<212> TYPE: DNA
<213> ORGANISM: Artificial
<220> FEATURE:
<223> OTHER INFORMATION: synthetic oligonucleotide probe

<400> SEQUENCE: 466
ttttcaaaca ctaattgcat atactcattt ttaggcatag gacccgtgtc t        51
```

```
<210> SEQ ID NO 467
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 467
gcaaaagaag aagacaaagc ca                                              22

<210> SEQ ID NO 468
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 468
ggttggagat tcatgagaac cttttttag gcataggacc cgtgtct                    47

<210> SEQ ID NO 469
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 469
atgtacccag taaaaaacca agc                                             23

<210> SEQ ID NO 470
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 470
cattgacacc attctttcga acatttttag gcataggacc cgtgtct                   47

<210> SEQ ID NO 471
<211> LENGTH: 52
<212> TYPE: DNA
<213> ORGANISM: Artificial
<220> FEATURE:
<223> OTHER INFORMATION: synthetic oligonucleotide probe

<400> SEQUENCE: 471
ttactcaagt caacatcaga taaatttatt tttaggcata ggacccgtgt ct             52

<210> SEQ ID NO 472
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 472
caatgtgtca tacgcttctt tcttttttta ggcataggac ccgtgtct                  48

<210> SEQ ID NO 473
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 473
```

```
cacccaaaca attagtggaa ttgtttttag gcataggacc cgtgtct              47
```

<210> SEQ ID NO 474
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 474

```
aagcctttaa cttgacttag tgtcattttt aggcatagga cccgtgtct            49
```

<210> SEQ ID NO 475
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 475

```
tcttgatctc atctattttg cttttttta ggcataggac ccgtgtct              48
```

<210> SEQ ID NO 476
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 476

```
ctcttcagcg ctaataaatg ataaattttt ctcttggaaa gaaagt               46
```

<210> SEQ ID NO 477
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 477

```
tgaattttct ctgcaagagt acaaattttt aggcatagga cccgtgtct            49
```

<210> SEQ ID NO 478
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 478

```
aagtactgcc tggccctcct ttttaggcat aggacccgtg tct                  43
```

<210> SEQ ID NO 479
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 479

```
gggccttcgc agggtttctt tttaggcata ggacccgtgt ct                   42
```

<210> SEQ ID NO 480
<211> LENGTH: 17
<212> TYPE: DNA
<213> ORGANISM: Artificial

```
<220> FEATURE:
<223> OTHER INFORMATION: synthetic oligonucleotide probe

<400> SEQUENCE: 480
ggacaaggcc tgggggg                                                          17

<210> SEQ ID NO 481
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 481
tccagcggga ggcacc                                                           16

<210> SEQ ID NO 482
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 482
caccttcaat gcccagctgt ttttaggcat aggacccgtg tct                             43

<210> SEQ ID NO 483
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 483
gctggcggat ccctttaggt ttttctcttg gaaagaaagt                                 40

<210> SEQ ID NO 484
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 484
cttggtgctc accctgcagt ttttaggcat aggacccgtg tct                             43

<210> SEQ ID NO 485
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 485
ctgctaggga tgaggttttg attttttctc ttggaaagaa agt                             43

<210> SEQ ID NO 486
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 486
ggaactgttt gggctttaag ttttttagg cataggaccc gtgtct                           46
```

```
<210> SEQ ID NO 487
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 487
aaggtctgct ggatcatctt ccttttagg cataggaccc gtgtct          46

<210> SEQ ID NO 488
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 488
gttccgcttc tcaccatctt tttttaggc ataggacccg tgtct           45

<210> SEQ ID NO 489
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 489
ccggcagtag ccgtctatga tttttaggca taggacccgt gtct            44

<210> SEQ ID NO 490
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 490
gacgcactcc tcctccctgt ttttaggcat aggacccgtg tct             43

<210> SEQ ID NO 491
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 491
gccaatgacc aggtccacag tttttaggc ataggacccg tgtct            45

<210> SEQ ID NO 492
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 492
agcgaggcgt actgctggtt tttaggcata ggacccgtgt ct              42

<210> SEQ ID NO 493
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 493
```

-continued acagcggtag gtctcctggt tttttctctt ggaaagaaag t                41

<210> SEQ ID NO 494
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 494
ctgagaggtg ggaccgcctt tttaggcata ggacccgtgt ct               42

<210> SEQ ID NO 495
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 495
gggcctccag gtttagcatg tttttctctt ggaaagaaag t                41

<210> SEQ ID NO 496
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 496
actcggccag gcaggtg                                           17

<210> SEQ ID NO 497
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 497
cgatgttggc gaagccgttt ttaggcatag gacccgtgtc t                41

<210> SEQ ID NO 498
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 498
aatgttccat ccttgaatga gttc                                   24

<210> SEQ ID NO 499
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 499
gtctgactct atgctgcagc tctttttct cttggaaaga aagt              44

<210> SEQ ID NO 500
<211> LENGTH: 47
<212> TYPE: DNA
<213> ORGANISM: Artificial

```
<220> FEATURE:
<223> OTHER INFORMATION: synthetic oligonucleotide probe

<400> SEQUENCE: 500
cctaggatgg atgatgagag agcttttag gcataggacc cgtgtct                    47

<210> SEQ ID NO 501
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 501
ggtcagccat gttctcagcc tttttaggc ataggacccg tgtct                      45

<210> SEQ ID NO 502
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 502
gggatctggg gcaggct                                                    17

<210> SEQ ID NO 503
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 503
gcgagagtgt tgaagaactt cattttttct cttggaaaga aagt                      44

<210> SEQ ID NO 504
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 504
ggctttgcgt cctgactagt cattttagg cataggaccc gtgtct                     46

<210> SEQ ID NO 505
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 505
tgatggacct gatctgcttg attttaggc ataggacccg tgtct                      45

<210> SEQ ID NO 506
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 506
gtcgggaatc tctgcgtaga tttttaggc ataggacccg tgtct                      45
```

```
<210> SEQ ID NO 507
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 507
tgctgctggt tggctgct                                                  18

<210> SEQ ID NO 508
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 508
cctgctcact cggctcaaac tttttttaggc ataggacccg tgtct                    45

<210> SEQ ID NO 509
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 509
ctgggatctg gaacatgctc tttttttaggc ataggacccg tgtct                    45

<210> SEQ ID NO 510
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 510
tggaaggcag aggcaggta                                                 19

<210> SEQ ID NO 511
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 511
cccccatccc ttcgtcgttt ttaggcatag gacccgtgtc t                        41

<210> SEQ ID NO 512
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 512
ccggagcctg agggcc                                                    16

<210> SEQ ID NO 513
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 513
```
cgtagtcaag gcacagctgg tttttaggca taggacccgt gtct    44

<210> SEQ ID NO 514
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 514
cgggtctggc ctggcag    17

<210> SEQ ID NO 515
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 515
ggagctgagg ctgtcggctt tttctcttgg aaagaaagt    39

<210> SEQ ID NO 516
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 516
cccacaggag gcctggg    17

<210> SEQ ID NO 517
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 517
gagctcgcgg ccatagcttt ttctcttgga aagaaagt    38

<210> SEQ ID NO 518
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 518
gcccgccagg cctcc    15

<210> SEQ ID NO 519
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 519
accgtagcgc ccccag    16

<210> SEQ ID NO 520
<211> LENGTH: 38
<212> TYPE: DNA
<213> ORGANISM: Artificial

```
<220> FEATURE:
<223> OTHER INFORMATION: synthetic oligonucleotide probe

<400> SEQUENCE: 520
agcgcctcca tgatggcttt ttctcttgga aagaaagt                              38

<210> SEQ ID NO 521
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 521
gcctggcgat gatgcttgtt tttctcttgg aaagaaagt                             39

<210> SEQ ID NO 522
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 522
tcctccgtcc ccgcg                                                       15

<210> SEQ ID NO 523
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 523
tgggccctca tctgtctgct ttttaggcat aggacccgtg tct                        43

<210> SEQ ID NO 524
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 524
cccctggctt cctctcccct tttctcttgg aaagaaagt                             39

<210> SEQ ID NO 525
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 525
gctgtgctgc ccagaggttt ttttaggcat aggacccgtg tct                        43

<210> SEQ ID NO 526
<211> LENGTH: 13
<212> TYPE: DNA
<213> ORGANISM: Artificial
<220> FEATURE:
<223> OTHER INFORMATION: synthetic oligonucleotide probe

<400> SEQUENCE: 526
gcgagcggcc ccg                                                         13
```

```
<210> SEQ ID NO 527
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 527
cctgctggtg actggcgttt tttctcttgg aaagaaagt                    39

<210> SEQ ID NO 528
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 528
tcaggacctc agtctcccct ctttttaggc ataggacccg tgtct             45

<210> SEQ ID NO 529
<211> LENGTH: 14
<212> TYPE: DNA
<213> ORGANISM: Artificial
<220> FEATURE:
<223> OTHER INFORMATION: synthetic oligonucleotide probe

<400> SEQUENCE: 529
tggggcccag gccc                                               14

<210> SEQ ID NO 530
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 530
agtcccttct taaaggagtc cactttttag gcataggacc cgtgtct           47

<210> SEQ ID NO 531
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 531
ggccaacggt ggccc                                              15

<210> SEQ ID NO 532
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 532
ctctctgcag agctggagtc ttttttctc ttggaaagaa agt                43

<210> SEQ ID NO 533
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 533
```

```
aaagggctg ggctcct                                                    17

<210> SEQ ID NO 534
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 534 cgtccctgc ggggc                                                      15

<210> SEQ ID NO 535
<211> LENGTH: 14
<212> TYPE: DNA
<213> ORGANISM: Artificial
<220> FEATURE:
<223> OTHER INFORMATION: synthetic oligonucleotide probe

<400> SEQUENCE: 535 gggggcgcc gagc                                                       14

<210> SEQ ID NO 536
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 536
ccggatctcc acagccctt tttaggcata ggacccgtgt ct                        42

<210> SEQ ID NO 537
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 537
gggtaggagc tgtggcgact ttttaggca taggaccgt gtct                       44

<210> SEQ ID NO 538
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 538
aaactcgtca ctcatcctcc gttttaggc ataggaccg tgtct                      45

<210> SEQ ID NO 539
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 539
gggctgtgag acaagatgt tattttagg cataggaccc gtgtct                     46

<210> SEQ ID NO 540
<211> LENGTH: 25
<212> TYPE: DNA
<213> ORGANISM: Artificial
```

```
<220> FEATURE:
<223> OTHER INFORMATION: synthetic oligonucleotide probe

<400> SEQUENCE: 540
tcttcaatac aaaatagggga tggtt                                              25

<210> SEQ ID NO 541
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 541
cggagacgac ccgatggctt tttaggcata ggacccgtgt ct                            42

<210> SEQ ID NO 542
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 542
tttgtgcagc gagggactgt ttttctcttg gaaagaaagt                               40

<210> SEQ ID NO 543
<211> LENGTH: 28
<212> TYPE: DNA
<213> ORGANISM: Artificial
<220> FEATURE:
<223> OTHER INFORMATION: synthetic oligonucleotide probe

<400> SEQUENCE: 543
aatcttgatt attataactc ctctcgat                                            28

<210> SEQ ID NO 544
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 544
ccccaatttg gaaagtgcat at                                                  22

<210> SEQ ID NO 545
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 545
ctgggccaga gctacatctt tattttttagg cataggaccc gtgtct                       46

<210> SEQ ID NO 546
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 546
catagaccct gtcagctgtc attcttttta ggcataggac ccgtgtct                      48
```

```
<210> SEQ ID NO 547
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 547
tctgcccctg ccaaatcttt ttttctcttg gaaagaaagt                              40

<210> SEQ ID NO 548
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 548
ctctgttgcc caactgcaaa tttttaggca taggacccgt gtct                         44

<210> SEQ ID NO 549
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 549
ctcagatgtt cttctccttt tggttttttct cttggaaaga aagt                        44

<210> SEQ ID NO 550
<211> LENGTH: 27
<212> TYPE: DNA
<213> ORGANISM: Artificial
<220> FEATURE:
<223> OTHER INFORMATION: synthetic oligonucleotide probe

<400> SEQUENCE: 550
catctgaaca cagagaggta agtgagc                                            27

<210> SEQ ID NO 551
<211> LENGTH: 28
<212> TYPE: DNA
<213> ORGANISM: Artificial
<220> FEATURE:
<223> OTHER INFORMATION: synthetic oligonucleotide probe

<400> SEQUENCE: 551
gatgataagc atttactaat aaaacaaa                                           28

<210> SEQ ID NO 552
<211> LENGTH: 51
<212> TYPE: DNA
<213> ORGANISM: Artificial
<220> FEATURE:
<223> OTHER INFORMATION: synthetic oligonucleotide probe

<400> SEQUENCE: 552
cagtgtaaag aggagtacat acagaggttt ttaggcatag gacccgtgtc t                 51

<210> SEQ ID NO 553
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 553
```

```
tgtggagaga atgttggcgt tttttaggca taggacccgt gtct            44

<210> SEQ ID NO 554
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 554
gatcacatat aaatggaagg ccatttttag gcataggacc cgtgtct         47

<210> SEQ ID NO 555
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 555
cttgtttgaa ctaaattgag gtgcttttc tcttggaaag aaagt            45

<210> SEQ ID NO 556
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 556
actctattta actctgaccc tggc                                  24

<210> SEQ ID NO 557
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 557
ggagggccga ggaggttttt ttaggcatag gacccgtgtc t               41

<210> SEQ ID NO 558
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 558 actgttttt cattcataaa gagcatttt ctcttggaaa gaaagt            46

<210> SEQ ID NO 559
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 559
gttaagatgc agatgtgaat ccctttttag gcataggacc cgtgtct         47

<210> SEQ ID NO 560
<211> LENGTH: 48
<212> TYPE: DNA
<213> ORGANISM: Artificial
```

```
<220> FEATURE:
<223> OTHER INFORMATION: synthetic oligonucleotide probe

<400> SEQUENCE: 560
ggattgccct gattatttac attttttta ggcataggac ccgtgtct        48

<210> SEQ ID NO 561
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 561
aaatcttaag cctgccagag ttttttttct cttggaaaga aagt            44

<210> SEQ ID NO 562
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 562
tggcctctct tgcggagtat ttttaggcat aggacccgtg tct              43

<210> SEQ ID NO 563
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 563
tataatcact tcctaatttt tcccattttt aggcatagga cccgtgtct        49

<210> SEQ ID NO 564
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 564
ttccttgatt ctgtgacttt attccttttt aggcatagga cccgtgtct        49

<210> SEQ ID NO 565
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 565 ggctttttt agagcccttg tttttctct tggaaagaaa gt                  42

<210> SEQ ID NO 566
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 566 ggcttttct tccgccgttt ttctcttgga aagaaagt                      38
```

```
<210> SEQ ID NO 567
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 567
tccacgccgt agctgtcatt ttttaggcat aggacccgtg tct          43

<210> SEQ ID NO 568
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 568
cggcgtcttg aacacaatgg                                    20

<210> SEQ ID NO 569
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 569
tgactgtcac gggctcgact ttttaggcat aggacccgtg tct          43

<210> SEQ ID NO 570
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 570
ccccgtttcc gcttcttgtt tttaggcata ggacccgtgt ct           42

<210> SEQ ID NO 571
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 571
tgaaaggcaa tggctcgctt tttaggcata ggacccgtgt ct           42

<210> SEQ ID NO 572
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 572
gcccgacctt cccaggagtt tttaggcata ggacccgtgt ct           42

<210> SEQ ID NO 573
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 573
```

```
caatctggcg gtgcacgttt ttctcttgga aagaaagt                               38

<210> SEQ ID NO 574
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 574
gccgctgcag gaagacgttt tttctcttgg aaagaaagt                              39

<210> SEQ ID NO 575
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 575
gcaaatccgc agctctgatg tttttaggca taggacccgt gtct                        44

<210> SEQ ID NO 576
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 576
gccctgctga acaccactga tttttaggca taggacccgt gtct                        44

<210> SEQ ID NO 577
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 577
tgcagacccc atcggtgatt tttaggcata ggacccgtgt ct                          42

<210> SEQ ID NO 578
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 578
gggctcggaa agcacagg                                                     18

<210> SEQ ID NO 579
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 579
aatctccagg tcctcgtagg gttttctct tggaaagaaa gt                           42

<210> SEQ ID NO 580
<211> LENGTH: 46
<212> TYPE: DNA
<213> ORGANISM: Artificial
```

```
<220> FEATURE:
<223> OTHER INFORMATION: synthetic oligonucleotide probe

<400> SEQUENCE: 580
cgcagagcaa gtagagctcc tcttttagg cataggaccc gtgtct                    46

<210> SEQ ID NO 581
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 581
atccatccgg cgcatctttt ttaggcatag gacccgtgtc t                        41

<210> SEQ ID NO 582
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 582
ggtcgcgagg caggtacg                                                  18

<210> SEQ ID NO 583
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 583
ccaaggacgt cgggcatc                                                  18

<210> SEQ ID NO 584
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 584
ccgctttcct tgttaattcg tttttctctt ggaaagaaag t                        41

<210> SEQ ID NO 585
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 585
tgtttgtgga tttcttgtca tagac                                          25

<210> SEQ ID NO 586
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 586
atgaggcctg gaagcagatc ttttaggca taggacccgt gtct                      44
```

```
<210> SEQ ID NO 587
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 587
gccaccggtg cacggc                                                       16

<210> SEQ ID NO 588
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 588
gtccctgctg gtcccgattt tttctcttgg aaagaaagt                              39

<210> SEQ ID NO 589
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 589
tttgctctcg atgccatggt ttttaggcat aggacccgtg tct                         43

<210> SEQ ID NO 590
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 590
tatgtcctct ttctgcacct tgt                                               23

<210> SEQ ID NO 591
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 591
tcggcctggg agaagtcatt tttaggcata ggacccgtgt ct                          42

<210> SEQ ID NO 592
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 592
gggtcagagc tgttcagctc ctttttaggc ataggacccg tgtct                       45

<210> SEQ ID NO 593
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 593
```

```
ggggagggac agcagcag                                                 18

<210> SEQ ID NO 594
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 594
aggggaattg cagagccc                                                 18

<210> SEQ ID NO 595
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 595
ttttgatgat gcccccactc tttttaggca taggacccgt gtct                    44

<210> SEQ ID NO 596
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 596
tgtcccttcc ccttccagt                                                19

<210> SEQ ID NO 597
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 597
aagaattcag gtctgagtgt ccagtttttc tcttggaaag aaagt                   45

<210> SEQ ID NO 598
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 598
ttgagctgcc tgaggtagaa cttttttctc ttggaaagaa agt                     43

<210> SEQ ID NO 599
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 599
gggtgggaca ggcacctc                                                 18

<210> SEQ ID NO 600
<211> LENGTH: 18
<212> TYPE: DNA
<213> ORGANISM: Artificial
```

```
<220> FEATURE:
<223> OTHER INFORMATION: synthetic oligonucleotide probe

<400> SEQUENCE: 600
ccattgagct gggggtgg                                                       18

<210> SEQ ID NO 601
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 601
agggtgccct tcttcttgtg                                                     20

<210> SEQ ID NO 602
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 602
ggagggatgg ggtggatg                                                       18

<210> SEQ ID NO 603
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 603
tgccaccaca tgggaccctt tttaggcata ggacccgtgt ct                            42

<210> SEQ ID NO 604
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 604
gggggcggtc gctgc                                                          15

<210> SEQ ID NO 605
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 605
cccagtgcag gtcagaggg                                                      19

<210> SEQ ID NO 606
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 606
tgtctgactc cttgttccgc ttttttctct tggaaagaaa gt                            42
```

```
<210> SEQ ID NO 607
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 607
agctggagaa gaagggtaag cttttttctc ttggaaagaa agt            43

<210> SEQ ID NO 608
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 608
caagagccag gagggtacca tttttaggca taggacccgt gtct            44

<210> SEQ ID NO 609
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 609
ctcctagaaa gatctactcc cccttttct cttggaaaga aagt             44

<210> SEQ ID NO 610
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 610
gaggtgaggg gactccaaag t                                     21

<210> SEQ ID NO 611
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 611
agagccacct ggagcatgag tttttaggca taggacccgt gtct            44

<210> SEQ ID NO 612
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 612
gctcaacact gagacgggct ctttttaggc ataggacccg tgtct           45

<210> SEQ ID NO 613
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 613
```

```
gctaatcaaa gtgcaatgaa ctgg                                           24

<210> SEQ ID NO 614
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 614
gggagccaaa gagggaaaag                                                20

<210> SEQ ID NO 615
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 615
agggtactga agggaaagac aag                                            23

<210> SEQ ID NO 616
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 616
cccactcaag ggggcctg                                                  18

<210> SEQ ID NO 617
<211> LENGTH: 27
<212> TYPE: DNA
<213> ORGANISM: Artificial
<220> FEATURE:
<223> OTHER INFORMATION: synthetic oligonucleotide probe

<400> SEQUENCE: 617
atcatatacc cctaacacag agataac                                        27

<210> SEQ ID NO 618
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 618
ccatctgttt acttctcaaa tgaaattttt aggcatagga cccgtgtct                49

<210> SEQ ID NO 619
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 619
gggtggtctg ctccagtacc tttttaggca taggacccgt gtct                     44

<210> SEQ ID NO 620
<211> LENGTH: 44
<212> TYPE: DNA
<213> ORGANISM: Artificial
```

```
<220> FEATURE:
<223> OTHER INFORMATION: synthetic oligonucleotide probe

<400> SEQUENCE: 620 tcaccccac agctagagga tttttaggca taggacccgt gtct                44

<210> SEQ ID NO 621
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 621
caccctgccc aaccttagag tttttaggca taggacccgt gtct                44

<210> SEQ ID NO 622
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 622
gccatgaggg caggcg                                               16

<210> SEQ ID NO 623
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 623
ggtccccagc tcagccctat ttttctcttg gaaagaaagt                     40

<210> SEQ ID NO 624
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 624
ccaccttccc cctgcctttt ttaggcatag gacccgtgtc t                   41

<210> SEQ ID NO 625
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 625
aggaaggtcg ctggacgatt ttttaggcat aggacccgtg tct                 43

<210> SEQ ID NO 626
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 626
ttgaggggcc agtgtctcc                                            19
```

```
<210> SEQ ID NO 627
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 627
tcacaagaca gaggggggta t                                              21

<210> SEQ ID NO 628
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 628
ggggctcctc aaaaggtaca g                                              21

<210> SEQ ID NO 629
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 629
ggtgaggccc cttcaaagtg                                                20

<210> SEQ ID NO 630
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 630
ggctgtgctc acttcagggt tttttaggca taggacccgt gtct                     44

<210> SEQ ID NO 631
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 631
ggcccagctg ctgctgtatt ttttaggcat aggacccgtg tct                      43

<210> SEQ ID NO 632
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 632
ctgagcattg acatcagcac c                                              21

<210> SEQ ID NO 633
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 633
```

```
tgcgaggtga agggcagttt tttctcttgg aaagaaagt                                  39

<210> SEQ ID NO 634
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 634
gtcctctgtg aactccgtga acttttttctc ttggaaagaa agt                            43

<210> SEQ ID NO 635
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 635
ggatagaggc taagtgtaga cacgttttta ggcataggac ccgtgtct                        48

<210> SEQ ID NO 636
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 636
ctctgttgac atcagcccca tttttaggca taggacccgt gtct                            44

<210> SEQ ID NO 637
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 637
cacttcaaca ggagtgacac cagtttttag gcataggacc cgtgtct                         47

<210> SEQ ID NO 638
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 638
ccggccatta cagggctctt tttaggcata ggacccgtgt ct                              42

<210> SEQ ID NO 639
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 639
gtcaggattt tgcaggtcca cttttaggc ataggacccg tgtct                            45

<210> SEQ ID NO 640
<211> LENGTH: 46
<212> TYPE: DNA
<213> ORGANISM: Artificial
```

```
<220> FEATURE:
<223> OTHER INFORMATION: synthetic oligonucleotide probe

<400> SEQUENCE: 640
tgtggccatt gtagttggta gcttttagg cataggaccc gtgtct                    46

<210> SEQ ID NO 641
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 641
gccccaggtg agctggta                                                  18

<210> SEQ ID NO 642
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 642
tcatcctcac tctctggcag c                                              21

<210> SEQ ID NO 643
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 643
gacgctggcc tccaaacatt tttaggcata ggacccgtgt ct                       42

<210> SEQ ID NO 644
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 644
cgatgcccag gtagccattt tttctcttgg aaagaaagt                           39

<210> SEQ ID NO 645
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 645
gggagaatag ccctggtagg taattttttct cttggaaaga aagt                    44

<210> SEQ ID NO 646
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 646
cggggtggtg caggact                                                   17
```

```
<210> SEQ ID NO 647
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 647
gccaggcagc cctgctcttt ttctcttgga aagaaagt                              38

<210> SEQ ID NO 648
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 648
caaggacacc aaaagctcca                                                  20

<210> SEQ ID NO 649
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 649
ccgggtgctt gggcg                                                       15

<210> SEQ ID NO 650
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 650
cttcaggatg gagtggaggt gttttctct tggaaagaaa gt                          42

<210> SEQ ID NO 651
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 651
tctgactctg tgtcatagct ctcctttta ggcataggac ccgtgtct                    48

<210> SEQ ID NO 652
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 652
gagtcaggac tcccacgctg tttttaggca taggacccgt gtct                       44

<210> SEQ ID NO 653
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 653
```

```
cacagtcatc atagggcagc tc                                          22

<210> SEQ ID NO 654
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 654
atctgaaggt tttctagtgt cagcttttttt aggcatagga cccgtgtct           49

<210> SEQ ID NO 655
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 655 cccttttgcac tcataacgtc atttttaggc ataggacccg tgtct                45

<210> SEQ ID NO 656
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 656
cgaggtgggt cactgtgtgt tac                                         23

<210> SEQ ID NO 657
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 657
caggtccacc tcgatcttgg tttttaggca taggacccgt gtct                  44

<210> SEQ ID NO 658
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 658
tactcagatc catcaccttc ttcattttta ggcataggac ccgtgtct              48

<210> SEQ ID NO 659
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 659
ccagactgtg ggcatgagca ttttttaggca taggacccgt gtct                 44

<210> SEQ ID NO 660
<211> LENGTH: 44
<212> TYPE: DNA
<213> ORGANISM: Artificial
```

```
<220> FEATURE:
<223> OTHER INFORMATION: synthetic oligonucleotide probe

<400> SEQUENCE: 660
cgcacagagc ctgctgtctt tttttaggca taggacccgt gtct                    44

<210> SEQ ID NO 661
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 661
gtccattcga gaaatcttca ggttttagg cataggaccc gtgtct                   46

<210> SEQ ID NO 662
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 662
gcccttctca ctggaggcac                                               20

<210> SEQ ID NO 663
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 663
actggctcta aggaaggcag attttaggc ataggacccg tgtct                    45

<210> SEQ ID NO 664
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 664
aggggccttc acagccat                                                 18

<210> SEQ ID NO 665
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 665
ctggtccctc gtagttacag atct                                          24

<210> SEQ ID NO 666
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 666
tgggccccac agaaacgttt ttaggcatag gacccgtgtc t                       41
```

```
<210> SEQ ID NO 667
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 667
atcgaaatcg gaagcctctc tttttctctt ggaaagaaag t          41

<210> SEQ ID NO 668
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 668
cctccgtaag gccctgggtt tttctcttgg aaagaaagt             39

<210> SEQ ID NO 669
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 669
tgacagtggg ataggtcttt cgtttttagg cataggaccc gtgtct     46

<210> SEQ ID NO 670
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 670
gaagcgcagc cgcacta                                     17

<210> SEQ ID NO 671
<211> LENGTH: 26
<212> TYPE: DNA
<213> ORGANISM: Artificial
<220> FEATURE:
<223> OTHER INFORMATION: synthetic oligonucleotide probe

<400> SEQUENCE: 671
tgcctctgaa gttttgtat catagt                            26

<210> SEQ ID NO 672
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 672
ttgctatcat ggatgggctg                                  20

<210> SEQ ID NO 673
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 673
```

| | |
|---|---|
| gttctttggc ctcttgctcc tttttctctt ggaaagaaag t | 41 |

<210> SEQ ID NO 674
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 674

| | |
|---|---|
| ttaaattggg cagtcatgtc cttttttagg cataggaccc gtgtct | 46 |

<210> SEQ ID NO 675
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 675

| | |
|---|---|
| catgcaggac acccaggttg tttttaggca taggacccgt gtct | 44 |

<210> SEQ ID NO 676
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 676

| | |
|---|---|
| ggaggtgact ggcttcaggg tttttctctt ggaaagaaag t | 41 |

<210> SEQ ID NO 677
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 677

| | |
|---|---|
| agctcccgct gctcgg | 16 |

<210> SEQ ID NO 678
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 678

| | |
|---|---|
| gcctagagcg gagccgcttt ttaggcatag gacccgtgtc t | 41 |

<210> SEQ ID NO 679
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 679

| | |
|---|---|
| cgagcattgc ttgcccattt ttctcttgga aagaaagt | 38 |

<210> SEQ ID NO 680
<211> LENGTH: 43
<212> TYPE: DNA
<213> ORGANISM: Artificial

```
<220> FEATURE:
<223> OTHER INFORMATION: synthetic oligonucleotide probe

<400> SEQUENCE: 680
gcagggagaa ggagccatct ttttaggcat aggacccgtg tct                    43

<210> SEQ ID NO 681
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 681
gcgcagatcc ccagctcttt ttaggcatag gacccgtgtc t                      41

<210> SEQ ID NO 682
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 682 cccccatcatg ttcttcttag tcatttttag gcataggacc cgtgtct               47

<210> SEQ ID NO 683
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 683
tttgatgccc ccggagattt tttctcttgg aaagaaagt                         39

<210> SEQ ID NO 684
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 684
cgggcagtcc tccatgggtt tttaggcata ggacccgtgt ct                     42

<210> SEQ ID NO 685
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 685
aggccgaggc ctggc                                                   15

<210> SEQ ID NO 686
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 686
gctgaaactc ggagttgtcg attttttaggc ataggacccg tgtct                 45
```

```
<210> SEQ ID NO 687
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 687
cgttccttcc ccagcctgtt tttctcttgg aaagaaagt                              39

<210> SEQ ID NO 688
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 688
acgtaaaggg atagggctgg tttttctctt ggaaagaaag t                           41

<210> SEQ ID NO 689
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 689
ccatggtggg aaactcatca tttttaggc ataggacccg tgtct                        45

<210> SEQ ID NO 690
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 690
gtcttcatca tcaaactgca gctttttag gcataggacc cgtgtct                      47

<210> SEQ ID NO 691
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 691
ggtgctggct tggggaca                                                     18

<210> SEQ ID NO 692
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 692
ggactgggac aggggctg                                                     18

<210> SEQ ID NO 693
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 693
```
tgccctggtt cagcagcttt tttctcttgg aaagaaagt                          39

<210> SEQ ID NO 694
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 694
ccaagcaagg cccccagttt ttaggcatag gacccgtgtc t                       41

<210> SEQ ID NO 695
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 695
cggatgccag gtctgtgaac atttttctct tggaaagaaa gt                      42

<210> SEQ ID NO 696
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 696
gataccatgg ctggagcagg                                               20

<210> SEQ ID NO 697
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 697
gggcctgggc cagagct                                                  17

<210> SEQ ID NO 698
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 698
ggtgggcttg ggggca                                                   16

<210> SEQ ID NO 699
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 699
ggtggggcca cagcctg                                                  17

<210> SEQ ID NO 700
<211> LENGTH: 49
<212> TYPE: DNA
<213> ORGANISM: Artificial

```
<220> FEATURE:
<223> OTHER INFORMATION: synthetic oligonucleotide probe

<400> SEQUENCE: 700
gaaggtctca tatgtccttt tacgtttttt aggcatagga cccgtgtct                    49

<210> SEQ ID NO 701
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 701
gcgagttata gcctcagggt actcttttta ggcataggac ccgtgtct                     48

<210> SEQ ID NO 702
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 702
cagctgggtc tgtgctgttg                                                    20

<210> SEQ ID NO 703
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 703
ggcacagcaa tgcgtcga                                                      18

<210> SEQ ID NO 704
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 704
aggagggcct ggggcta                                                       17

<210> SEQ ID NO 705
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 705
ggtggaggcc ggggg                                                         15

<210> SEQ ID NO 706
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 706
ggcaggggct ggagcct                                                       17
```

```
<210> SEQ ID NO 707
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 707
ggggcaggac ttgggga                                                    17

<210> SEQ ID NO 708
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 708
aggactcttc ttcatgatgc tcttttttc tcttggaaag aaagt                      45

<210> SEQ ID NO 709
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 709
tgatctgccc agaaggaaac attttctct tggaaagaaa gt                         42

<210> SEQ ID NO 710
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 710
gcagcagggc ctctgacag                                                  19

<210> SEQ ID NO 711
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 711
ttctcctcaa tccggtgacg tttttaggca taggacccgt gtct                      44

<210> SEQ ID NO 712
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 712
ggcctctggg ctgtcactag tttttaggca taggacccgt gtct                      44

<210> SEQ ID NO 713
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 713
```

```
gtgggggggcc acaggta                                                    17

<210> SEQ ID NO 714
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 714
gaagctgagc tgcgggaa                                                    18

<210> SEQ ID NO 715
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 715
catcagcatg ggctcagttg t                                                21

<210> SEQ ID NO 716
<211> LENGTH: 13
<212> TYPE: DNA
<213> ORGANISM: Artificial
<220> FEATURE:
<223> OTHER INFORMATION: synthetic oligonucleotide probe

<400> SEQUENCE: 716
ggggccgggg cca                                                         13

<210> SEQ ID NO 717
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 717
agttgatggt gctcagggat gttttttaggc ataggacccg tgtct                     45

<210> SEQ ID NO 718
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 718
tcggtgggtc cgctgaattt ttaggcatag gacccgtgtc t                          41

<210> SEQ ID NO 719
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 719
ccaggattat agccccttat acatttttct cttggaaaga aagt                       44

<210> SEQ ID NO 720
<211> LENGTH: 25
<212> TYPE: DNA
<213> ORGANISM: Artificial
```

```
<220> FEATURE:
<223> OTHER INFORMATION: synthetic oligonucleotide probe

<400> SEQUENCE: 720
tgtcacatga agtataccca ggttt                                             25

<210> SEQ ID NO 721
<211> LENGTH: 28
<212> TYPE: DNA
<213> ORGANISM: Artificial
<220> FEATURE:
<223> OTHER INFORMATION: synthetic oligonucleotide probe

<400> SEQUENCE: 721
tctggattaa atattgtatg agtcaaag                                          28

<210> SEQ ID NO 722
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 722
gcgaagccga ccaccatttt ttaggcatag gacccgtgtc t                           41

<210> SEQ ID NO 723
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 723
tttccatttg tgaccaactg aattttagg cataggaccc gtgtct                       46

<210> SEQ ID NO 724
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 724
tcaggccttc ccaaatatgg tttttctctt ggaaagaaag t                           41

<210> SEQ ID NO 725
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 725
catagttgca gattttgacc tgagtttta ggcataggac ccgtgtct                     48

<210> SEQ ID NO 726
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 726
ctgcttggcg gattagctct ttttaggcat aggacccgtg tct                         43
```

```
<210> SEQ ID NO 727
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 727
ggttgctcta atatttgaag gtatgttttt ctcttggaaa gaaagt                    46

<210> SEQ ID NO 728
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 728
aaggatccaa atgaaacatt tgttttttag gcataggacc cgtgtct                   47

<210> SEQ ID NO 729
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 729
ggccatctgc tgttggcatt tttaggcata ggacccgtgt ct                        42

<210> SEQ ID NO 730
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 730
gtgttttccc accaggctgt tttttaggca taggacccgt gtct                      44

<210> SEQ ID NO 731
<211> LENGTH: 52
<212> TYPE: DNA
<213> ORGANISM: Artificial
<220> FEATURE:
<223> OTHER INFORMATION: synthetic oligonucleotide probe

<400> SEQUENCE: 731
ggtaagactt cttgttcttt tcactagatt tttaggcata ggacccgtgt ct             52

<210> SEQ ID NO 732
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 732
gtgccatctg tggttgaaat actttttag gcataggacc cgtgtct                    47

<210> SEQ ID NO 733
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 733
```
ggatgggcct tcacatacat aac                                              23

<210> SEQ ID NO 734
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 734
ggcaccaggt agtccaccat gttttaggc ataggacccg tgtct                       45

<210> SEQ ID NO 735
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 735
agtgcagatc ccatcctcac a                                                21

<210> SEQ ID NO 736
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 736
tttttcccga tctcccagct ttttctcttg gaaagaaagt                            40

<210> SEQ ID NO 737
<211> LENGTH: 26
<212> TYPE: DNA
<213> ORGANISM: Artificial
<220> FEATURE:
<223> OTHER INFORMATION: synthetic oligonucleotide probe

<400> SEQUENCE: 737
tccagtgttt caaatacttt tttctt                                           26

<210> SEQ ID NO 738
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 738
ggaaacgaaa tcctctctgt tta                                              23

<210> SEQ ID NO 739
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 739
gggcatgcag gtggatattt tttttctctt ggaaagaaag t                          41

<210> SEQ ID NO 740
<211> LENGTH: 45
<212> TYPE: DNA
<213> ORGANISM: Artificial

```
<220> FEATURE:
<223> OTHER INFORMATION: synthetic oligonucleotide probe

<400> SEQUENCE: 740
cttctgcttg caaataggca attttttaggc ataggacccg tgtct            45

<210> SEQ ID NO 741
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 741 ggtcaggggtg caccaagagt tttttaggca taggacccgt gtct             44

<210> SEQ ID NO 742
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 742
cgcctctgtc attcgtgctt ttttaggcat aggacccgtg tct               43

<210> SEQ ID NO 743
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 743
gtccttgggt ccagcagtta ctttttctct tggaaagaaa gt                42

<210> SEQ ID NO 744
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 744
tgccggtccc ctccac                                             16

<210> SEQ ID NO 745
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 745
caataacctt tgctggtccc attttttaggc ataggacccg tgtct            45

<210> SEQ ID NO 746
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 746
ggcgtcgttt ccagctctg                                          19
```

```
<210> SEQ ID NO 747
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 747
gggccttgag gtgctttgtt tttctcttgg aaagaaagt                    39

<210> SEQ ID NO 748
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 748
gatgctgaca ctccatgcag atttttaggc ataggacccg tgtct            45

<210> SEQ ID NO 749
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 749
gcgctggctc gatctcagtt                                        20

<210> SEQ ID NO 750
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 750
gtgggactga ctttccctga gttttttaggc ataggacccg tgtct           45

<210> SEQ ID NO 751
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 751
gagtcccaaa atacacgcag c                                      21

<210> SEQ ID NO 752
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 752
cgtccccgtc ctgtcccttt ttaggcatag gacccgtgtc t                41

<210> SEQ ID NO 753
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 753
```

```
cgcgagggat ctgacttgga tttttctctt ggaaagaaag t                    41

<210> SEQ ID NO 754
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 754
ggcccgggcg cactt                                                 15

<210> SEQ ID NO 755
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 755
tgcaaaagcc cttgttttct g                                          21

<210> SEQ ID NO 756
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 756
gccaggatgt tcttgcagga tttttaggca taggacccgt gtct                 44

<210> SEQ ID NO 757
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 757
acgctggtga caggaaggag tttttaggca taggacccgt gtct                 44

<210> SEQ ID NO 758
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 758
caatgaaaca cttctggcag tatcttttta ggcataggac ccgtgtct             48

<210> SEQ ID NO 759
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 759
catgaaatct ctgattctga gcttttttc tcttggaaag aaagt                 45

<210> SEQ ID NO 760
<211> LENGTH: 42
<212> TYPE: DNA
<213> ORGANISM: Artificial
```

```
<220> FEATURE:
<223> OTHER INFORMATION: synthetic oligonucleotide probe

<400> SEQUENCE: 760
ggaggctggt gctgaggctt tttaggcata ggacccgtgt ct                           42

<210> SEQ ID NO 761
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 761
gctcctcgct gcggcagttt ttctcttgga aagaaagt                                38

<210> SEQ ID NO 762
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 762
cggcttttct gcacttgctt ttttctcttg gaaagaaagt                              40

<210> SEQ ID NO 763
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 763
tggaggaggc ctctgctgt                                                     19

<210> SEQ ID NO 764
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 764
agatcccatt aaatgtcctg gtattttag gcataggacc cgtgtct                       47

<210> SEQ ID NO 765
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 765
tgttctggaa cctggacgct tttttaggca taggacccgt gtct                         44

<210> SEQ ID NO 766
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 766
tctctgtact cgatgaaaca cagtg                                              25
```

```
<210> SEQ ID NO 767
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 767
tgtggttcga ggcacatctc tttttaggc ataggacccg tgtct                45

<210> SEQ ID NO 768
<211> LENGTH: 17
<212> TYPE: DNA
<213> ORGANISM: Artificial
<220> FEATURE:
<223> OTHER INFORMATION: synthetic oligonucleotide probe

<400> SEQUENCE: 768
tggcaagaat gcgggga                                              17

<210> SEQ ID NO 769
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 769
gcagcagcaa aatgtttgtt t                                         21

<210> SEQ ID NO 770
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 770 agtcctttg aagcaagtac tgcttttag gcataggacc cgtgtct              47

<210> SEQ ID NO 771
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 771
caggagtccg tgcagcttg                                            19

<210> SEQ ID NO 772
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 772
cttcaaacat ggtgcttcca attttaggc ataggacccg tgtct                45

<210> SEQ ID NO 773
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 773
```

```
gctcttctgt cctttggcc tttttaggc ataggacccg tgtct            45

<210> SEQ ID NO 774
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 774
agacaggcag ccagcagg                                        18

<210> SEQ ID NO 775
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 775
ggggctccgg acgagc                                          16

<210> SEQ ID NO 776
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 776
ccccaggcac ggaatggttt ttctcttgga aagaaagt                  38

<210> SEQ ID NO 777
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 777
gggtgccgca ttccct                                          16

<210> SEQ ID NO 778
<211> LENGTH: 26
<212> TYPE: DNA
<213> ORGANISM: Artificial
<220> FEATURE:
<223> OTHER INFORMATION: synthetic oligonucleotide probe

<400> SEQUENCE: 778
tctaggtata cctcaaactc caaaag                               26

<210> SEQ ID NO 779
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 779
atgtaccgaa tttgtttgtc aattttttta ggcataggac ccgtgtct       48

<210> SEQ ID NO 780
<211> LENGTH: 43
<212> TYPE: DNA
<213> ORGANISM: Artificial
```

```
<220> FEATURE:
<223> OTHER INFORMATION: synthetic oligonucleotide probe

<400> SEQUENCE: 780
cgttctgaag aggtgagtgg cttttttctc ttggaaagaa agt                    43

<210> SEQ ID NO 781
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 781
caagtctcct cattgaatcc agatttttta ggcataggac ccgtgtct               48

<210> SEQ ID NO 782
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 782
aacaacataa gttctgtgcc cagtttttag gcataggacc cgtgtct                47

<210> SEQ ID NO 783
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 783
ccatctttgg aaggttcagg t                                            21

<210> SEQ ID NO 784
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 784
ccttttcttg caggaactgg attttttctc ttggaaagaa agt                    43

<210> SEQ ID NO 785
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 785
catctttgga atcttctcct ggtttttagg cataggaccc gtgtct                 46

<210> SEQ ID NO 786
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 786
caggactttt gtactcatct gcactttta ggcataggac ccgtgtct                48
```

```
<210> SEQ ID NO 787
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 787
ttgttacatg tctcctttct caggtttta ggcataggac ccgtgtct                48

<210> SEQ ID NO 788
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 788
gctgagatgc cgtcgaggtt tttctcttgg aaagaaagt                         39

<210> SEQ ID NO 789
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 789
tgctgctttc acacatgtta ctc                                          23

<210> SEQ ID NO 790
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 790
tggaagcatc catcttttc agttttagg cataggaccc gtgtct                   46

<210> SEQ ID NO 791
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 791
ccttaaagct gcgcagaatg tttttctctt ggaaagaaag t                      41

<210> SEQ ID NO 792
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 792
gggtactggg gcagggaa                                                18

<210> SEQ ID NO 793
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 793
```
gtctgtgtgg ggcggcta                                                        18

<210> SEQ ID NO 794
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 794
ccactggttc tgtgcctgca                                                      20

<210> SEQ ID NO 795
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 795
agatgagttg tcatgtcctg cagtttttag gcataggacc cgtgtct                        47

<210> SEQ ID NO 796
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 796
accagtgatg attttcacca ggtttttagg cataggaccc gtgtct                         46

<210> SEQ ID NO 797
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 797
ggcagcaggc aacaccagtt tttaggcata ggacccgtgt ct                             42

<210> SEQ ID NO 798
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 798
acatttgccg aagagccctt ttttaggcat aggacccgtg tct                            43

<210> SEQ ID NO 799
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 799
catttgtggt tgggtcaggg ttttaggca taggacccgt gtct                            44

<210> SEQ ID NO 800
<211> LENGTH: 22
<212> TYPE: DNA
<213> ORGANISM: Artificial

```
<220> FEATURE:
<223> OTHER INFORMATION: synthetic oligonucleotide probe

<400> SEQUENCE: 800
aaggaatgcc cattaacaac aa                                            22

<210> SEQ ID NO 801
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 801
tggacaggtt tctgaccaga agtttttagg cataggaccc gtgtct                  46

<210> SEQ ID NO 802
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 802
tgttttctgc cagtgcctct tttttaggc ataggacccg tgtct                    45

<210> SEQ ID NO 803
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 803
actctcaaat ctgttctgga ggtacttttt aggcatagga cccgtgtct               49

<210> SEQ ID NO 804
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 804
agctctggct tgttcctcac tttttaggc ataggacccg tgtct                    45

<210> SEQ ID NO 805
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 805
cgctcatact tttagttctc catagagttt ttctcttgga aagaaagt                48

<210> SEQ ID NO 806
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 806
caatctgagg tgcccatgct tttttctctt ggaaagaaag t                       41
```

```
<210> SEQ ID NO 807
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 807
caggctggac tgcaggaact tttttaggca taggacccgt gtct                    44

<210> SEQ ID NO 808
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 808
gtggttattg catctagatt ctttgttttt aggcatagga cccgtgtct               49

<210> SEQ ID NO 809
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 809
gcttcgtcag caggctgg                                                 18

<210> SEQ ID NO 810
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 810
cgagaagatg atctgactgc ctgttttttct cttggaaaga aagt                   44

<210> SEQ ID NO 811
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 811
cagaagaggt tgagggtgtc tgattttag gcataggacc cgtgtct                  47

<210> SEQ ID NO 812
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 812
gcggctgatg gtgtgggttt ttaggcatag gacccgtgtc t                       41

<210> SEQ ID NO 813
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 813
```

```
aggtacaggc cctctgatgg tttttaggca taggacccgt gtct          44

<210> SEQ ID NO 814
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 814
gctgcccctc agcttgagtt tttctcttgg aaagaaagt                39

<210> SEQ ID NO 815
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 815
tcgggccgat tgatctcatt tttctcttgg aaagaaagt                39

<210> SEQ ID NO 816
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 816
ggcggttcag ccactggatt tttaggcata ggacccgtgt ct            42

<210> SEQ ID NO 817
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 817
aggcttgtca ctcggggtt                                     19

<210> SEQ ID NO 818
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 818
tctccagctg gaagacccc                                     19

<210> SEQ ID NO 819
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 819
caccaccagc tggttatctc tc                                 22

<210> SEQ ID NO 820
<211> LENGTH: 45
<212> TYPE: DNA
<213> ORGANISM: Artificial
```

```
<220> FEATURE:
<223> OTHER INFORMATION: synthetic oligonucleotide probe

<400> SEQUENCE: 820
ggccagaggg ctgattagag atttttaggc ataggacccg tgtct          45

<210> SEQ ID NO 821
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 821 aggaggggt aataaaggga t                                      21

<210> SEQ ID NO 822
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 822
ggtttgctac aacatgggct acttttagg cataggaccc gtgtct           46

<210> SEQ ID NO 823
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 823
agactcggca aagtcgagat agttttagg cataggaccc gtgtct           46

<210> SEQ ID NO 824
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 824
cccccaattc tcttttgag cttttctct tggaaagaaa gt                42

<210> SEQ ID NO 825
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 825
tggcaggggc tcttgatg                                         18

<210> SEQ ID NO 826
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 826
gtctggtagg agacggcgat ttttctctt ggaaagaaag t                41
```

```
<210> SEQ ID NO 827
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 827
gcttgggttc cgaccctaag tttttaggca taggacccgt gtct           44

<210> SEQ ID NO 828
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 828
tggggcaggg gaggc           15

<210> SEQ ID NO 829
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 829
gtttgggaag gttggatgtt c           21

<210> SEQ ID NO 830
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 830
atcccaaagt agacctgccc tttttaggca taggacccgt gtct           44

<210> SEQ ID NO 831
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 831
cccctctggg gtctccctc           19

<210> SEQ ID NO 832
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 832
caggagggca ttggcccttt ttaggcatag gacccgtgtc t           41

<210> SEQ ID NO 833
<211> LENGTH: 45
<212> TYPE: DNA
<213> ORGANISM: Artificial
<220> FEATURE:
<223> OTHER INFORMATION: synthetic oligonucleotide probe
```

-continued

<400> SEQUENCE: 833
gcagagagga ggttgacctt gttttttaggc ataggacccg tgtct         45

<210> SEQ ID NO 834
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 834
gtcctcctca cagggcaatg tttttaggca taggacccgt gtct          44

<210> SEQ ID NO 835
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 835
tcccagatag atgggctcat acttttttctc ttggaaagaa agt           43

<210> SEQ ID NO 836
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 836
cagggcttgg cctcagcttt ttaggcatag gacccgtgtc t              41

<210> SEQ ID NO 837
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 837
tgaggagcac atgggtggag tttttaggca taggacccgt gtct           44

<210> SEQ ID NO 838
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 838
tgaagaggac ctgggagtag atg                                 23

<210> SEQ ID NO 839
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 839
gcgctgagtc ggtcaccct                                      19

-continued

```
<210> SEQ ID NO 840
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 840
agctccacgc cattggcttt ttaggcatag gacccgtgtc t                    41

<210> SEQ ID NO 841
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 841
gggcagcctt ggccct                                                16
```